US011305282B2

(12) United States Patent
Barany

(10) Patent No.: US 11,305,282 B2
(45) Date of Patent: Apr. 19, 2022

(54) DEVICES, PROCESSES, AND SYSTEMS FOR DETERMINATION OF NUCLEIC ACID SEQUENCE, EXPRESSION, COPY NUMBER, OR METHYLATION CHANGES USING COMBINED NUCLEASE, LIGASE, POLYMERASE, AND SEQUENCING REACTIONS

(71) Applicant: Cornell University, Ithaca, NY (US)

(72) Inventor: Francis Barany, New York, NY (US)

(73) Assignee: CORNELL UNIVERSITY, Ithaca, NY (US)

( * ) Notice: Subject to any disclaimer, the term of this patent is extended or adjusted under 35 U.S.C. 154(b) by 0 days.

(21) Appl. No.: 16/498,893

(22) PCT Filed: Mar. 29, 2018

(86) PCT No.: PCT/US2018/025213
§ 371 (c)(1),
(2) Date: Sep. 27, 2019

(87) PCT Pub. No.: WO2018/183723
PCT Pub. Date: Oct. 4, 2018

(65) Prior Publication Data
US 2020/0038871 A1    Feb. 6, 2020

Related U.S. Application Data

(60) Provisional application No. 62/478,412, filed on Mar. 29, 2017.

(51) Int. Cl.
*C12Q 1/6869*    (2018.01)
*B01L 3/00*    (2006.01)

(52) U.S. Cl.
CPC ...... *B01L 3/502761* (2013.01); *C12Q 1/6869* (2013.01); *B01L 2200/027* (2013.01);
(Continued)

(58) Field of Classification Search
CPC .......... C12Q 1/6837; B01J 2219/00317; B01J 2219/00644; B01L 3/502761;
(Continued)

(56) References Cited

U.S. PATENT DOCUMENTS 5,726,026 A * 3/1998 Wilding ............. B01D 67/0062
366/DIG. 3
5,827,480 A    10/1998 Haff et al.
(Continued)

FOREIGN PATENT DOCUMENTS

CN    1942590 A    4/2007
EP    3168624 A1    5/2017
(Continued)

OTHER PUBLICATIONS

He et al., "Improved lysis of single bacterial cells by a modified alkaline-thermal shock procedure", (2016) BioTechniques 60: 12-135 (Year: 2016).*

(Continued)

*Primary Examiner* — Jehanne S Sitton
*Assistant Examiner* — Daniel W Nielsen
(74) *Attorney, Agent, or Firm* — Troutman Pepper Hamilton Sanders LLP

(57) ABSTRACT

The present invention relates to methods, devices, instruments, processes, and systems for the highly specific, targeted molecular analysis of regions of human genomes and transcriptomes from the blood, i.e. from cell free circulating DNA, exosomes, microRNA, lncRNA, circulating tumor cells, or total blood cells. The technology enables highly sensitive identification and enumeration of mutation, expression, copy number, translocation, alternative splicing, and methylation changes using spatial multiplexing and combined nuclease, ligation, polymerase, and sequencing reactions. Such technology may be used for non-invasive early (Continued)

detection of cancer, non-invasive cancer prognosis, and monitoring both treatment efficacy and disease recurrence of cancer.

25 Claims, 54 Drawing Sheets

Specification includes a Sequence Listing.

(52) U.S. Cl.
CPC ... *B01L 2200/0668* (2013.01); *B01L 2200/16* (2013.01); *B01L 2300/087* (2013.01); *B01L 2300/0819* (2013.01); *B01L 2300/0864* (2013.01); *B01L 2300/165* (2013.01); *B01L 2300/1805* (2013.01); *B01L 2400/0622* (2013.01)

(58) Field of Classification Search
CPC .......... B01L 2200/027; B01L 2200/16; B01L 2200/0668; B01L 2300/0819; B01L 2300/0864; B01L 2300/087; B01L 1/68
See application file for complete search history.

(56) References Cited

U.S. PATENT DOCUMENTS

| | | | | |
|---|---|---|---|---|
| 6,716,629 | B2* | 4/2004 | Hess | B01J 19/0046 435/420 |
| 8,673,238 | B2 | 3/2014 | Dority et al. | |
| 8,728,765 | B2 | 5/2014 | Ching et al. | |
| 8,900,828 | B2 | 12/2014 | Smith et al. | |
| 9,333,463 | B2 | 5/2016 | Puleo et al. | |
| 9,518,299 | B2 | 12/2016 | O'Keefe et al. | |
| 2002/0164820 | A1* | 11/2002 | Brown | B01L 3/5088 436/180 |
| 2004/0109793 | A1* | 6/2004 | McNeely | B01F 11/0045 422/400 |
| 2005/0082204 | A1 | 4/2005 | Schwartz et al. | |
| 2007/0183935 | A1* | 8/2007 | Clemmens | C12M 23/42 422/400 |
| 2009/0148933 | A1* | 6/2009 | Battrell | B01F 13/0059 435/287.2 |
| 2011/0008223 | A1 | 1/2011 | Tsao et al. | |
| 2012/0071358 | A1 | 3/2012 | Zhou et al. | |
| 2014/0087958 | A1 | 3/2014 | Chang et al. | |
| 2015/0099642 | A1 | 4/2015 | Barany et al. | |
| 2015/0353997 | A1* | 12/2015 | Duffy | C12Q 1/6837 506/9 |
| 2016/0319334 | A1 | 11/2016 | Barany et al. | |

FOREIGN PATENT DOCUMENTS

| | | | | |
|---|---|---|---|---|
| JP | H07-51099 | A | 2/1995 | |
| JP | H09-509498 | A | 9/1997 | |
| JP | 2004279336 | A | 10/2004 | |
| JP | 2010-66195 | A | 3/2010 | |
| JP | 2014533096 | A | 12/2014 | |
| JP | 2016-523365 | A | 8/2016 | |
| WO | 96/14934 | A1 | 5/1996 | |
| WO | WO-9940174 | A1 * | 8/1999 | ....... G01N 27/44743 |
| WO | 2005/080606 | A1 | 9/2005 | |
| WO | 2013045700 | A1 | 4/2013 | |
| WO | 2014/052671 | A1 | 4/2014 | |
| WO | 2014/210207 | A1 | 12/2014 | |
| WO | 2016/006208 | A1 | 1/2016 | |
| WO | 2016/154337 | A2 | 9/2019 | |

OTHER PUBLICATIONS

International Search Report and Written Opinion for corresponding Application No. PCT/US2018/025213 (dated Jul. 17, 2018).
Ben Butkus, "Cepheid Plans 1,000-Target PCR, Protein Detection, FFPE Analysis, Other Upgrades to GeneXpert," Genomeweb, Sep. 27, 2012 (https://www.genomeweb.com/pcrsample-prep/cepheid-plans-1000-target-pcr-protein-detection-ffpe-analysis-other-upgrades-gen).
Notice of Reasons for Rejection in Japanese Patent Application No. 2019-553187 (dated Sep. 29, 2021).
Wang et al., "Fully Integrated Thermoplastic Genosensor for the Highly Sensitive Detection and Identification of Multi-Drug-Resistant Tuberculosis," Microfluidics 124(18): 4425-4429 (2012).
Office Action in corresponding CN 201880034449.6 (dated Jul. 2, 2021).
Extended European Search Report and Opinion in EP 18774654.0 (dated Dec. 15, 2020).
Merriam-Webster, "Definition of Array (noun)" (https://www.merriam-webster.com/dictionary/array); archived at Wayback Machine (https://web.archive.org/); capture dated Dec. 6, 2017.

* cited by examiner

A. 24, 48, 96 columns ($A_1$ to $A_{ii}$) x 16, 32, 64 rows ($B_1$ to $B_v$)

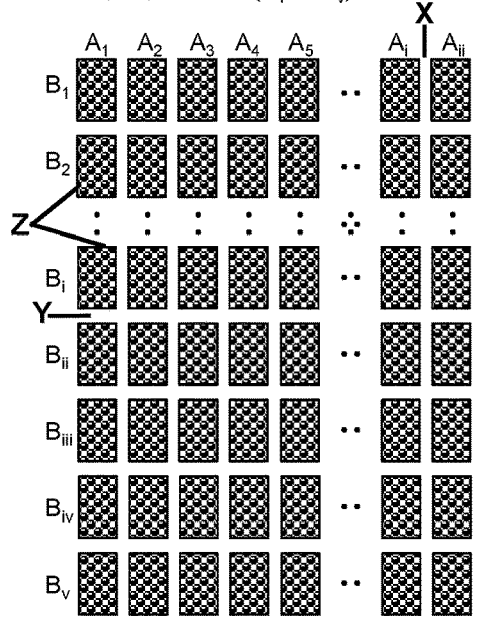

Each subdivision Z illustrated is 400 x 600 micron. Additional 100 um wide ridges X and Y between subdivisions. For Cartesian packing, a given subdivision with 50 micron pore will contain 6 x 4 = 24 micro-pores.

B. 24, 48, 96 columns ($A_1$ to $A_{ii}$) x 32, 64, 128 rows ($B_1$ to $B_{ix}$)

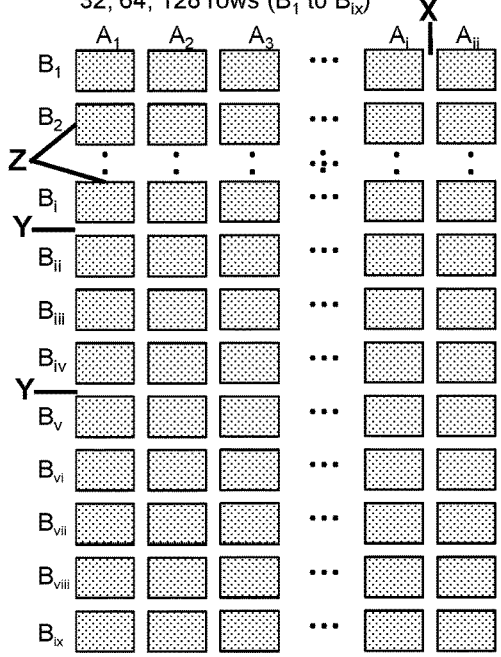

Each subdivision Z illustrated is 600 x 400 micron. Additional 100 um wide ridges X and Y between subdivisions. For hexagonal packing, a given subdivision with 5 micron pore will contain 60 x 46 = 2,760 micro-pores.

C. 48, 96 columns ($A_1$ to $A_{ii}$) x 48, 96 rows ($B_1$ to $B_{ii}$)

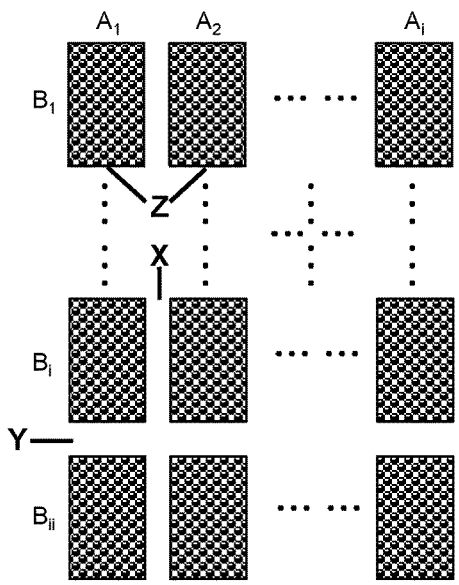

Each subdivision Z illustrated is 800 x 1,200 micron. Additional 200 um wide ridges X and Y between subdivisions. For hexagonal packing, A given subdivision with 50 micron pore will contain 12 x 8 = 96 micro-wells.

D. 24, 48, 96 columns ($A_1$ to $A_{ii}$) x 16, 32, 64 rows ($B_1$ to $B_v$), or Double 48, 64 columns x Double 48, 64 rows

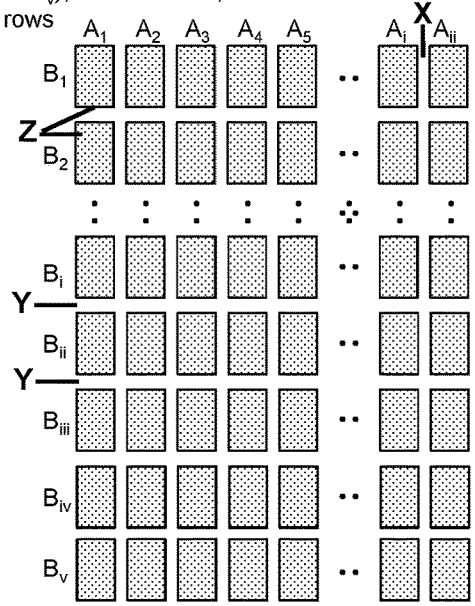

Each subdivision Z illustrated is 400 x 600 micron. Additional 100 um wide ridges X and Y between subdivisions. For hexagonal packing, a given subdivision with 5 micron pore will contain 60 x 46 = 2,760 micro-pores.

Figures 1A-1D

A. Hydrophobic plate with 50 um hydrophilic micro-wells. Each section is 1.2 mm x 0.8 mm, contains 96 micro-wells.

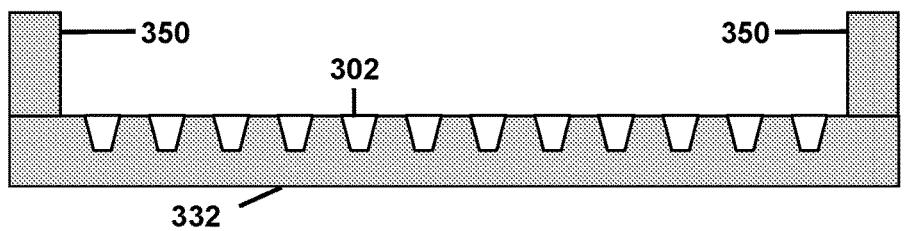

B. Fill with with 1-4 UniTaq primer sets (or alternatively, 1-4 universal tag primer sets with mutation or methylation-specific Taqman probes) using acoustic droplet ejection.

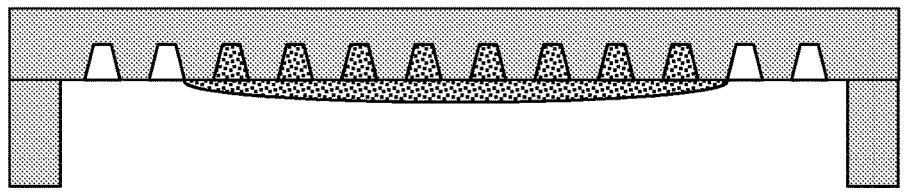

C. Centrifuge. Aqueous liquid spreads to empty micro-wells.

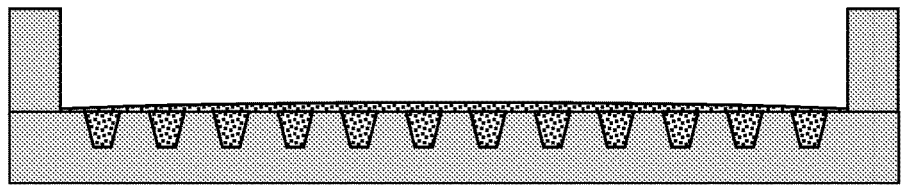

D. After centrifugation, droplets will avoid hydrophobic surface.

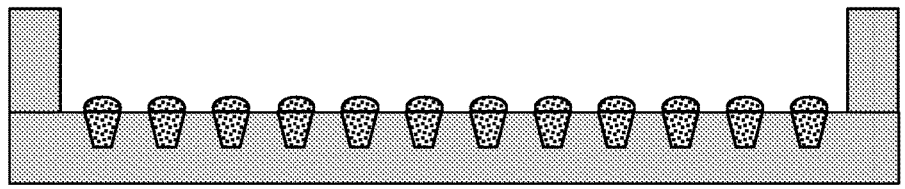

E. Evaporate Aqueous solution.

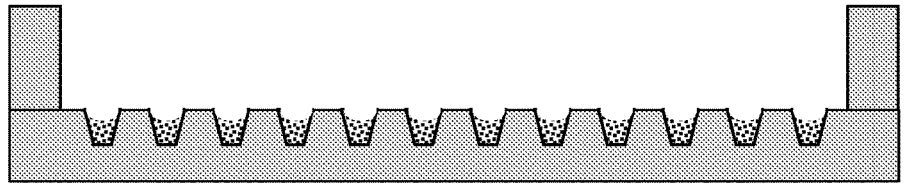

F. Leaving dried primer/probe sets in wells.

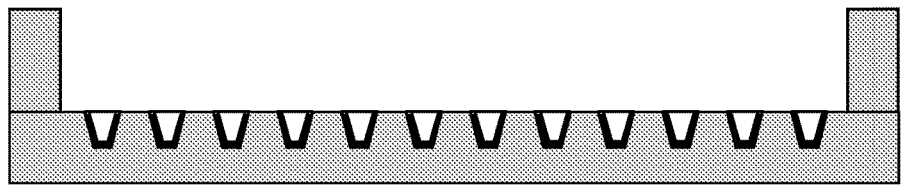

Figure 14

A. Hydrophobic plate with 50 um hydrophilic microwells. Each section is 1.2 mm x 0.8 mm, contains 96 microwells.
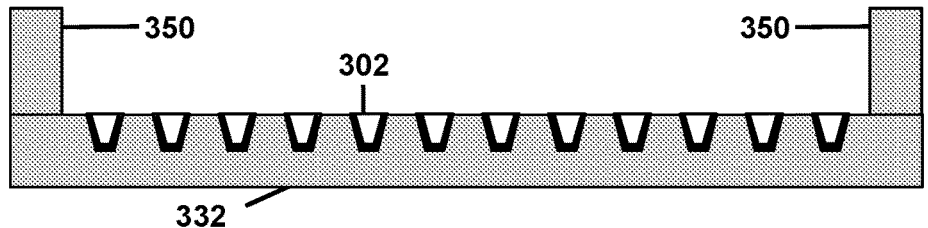
B. Fill TaqMan reaction with target DNA using acoustic droplet ejection.
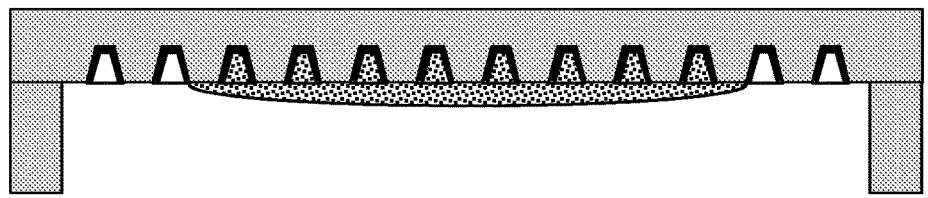
C. Overlay with mineral oil.
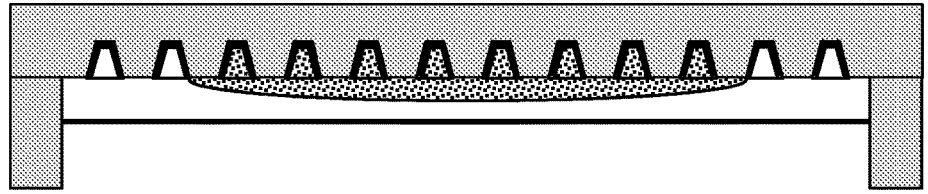
D. Centrifuge. Denser aqueous liquid spreads to empty microwells.
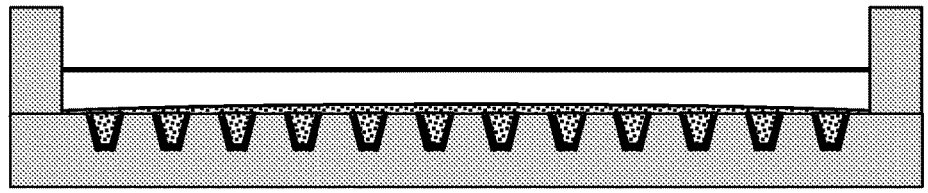
E. Move plate to thermocycler. Droplets separate. Amplify.
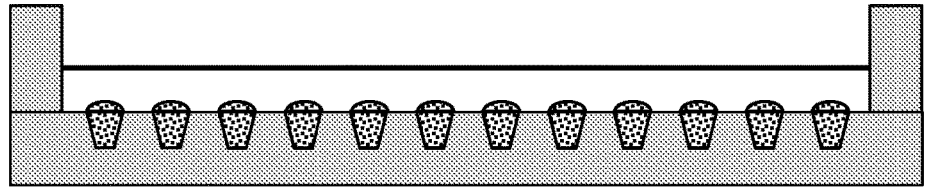
Figure 15

A. PCR-PCR-qPCR (Taqman) for unknown pathogen identification and quantification. Isolate genomic DNA. For RNA viruses, an initial reverse-transcriptase step generates cDNA.

B. Perform initial limited cycle multiplexed amplification of pathogen-specific regions in an Initial Reaction Chamber. Primers contain identical 8-11 base tails to prevent primer dimers.

C. Distribute initial PCR products into 24, 36, or 48 Primary PCR Reaction Chambers. Perform limited cycle nested PCR using primers with Universal tag tails. Primers are unblocked with RNaseH2 only when bound to correct target.

D. PCR products comprise of Ai tag sequence, pathogen-specific sequence, and Ci' tag sequence. Distribute products of each Primary PCR Reaction Chamber into 384 or 768 micro-pores.

E. Amplify authentic pathogen-specific products with Tag-specific primers (Ai and Ci). Each Taqman probe spans a unique pathogen-specific sequence.

F. The 5'->3' nuclease activity of Taq polymerase liberates the fluorescent group to generate signal.

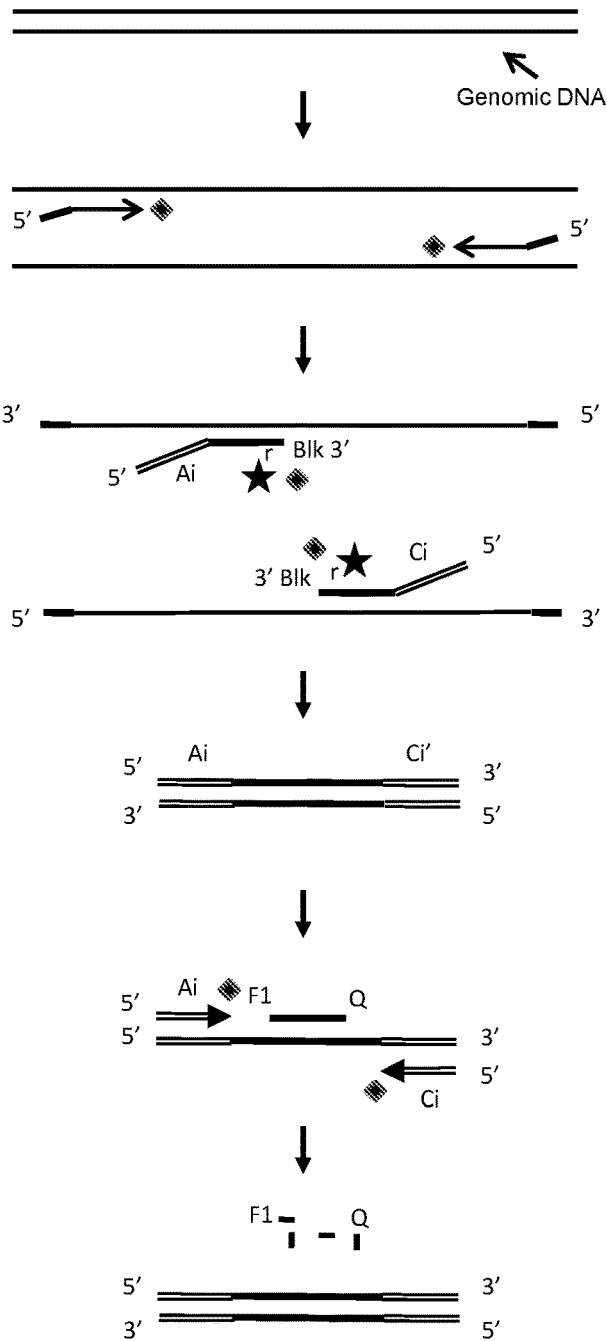

Figure 16

A. PCR-PCR-qPCR (UniTaq) for unknown pathogen identification and quantification. Isolate genomic DNA. For RNA viruses, an initial reverse-transcriptase step generates cDNA.

B. Perform initial limited cycle multiplexed amplification of pathogen-specific regions in an Initial Reaction Chamber. Primers contain identical 8-11 base tails to prevent primer dimers.

C. Distribute initial PCR products into 24, 36, or 48 Primary PCR Reaction Chambers. Perform limited cycle nested PCR using primers with UniTaq tails. Primers are unblocked with RNaseH2 only when bound to correct target.

D. PCR products comprise of Ai tag sequence, pathogen-specific sequence, Bi', and Ci' tag sequence. Distribute products of each Primary PCR Reaction Chambers into 384 or 768 micro-pores.

E. Amplify authentic pathogen-specific products with UniTaq-specific primers (F1-Bi-Q-Ai and Ci).

F. Double-stranded DNA products of PCR; the polymerase blocker stops extension of the bottom strand.

G. After the denaturation step, as the temperature decreases, a hairpin forms between Bi and Bi'. The 5'->3' nuclease activity of Taq polymerase extends primer Ci and liberates the fluorescent group to generate signal.

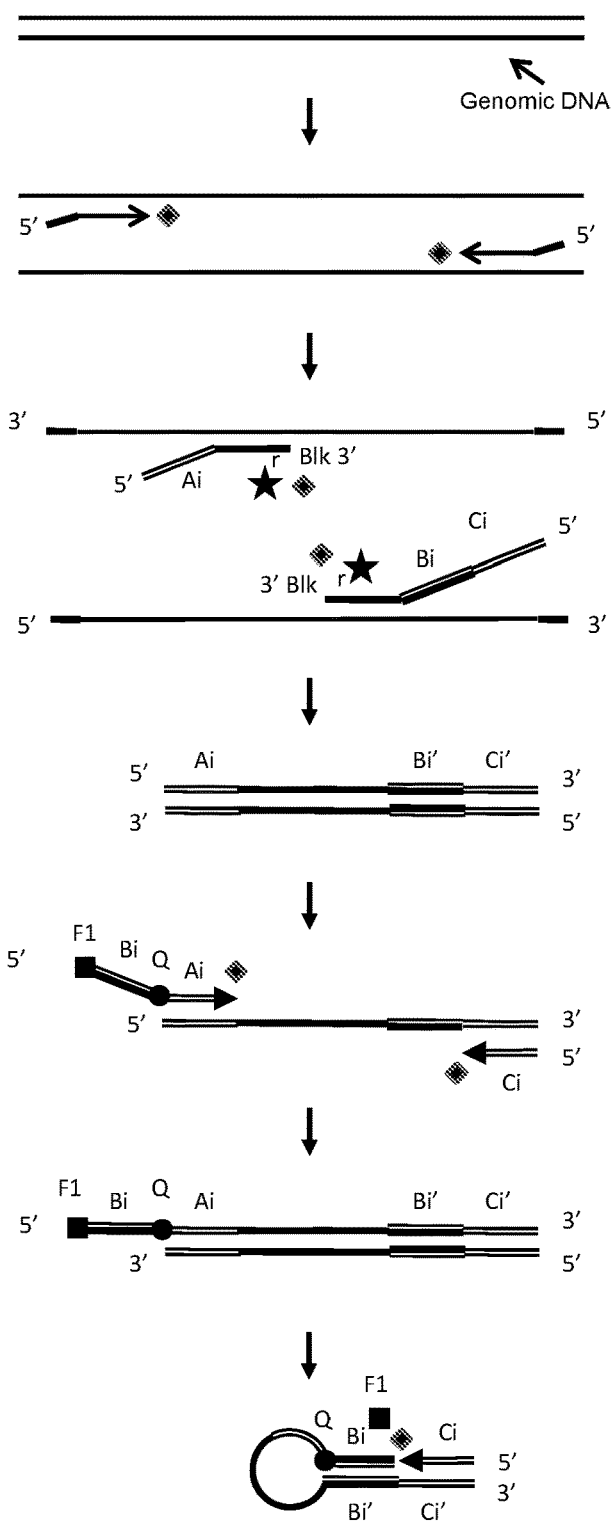

Figure 17

A. PCR-PCR-qPCR (UniRq) for unknown pathogen identification and quantification. Isolate genomic DNA. For RNA viruses, an initial reverse-transcriptase step generates cDNA.

B. Perform initial limited cycle multiplexed amplification of pathogen-specific regions in an Initial Reaction Chamber. Primers contain identical 8-11 base tails to prevent primer dimers.

C. Distribute initial PCR products into 24, 36, or 48 Primary PCR Reaction Chambers. Perform limited cycle nested PCR using primers with UniTaq tails. Primers are unblocked with RNaseH2 only when bound to correct target.

D. PCR products comprise of Ai-Bi'-ti' tag sequence, pathogen-specific sequence with ti-tj, and tj'- Bj'-Ci' tag sequence. Distribute products of each Primary PCR Reaction Chambers into 384 or 768 micro-pores.

E. Amplify authentic pathogen-specific products with UniTaq-specific primers (F1-r-Bj,Bi-Q-Ai, and Ci), using polymerase with strand-displacing activity, and lacking 5'-3' nuclease activity.

F. Double-stranded DNA products of PCR; the polymerase blocker stops extension of the bottom strand.

G. After the denaturation step, as the temperature decreases, 4 hairpins form between pathogen-specific sequences (ti & ti'; tj & tj'), Bi & Bi', and Bj & Bj'. This renders the ribose base in the Bj sequence double-stranded, enabling RNaseH2 to liberate the fluorescent group and generate signal. Primer dimer lacks pathogen-specific sequences, would not form all hairpins, and thus RNaseH2 would not liberate signal.

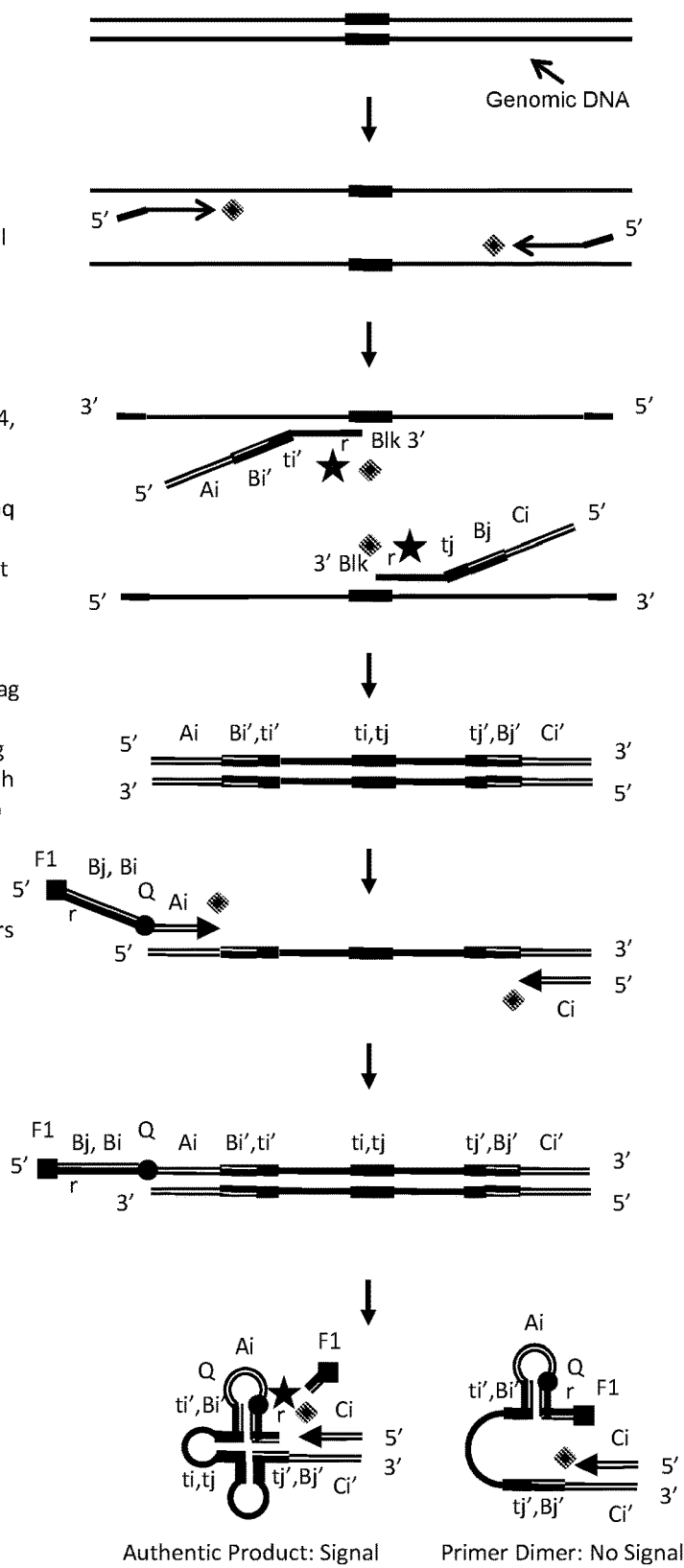

Figure 18

A. PCR-LDR-qPCR (Taqman) for unknown pathogen identification and quantification. Isolate genomic DNA. For RNA viruses, an initial reverse-transcriptase step generates cDNA.

B. Perform initial multiplexed amplification of pathogen-specific regions in an Initial Reaction Chamber. Primers contain identical 8-11 base tails to prevent primer dimers C. Distribute initial PCR products into 24, 36, or 48 Primary LDR Reaction Chambers.

D. Pathogen-specific ligation oligonucleotides contain tags (Ai and Ci') for subsequent PCR amplification. Ligase covalently seals the two oligonucleotides together.

E. Distribute ligation products of each Primary LDR Reaction Chamber into 384 or 768 micropores. Amplify authentic pathogen-specific products with Tag-specific primers (Ai and Ci). Each Taqman probe spans a unique pathogen-specific sequence.

F. The 5'->3' nuclease activity of Taq polymerase liberates the fluorescent group to generate signal.

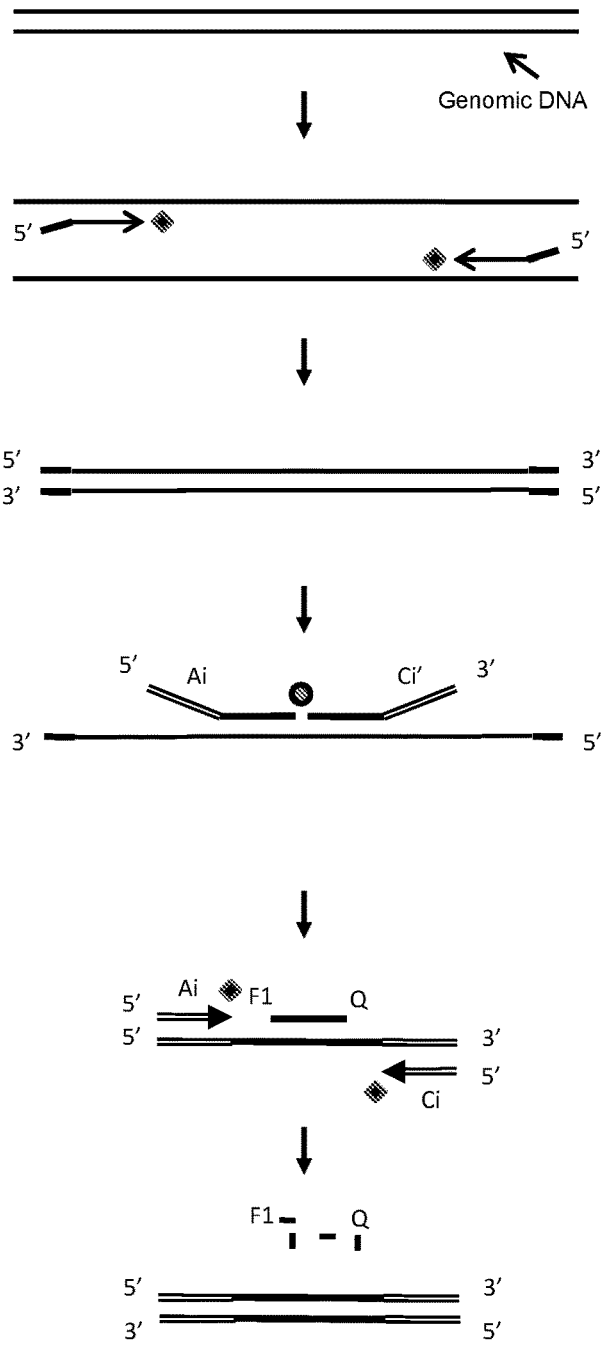

Figure 19

A. PCR-LDR-qPCR (UniTaq) for unknown pathogen identification and quantification. Isolate genomic DNA. For RNA viruses, an initial reverse-transcriptase step generates cDNA.

B. Perform initial multiplexed amplification of pathogen-specific regions in an Initial Reaction Chamber. Primers contain identical 8-11 base tails to prevent primer dimers C. Distribute initial PCR products into 24, 36, or 48 Primary LDR Reaction Chambers.

D. Pathogen-specific ligation oligonucleotides contain tags (Ai, Bi'-Ci') for subsequent PCR amplification. Ligase covalently seals the two oligonucleotides together.

E. Distribute ligation products of each Primary LDR Reaction Chamber into 384 or 768 micro-pores. Amplify authentic pathogen-specific products with UniTaq-specific primers (F1-Bi-Q-Ai and Ci).

F. Double-stranded DNA products of PCR; the polymerase blocker stops extension of the bottom strand.

G. After the denaturation step, as the temperature decreases, a hairpin forms between Bi and Bi'. The 5'->3' nuclease activity of Taq polymerase extends primer Ci and liberates the fluorescent group to generate signal.

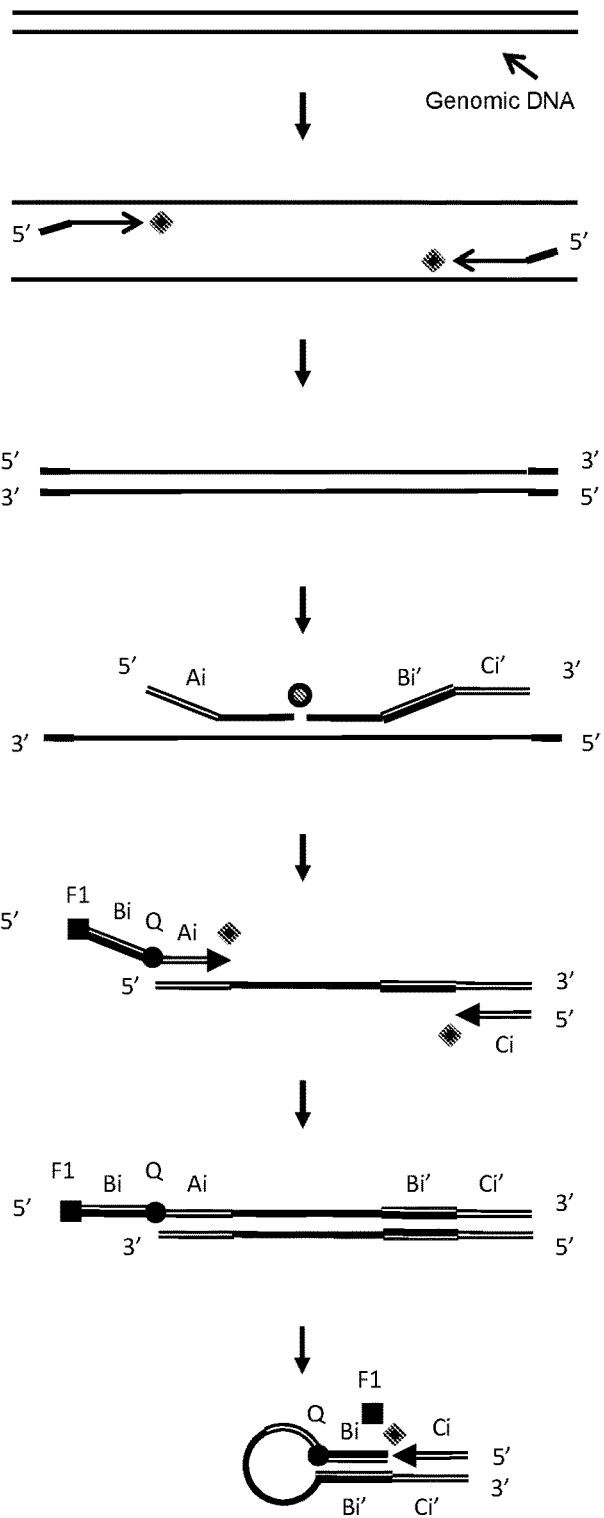

Figure 20

A. PCR-LDR-qPCR (UniSpTq) for unknown pathogen identification and quantification. Isolate genomic DNA. For RNA viruses, an initial reverse-transcriptase step generates cDNA.

B. Perform initial multiplexed amplification of pathogen-specific regions in an Initial Reaction Chamber. Primers contain identical 8-11 base tails to prevent primer dimers C. Distribute initial PCR products into 24, 36, or 48 Primary LDR Reaction Chambers.

D. Pathogen-specific ligation oligonucleotides contain tags (Ai-Bi'-zi; zi'-Bj'-Ci') for subsequent PCR amplification. Ligase covalently seals the two oligonucleotides together.

E. Distribute ligation products of each Primary LDR Reaction Chamber into 384 or 768 micro-pores. Amplify authentic pathogen-specific products with UniTaq-specific primers (F1-Bj,Bi-Q-Ai and Ci).

F. Double-stranded DNA products of PCR; the polymerase blocker stops extension of the bottom strand.

G. After the denaturation step, as the temperature decreases, 3 hairpins forms between Bi & Bi', zi & zi', and Bj & Bj'. The 5'->3' nuclease activity of Taq polymerase extends primer Ci and liberates the fluorescent group to generate signal. As soon as polymerase has traversed Bj', the short zi-zi' stem falls apart and polymerase continues extending to create the dsDNA product.

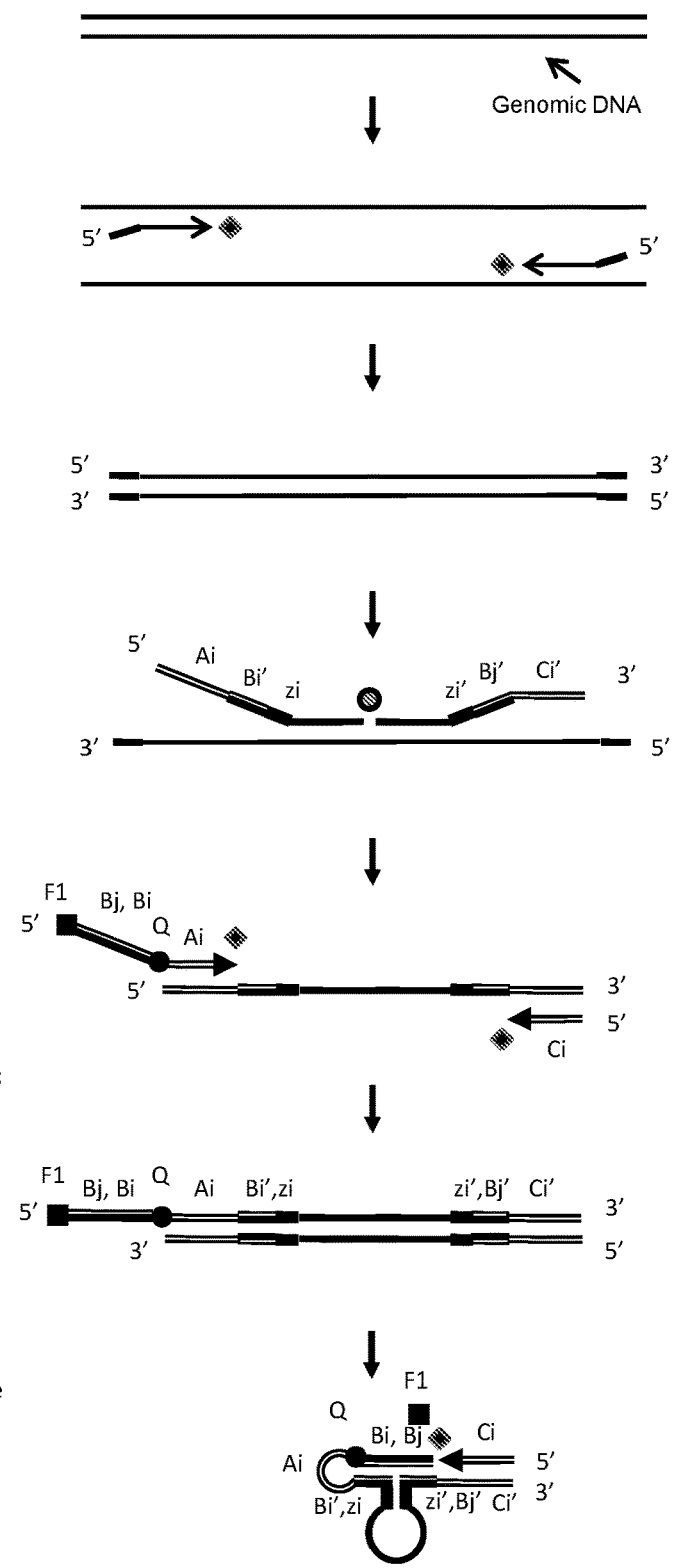

Figure 21

A. PCR-qLDR (UniLDq) for unknown pathogen identification and quantification. Isolate genomic DNA. For RNA viruses, an initial reverse-transcriptase step generates cDNA.

B. Perform initial multiplexed amplification of pathogen-specific regions in an Initial Reaction Chamber. Primers contain identical 8-11 base tails to prevent primer dimers C. Distribute initial PCR products into into 384 or 768 micro-pores.

D. Pathogen-specific ligation oligonucleotides have tags (Bi'-ti'; tj'-Bj') for subsequent detection. (When detecting specific SNPs or mutations, blocking LNA or PNA Wt probes suppress ligation to Wt sequence.) Upstream ligation primer contains block, which may be removed by cleaving ribose base with RNaseH2 only when hybridized to target.

E. Ligase covalently seals the two oligonucleotides together.

F. In the presence of probe (F1-r-Bj,Bi-Q), and after the denaturation step, as the temperature decreases, 4 double-stranded stems form between probe and pathogen-specific sequences (ti & ti'; tj & tj'), Bi & Bi', and Bj & Bj'. This renders the ribose base in the Bj sequence double-stranded, enabling RNaseH2 to liberate the fluorescent group and generate signal. The cleaved probe dissociates from the product and new probe can hybridize to generate additional signal. Unligated LDR primers would not form all hairpins, and thus RNaseH2 would not liberate signal.

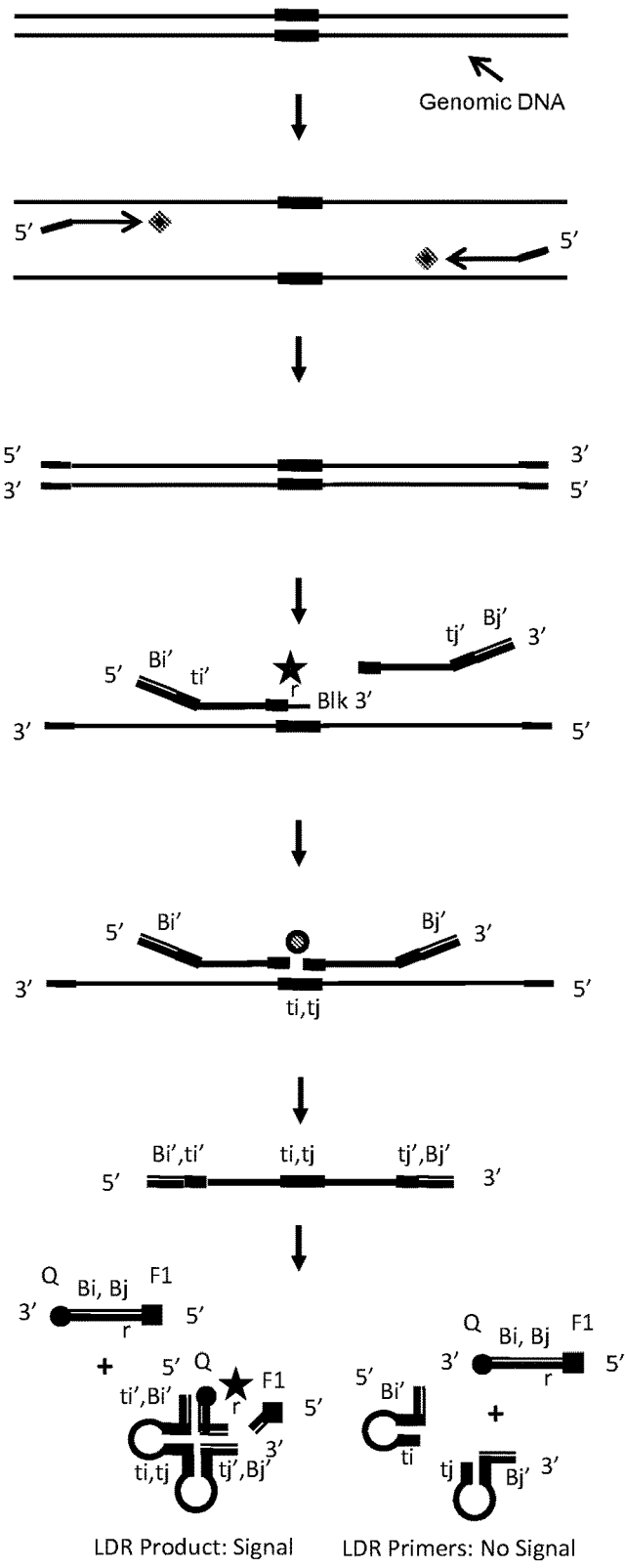

Figure 22

A. PCR-qLDR (TsLDq) for unknown pathogen identification and quantification. Isolate genomic DNA. For RNA viruses, an initial reverse-transcriptase step generates cDNA.

B. Perform initial multiplexed amplification of pathogen-specific regions in an Initial Reaction Chamber. Primers contain identical 8-11 base tails to prevent primer dimers C. Distribute initial PCR products into into 384 or 768 micro-pores.

D. Pathogen-specific ligation oligonucleotides have tags (Bi' and tj') for subsequent detection. (When detecting specific SNPs or mutations, blocking LNA or PNA Wt probes suppress ligation to Wt sequence.) Upstream ligation primer contains block, which may be removed by cleaving ribose base with RNaseH2 only when hybridized to target.

E. Ligase covalently seals the two oligonucleotides together.

F. In the presence of probe (F1-r-pathogen sequence-Bi-Q), and after the denaturation step, as the temperature decreases, 2 double-stranded stems form between pathogen-specific sequences (ti,tj & ti',tj'), and Bi & Bi'. This renders the ribose base in the pathogen sequence double-stranded, enabling RNaseH2 to liberate the fluorescent group and generate signal. The cleaved probe dissociates from the product and new probe can hybridize to generate additional signal. Unligated LDR primers would not form both stems, and thus RNaseH2 would not liberate signal.

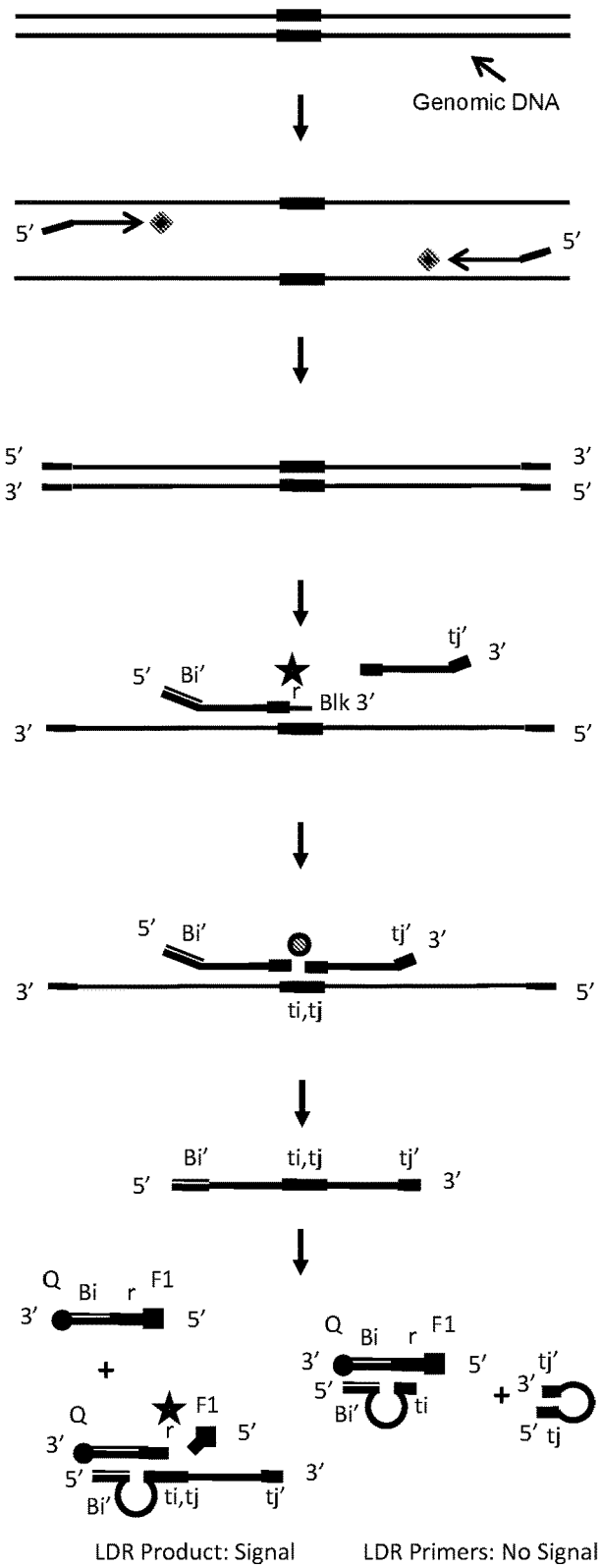

Figure 23

A. Unknown pathogen identification and quantification; using Multiplexed PCR - Nested PCR - UniTaq detection. (Alternatively, Multiplexed PCR – Nested PCR - Real-time-PCR with target-specific Taqman probes.)

B. Preparation: Rows are pre-filled with 1-4 UniTaq primer sets (or alternatively, 1-4 universal tag primer sets with target-specific Taqman probes). Primers are distributed into each row and dried down into individual micro-pores.

C. Preparation: Pre-fill pre-chambers to columns with nested PCR primer sets with either UniTaq or universal tag sequences on their 5' ends, and dry down.

D. Multiplexed PCR amplification (or reverse-transcription-PCR for RNA targets) for 9 cycles in an Initial Reaction Chamber to generate 512 copies of each original target.

E. Distribute initial multiplex reaction into 24 Primary PCR Reaction Chambers, with average distribution of 20 copies of each original pathogen in each Primary PCR Reaction Chamber. Perform 5 cycles of nested PCR using target-specific primers with UniTaq or universal tags in groups of 16, 32, or 64 primer sets, to generate an average of 640 copies of each pathogen-specific target per Primary PCR Reaction Chamber.

F. Distribute nested PCR products of each Primary PCR Reaction Chamber into mixing chambers and then into 384 or 768 micro-pores of each column. Universal or UniTaq primers in each row will amplify only those products from each column with the correct tags. Ct values across micro-pores will provide approximate copy information for pathogen-specific targets.

A. For Unknown pathogen identification and typing; using Multiplexed PCR - LDR- UniTaq detection or - Real-time-PCR.

B. Prepare rows as above, and pre-fill chambers to columns with LDR probe sets with either UniTaq or universal tag sequences on their non-ligating 5' (upstream) and 3' (downstream) ends, and dry down.

C. Multiplexed PCR amplification (or reverse-transcription-PCR for RNA targets) for 30 cycles to amplify original target in an Initial Reaction Chamber.

D. Distribute initial multiplex reaction into 24 Primary LDR Reaction Chambers, while diluting 10-fold. Perform 20 cycles of LDR using allele-specific probes with UniTaq or universal tags in groups of 16, 32, or 64 probe sets.

E. Distribute LDR products of each Primary LDR Reaction Chamber into mixing chambers and then into 384 or 768 micro-pores of each column. Universal or UniTaq primers in each row will amplify only those products from each column with the correct tags. Ct values across micro-pores will provide approximate copy information for pathogen-specific targets initially present at high abundance.

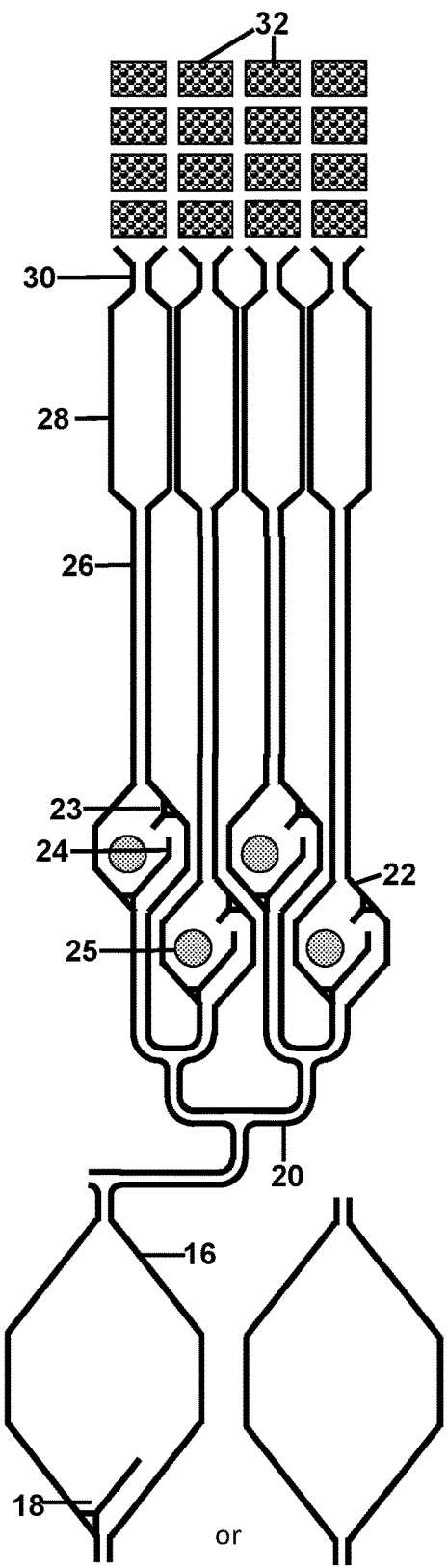

Valve 3    Valve 5

24-48 Columns, thousands of Micro-pores:
Rows are pre-filled with 1-4 UniTaq primer sets (or alternatively, 1-4 universal tag primer sets with target-specific Taqman probes). Primers are distributed into each row and dried down into individual micro-pores.

Heating Element 4

Narrow 24-48 mixing Chambers 28

Valve 4

Secondary 24-48 multiplex Reaction Chambers 22

Heating Element 3

Primary 24-48 multiplex PCR Reaction Chambers 16

Heating Element 2

Initial multiplex Reaction Chamber 10

Heating Element 1

Valve 1

Valve 2

Figures 25A-25B

A. PCR-PCR-qPCR (Taqman) for unknown bacterial pathogen identification directly from blood. Isolate genomic DNA.

B. Distribute initial sample into 24, 36, or 48 Primary PCR Reaction Chambers (columns). Perform initial multiplexed amplification of pathogen-specific regions. Use tandem or more PCR primer sets. Primers contain identical 8-11 base tails to prevent primer dimers.

C. Perform nested PCR using primers with Universal tag tails in Secondary PCR Reaction Chambers. Primers are unblocked with RNaseH2 only when bound to correct target.

D. PCR products comprise of Ai tag sequence, pathogen-specific sequence, and Ci tag sequence. Distribute products of each Secondary PCR Reaction Chamber into 384 or 768 micro-pores (16 or 32 rows). Universal tag primers in each row will amplify only those products from each Secondary PCR Reaction Chamber (columns) with the correct tags.

E. Amplify authentic pathogen-specific products with Tag-specific primers (Ai and Ci). Each Taqman probe spans a unique pathogen-specific sequence.

F. The 5'->3' nuclease activity of Taq polymerase liberates the fluorescent group to generate signal.

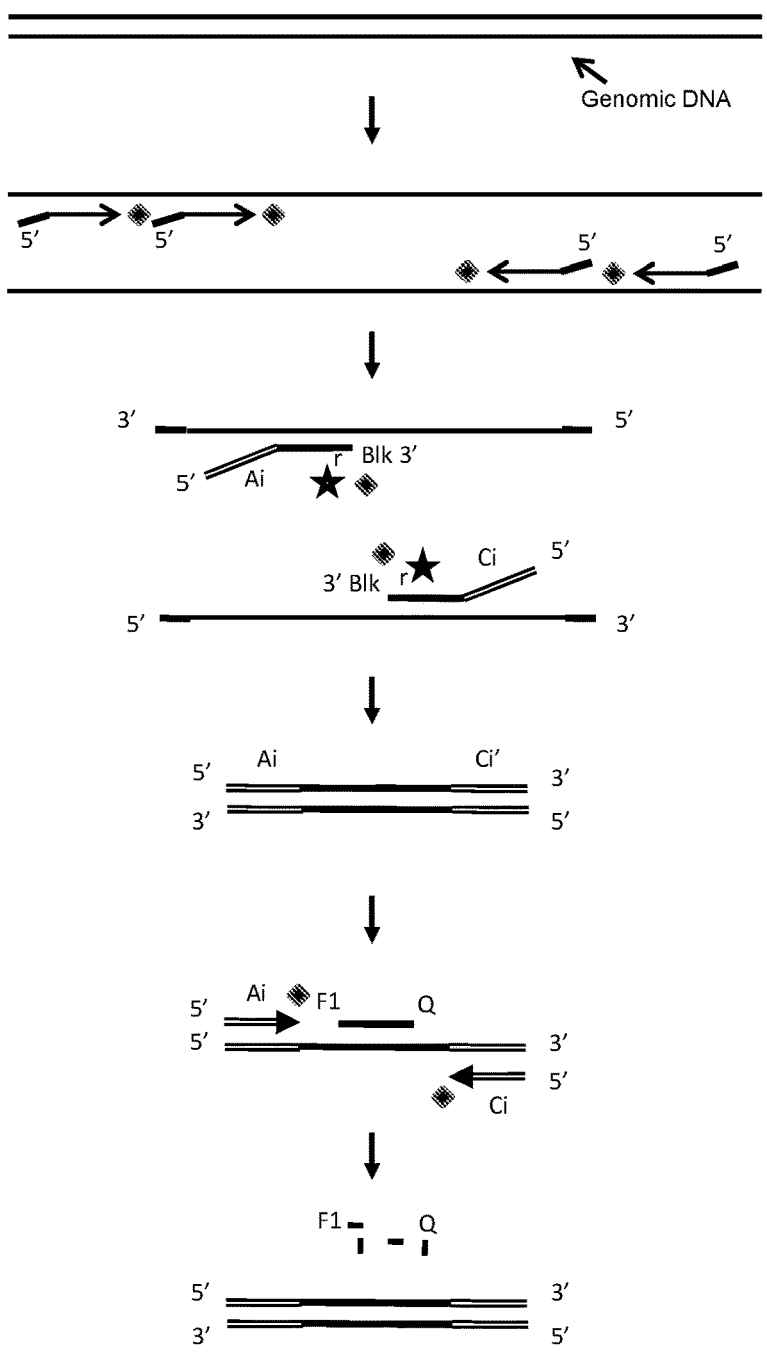

Figure 26

A. PCR-PCR-qPCR (UniTaq) for unknown bacterial pathogen identification directly from blood. Isolate genomic DNA.

B. Distribute initial sample into 24, 36, or 48 Primary PCR Reaction Chambers (columns). Perform initial multiplexed amplification of pathogen-specific regions. Use tandem or more PCR primer sets. Primers contain identical 8-11 base tails to prevent primer dimers.

C. Perform nested PCR using primers with Universal tag tails in Secondary PCR Reaction Chambers. Primers are unblocked with RNaseH2 only when bound to correct target.

D. PCR products comprise of Ai tag sequence, pathogen-specific sequence, Bi', and Ci tag sequence. Distribute products of each Secondary PCR Reaction Chamber into 384 or 768 micro-pores (16 or 32 rows). UniTaq primers in each row will amplify only those products from each Secondary PCR Reaction Chamber (columns) with the correct tags.

E. Amplify authentic pathogen-specific products with UniTaq-specific primers (F1-Bi-Q-Ai and Ci).

F. Double-stranded DNA products of PCR; the polymerase blocker stops extension of the bottom strand.

G. After the denaturation step, as the temperature decreases, a hairpin forms between Bi and Bi'. The 5'->3' nuclease activity of Taq polymerase extends primer Ci and liberates the fluorescent group to generate signal.

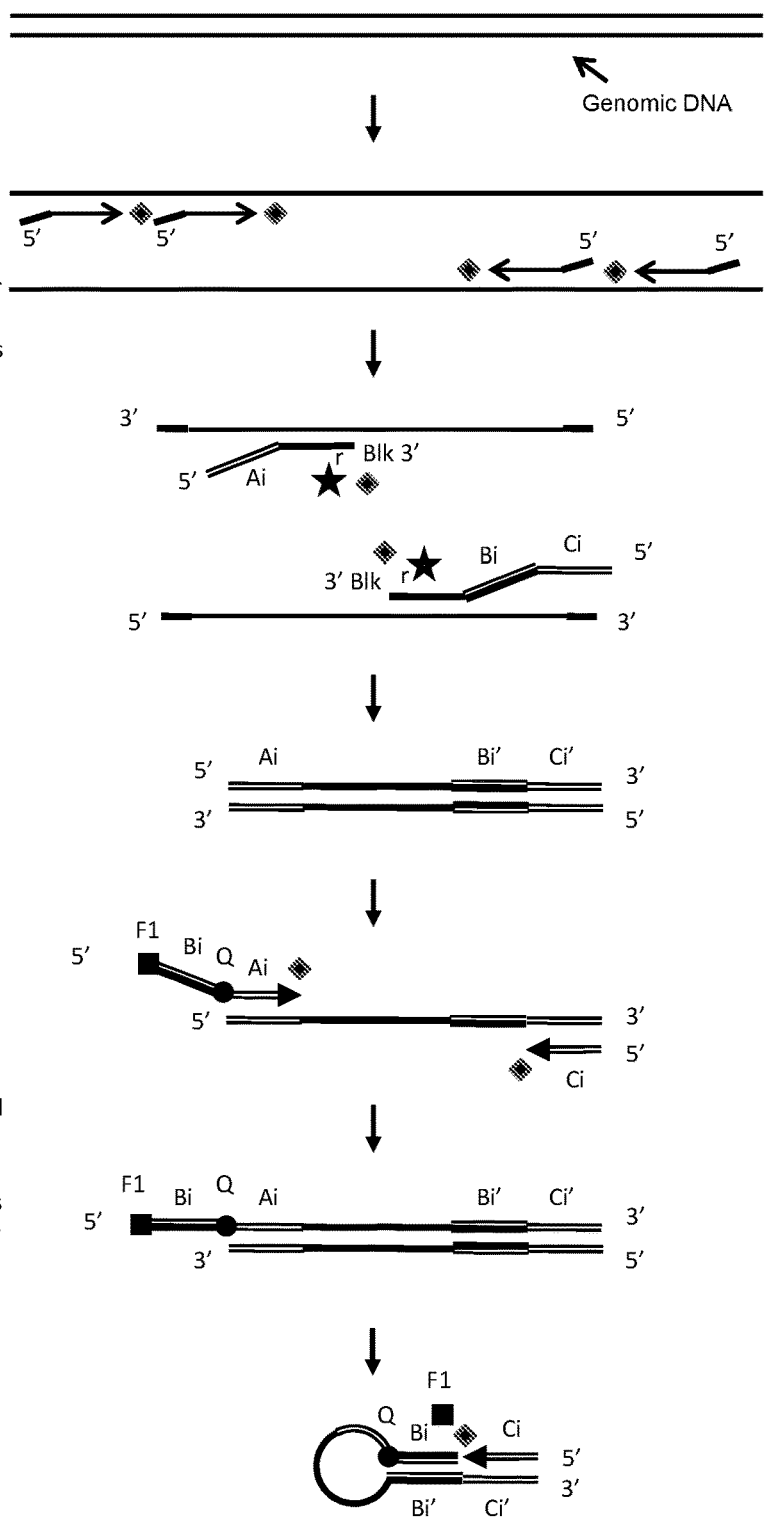

Figure 27

A. PCR-LDR-qPCR (Taqman) reaction (with optional carryover prevention) to detect low-level mutation. Isolate genomic or cfDNA.

B. Distribute initial sample into 24, 36, or 48 Primary PCR Reaction Chambers (columns). Treat with UDG for carryover prevention. Upstream locus primers contain ribose bases (r), which are removed with RNaseH2 only when bound to target, thus unblocking primer. Blocking LNA or PNA Wt probes facilitate preferential amplification of mutation containing regions using PCR (and dUTP). Downstream primers contain identical 8-11 base tails to prevent primer dimers.

C. PCR products incorporate dU, allowing for carryover prevention. Distribute products into Secondary LDR Reaction Chambers.

D. Mutation-specific ligation oligonucleotides (Mt) contain tags (Ai, Ci') for subsequent PCR amplification. Blocking LNA or PNA Wt probes suppress ligation to Wt sequence. Upstream ligation primer contains block, which may be removed by cleaving ribose base with RNaseH2 only when hybridized to target.

E. Ligase covalently seals the unblocked mutation-specific upstream and phosphorylated downstream oligonucleotides together in each Secondary LDR Reaction Chamber.

F. Add Taqman mastermix with UDG for carryover prevention, which also destroys original target amplicons. Distribute products of each Secondary LDR Reaction Chamber into 384 or 768 micro-pores. Only authentic LDR products will amplify, when using PCR (and dUTP) with tag-specific primers (Ai, Ci'). Each Taqman probe spans the ligation junction.

G. The 5'->3' nuclease activity of Taq polymerase liberates the fluorescent group to generate signal. (PCR products incorporate dU, allowing for carryover prevention.)

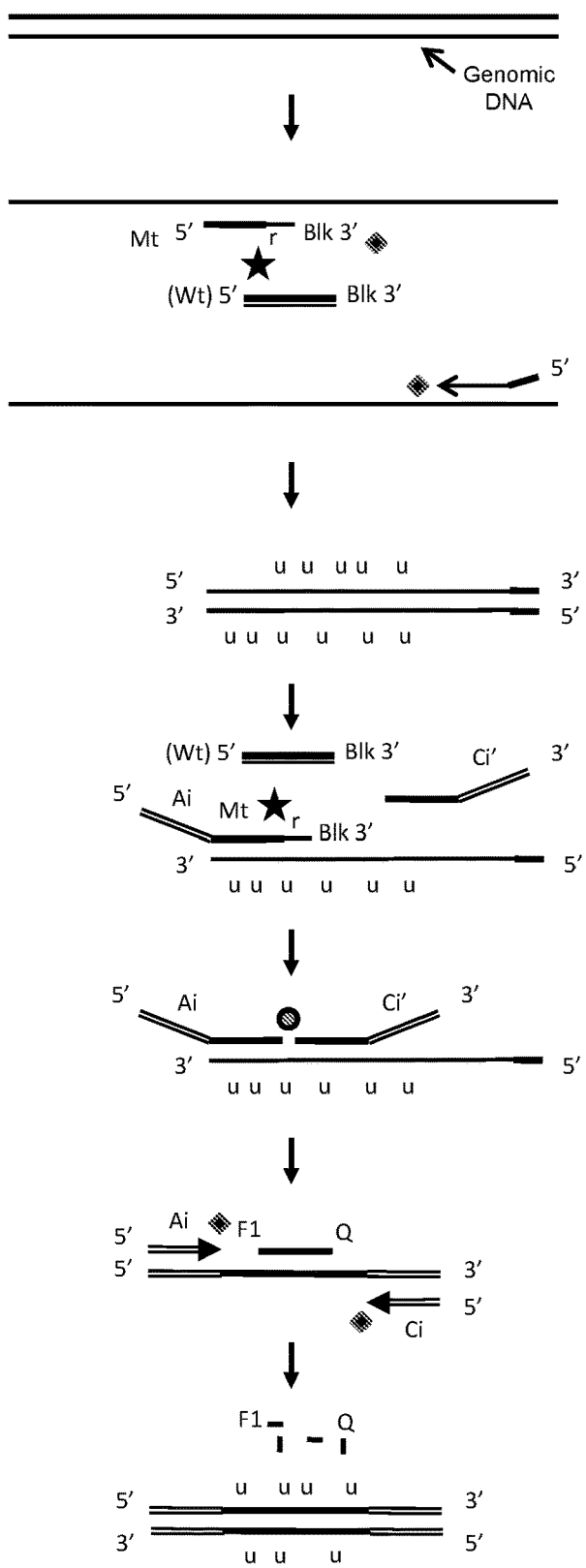

Figure 28

A. PCR-LDR-qPCR (UniTaq) reaction (with optional carryover prevention) to detect low-level mutation. Isolate genomic or cfDNA.

B. Distribute initial sample into 24, 36, or 48 Primary PCR Reaction Chambers (columns). Treat with UDG for carryover prevention. Upstream locus primers contain ribose bases (r), which are removed with RNaseH2 only when bound to target, thus unblocking primer. Blocking LNA or PNA Wt probes facilitate preferential amplification of mutation containing regions using PCR (and dUTP). Downstream primers contain identical 8-11 base tails to prevent primer dimers.

C. PCR products incorporate dU, allowing for carryover prevention. Distribute products into Secondary LDR Reaction Chambers.

D. Mutation-specific ligation oligonucleotides (Mt) contain tags (Ai, Bi', Ci') for subsequent PCR amplification. Blocking LNA or PNA Wt probes suppress ligation to Wt sequence. Upstream ligation primer contains block, which may be removed by cleaving ribose base with RNaseH2 only when hybridized to target.

E. Ligase covalently seals the unblocked mutation-specific upstream and phosphorylated downstream oligonucleotides together in each Secondary LDR Reaction Chamber.

F. Add Taqman mastermix with UDG for carryover prevention, which also destroys original target amplicons. Distribute products of each Secondary LDR Reaction Chamber into 384 or 768 micro-pores. Only authentic LDR products will amplify, when using PCR (and dUTP) with Unitaq-specific primers (F1-Bi-Q-Ai, Ci).

G. Double-stranded DNA products of PCR; the polymerase blocker stops extension of the bottom strand.

H. After the denaturation step, as the temperature decreases, a hairpin forms between Bi and Bi'. The 5'->3' nuclease activity of Taq polymerase extends primer Ci and liberates the fluorescent group to generate signal. (PCR products incorporate dU, allowing for carryover prevention.)

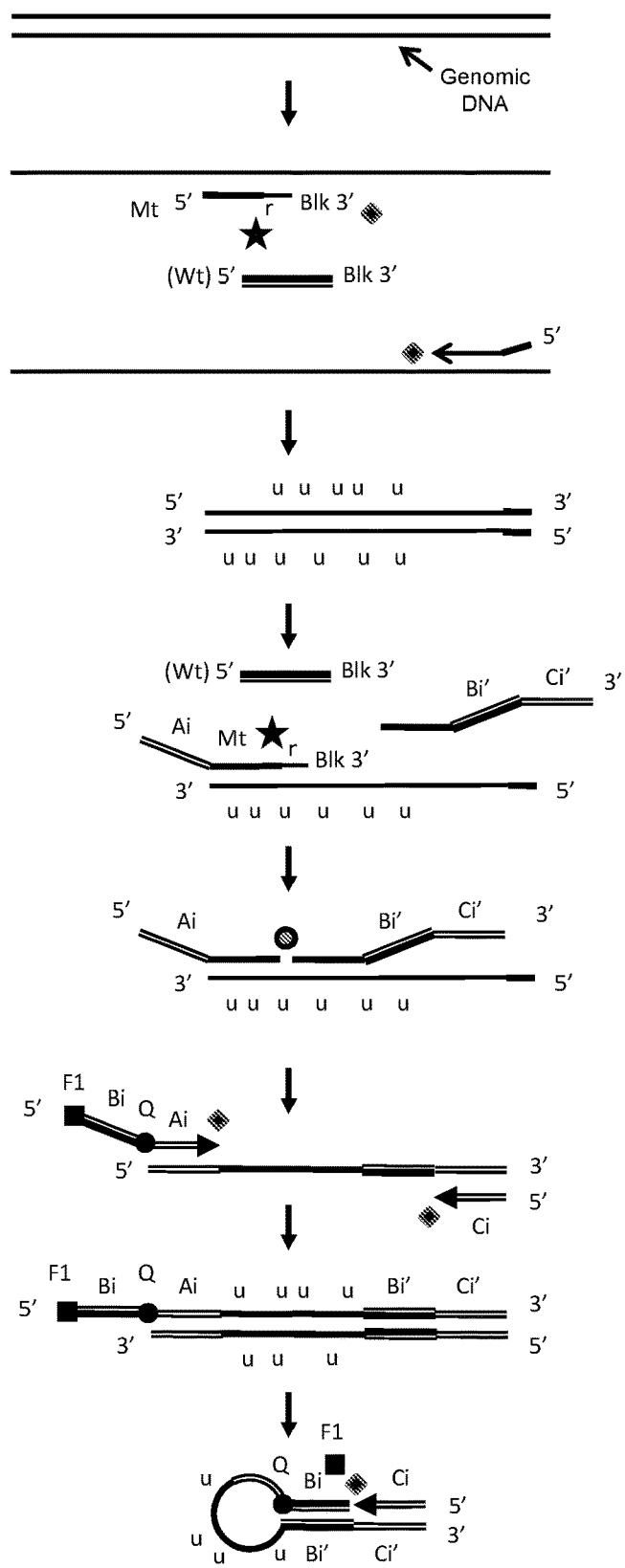

Figure 29

A. Mutations and Methylations at low-level in plasma; using Multiplexed PCR - LDR- UniTaq detection. (Alternatively, Multiplexed PCR – LDR- Real-time-PCR with mutation or methylation-specific Taqman probes.)

B. Preparation: Rows are pre-filled with 1-4 UniTaq primer sets (or alternatively, 1-4 universal tag primer sets with mutation or methylation-specific Taqman probes). Primers are distributed into each row and dried down into individual micro-pores.

C. Preparation: Pre-fill pre-chambers to columns with LDR primer sets with either UniTaq or universal tag sequences on their non-ligating 5' (upstream) and 3' (downstream) ends, and dry down. (Alternatively, when using identical LDR primer sets in each pre-chamber, they may be added after the PCR step.)

D. Digest half of cfDNA with Bsh1236I to cleave unmethylated DNA in the Initial Reaction Chamber. Treat with Bisulfite. Re-purify DNA strands.

E. Distribute initial cfDNA and Bsh1236I/bisulfite treated cfDNA into 24 Primary PCR Reaction Chambers. Highest level of DNA in plasma = 10,000 genome equivalents. After Bsh1236I/bisulfite treatment, about 200 genome equivalents. On average, 400 copies of each untreated target, and 8 copies of each Bsh1236I/bisulfite treated target per Primary PCR Reaction Chamber, with at most 1 mutation or methylated fragment per Primary PCR Reaction Chambers. Perform 30-40 cycles of locus-specific PCR with blocking PNA or LNA to reduce amplification of wild-type DNA (for mutation detection, optional for methylation detection).

F. Dilute products of each Primary PCR Reaction Chamber into pre-dried LDR primers and buffers of each Secondary LDR Reaction Chamber. Perform 20 cycles of LDR using mutation-specific or methylation-specific primers with UniTaq tags, in groups of 16, 32, or 64 primer sets. LDR primers for different methylation regions, i.e. top and bottom strand of the same promoter region may be designed to give the same signal in the same Secondary LDR Reaction Chamber.

G. Add Taqman master-mix with UDG and distribute LDR products into each mixing chamber, and into 384 or 768 micro-pores of each column. Universal or UniTaq primers in each row will amplify only those products from each column with the correct tags. Presence or absence of specific mutations or methylations in each of the 24 columns allows for enumerating the number of low-level mutations and specific methylation in cfDNA from plasma.

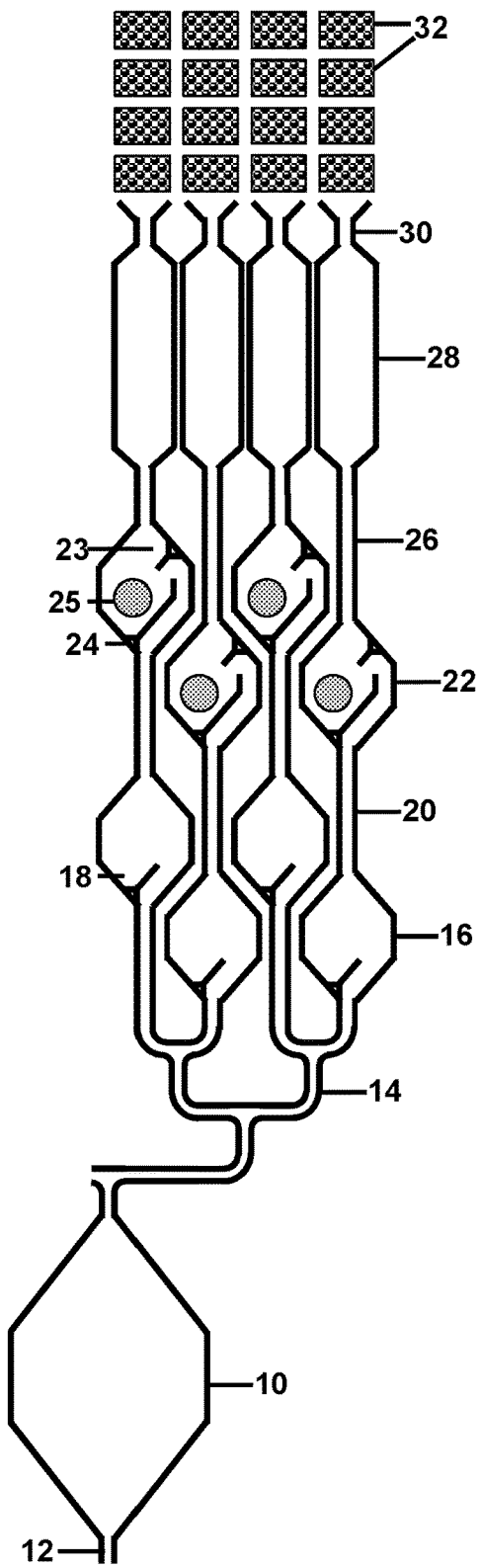

Figure 30

A. PCR-LDR-qPCR (Taqman) reaction (with optional carryover prevention) to detect methylation. Isolate genomic or cfDNA. Treat with Bsh1236I (CG^CG) and UNG (37oC, 30-60 minutes) to completely digest unmethylated DNA and prevent carryover in an Initial Reaction Chamber. Treat with bisulfite, which renders the strands non-complementary.

B. Distribute bisulfite treated sample into 24, 36, or 48 Primary PCR Reaction Chambers (columns) and PCR amplify. Upstream locus primers contain ribose bases (r), which are removed with RNaseH2 only when bound to target, thus unblocking primer. Downstream primers contain identical 8-11 base tails to prevent primer dimers.

C. PCR products incorporate dU, allowing for carryover prevention. Distribute products into Secondary LDR Reaction Chambers D. Methylation-specific ligation oligonucleotides contain tags (Ai, Ci') for subsequent PCR amplification. Upstream ligation primer contains block, which may be removed by cleaving ribose base with RNaseH2 only when hybridized to target.

E. Ligase covalently seals the unblocked mutation-specific upstream and phosphorylated downstream oligonucleotides together in each Secondary LDR Reaction Chamber.

F. Add Taqman mastermix with UDG for carryover prevention, which also destroys original target amplicons. Distribute products of each Secondary LDR Reaction Chamber into 384 or 768 micro-pores. Only authentic LDR products will amplify, when using PCR (and dUTP) with tag-specific primers (Ai, Ci'). Each Taqman probe spans the ligation junction.

G. The 5'->3' nuclease activity of Taq polymerase liberates the fluorescent group to generate signal. (PCR products incorporate dU, allowing for carryover prevention.)

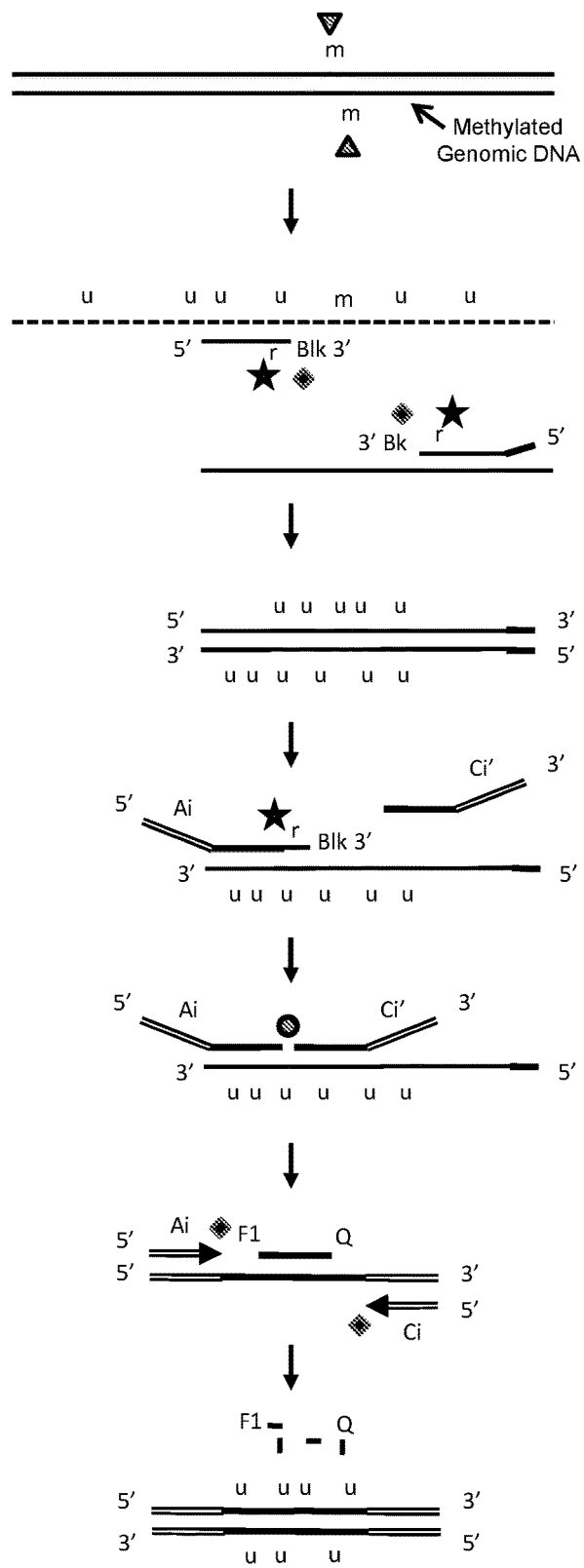

Figure 31

A. PCR-LDR-qPCR (UniTaq) reaction (with optional carryover prevention) to detect methylation. Isolate genomic or cfDNA. Treat with Bsh1236I (CG^CG) and UNG (37oC, 30-60 minutes) to completely digest unmethylated DNA and prevent carryover in an Initial Reaction Chamber. Treat with bisulfite, which renders the strands non-complementary.

B. Distribute bisulfite treated sample into 24, 36, or 48 Primary PCR Reaction Chambers (columns) and PCR amplify. Upstream locus primers contain ribose bases (r), which are removed with RNaseH2 only when bound to target, thus unblocking primer. Downstream primers contain identical 8-11 base tails to prevent primer dimers.

C. PCR products incorporate dU, allowing for carryover prevention. Distribute products into Secondary LDR Reaction Chambers.

D. Methylation-specific ligation oligonucleotides contain tags (Ai, Bi-Ci') for subsequent PCR amplification. Upstream ligation primer contains block, which may be removed by cleaving ribose base with RNaseH2 only when hybridized to target.

E. Ligase covalently seals the unblocked mutation-specific upstream and phosphorylated downstream oligonucleotides together in each Secondary LDR Reaction Chamber.

F. Add Taqman mastermix with UDG for carryover prevention, which also destroys original target amplicons. Distribute products of each Secondary LDR Reaction Chamber into 384 or 768 micro-pores. Only authentic LDR products will amplify, when using PCR (and dUTP) with Unitaq-specific primers (F1-Bi-Q-Ai, Ci).

G. Double-stranded DNA products of PCR; the polymerase blocker stops extension of the bottom strand.

H. After the denaturation step, as the temperature decreases, a hairpin forms between Bi and Bi'. The 5'->3' nuclease activity of Taq polymerase extends primer Ci and liberates the fluorescent group to generate signal.

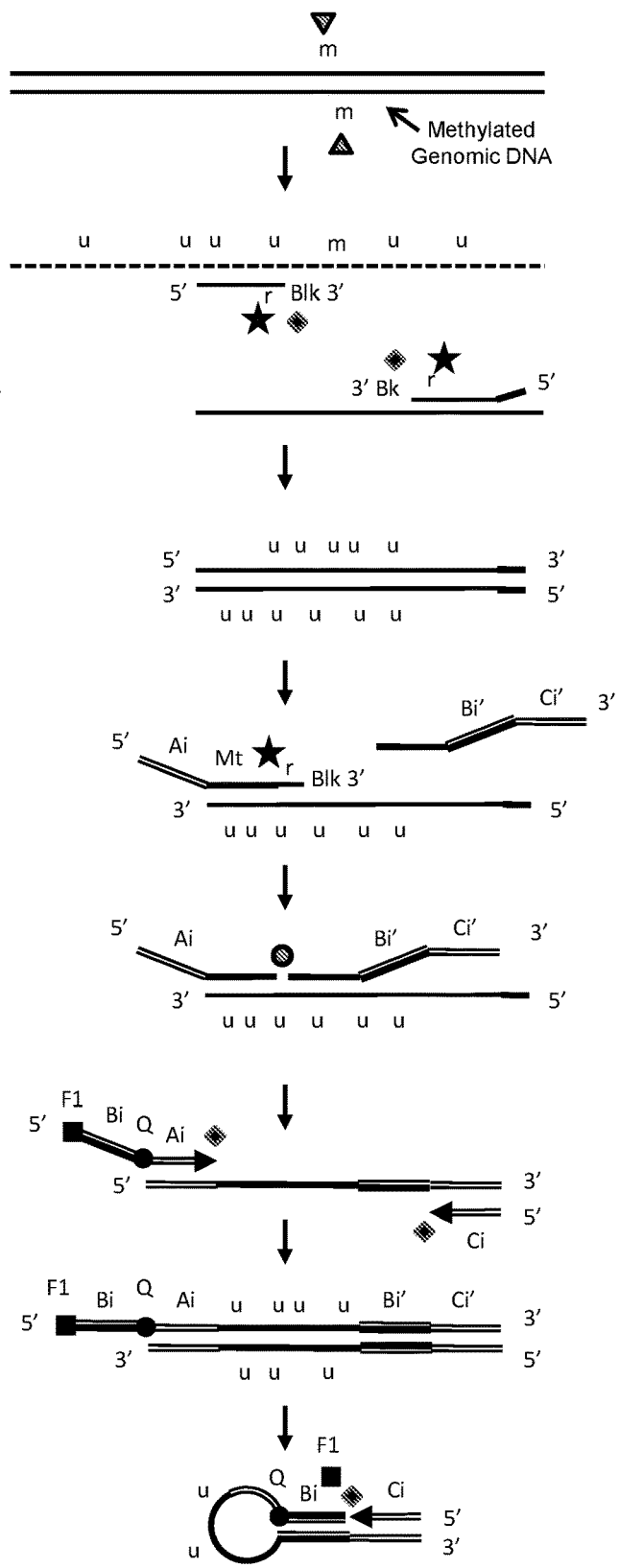

Figure 32

A. RT-PCR-PCR-qPCR (Taqman) to quantify wt and alternatively spliced (3a vs. 3b) transcript. Isolate mRNA.

B. Use reverse-transcriptase to make cDNA copy with 3' transcript-specific primers. Activate Taq polymerase and perform limited cycle PCR amplification (i.e. 7 cycles) to maintain relative ratios of different amplicons in an Initial Reaction Chamber. Primers contain identical 8-11 base tails to prevent primer dimers. Distribute initial multiplexed products into 6 Primary PCR Reaction Chambers.

C. Perform nested PCR (i.e. 10 cycles) using exon junction-specific primers with Universal tag tails (Ai; Aj; and Bi-Ci). Differentially dilute products.

D. PCR products comprise of Ai or Aj tag sequence, exon-junction-specific sequence, Bi', and Ci tag sequence. Differentially dilute products from each of the 6 Primary PCR Reaction Chambers into 4 Secondary PCR Reaction Chambers for a total of 24 chambers. Distribute products of each Secondary PCR Reaction Chamber into 384 or 768 micro-pores (16 or 32 rows). UniTaq primers in each row will amplify only those products from each Secondary PCR Reaction Chamber (columns) with the correct tags.

E. Double-stranded DNA products of PCR (not shown); the polymerase blocker stops extension of the bottom strand.

F. After the denaturation step, as the temperature decreases, a hairpin forms between Bi and Bi'. The 5'->3' nuclease activity of Taq polymerase extends primer Ci and liberates the fluorescent group to generate signal.

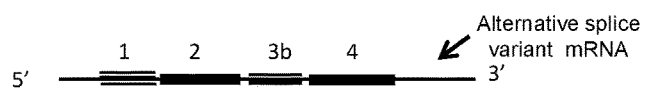
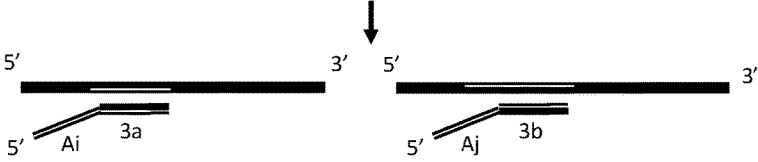
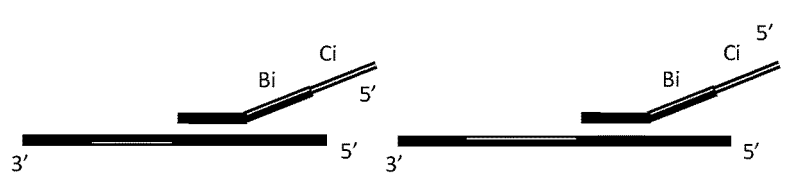
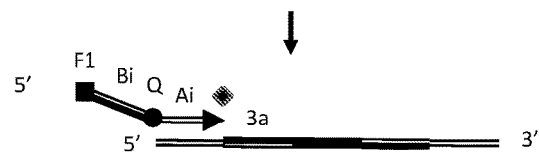
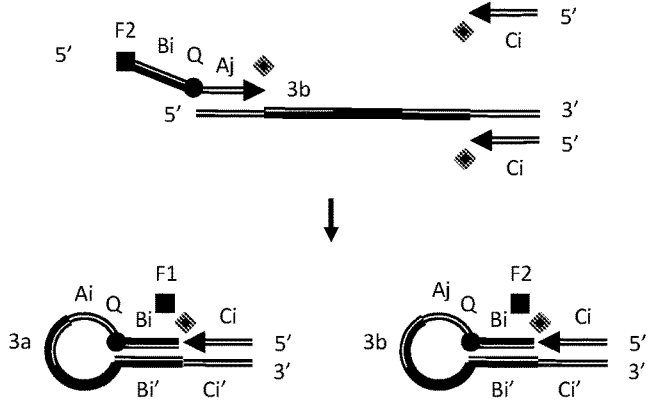

Figure 33

A. Exact enumeration of both rare and over-expressed lncRNA, mRNA, or splice variants; using Multiplexed RT-PCR - Nested PCR - UniTaq detection. (Alternatively, Multiplexed RT-PCR – Nested PCR - Real-time-PCR with target-specific Taqman probes.)

B. Preparation: Rows are pre-filled with 1-4 UniTaq primer sets (or alternatively, 1-4 universal tag primer sets with target-specific Taqman probes). Primers are distributed into each row and dried down into individual micro-pores.

C. Preparation: Pre-fill reaction chambers to columns with nested PCR primer sets with either UniTaq or universal tag sequences on their 5' ends, and dry down.

D. Multiplexed reverse-transcription PCR amplification for 7 cycles to generate 128 copies of each original target in an Initial Reaction Chamber.

E. Distribute initial multiplex reaction into 6 Primary PCR Reaction Chambers, with average distribution of 20 copies in each Primary PCR Reaction Chamber of each original transcript. Perform 10 cycles of nested PCR using target-specific primers with UniTaq or universal tags in groups of 16, 32, or 64 primer sets. Each Primary PCR Reaction Chamber is designed to retain a certain percentage of liquid volume after draining. Perform 3 cycles of filling and draining to differentially dilute products.

F. Dilute products from each of 6 Primary PCR Reaction Chambers into 4 Secondary Chambers each (= 24 total). Each Secondary Chamber is designed to retain a certain percentage of liquid volume after draining. Perform 3 cycles of filling and draining to differentially dilute products.

G. Distribute nested PCR products into each mixing chamber and then into 384 or 768 micro-pores of each column. Universal or UniTaq primers in each row will amplify only those products from each column with the correct tags. Poisson distribution in micro-pores will enumerate low-copy, medium-copy, and high-copy lncRNA, mRNA, or splice variants.

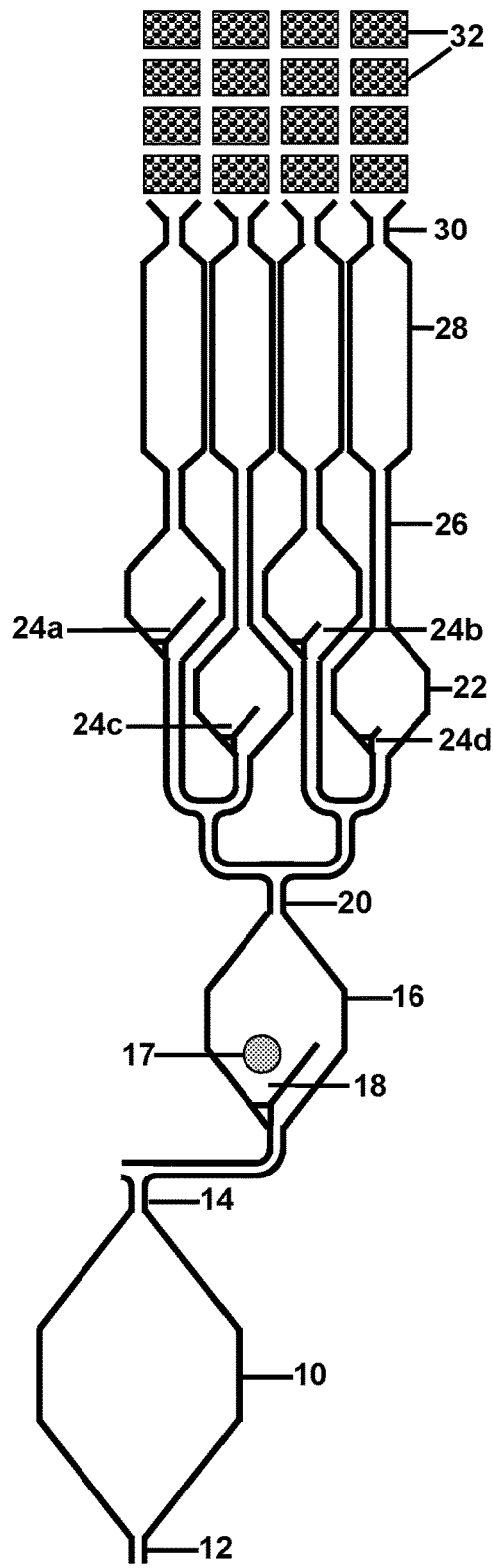

Figure 34

A. Primer design for sequencing and identifying mutations in one target strand in unknown pathogens. Isolate genomic DNA. For RNA viruses, an initial reverse-transcriptase step generates cDNA. PCR amplify target regions in an Initial Reaction Chamber.

B. Distribute sample into 24, 36, or 48 Primary PCR Reaction Chambers. Nested, locus-specific primers are unblocked with RNaseH2 only when bound to target. Perform 2 - 3 cycles of amplification with strand-displacement thermostable polymerase. One primer contains a target-specific region and first tag sequence, the second primer contains a target-specific region, fragment identifier, dU, and a second tag sequence.

C. Treat with UDG (uracil DNA glycosylase) and optionally, APE1 (human apurinic endonuclease) to destroy original primers and portion of primers in products.

D. Distribute products into micro-pores or beads into micro-pores containing immobilized second tag sequence primers. In the presence of both first and second tag primers, products are PCR amplified in micro-pores such that a given micro-pore generally contains zero or one clonal amplification of a given region, but may contain multiple clonal amplicons from different regions. After denaturation, and removal of unbound fragments, remaining tethered single-stranded target DNA is suitable for primer-directed sequencing.

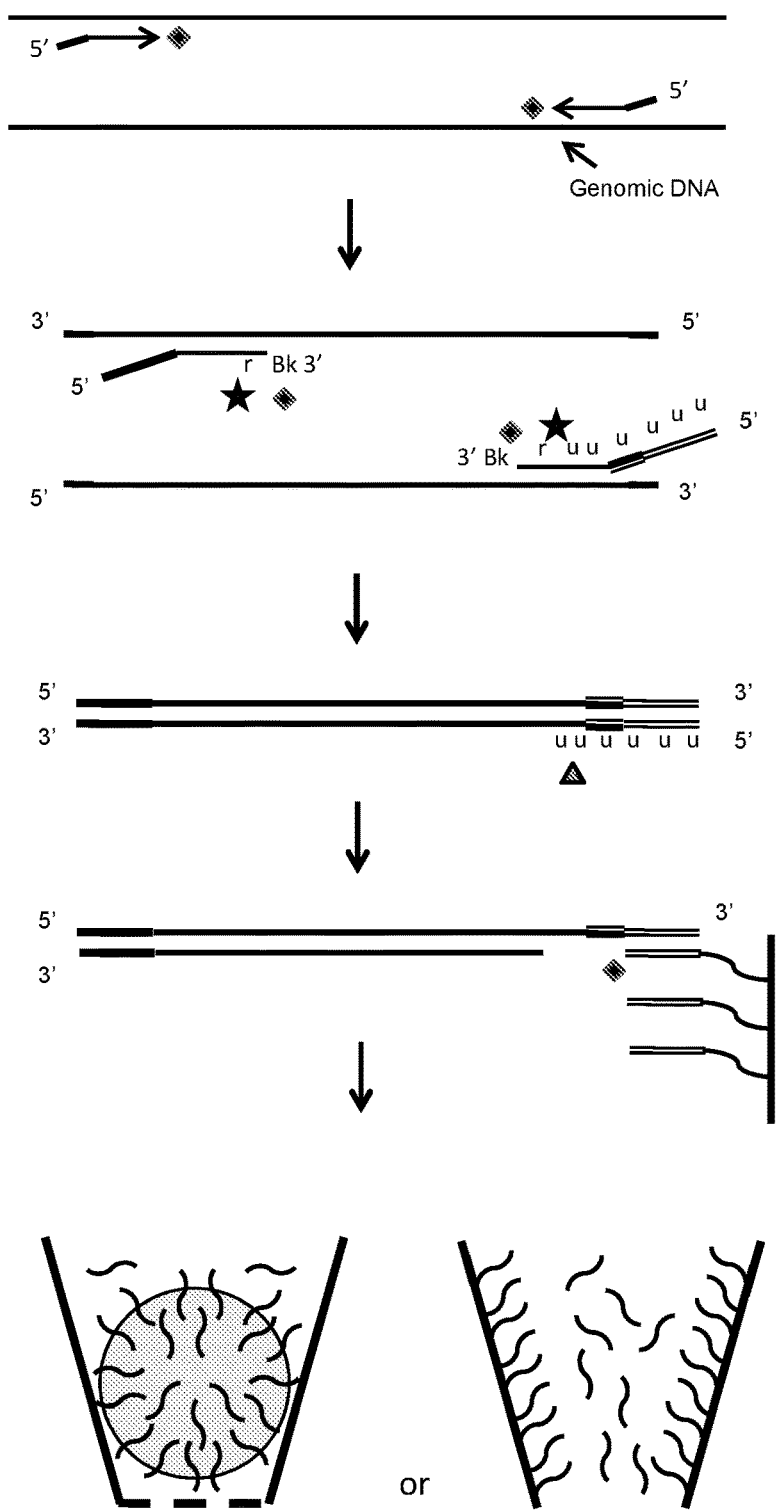

Figure 35

A. Distribute products into micro-pores or beads into micro-pores containing immobilized second tag sequence primers. In the presence of both first and second tag primers, products are PCR amplified in micro-pores such that a given micro-pore generally contains zero or one clonal amplification of a given region, but may contain multiple clonal amplicons from different regions.

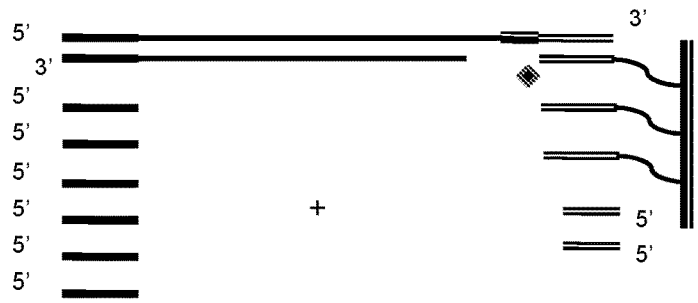

B. In solution first tag primer is in excess of both second tag primers. Immobilized primer is longer than in solution second tag primer. Optionally, at end of PCR cycles, hybridization temperature are above Tm of shorter tag primer to favor synthesis of single stranded products to hybridize to immobilized primer and drive extension of such primers to completion.

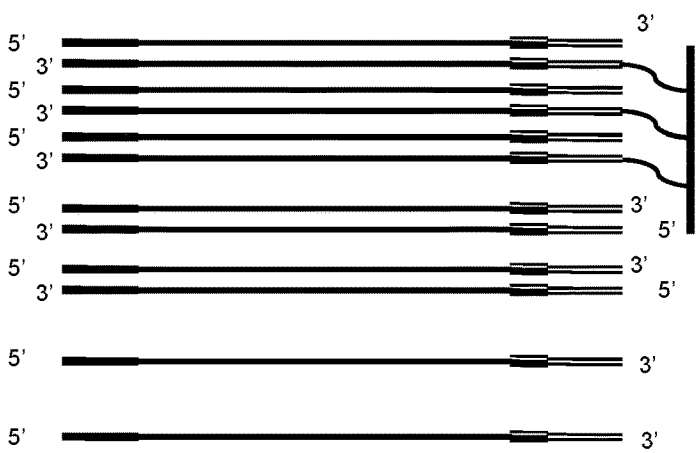

C. After denaturation, and removal of unbound fragments, remaining tethered single-stranded target DNA is suitable for primer-directed sequencing.

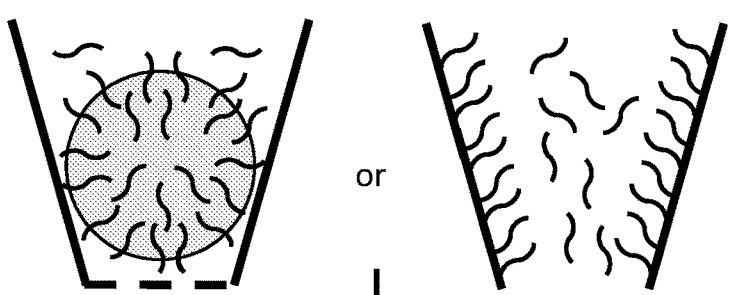

D. A gene-specific (GS) primer may be used for sequencing. Alternatively, a first set of 8-16 sequencing primers may comprise a common 5' sequence (16 bases), and variable 3' sequences (8 bases). Or, a second set of 64-256 sequencing primers may comprise a common 5' sequence (8 bases), a variable middle sequence (8 bases, 8-16 variants) and hyper-variable 3' sequences (8 bases, 64-256 variants).

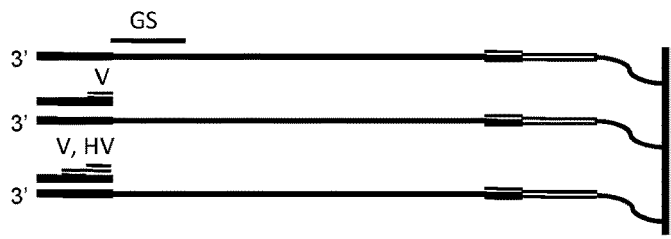

Figure 36

A. Distribute products into micro-pores or beads into micro-pores containing immobilized second tag sequence primers. In the presence of both first and second tag primers, products are amplified in micro-pores such that a given micro-pore generally contains zero or one clonal amplification of a given region, but may contain multiple clonal amplicons from different regions.

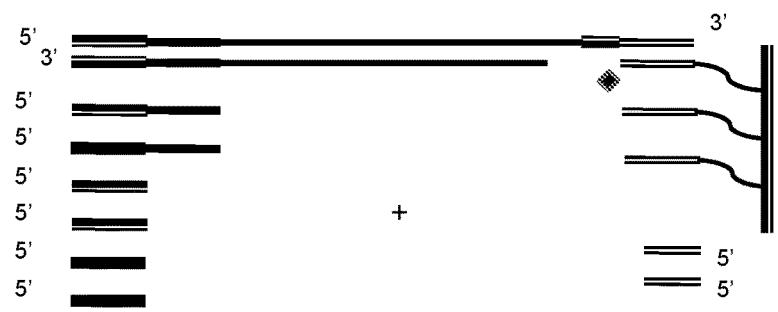

B. In solution first tag primers comprise two different 5' portions, and with added 5' portion primers, which are in excess of both second tag primers. Immobilized primer is longer than in solution second tag primer. Using strand-displacement polymerase lacking 5'-3' nuclease activity, perform combined isothermal and thermo-cycling amplification. Re-annealing of products with different 5' portions enables strand displacement amplification and helps drive extension of immobilized primers to completion.

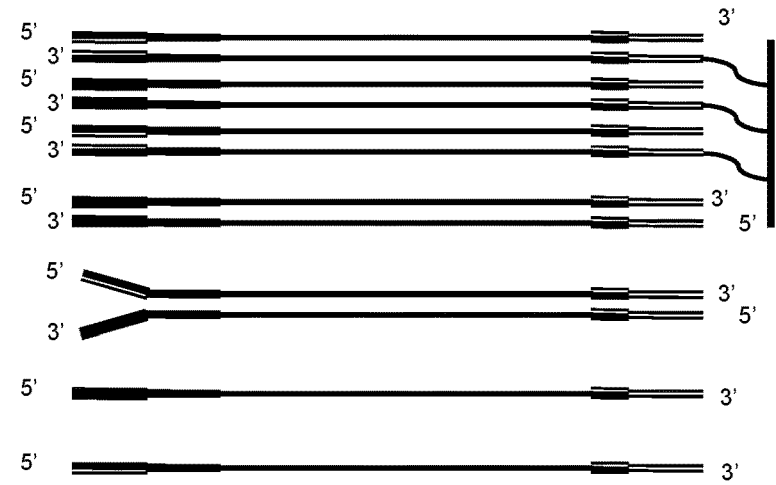

C. After denaturation, and removal of unbound fragments, remaining tethered single-stranded target DNA is suitable for primer-directed sequencing.

D. A gene-specific (GS) primer may be used for sequencing. Alternatively, a first set of 8-16 sequencing primers may comprise a common 5' sequence (16 bases), and variable 3' sequences (8 bases). Or, a second set of 64-256 sequencing primers may comprise a common 5' sequence (8 bases), a variable middle sequence (8 bases, 8-16 variants) and hyper-variable 3' sequences (8 bases, 64-256 variants).

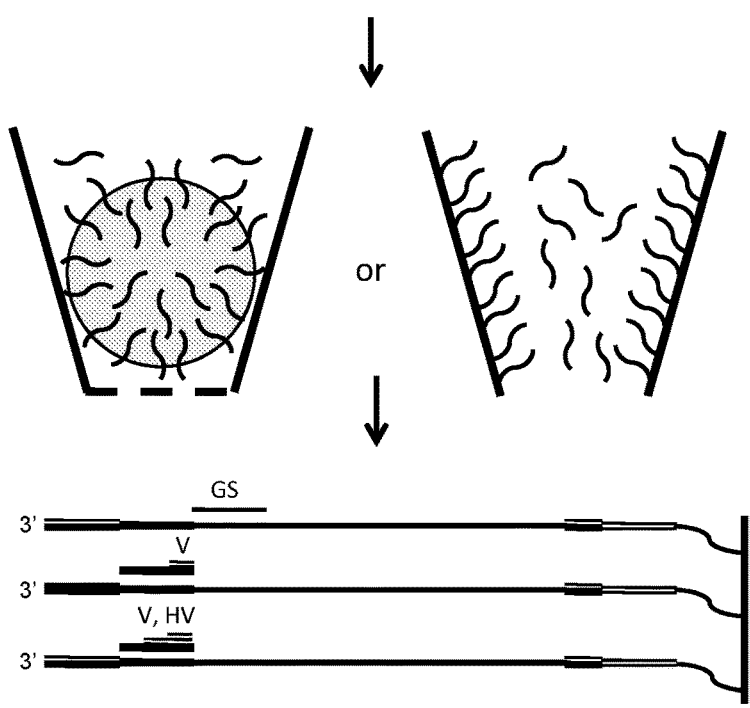

Figure 37

A. Distribute products into micro-pores or beads into micro-pores containing immobilized second tag sequence primers. In the presence of both first and second tag primers, products are amplified in micro-pores such that a given micro-pore generally contains zero or one clonal amplification of a given region, but may contain multiple clonal amplicons from different regions.

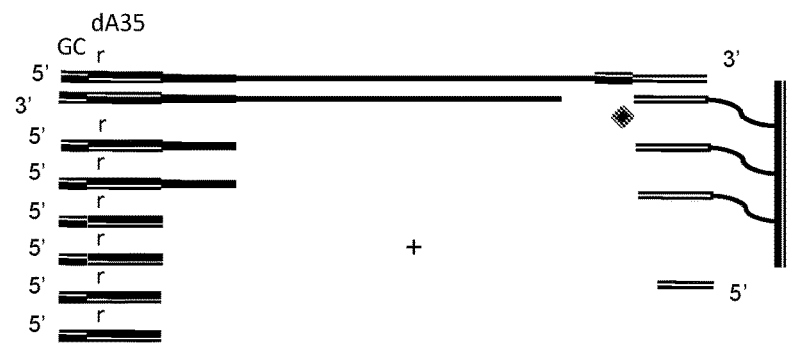

B. In solution first tag primer comprises dA35, and with added dA35 with GC rich toehold primer, are in excess of both second tag primers. Immobilized primer is longer than in solution second tag primer. Using strand-displacement polymerase lacking 5'-3' nuclease activity, perform isothermal and/or thermo-cycling amplification. Primer toehold is released with RNaseH2 only when bound to target. Excess single-stranded product hybridizes to immobilized primer and helps drive extension of immobilized primers to completion.

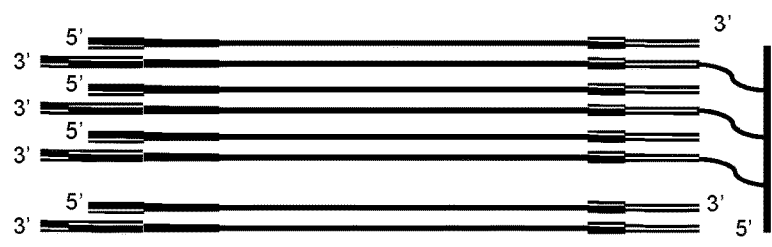

C. After denaturation, and removal of unbound fragments, remaining tethered single-stranded target DNA is suitable for primer-directed sequencing.

D. A gene-specific (GS) primer may be used for sequencing. Alternatively, a first set of 8-16 sequencing primers may comprise a common 5' sequence (16 bases), and variable 3' sequences (8 bases). Or, a second set of 64-256 sequencing primers may comprise a common 5' sequence (8 bases), a variable middle sequence (8 bases, 8-16 variants) and hyper-variable 3' sequences (8 bases, 64-256 variants).

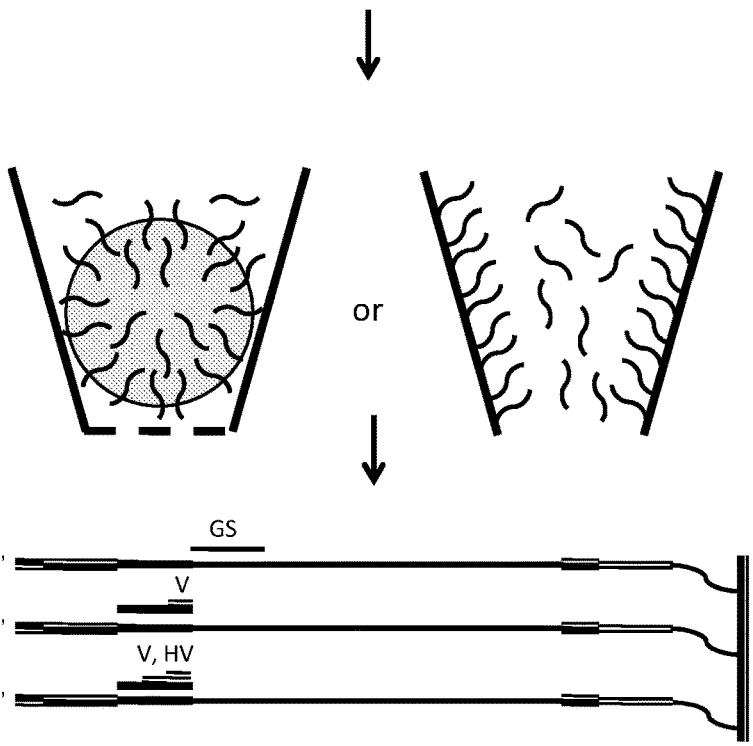

Figure 38

A. Unknown pathogen identification, quantification and genotyping; using Multiplexed PCR - Nested PCR – sequencing.

B. Preparation: Rows are pre-filled with one or more universal tag primer sets, where one primer is immobilized and the other primer is bound, but released at higher temperature. Primers are distributed into each row and dried down into individual micro-pores.

C. Preparation: Pre-fill pre-chambers to columns with nested PCR primer sets with universal tag sequences on their 5' ends, and dry down.

D. Multiplexed PCR amplification (or reverse-transcription-PCR for RNA targets) for 10 cycles to generate 1,024 copies of each original target in an Initial Reaction Chamber.

E. Distribute initial multiplex reaction into 48 Primary PCR Reaction Chambers, with average distribution of 20 copies in each Primary PCR Reaction Chamber of each original pathogen. Perform 5 cycles of nested PCR using target-specific primers with universal tags in groups of 32, or 64 primer sets, with average of 640 copies of each pathogen. Remove universal primer sequence from product with UDG/APE1, facilitates hybridization to immobilized primer in micro-pore.

F. Distribute nested PCR products with single-stranded tails into mixing chambers and then into micro-pores of each column. PCR amplify one or more products in each micro-pore and melt off non-anchored strand. Universal primers in each row will amplify only those products from each column with the correct tags.

G. Add either target-specific, or universal tag-specific sequencing primers. Perform sequencing-by-synthesis. Poisson distribution in micro-pores will enumerate target sequences, while direct sequence information will identify variant pathogens.

H. Alternative approach, where all micro-pores are pre-filled with a single universal primer, which is immobilized, and micro-pores are dried.

I. Preparation: Pre-fill pre-chambers to columns with nested PCR primer sets with 8-12 unique tag sequence on one primer of the set, and universal sequences on their 5' ends, and dry down.

J. Initial multiplexed PCR amplification, distribution into 48 Primary PCR Reaction Chambers, nested PCR using target-specific primers, distribution into mixing chambers and then into micro-pores, and PCR amplification in micro-pores is as described above.

K. Add either target-specific, or universal primers with unique tag-specific portions as sequencing primers. Perform sequencing-by-synthesis. Poisson distribution in micro-pores will enumerate target sequences, while direct sequence information will identify variant pathogens

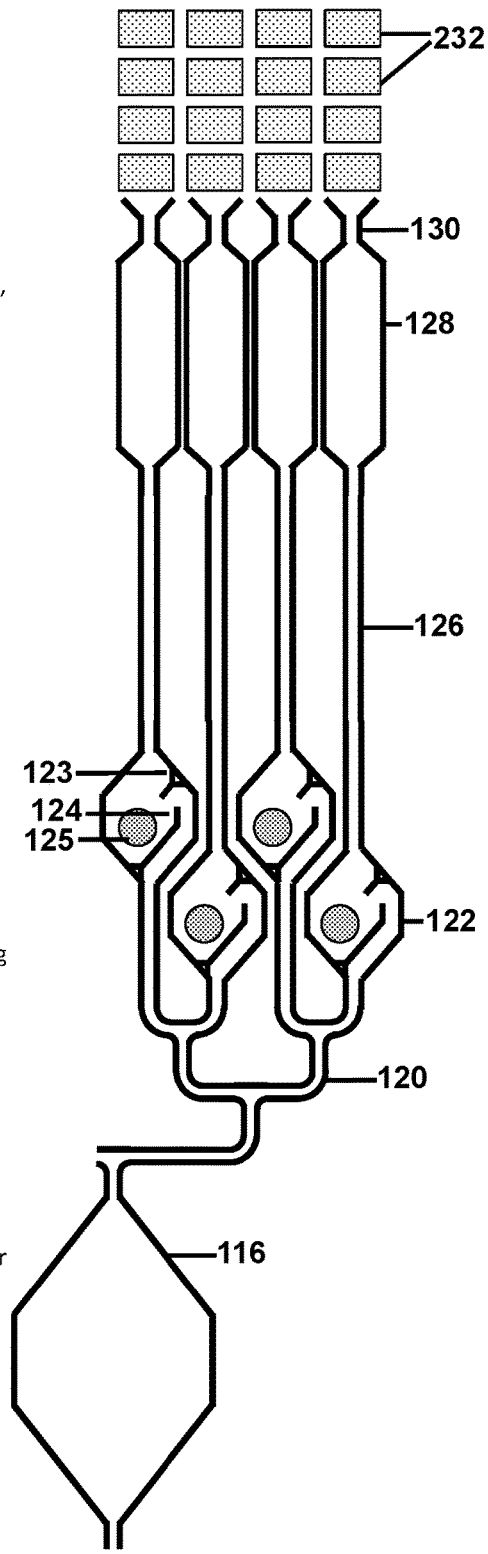

Figure 39

A. Primer design for sequencing and identifying mutations in one target strand. cfDNA of average length of about 160 bp.

B. Distribute sample into 24, 36, or 48 Primary PCR Reaction Chambers. Locus-specific primers are unblocked with RNaseH2 only when bound to target. Perform 2 - 3 cycles of amplification with strand-displacement thermostable polymerase. One primer contains a target-specific region and first tag sequence, the second primer contains a target-specific region, fragment identifier, dU, and a second tag sequence.

C. Treat with UDG (uracil DNA glycosylase) and optionally, APE1 (human apurinic endonuclease) to destroy original primers and portion of primers in products.

D. Distribute products into micro-pores or beads into micro-pores containing immobilized second tag sequence primers. In the presence of both first and second tag primers, products are PCR amplified in micro-pores such that a given micro-pore generally contains zero or one clonal amplification of a given region, but may contain multiple clonal amplicons from different regions. After denaturation, and removal of unbound fragments, remaining tethered single-stranded target DNA is suitable for primer-directed sequencing.

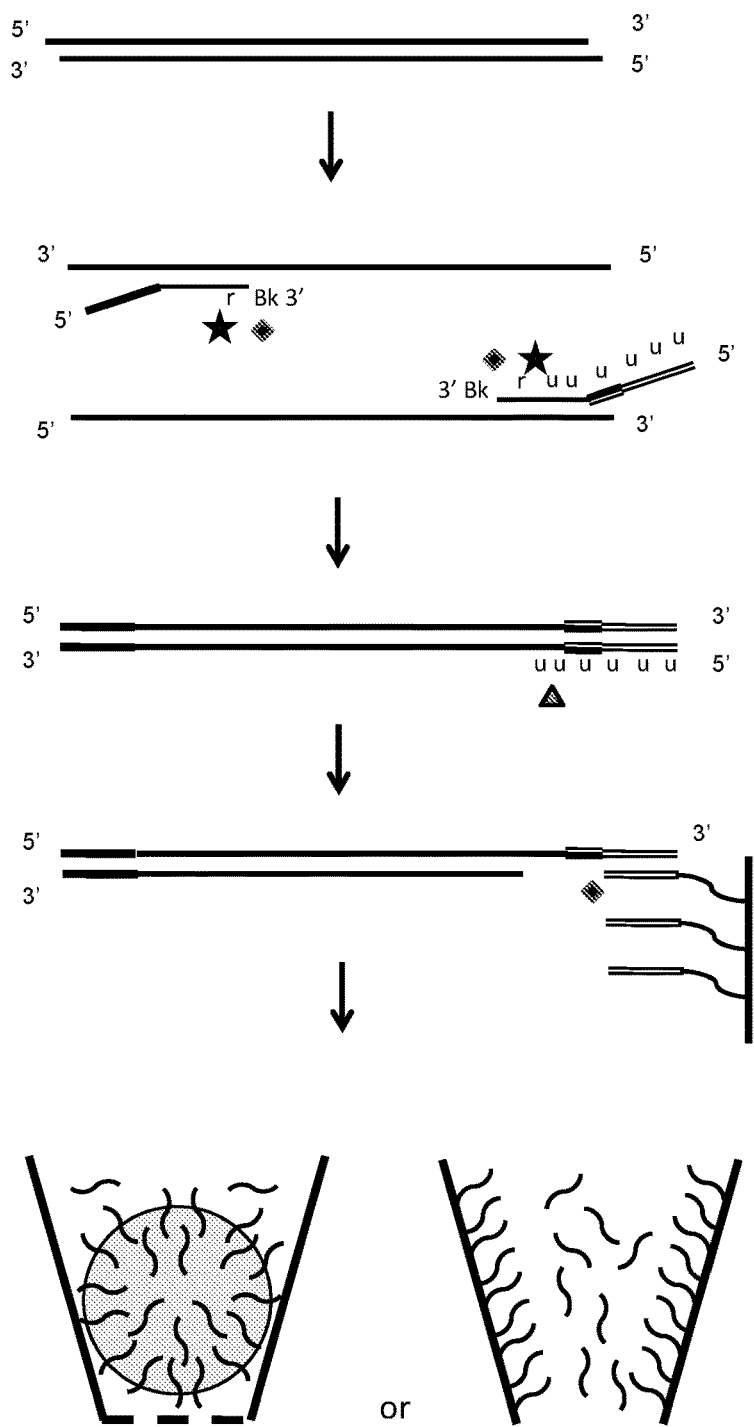

Figure 40

A. Primer design for sequencing and identifying mutations in one target strand, across overlapping fragments. cfDNA of average length of about 160 bp.

B. Distribute sample into 24, 36, or 48 Primary PCR Reaction Chambers. Locus-specific primers are unblocked with RNaseH2 only when bound to target. Perform 2 - 3 cycles of amplification with strand-displacement thermostable polymerase. One primer contains a target-specific region and first tag sequence, the second primer contains a target-specific region, fragment identifier, dU, and a second tag sequence, which differs slightly from first tag sequence.

C. Treat with UDG (uracil DNA glycosylase) and optionally, APE1 (human apurinic endonuclease) to destroy original primers and portion of primers in products.

D. Anneal biotinylated primer containing second tag sequence. Strand displacement polymerase extends to form full length double-stranded copy of fragment.

E. Both extended and free biotinylated primers are captured on streptavidin coated beads to be distributed in micro-pores, or directly on streptavidin coated micro-pores. In the presence of both first and second tag primers, longer products are PCR amplified in micro-pores such that a given micro-pore generally contains zero or one clonal amplification of a given region. Shorter products form panhandles and do not amplify. After denaturation, and removal of unbound fragments, remaining tethered single-stranded target DNA is suitable for primer-directed sequencing.

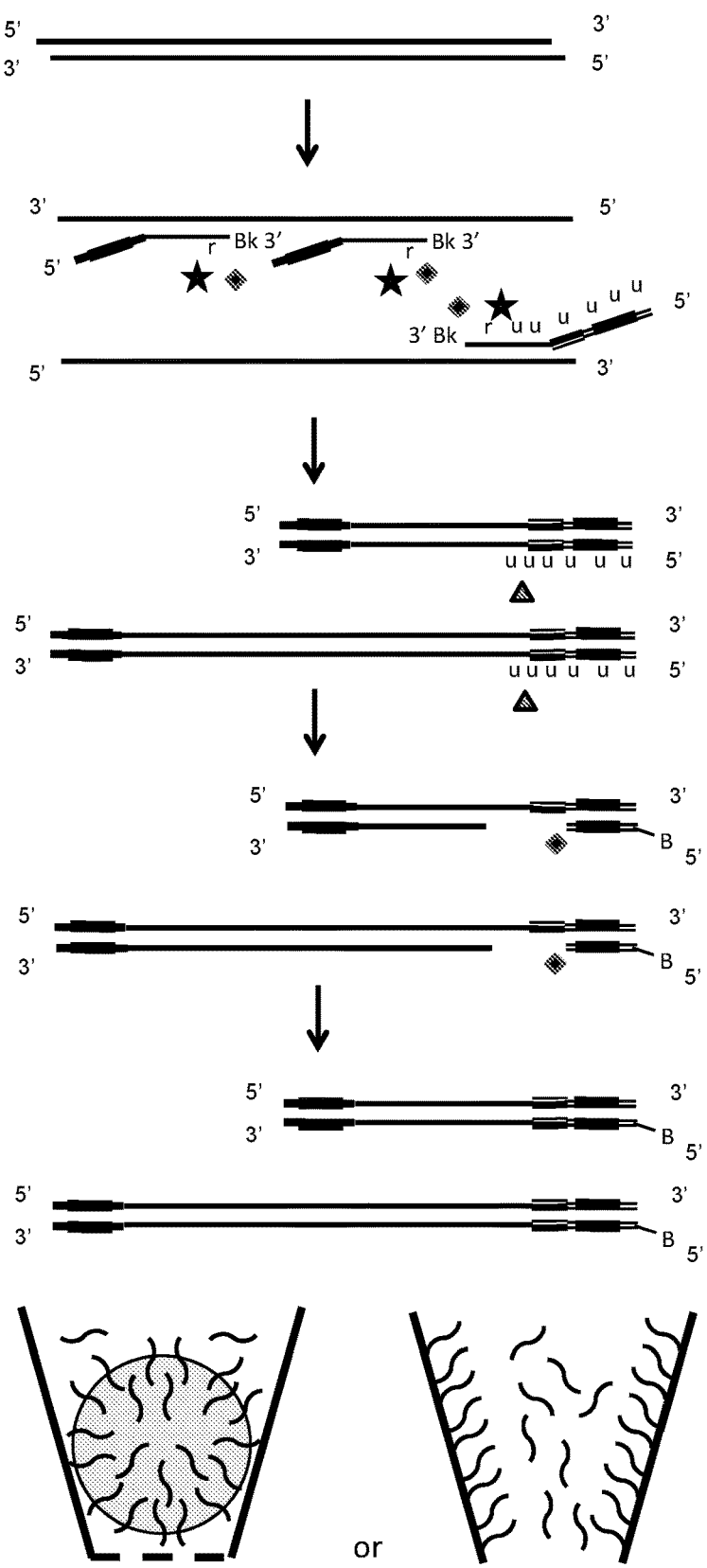

Figure 41

A. Primer design for sequencing and identifying mutations in one target strand, across overlapping fragments. cfDNA of average length of about 160 bp.

B. Distribute sample into 24, 36, or 48 Primary PCR Reaction Chambers. Locus-specific primers are unblocked with RNaseH2 only when bound to target. Perform 2 - 3 cycles of amplification with strand-displacement thermostable polymerase. One primer contains a target-specific region and first tag sequence, the second primer contains a target-specific region, fragment identifier, dU, and a second tag sequence, which differs slightly from first tag sequence.

C. Treat with UDG (uracil DNA glycosylase) and optionally, APE1 (human apurinic endonuclease) to destroy original primers and portion of primers in products.

D. Distribute products into micro-pores or beads into micro-pores containing immobilized second tag sequence primers. In the presence of both first and second tag primers, longer products are PCR amplified in micro-pores such that a given micro-pore generally contains zero or one clonal amplification of a given region. Shorter products form panhandles and do not amplify. After denaturation, and removal of unbound fragments, remaining tethered single-stranded target DNA is suitable for primer-directed sequencing.

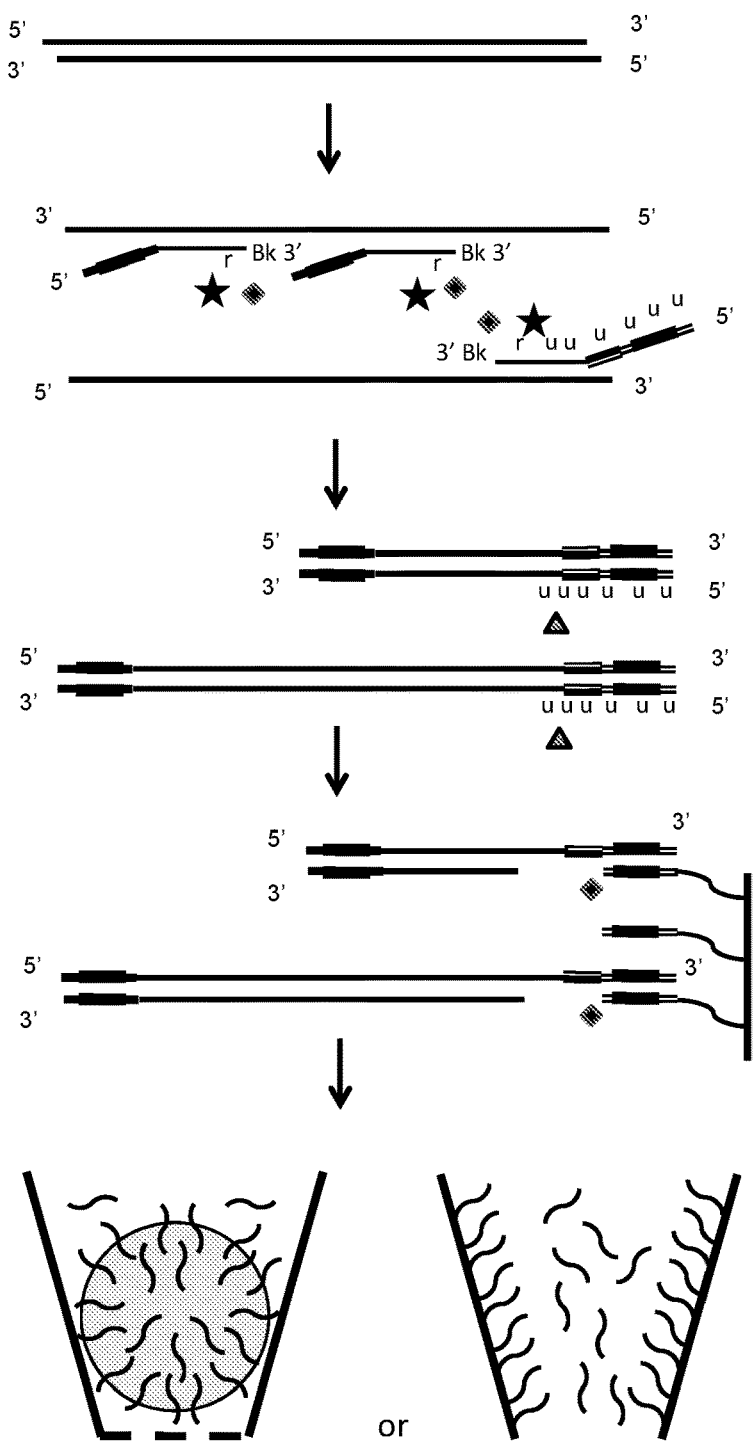

Figure 42

A. Close-up illustrating primer design where shorter amplicons form panhandles, which do not amplify, while the desired longer products amplify on the solid support. Illustrated with capture of biotin primer.

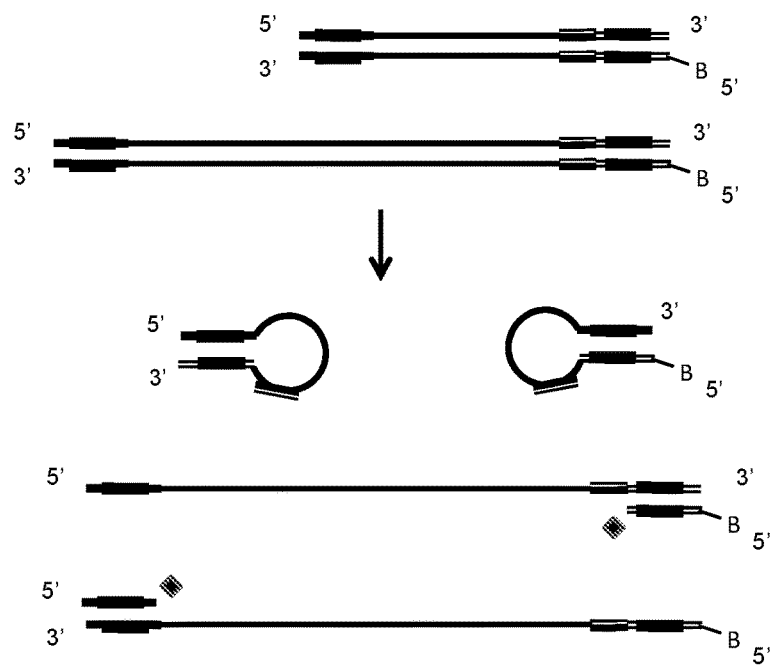

B. Close-up illustrating primer design where shorter amplicons form panhandles, which do not amplify, while the desired longer products amplify on the solid support. Illustrated with primers immobilized to the solid support.

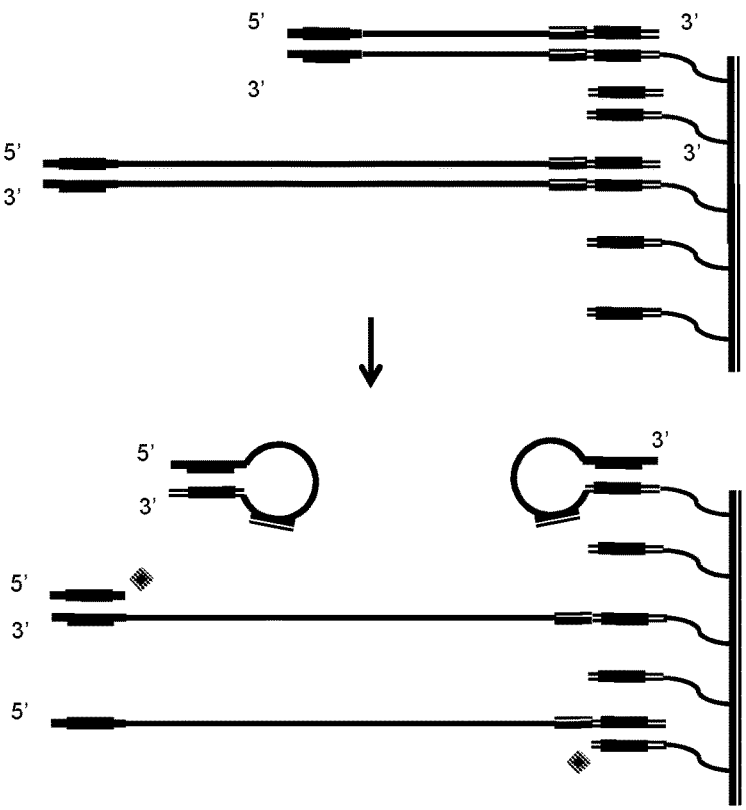

Figure 43

A. Primer design for sequencing and identifying mutations in one target strand, across overlapping fragments. cfDNA of average length of about 160 bp.

B. Distribute sample into 24, 36, or 48 Primary PCR Reaction Chambers. Locus-specific primers are unblocked with RNaseH2 only when bound to target. Perform 2 - 3 cycles of amplification with strand-displacement thermostable polymerase. One primer contains a target-specific region and first tag sequence, the second primer contains a target-specific region, fragment identifier, dU, and a second tag sequence.

C. Treat with UDG (uracil DNA glycosylase) and optionally, APE1 (human apurinic endonuclease) to destroy original primers and portion of primers in products.

D. Distribute products into micro-pores or beads into micro-pores containing immobilized second tag sequence primers. In the presence of both first and second tag primers, longer products are PCR amplified in micro-pores such that a given micro-pore generally contains zero or one clonal amplification of a given region. Shorter products form panhandles, or are missing a second tag sequence and do not amplify. After denaturation, and removal of unbound fragments, remaining tethered single-stranded target DNA is suitable for primer-directed sequencing.

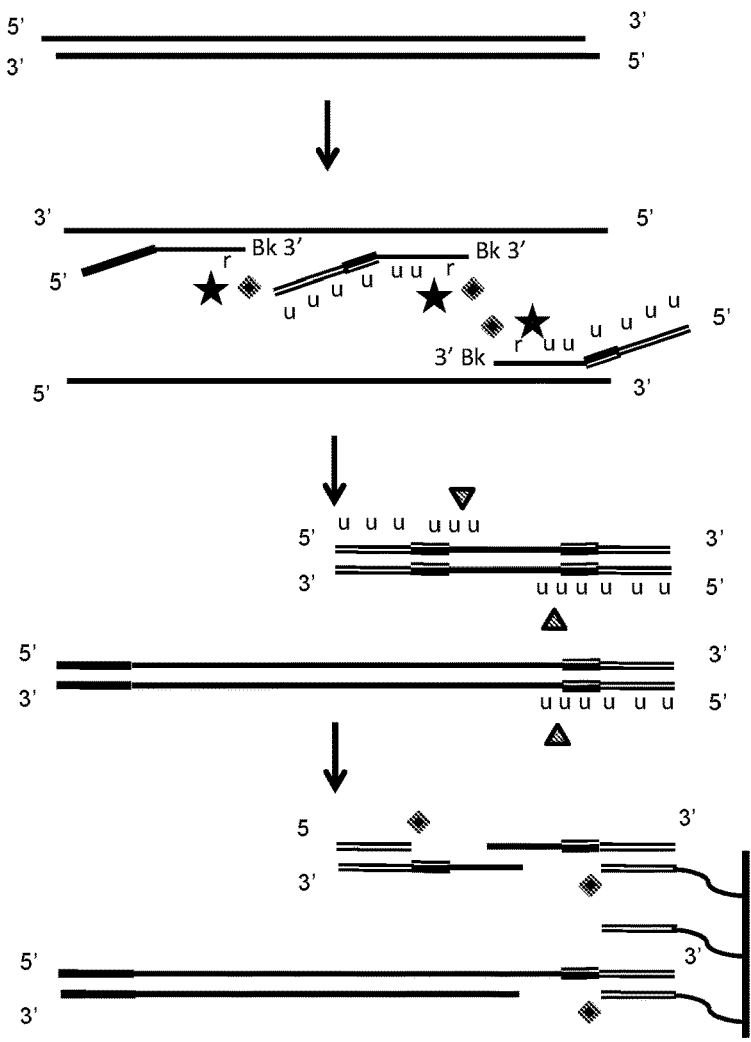

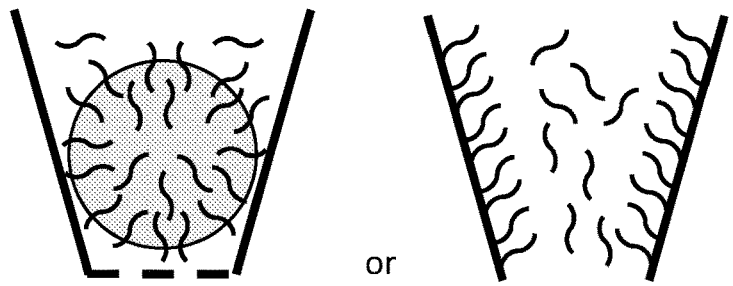

Figure 44

A. Primer design for sequencing and identifying mutations in one target strand, across overlapping fragments. cfDNA of average length of about 160 bp.

B. Distribute sample into 24, 36, or 48 Primary PCR Reaction Chambers. Locus-specific primers are unblocked with RNaseH2 only when bound to target. Perform 2 - 3 cycles of amplification with strand-displacement thermostable polymerase. One primer contains a target-specific region and first tag sequence, the second primer contains a target-specific region, fragment identifier, dU, and a second tag sequence.

C. Treat with UDG (uracil DNA glycosylase) and optionally, APE1 (human apurinic endonuclease) to destroy original primers and portion of primers in products.

D. Distribute products into micro-pores or beads into micro-pores containing immobilized second tag sequence primers. In the presence of both first and second tag primers, longer products are PCR amplified in micro-pores such that a given micro-pore generally contains zero or one clonal amplification of a given region. Shorter products form panhandles, or are missing a second tag sequence and do not amplify. After denaturation, and removal of unbound fragments, remaining tethered single-stranded target DNA is suitable for primer-directed sequencing.

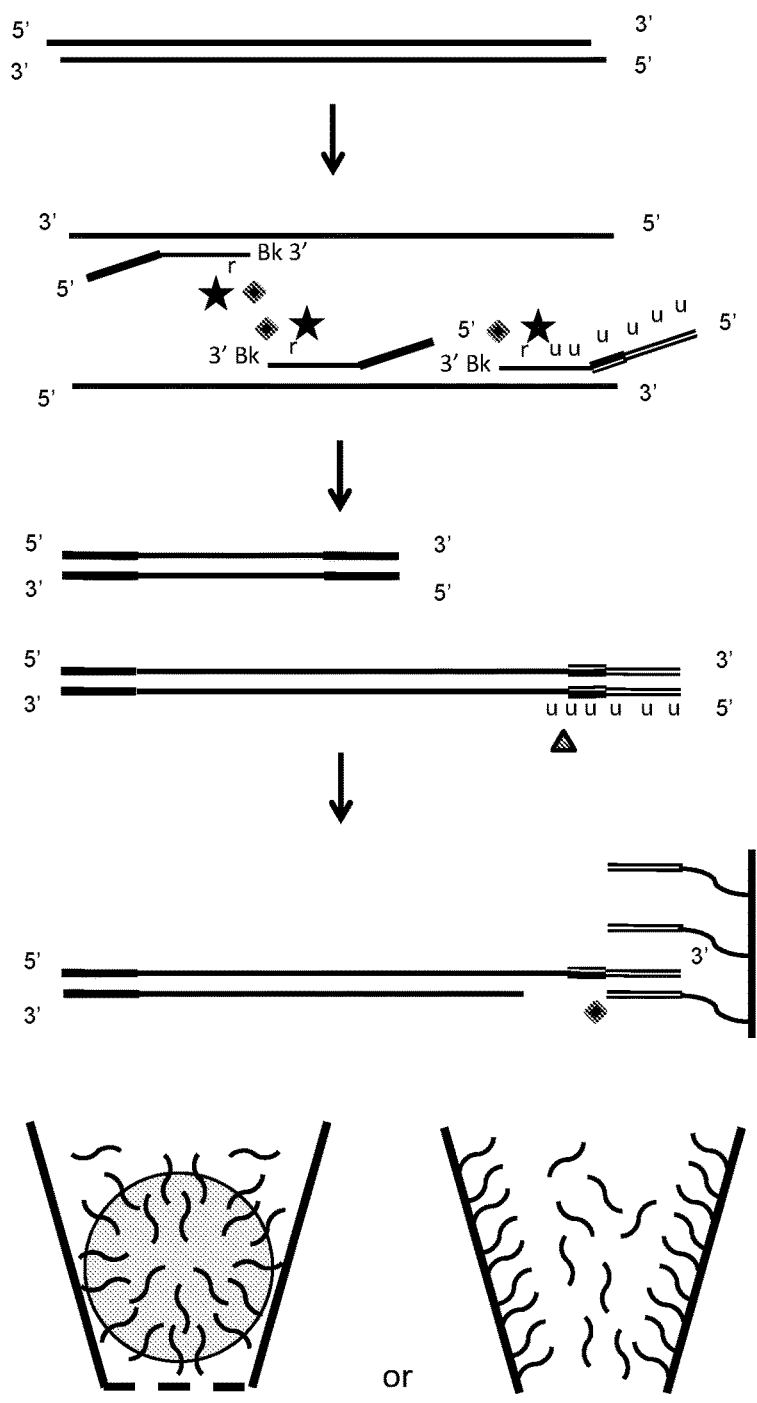

Figure 45

A. Primer design for sequencing and identifying mutations in both target strands, across overlapping fragments. cfDNA of average length of about 160 bp.

B. Distribute sample into 24, 36, or 48 Primary PCR Reaction Chambers. Locus-specific primers are unblocked with RNaseH2 only when bound to target. Perform 2-3 cycles of amplification with Taq polymerase. All primers contain dU, target-specific region, fragment identifier, and the same first tag sequences. 5'-3' proofreading activity will destroy most smaller fragments.

C. Treat with UDG (uracil DNA glycosylase) and optionally, APE1 (human apurinic endonuclease) to destroy original primers and portion of primers in both short and long products.

D. Distribute products into wells or beads into wells containing immobilized first tag sequence primers. Strand displacement polymerase extends to form double-stranded copy of both strands.

E. Nested, target-specific primers are unblocked with RNaseH2 only when bound to target. Perform 1-2 cycles of amplification with strand-displacement thermostable polymerase. Nested target-specific primer contain second tag sequence.

F. In the presence of both first and second tag primers, longer products are PCR amplified in micro-pores such that a given micro-pore generally contains zero or one clonal amplification of a given region. After denaturation, and removal of unbound fragments, remaining tethered single-stranded target DNA is suitable for primer-directed sequencing.

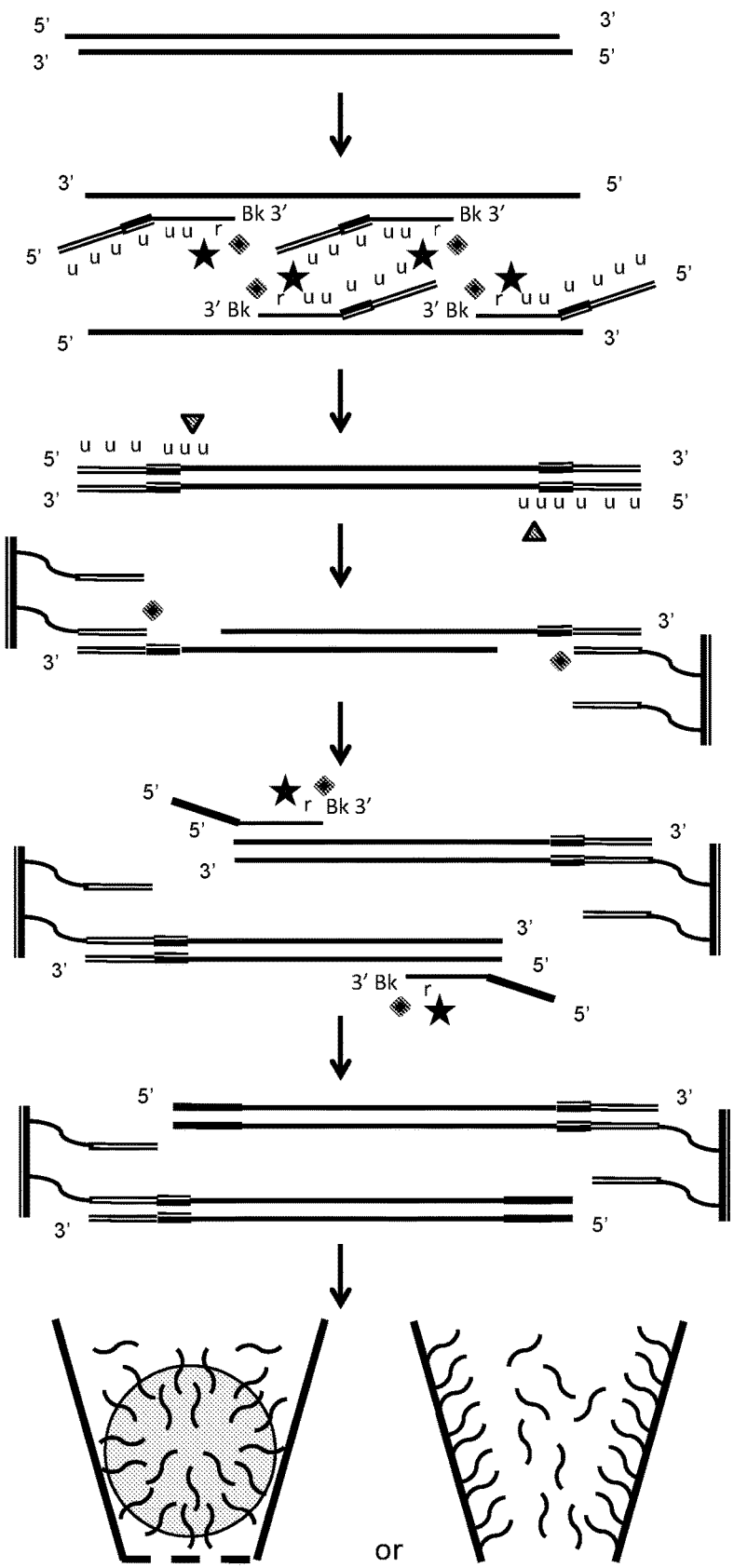

Figure 46

A. Primer design for identifying SNPs and enumerating copy number of both locus-specific strands. cfDNA of average length of about 160 bp.

B. Distribute sample into 24, 36, or 48 Primary PCR Reaction Chambers. Locus-specific primers are unblocked with RNaseH2 only when bound to target. Perform 3 cycles of amplification with strand-displacement thermostable polymerase. Both primers contain dU, target-specific region, fragment identifier, and the same first tag sequences.

C. Treat with UDG (uracil DNA glycosylase) and optionally, APE1 (human apurinic endonuclease) to destroy original primers and portion of primers in products.

D. Distribute products into wells or beads into wells containing immobilized first tag sequence primers. Strand displacement polymerase extends to form double-stranded copy of fragments.

E. Nested, target-specific primers are unblocked with RNaseH2 only when bound to target. Perform 1-2 cycles of amplification. Nested primers contain second tag sequence, with optional variable regions.

F. In the presence of both first and second tag primers, products are PCR amplified in micro-pores. After denaturation, and removal of unbound fragments, remaining tethered single-stranded target DNA is suitable for primer-directed sequencing.

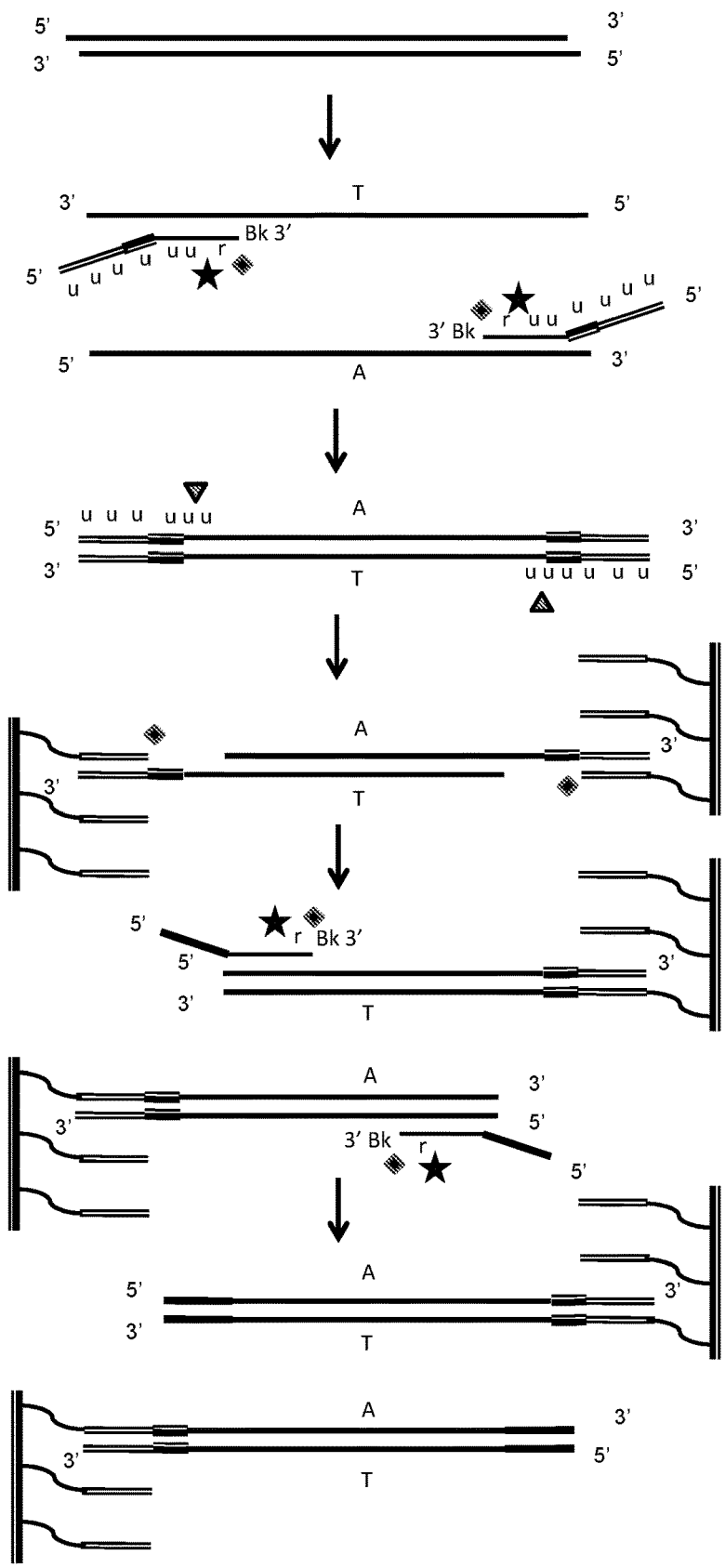

Figure 47

A. For identifying unknown mutations at low-abundance in plasma; using Fragment identifier PCR - sequencing.

B. Preparation: All micro-pores are pre-filled with a single universal primer, which is immobilized, and micro-pores are dried.

C. Distribute initial sample into 48 Primary PCR Reaction Chambers. Highest level of DNA in plasma = 10,000 genome equivalents. On average, 200 copies of each target per Primary PCR Reaction Chamber, with at most 1 mutation. Perform 3 cycles of fragment identifier PCR for both strands, each strand covering slightly different sequences. Yields 4 copies of top strand, and 4 copies of bottom strand.

D. Treat with UDG/APE1 and distribute Fragment identifier PCR products with single-stranded tails into mixing chambers and then micro-pores of each column. PCR amplify one or more products in each micro-pore using nested target-specific primers and universal primers and melt off non-anchored strand.

E. Add either target-specific, or universal primers with unique tag-specific portions as sequencing primers. Perform sequencing-by-synthesis. Generate about 80 bases of sequence information, plus 10 bases of unique fragment identifier barcode, for accurate enumeration of each mutation, with verification on both strands.

A. For non-invasive prenatal testing of trisomy in plasma; using Fragment identifier PCR - sequencing.

B. Preparation: All micro-pores are pre-filled with a single universal primer, which is immobilized, and micro-pores are dried.

C. Adjust DNA in plasma/ sample to 2,000 genome equivalents. Distribute initial sample into 48 Primary PCR Reaction Chambers. On average, 40 copies of each locus per Primary PCR Reaction Chamber, with different SNPs. Perform 3 cycles of fragment identifier PCR for both strands, each strand covering slightly different sequences. Yields 4 copies of top strand, and 4 copies of bottom strand.

D. Treat with UDG/APE1 and distribute Fragment identifier PCR products with single-stranded tails into mixing chambers and then micro-pores of each column. PCR amplify one or more products in each micro-pore using nested locus-specific primers and universal primers and melt off non-anchored strand.

E. Add either target-specific, or universal primers with unique tag-specific portions as sequencing primers. Perform sequencing-by-synthesis. Generate about 50 bases of sequence information, plus 10 bases of unique fragment identifier barcode, for accurate enumeration of each SNP and chromosomal copy number, with verification on both strands.

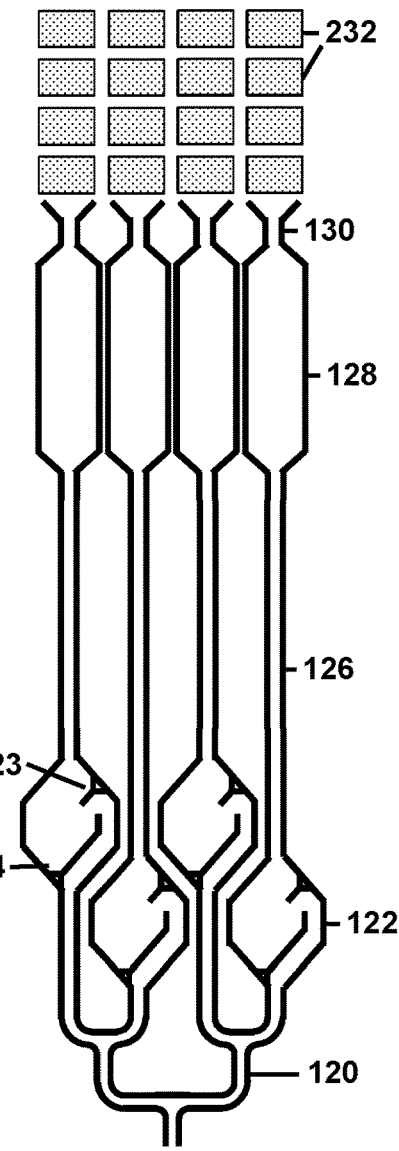

Figure 48

A. Primer design for sequencing and identifying methylation in one target strand. cfDNA of average length of about 160 bp. Treat with Bsh1236I (CG^CG) to completely digest unmethylated DNA in an Initial Reaction Chamber. Treat with bisulfite, which renders the strands non-complementary.

B. Distribute sample into 24, 36, or 48 Primary PCR Reaction Chambers. Locus-specific primers are unblocked with RNaseH2 only when bound to target. Perform 2 - 3 cycles of amplification with strand-displacement thermostable polymerase. One primer contains a target-specific region and first tag sequence, the second primer contains a target-specific region, fragment identifier, dU, and a second tag sequence.

C. Treat with UDG (uracil DNA glycosylase) and optionally, APE1 (human apurinic endonuclease) to destroy original primers and portion of primers in products.

D. Distribute products into micro-pores or beads into micro-pores containing immobilized second tag sequence primers. In the presence of both first and second tag primers, products are PCR amplified in micro-pores such that a given micro-pore generally contains zero or one clonal amplification of a given region, but may contain multiple clonal amplicons from different regions. After denaturation, and removal of unbound fragments, remaining tethered single-stranded target DNA is suitable for primer-directed sequencing.

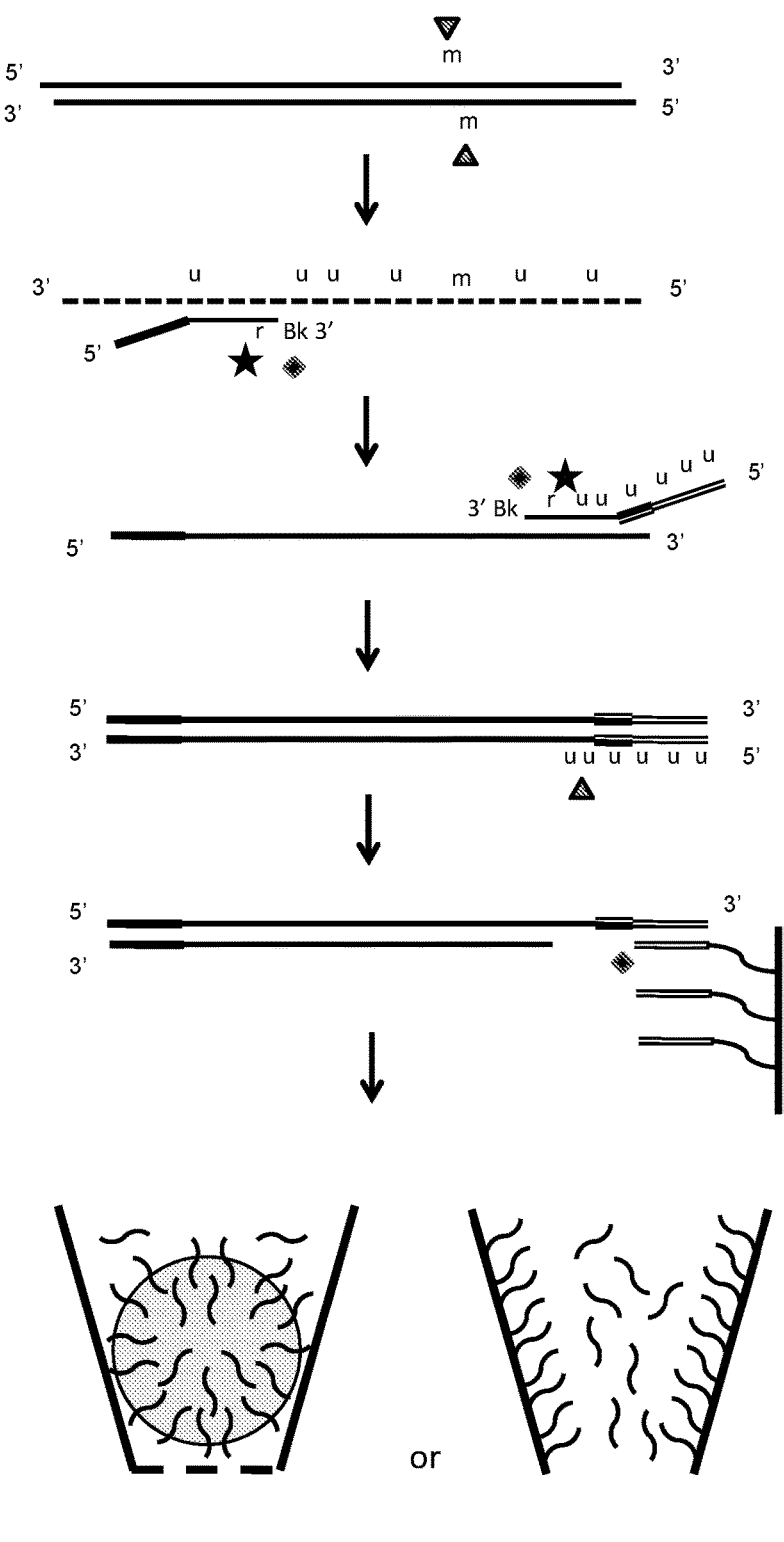

Figure 51

A. For identifying low-abundance unknown mutations and methylations in plasma; using Fragment identifier PCR - sequencing.

B. Preparation: All micro-pores are pre-filled with a single universal primer, which is immobilized, and micro-pores are dried.

C. Divide initial sample in half, and mix other half with buffer, primers, reagents, and polymerase, and distribute into first set of 48 Primary PCR Reaction Chambers. Highest level of DNA in plasma = 10,000 genome equivalents. On average, 200 copies of each target per Primary PCR Reaction Chamber, with at most 1 mutation. Perform 3 cycles of fragment identifier PCR for both strands, each strand covering slightly different sequences. Yields 4 copies of top strand, and 4 copies of bottom strand.

D. Treat with UDG and distribute Fragment identifier PCR products with single-stranded tails into 48 Secondary Chambers, while draining and washing out the Primary PCR Reaction Chambers with several washes.

E. Digest second half of sample with Bsh1236I in an Initial Reaction Chamber. Treat with Bisulfite. Re-purify DNA strands.

F. Mix with primers, reagents, and polymerase, and distribute bisulfite treated sample into first set of 48 Primary PCR Reaction Chambers. On average, after endonuclease treatment, 4 copies of each target per Primary PCR Reaction Chamber, with at most 1 is methylated. Perform 3 cycles of fragment identifier PCR for both strands, each strand covering slightly different sequences. Yields 4 copies of top strand, and 4 copies of bottom strand of originally methylated DNA.

G. Treat with UDG/APE1, combine with earlier mutation-specific products in set of 48 Secondary Reaction Chambers, add fresh reagents, polymerase and nested primers, mix in 48 mixing chambers, and distribute Fragment identifier PCR products into micro-pores of each column. PCR amplify one or more products in each micro-pore and melt off non-anchored strand.

H. Add either target-specific, or universal primers with unique tag-specific portions as sequencing primers. Perform sequencing-by-synthesis. Generate about 80 bases of sequence information, plus 10 bases of unique fragment identifier barcode, for accurate enumeration of each mutation or methylated region, with verification on both strands.

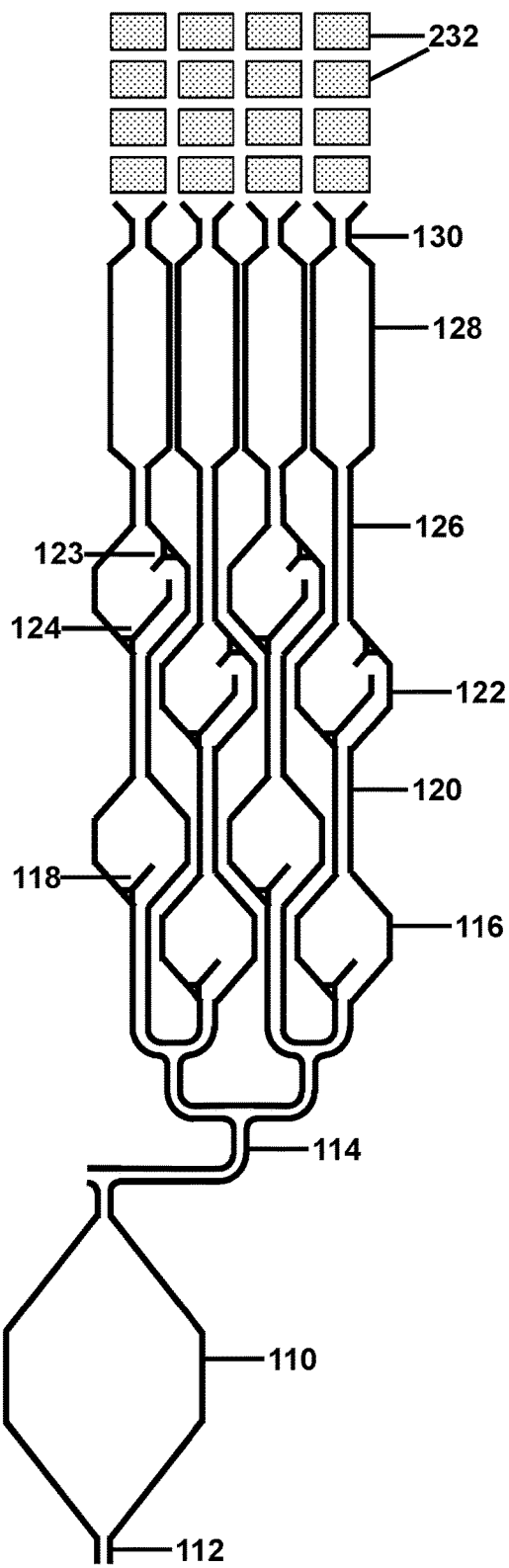

Figure 52

A. Primer design for sequencing low- and medium-abundance lncRNA, mRNA, and splice-site variants, isolated from CTC's or exosomes. Use reverse-transcriptase to make cDNA copies with 3' transcript-specific primers in an Initial Reaction Chamber.

B. Distribute sample into 24 Primary PCR Reaction Chambers. Transcript-specific primers are unblocked with RNaseH2 only when bound to cDNA or complement. Perform 2 - 3 cycles of amplification with strand-displacement thermostable polymerase. One primer contains a transcript-specific region and first tag sequence, the second primer contains a transcript-specific region, transcript identifier, dU, and a second tag sequence.

C. Treat with UDG (uracil DNA glycosylase) and optionally, APE1 (human apurinic endonuclease) to destroy original primers and portion of primers in products.

D. Differentially dilute products from each of the 24 Primary PCR Reaction Chambers into two Secondary Chambers = 48 total. Distribute products into micro-pores or beads into micro-pores containing immobilized second tag sequence primers. In the presence of both first and second tag primers, products are PCR amplified in micro-pores such that a given micro-pore generally contains zero or one clonal amplification of a given region, but may contain multiple clonal amplicons from different regions. After denaturation, and removal of unbound fragments, remaining tethered single-stranded target DNA is suitable for primer-directed sequencing.

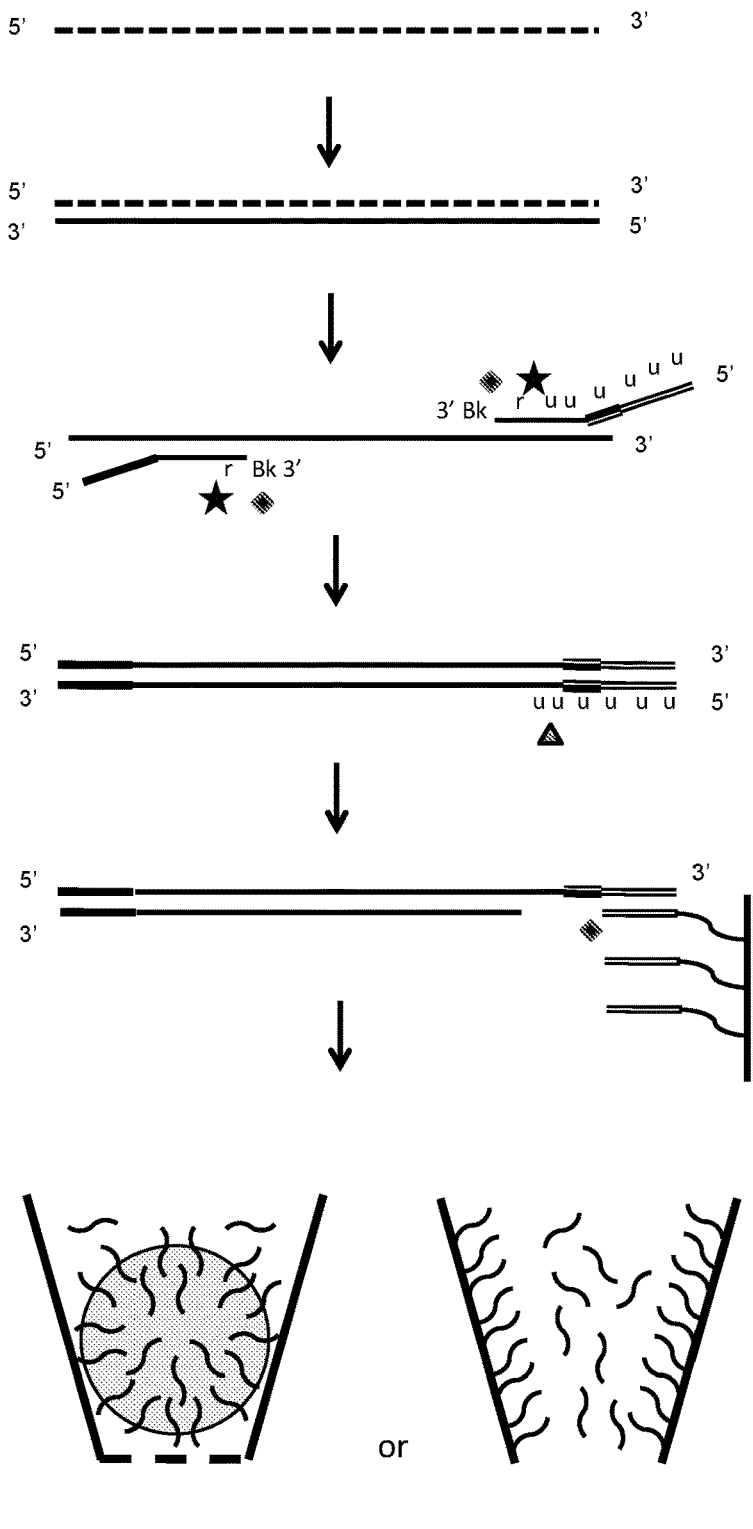

Figure 53

A. Exact enumeration of low-abundance, medium-abundance, and over-expressed lncRNA, mRNA, splice variants, or gene-fusions; using Multiplexed RT-PCR - Nested PCR - UniTaq detection. (Alternatively, Multiplexed PCR – Nested PCR - Real-time-PCR with transcript-specific Taqman probes.)

B. Preparation: Rows are pre-filled with 1-4 UniTaq primer sets (or alternatively, 1-4 universal tag primer sets with target-specific Taqman probes). Primers are distributed into each row and dried down into individual micro-pores.

C. Preparation: Pre-fill reaction chambers to columns with nested PCR primer sets with either UniTaq or universal tag sequences on their 5' ends, and dry down.

D. Initial multiplexed reverse-transcription PCR amplification for 9 cycles to generate 512 copies of each original transcript in an Initial Reaction Chamber.

E. Distribute initial multiplex reaction into 24 Primary PCR Reaction Chambers, with average distribution of 20 copies in each Primary PCR Reaction Chamber of each original transcript. Perform 10 cycles of nested PCR using transcript-specific primers with UniTaq or universal tags in groups of 16, 32, or 64 primer sets. Each Primary PCR Reaction Chamber is designed to retain a certain percentage of liquid volume after draining. Perform 3 cycles of filling and draining to differentially dilute products.

F. Dilute products from each of 24 Primary PCR Reaction Chambers into 2 Secondary Reaction Chambers (= 48 total). Each Secondary Reaction Chamber is designed to retain a certain percentage of liquid volume after draining. Perform 2 cycles of filling and draining to differentially dilute products.

G. Distribute nested PCR products into mixing chambers and then into micro-pores of each column. Universal or UniTaq primers in each row will amplify only those products from each column with the correct tags. Poisson distribution in micro-pores will enumerate low-abundance, medium-abundance, and over-expressed lncRNA, mRNA, splice variants, or gene-fusions.

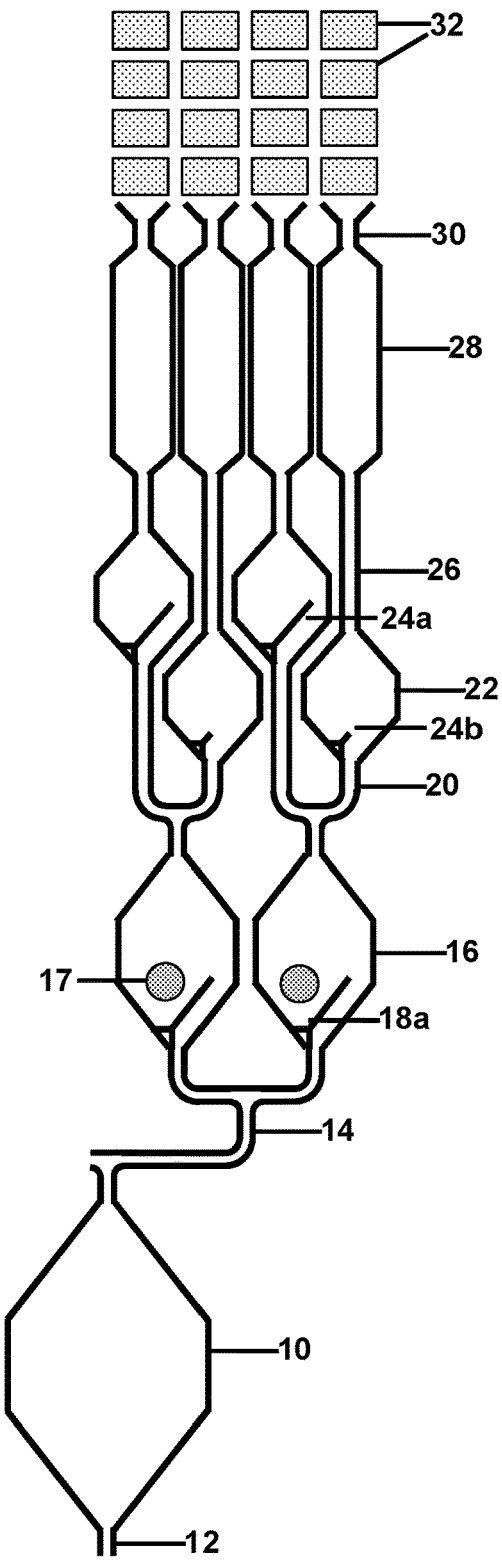

Figure 54

DEVICES, PROCESSES, AND SYSTEMS FOR DETERMINATION OF NUCLEIC ACID SEQUENCE, EXPRESSION, COPY NUMBER, OR METHYLATION CHANGES USING COMBINED NUCLEASE, LIGASE, POLYMERASE, AND SEQUENCING REACTIONS

This application is a national stage application under 35 U.S.C. § 371 of PCT Application No. PCT/US2018/025213, filed Mar. 29, 2018, which claims the benefit of U.S. Provisional Patent Application Ser. No. 62/478,412, filed Mar. 29, 2017, which are hereby incorporated by reference in their entirety.

FIELD OF THE INVENTION

The present invention relates to devices, processes, and systems for determination of nucleic acid sequence, expression, copy number, or methylation changes using combined nuclease, ligation, polymerase, and sequencing reactions.

BACKGROUND OF THE INVENTION

Advances in DNA sequencing hold the promise to standardize and develop non-invasive molecular diagnosis to improve prenatal care, transplantation efficacy, cancer and other disease detection and individualized treatment. Currently, patients with predisposing or early disease are not identified, and those with disease are not given the best treatment—all because of failures at the diagnostic level.

In the cancer field, there is a need to develop such technology for early detection, guiding therapy, and monitoring for recurrence—all from a blood sample. This includes the need to develop: (i) high sensitivity detection of single base mutation, small insertion, and small deletion mutations in known genes (when present at 1% to 0.01% of cell-free DNA); (ii) high sensitivity detection of promoter hypermethylation and hypomethylation (when present at 1% to 0.01% of cell-free DNA); (iii) accurate quantification of tumor-specific mRNA, lncRNA, and miRNA isolated from tumor-derived exosomes or RISC complex, or circulating tumor cells in blood; (iv) accurate quantification of tumor-specific copy changes in DNA isolated from circulating tumor cells; (v) accurate quantification of mutations, promoter hypermethylation and hypomethylation in DNA isolated from circulating tumor cells. All these (except quantification of tumor-specific copy changes in DNA isolated from circulating tumor cells) require focusing the sequencing on targeted genes or regions of the genome. Further, determination of the sequence information or methylation status from both strands of the original fragment provides critically needed confirmation of rare events.

Normal plasma contains nucleic acids released from normal cells undergoing normal physiological processes (i.e. exosomes, apoptosis). There may be additional release of nucleic acids under conditions of stress, inflammation, infection, or injury. In general, DNA released from apoptotic cells is an average of 160 bp in length, while DNA from fetal cells is an average of about 140 bp. Plasma from a cancer patient contains nucleic acids released from cancer cells undergoing abnormal physiological processes, as well as within circulating tumor cells (CTCs). Likewise, plasma from a pregnant woman contains nucleic acids released from fetal cells.

There are several challenges for developing reliable diagnostic and screening tests. The first challenge is to distinguish those markers emanating from the tumor or fetus that are indicative of disease (i.e. early cancer) vs. presence of the same markers emanating from normal tissue. There is also a need to balance the number of markers examined and the cost of the test, with the specificity and sensitivity of the assay. This is a challenge that needs to address the biological variation in diseases such as cancer. In many cases the assay should serve as a screening tool, requiring the availability of secondary diagnostic follow-up (i.e. colonoscopy, amniocentesis). Compounding the biological problem is the need to reliably detect nucleic acid sequence mutation or promoter methylation differences, or reliably quantify DNA or RNA copy number from either a very small number of initial cells (i.e. from CTCs), or when the cancer or fetus-specific signal is in the presence of a far larger amount of nucleic acid emanating from normal cells. Finally, there is the technical challenge to distinguish true signal resulting from detecting the desired disease-specific nucleic acid differences vs. false signal generated from normal nucleic acids present in the sample vs. false signal generated in the absence of the disease-specific nucleic acid differences.

By way of an example, consider the challenge of detecting, in plasma, the presence of circulating tumor DNA harboring a mutation in the p53 gene or a methylated promoter region. Such a sample will contain a far larger amount of cell-free DNA arising from normal cells, where the tumor DNA may only comprise 0.01% of the total cell-free DNA. Thus, in attempting to find the presence of such mutant DNA by total sequencing, one would need to sequence 100,000 genomes to identify 10 genomes harboring the mutations. This would require sequencing 300,000 GB of DNA, a task beyond the reach of current sequencing technology, not to mention the enormous data-management issues. To circumvent this problem, many groups have attempted to capture specific target regions or to PCR amplify the regions in question. Sequence capture has suffered from dropout, such that maybe 90-95% of the desired sequences are captured, but desired fragments are missing. Alternatively, PCR amplification provides the risk of introducing a rare error that is indistinguishable from a true mutation. Further, PCR loses methylation information. While bisulfite treatment has been traditionally used to determine the presence of promoter methylation, it is also destructive of the DNA sample and lacks the ability to identify multiple methylation changes in cell-free DNA.

There are several different approaches for reducing error rate and improving the accuracy of sequencing runs. A consensus accuracy may be achieved in the presence of high error rates by sequencing the same region of DNA 30 to 100 times. However, a high error rate makes it extremely difficult to identify a sequence variant in low abundance, for example when trying to identify a cancer mutation in the presence of normal DNA. Therefore, a low error rate is required to detect a mutation in relatively low abundance. The first approach termed tagged-amplicon deep sequencing (TAm-Seq) method (Forshew et al., "Noninvasive Identification and Monitoring of Cancer Mutations by Targeted Deep Sequencing of Plasma DNA," Sci Transl Med. 4(136):136 (2012)) is based on designing primers to amplify 5995 bases that cover select regions of cancer-related genes, including TP53, EGFR, BRAF, and KRAS. This approach is able identify mutations in the p53 gene at frequencies of 2% to 65%. In this approach, primers are designed to pre-amplify the DNA (for 15 cycles) in a multiplexed reaction with many PCR primers. This creates both desired and undesired products, so it is followed with single-plex PCR to further amplify each of the desired products. The fragments are subjected to a final barcoding PCR step prior to standard next-generation sequencing. The advantage of this approach is it uses the time tested multiplexed PCR-PCR, which is unparalleled for amplification of low numbers of starting nucleic acids. The disadvantage is that this approach is unable to distinguish a true mutation from a PCR error in the early rounds of amplification. Thus, while the sensitivity of 2% (i.e. detecting one mutant allele in 50 wt alleles) is sufficient for evaluating late-stage cancers prior to making a treatment decision, it is not sensitive enough for early detection.

A variation of the first approach is termed Safe-Sequencing System "Safe-SeqS" (Kinde et al., "Detection and Quantification of Rare Mutations with Massively Parallel Sequencing," *Proc Natl Acad Sci USA* 108(23):9530-5 (2011)), where randomly sheared genomic DNA is appended onto the ends of linkers ligated to genomic DNA. The approach demonstrated that the most mutations described from genomic sequencing are actually errors, and reduced presumptive sequencing errors by at least 70-fold. Likewise, an approach called ultrasensitive deep sequencing (Narayan et al., "Ultrasensitive Measurement of Hotspot Mutations in Tumor DNA in Blood Using Error-suppressed Multiplexed Deep Sequencing," *Cancer Res.* 72(14):3492-8 (2012)) appends bar codes onto primers for a nested PCR amplification. Presumably, a similar system of appending barcodes was developed to detect rare mutations and copy number variations that depends on bioinformatics tools (Talasaz, A.; Systems and Methods to Detect Rare Mutations and Copy Number Variation, US Patent Application Publication No. US 2014/0066317 A1). Paired-end reads are used to cover the region containing the presumptive mutation. This method was used to track known mutations in plasma of patients with late stage cancer. These approaches require many reads to establish consensus sequences. These methods require extending across the target DNA, and, thus, it would be impossible to distinguish true mutation, from polymerase generated error, especially when copying across a damaged base, such as deaminated cytosine. Finally, these methods do not provide information on methylation status of CpG sites within the fragment.

The second approach termed Duplex sequencing (Schmitt et al., "Detection of Ultra-Rare Mutations by Next-Generation Sequencing," *Proc Natl Acad Sci USA* 109(36):14508-13 (2012)) is based on using duplex linkers containing 12 base randomized tags. By amplifying both top and bottom strands of input target DNA, a given fragment obtains a unique identifier (comprised of 12 bases on each end) such that it may be tracked via sequencing. Sequence reads sharing a unique set of tags are grouped into paired families with members having strand identifiers in either the top-strand or bottom-strand orientation. Each family pair reflects the amplification of one double-stranded DNA fragment. Mutations present in only one or a few family members represent sequencing mistakes or PCR-introduced errors occurring late in amplification. Mutations occurring in many or all members of one family in a pair arise from PCR errors during the first round of amplification such as might occur when copying across sites of mutagenic DNA damage. On the other hand, true mutations present on both strands of a DNA fragment appear in all members of a family pair. Whereas artifactual mutations may co-occur in a family pair with a true mutation, all except those arising during the first round of PCR amplification can be independently identified and discounted when producing an error-corrected single-strand consensus sequence. The sequences obtained from each of the two strands of an individual DNA duplex can then be compared to obtain the duplex consensus sequence, which eliminates remaining errors that occurred during the first round of PCR. The advantage of this approach is that it unambiguously distinguishes true mutations from PCR errors or from mutagenic DNA damage, and achieves an extraordinarily low error rate of $3.8 \times 10^{-10}$. The disadvantage of this approach is that many fragments need to be sequenced to obtain at least five members of each strand in a family pair (i.e. minimum of 10 sequence reads per original fragment, but often requiring far more due to fluctuations). Further, the method has not been tested on cfDNA, which tend to be smaller than fragments generated from intact genomic DNA, and thus would require sequencing more fragments to cover all potential mutations. Finally, the method does not provide information on methylation status of CpG sites within the fragment.

The third approach, termed smMIP for Single Molecule Molecular Inversion Probes (Hiatt et al., "Single Molecule Molecular Inversion Probes for Targeted, High-Accuracy Detection of Low-Frequency Variation," *Genome Res.* 23(5):843-54 (2013) combines single molecule tagging with multiplex capture to enable highly sensitive detection of low-frequency subclonal variation. The method claims an error rate of $2.6 \times 10^{-5}$ in clinical specimens. The disadvantage of this approach is that many fragments need to be sequenced to obtain at least five members of each strand in a family pair (i.e. minimum of 10 sequence reads per original fragment, but often requiring far more due to fluctuations). Also, the method requires extending across the target DNA, and thus it would be impossible to distinguish true mutation, from polymerase-generated error, especially when copying across a damaged base, such as deaminated cytosine. Further, the method has not been tested on cfDNA, which tend to be smaller than fragments generated from intact genomic DNA, and thus would require sequencing more fragments to cover all potential mutations. Finally, the method does not provide information on methylation status of CpG sites within the fragment.

The fourth approach, termed circle sequencing (Lou et al., "High-throughput DNA Sequencing Errors are Reduced by Orders of Magnitude Using Circle Sequencing," *Proc Natl Acad Sci USA* 110(49):19872-7 (2013); Acevedo et al., "Mutational and Fitness Landscapes of an RNA Virus Revealed Through Population Sequencing," *Nature* 2014 505(7485):686-90 (2014); and Acevedo et al., "Library Preparation for Highly Accurate Population Sequencing of RNA Viruses," *Nat Protoc.* 9(7):1760-9 (2014)) is based on shearing DNA or RNA to about 150 bases, denaturing to form single strands, circularizing those single strands, using random hexamer primers and phi29 DNA polymerase for rolling circle amplification (in the presence of Uracil-DNA glycosylase and Formamidopyrimidine-DNA glycosylase), re-shearing the products to about 500 bases, and then proceeding with standard next generation sequencing. The advantage of this approach is that the rolling circle amplification makes multiple tandem copies off the original target DNA, such that a polymerase error may appear in only one copy, but a true mutation appears in all copies. The read families average 3 copies in size, because the copies are physically linked to each other. The method also uses Uracil-DNA glycosylase and Formamidopyrimidine-DNA glycosylase to remove targets containing damaged bases, to eliminate such errors. The advantage of this technology is that it takes the sequencing error rate from a current level of about 0.1 to $1 \times 10^{-2}$, to a rate as low as $7.6 \times 10^{-6}$. The latter error rate is now sufficient to distinguish cancer mutations in plasma in the presence of 100 to 10,000-fold excess of wild-type DNA. A further advantage is that 2-3 copies of the same sequence are physically linked, allowing for verification of a true mutation from sequence data generated from a single fragment, as opposed to at least 10 fragments using the Duplex sequencing approach. However, the method does not provide the ability to determine copy number changes, nor provide information on methylation status of CpG sites within the fragment.

The fifth approach, developed by Complete Genomics (Drmanac et al., "Human Genome Sequencing Using Unchained Base Reads on Self-Assembling DNA Nanoarrays," *Science* 327(5961):78-81 (2010)) is based on using ligation reads on nanoball arrays. About 400 nucleotides of genomic DNA are circularized with linkers, cleaved, recircularized with additional linkers, and ultimately recircularized to contain about four linkers. The DNA undergoes rolling circle amplification using phi 29 DNA Polymerase to generate nanoballs. These are then placed onto an array, and sequenced using a ligation-based approach. The salient point of this approach, of relevance herein, is that multiple tandem copies of the same sequence may be generated and subsequently sequenced off a single rolling circle amplification product. Since the same sequence is interrogated multiple times by either ligase or polymerase (by combining rolling circle with other sequencing by synthesis approaches), the error rate per base may be significantly reduced. As such, sequencing directly off a rolling circle product provides many of the same advantages of the circle sequencing approach described above.

The sixth approach, termed SMRT—single molecule real time—sequencing (Flusberg et al., "Direct Detection of DNA Methylation During Single-Molecule, Real-Time Sequencing," *Nat Methods* 7(6):461-5 (2010)) is based on adding hairpin loops onto the ends of a DNA fragment, and allowing a DNA polymerase with strand-displacement activity to extend around the covalently closed loop, providing sequence information on the two complementary strands. Specifically, single molecules of polymerase catalyze the incorporation of fluorescently labeled nucleotides into complementary nucleic acid strands. The polymerase slows down or "stutters" when incorporating a nucleotide opposite a methylated base, and the resulting fluorescence pulses allow direct detection of modified nucleotides in the DNA template, including $N^6$-methyladenine, 5-methylcytosine and 5-hydroxymethylcytosine. The accuracy of the approach has improved, especially as the polymerase may traverse around the closed loop several times, allowing for determination of a consensus sequence. Although the technique is designed to provide sequence information on "dumbbell" shaped substrates (containing mostly the two complementary sequences of a linear fragment of DNA), it may also be applied to single-stranded circular substrates.

Several research groups and companies have developed kits to amplify specific target sequences while appending a unique molecule identifier (UMI) or barcode to each fragment.

An elegant approach termed SiMSen-Seq (Simple, Multiplexed, PCR-based barcoding of DNA for Sensitive mutation detection using Sequencing) uses two round of PCR with high fidelity polymerase to append a hairpin-protected barcode to each fragment, as well as external universal primers (Ståhlberg et al., "Simple, Multiplexed, PCR-based Barcoding of DNA Enables Sensitive Mutation Detection in Liquid Biopsies Using Sequencing," *Nucleic Acids Res.* 44(11):e105) (2016)). In this approach, one primer contains an adapter stem to "hide" the barcode from the target DNA, such that the primer hybridization to the target is not misdirected by random bases in the barcode sequence. The other primer is a regular primer with an Illumina adapter sequence on the end. After two rounds of amplification with a high-fidelity polymerase, adapter, and barcode are appended to target fragments. After protease treatment and dilution, a second PCR is performed using Illumina adapters containing patient identifier barcodes. The approach did identify hot spot positions for raw sequencing errors, and currently is designed to barcode only one strand.

In the ThruPLEX Tag-seq Kit (Rubicon Genomics), stem-loop adapters are ligated to the ends of double-stranded DNA. As with standard Y adapters, genomic DNA is repaired to yield blunt ends. In the next step, stem-loop adaptors containing unique molecular tags (UMI) with blocked 5' ends are ligated to the 5' end of the DNA, leaving a nick at the 3' end of the target fragment. The stem-loop adaptors do not have single-strand overhangs preventing ligation to each other, both of which contribute to non-specific background found with many other NGS preparations. Instead, the stem-loop adapters contain a cleavable replication stop base. In the final step, the 3' ends of the DNA are extended to complete library synthesis and Illumina-compatible indexes are added through a high-fidelity amplification. Any remaining free adaptors are degraded. Ligation reactions can be inefficient, which creates the potential of lower yields when mutational sample input is limited. Further, this approach does not select for specific targets.

In the NEBNext Direct target enrichment approach (New England Biolabs), DNA is fragmented to about 150-200 bp in length. The fragmented DNA is rapidly hybridized to biotinylated oligonucleotide "baits" that define the 3' end of each target of interest. Such oligonucleotide baits are designed for both the top and bottom strands of each target. The bait-target hybrids are bound to streptavidin beads, and any 3' off target sequence is trimmed enzymatically, to generate a blunt end. This combination of a short hybridization time with the enzymatic removal of 3' off target sequence enables greater sequencing efficiency relative to conventional hybridization-based enrichment methods. The trimmed targets are then converted into Illumina-compatible libraries that include unique molecular identifiers (UMI) and a sample barcode. This conversion is accomplished as follows. The blunt end is dA-tailed with terminal transferase, allowing for ligation of a hairpinned loop sequence to the single-stranded dA overhang. Next, the probe is extended with a DNA polymerase to generate a copy of the original fragment and generate double-stranded DNA with random 5' ends. These ends are blunted (with T4 polymerase or DNA polymerase 1), and the 5' end either contained a phosphate from the original fragmentation, or a phosphate is added using T4 kinase. This new end is now suitable for ligating on an adapter to the original target strand comprising a UMI sequence. The adapter hairpin loop is then cleaved, thus creating a top strand comprising of a 5' adapter sequence, an UMI sequence, a stretch of 5' target sequence, the desired target region up to the 3' end complementary to the bait, a polydA sequence, and then a 3' adapter sequence. This top strand may then be melted off the streptavidin beads, purified, and then is suitable for amplification with Illumina or Ion Torrent adapters containing patient identifier barcodes. Sequence-ready libraries are generated within one day. The procedure is compatible with most automated liquid handling instruments. Although the technique is designed to be highly efficient in capturing just the desired fragments, it is also a lengthy, multi-step procedure, with the potential of lower yields when mutational sample input is limited.

In the QIAseq targeted RNA sequencing approach (Qiagen Inc.) unique identifiers are appended to RNA sequences, allowing for their precise enumeration. After purifying the RNA sample, reverse transcriptase is used to synthesize cDNA. A composite primer comprising of a first 5' universal sequence, an internal 12-base molecular tag (i.e. a UMI) and a gene-specific 3' portion is used to make an extension product off the cDNA. After extension, the reaction is cleaned up to remove unreacted primers. This is followed by a first stage PCR using a universal primer and a second gene-specific primer comprising a second 5' universal sequence. According to the manufacturer, the first gene-specific primers and the second gene-specific primers "never see each other, thereby minimizing primer dimers." After the first PCR, there is an additional reaction clean-up step. This is followed by a second-stage PCR, using the universal adapter sequences to append Illumina or Ion Torrent adapters containing patient identifier barcodes. Sequence-ready libraries are generated within 6 hours. Since each initial cDNA molecule has presumably been extended by a primer comprising an UMI, one can count how many original transcripts of each RNA molecule are present by matching transcript with unique UMI, and thus distinguish 5 replicates of 1 transcript from 5 unique transcripts of the same gene. The technique is designed to enumerate RNA fragments as in RNA-seq, but for very specific desired fragments. Although it may also be adapted to identify low-abundant mutations, the multi-wash procedure creates the potential of lower yields when mutational sample input is limited.

In the Oncomine Cell-Free DNA assays for liquid biopsy clinical research (ThermoFisher Scientific), a two-step PCR reaction is used to amplify target sequences directly from cfDNA. Both forward and reverse composite primers comprise a first/second 5' universal sequence, an internal unique molecular tag (i.e. a UMI) and a gene-specific 3' portion. After exactly two cycles of PCR two composite double-stranded products are formed. The first product comprises the top-strand primer extension product, the top-strand target sequence, and the complement of the bottom-strand primer including the second universal sequence; hybridized to the initial extension of the bottom-strand primer including the bottom-strand target sequence. The second product comprises the bottom-strand primer extension product, the bottom-strand target sequence, and the complement of the top-strand primer including the first universal sequence; hybridized to the initial extension of the top-strand primer including the top-strand target sequence. Thus, both a top and a bottom strand contain universal adapter sequences and unique UMI sequences arising from each initial target strand. The target amplicons are then captured on a solid support purified from the gene-specific primers. The products are released from the solid support and then are suitable a second-stage PCR, using the universal adapter sequences to append Ion Torrent adapters containing patient identifier barcodes. Sequence-ready libraries are generated within a few hours, and then may be combined for further template preparation using emulsion PCR on beads. This approach is very rapid and robust; however, it does require the extra step of physically removing initial gene-specific primers, as well as a cleanup/size selection after the second PCR step (presumably to eliminate primer dimers), and it is unclear if this procedure creates the potential of lower yields when mutational sample input is limited.

The present invention is directed at overcoming these and other deficiencies in the art.

SUMMARY OF THE INVENTION

One aspect of the present invention relates to a system for identifying a plurality of nucleic acid molecules in a sample. This system comprises an inlet port and a cartridge. The cartridge defines a space containing multiple primary reaction chambers fluidically coupled to the inlet port to receive material from the inlet port and produce primary reaction chamber products from the material. The space also contains a product capture housing enclosing a solid support with a plurality of separate columns of a plurality of product capture subunits with each separate product capture subunit comprising an array of a plurality of individual hydrophilic micro-pores or micro-wells separated by hydrophobic surfaces where primary reaction products are further reacted to create array products. The array products are detected in the micro-pores or micro-wells, where one or more of the columns of separate product capture subunits receive material which has passed through one of the multiple primary reaction chambers.

Another aspect of the present invention relates to a system for identifying a plurality of nucleic acid molecules in a sample. The system includes: an inlet port; an outlet port; and a cartridge comprising an array of micro-pores or micro-wells, with the cartridge fluidically coupling the inlet port and the outlet port. The cartridge defines a space containing multiple primary reaction chambers fluidically coupled to the inlet port to receive material from the inlet port and produce primary reaction chamber products from the material. The space also contains multiple secondary reaction chambers, one or more of which are fluidically coupled to one of the multiple primary reaction chambers to receive material from one of the multiple primary reaction chambers, and to produce secondary reaction chamber products. At least some of the multiple primary and secondary reaction chambers are configured to maintain a trough of liquid in the multiple primary and secondary reaction chambers to facilitate mixing of sample, reagents, and/or product reactants for generating subsequent reaction chamber or array products. The space also contains multiple mixing chambers each fluidically coupled to one of the multiple secondary reaction chambers to receive material from one of the multiple secondary reaction chambers and to discharge material to the product capture housing so that each column of separate product capture subunits is fluidically coupled to one of the one or more mixing chamber to receive material from one of the one or more mixing chambers. The space also contains a product capture housing enclosing a solid support with a plurality of separate columns of a plurality of product capture subunits with each separate product capture subunit comprising an array of a plurality of individual hydrophilic micro-pores or micro-wells separated by hydrophobic surfaces where secondary reaction products are further reacted to create array products. The array products are detected in the micro-pores or micro-wells, where one or more of the columns of separate product capture subunits receive material which has passed through one of the multiple primary reaction chambers.

Another aspect of the present invention relates to a system for identifying a plurality of nucleic acid molecules in a sample. The system includes: an inlet port; an outlet port; and a cartridge fluidically coupling the inlet port and the outlet port. The cartridge defines a space containing a product capture housing enclosing a solid support with a plurality of separate columns of product capture subunits. Each separate product capture subunit comprises an array of a plurality of individual hydrophilic micro-pores separated by hydrophobic surfaces each having opposed first and second open ends with the first end having a large diameter and the second end having a diameter which is smaller than that of the first end. The product capture housing comprises a plurality of fluid channels to permit material to pass from the inlet port through a column of the product capture subunits into contact with the array of micro-pores in those subunits, and to the outlet port, where the plurality of fluid channels are located above and below the solid support.

A further aspect of the present invention relates to a method for preparing a system for identifying a plurality of nucleic acid molecules in a sample. The method comprises providing the system of the present invention and applying universal tag or capture oligonucleotide primers or probes to the micro-pores or micro-wells of the product capture subunits on the solid support within the product capture housing. As a result, the universal tag or capture oligonucleotide primers or probes are retained within the micro-pores or micro-wells.

Another embodiment of the present invention relates to a process of identifying a plurality of nucleic acid molecules in a sample using the system of the present invention. Following filling of the one or more primary reaction chambers and/or the one or more secondary reaction chambers, (if present), the process comprises conducting the primary and/or secondary reactions in the system and detecting the presence of target nucleic acid molecules in the sample in the micro-wells or micro-pores based on carrying out the primary and/or secondary reactions.

Another embodiment of the present invention relates to a process of identifying a plurality of nucleic acid molecules in a sample using the system of the present invention. Following the carrying out the primary and/or secondary reactions, the products of such reactions are amplified in the micro-wells or micro-pores under conditions where a polymerase, exonuclease, endonuclease, or ribonuclease cleaves one or more probes comprising a quencher and fluorescent group in a target-specific manner, such that fluorescent groups are liberated to generate signal if the target nucleic acid molecules are present in the sample.

Another embodiment of the present invention relates to a process of identifying a plurality of nucleic acid molecules in a sample using the system of the present invention. The process comprises providing a sample containing a plurality of target nucleic acid molecules, and then contacting the sample with a set of primary oligonucleotide primers having a first portion complementary to a portion of the target nucleic acid molecules and a second portion and a polymerase to form a polymerase chain reaction mixture. This mixture is subjected to a polymerase chain reaction in the primary reaction chambers to produce a set of amplification products. The amplification products are passed to the product capture housing enclosing a solid support with a plurality of separate columns of a plurality of capture subunits with each separate product capture subunit comprising an array of a plurality of individual micro-pores containing immobilized captures probes complementary to the second portion. The target nucleic acid molecules are captured and copied onto the immobilized capture probes. The nucleotide sequence of the immobilized target nucleic acid molecules is obtained by carrying out sequencing reactions in the micro-pores.

The present invention also relates to a process for preparing a microtiter plate for identifying a plurality of nucleic acid molecules in a sample. This involves providing a microtiter plate with a plurality of separate rows and columns of product capture subunits with each separate product capture subunit comprising an array of a plurality of individual hydrophilic micro-wells separated by hydrophobic surfaces. The micro-wells of the microtiter plate are filled with an aqueous liquid containing oligonucleotide primers and/or probes. The microtiter plate is centrifuged to spread the aqueous liquid to unfilled micro-wells in each separate product capture subunit in the microtiter plates. Centrifuging is then terminated to urge the aqueous liquid out of contact with the hydrophobic surfaces. The aqueous liquid is evaporated, and the micro-wells are dried so that the oligonucleotide primers are left in the micro-wells.

Another aspect of the present invention relates to a system for identifying a plurality of nucleic acid molecules in a sample. This system comprises an inlet port; an outlet port; and a cartridge fluidically coupled to the inlet port and the outlet port. The cartridge defines a space containing a product capture housing enclosing a solid support with a plurality of separate columns of product capture subunits. Each separate product capture subunit comprises an array of a plurality of individual hydrophilic micro-pores separated by hydrophobic surfaces each having opposed first and second open ends with the first end having a large diameter and the second end having a diameter which is smaller than that of the first end. The product capture housing comprises a plurality of fluid channels to permit material to pass from the inlet port through a column of the product capture subunits into contact with the array of micro-pores in those subunits, and to the outlet port, wherein the plurality of fluid channels are located above and below the solid support.

The present invention provides a set of devices, chambers, and assays for determining the cause of disease directly from a blood sample. Nucleic acids are purified from the clinical sample, targeted regions are subjected to a series of amplification reactions, and targets are identified or enumerated using either real-time PCR or sequencing as a readout.

This invention aims to help address the major diagnostic clinical challenges facing the U.S. and the world. The largest unmet need is to detect cancer at the earliest stage. An accessible and accurate early detection test has the potential to save over 300,000 lives annually in the U.S. and over 4,000,000 lives globally; it can save $300 billion in annual healthcare costs in the U.S. alone. One potential solution to this challenge is to provide a process and system for assaying multiple DNA mutational and methylation changes simultaneously, at the single-molecule level of sensitivity, as described in the present application. The same assay may also be used to monitor "cancer marker load" in the blood, to monitor how effectively a given treatment is killing residual cancer cells after surgery. A related challenge is to monitor the patient for early recurrence of the cancer, at a time when alternative treatments may still be effective. The present invention provides the flexibility to track cancer markers using either Taqman™ assays, sequencing, or both.

Infectious disease testing is migrating from single pathogen detection to symptom-based, or blood-borne pathogen detection. The present invention has the potential to provide accurate viral or bacterial load values for hundreds of targets simultaneously, to guide physicians to make clinically actionable decisions. For example, a patient suffering from a respiratory illness may be simultaneously tested for: all strains of influenza and Parainfluenza viruses, Adenovirus, Coronavirus, Rhinovirus, Enterovirus, Respiratory Syncytial Virus, *Mycobacterium tuberculosis*, *Streptococcus pneumoniae*, Group A Strep, *Mycoplasma pneumoniae*, *Haemophilus Influenzae*, etc. For blood-borne pathogens, the present invention may be used to distinguish: *Staphylococcus*, MRSA, *Streptococcus*, *Enterococcus* (VRE), *Listeria*, *Acinetobacter*, *Enterobacter*, *E. coli* (including toxin producers), *Klebsiella* (including KPC's), *Pseudomonas*, *Proteus*, *Candida*, *Cryptococcus*, *Neisseria*, *Haemophilus*, etc. International travelers with symptoms of fever may be tested to distinguish Zika virus from viral hemorrhagic fevers (Dengue, Yellow Fever, West Nile, arenaviruses, filoviruses, bunyaviruses, and other flaviviruses) or other viruses (Influenza, RSV, SARS, Chikungunya, rubella, measles, parvovirus, enterovirus, adenovirus, and alphavirus infection), or parasitic causes (malaria) or bacterial causes (group A *streptococcus, rickettsia, borrelia*, leptospirosis).

Non-invasive Prenatal Testing is currently being used to distinguish chromosomal copy anomalies using either chromosomal fragment counting via direct sequencing, or ligation-based detection with array-based quantification. The present invention's ability to accurately identify and enumerate targets at the single-molecule level would provide an opportunity to provide highly accurate results at lower costs. As an example, the enabling of more complete blood-based testing for life-threatening autosomal and X-linked recessive Mendelian disorders: Trisomy 21, 18, 13, Turner Syndrome, Kleinfelder Syndrome (Chromosomal copy anomalies); Duchenne and Beckers Muscular dystrophies, Cystic Fibrosis, and other inherited diseases.

BRIEF DESCRIPTION OF THE DRAWINGS

FIGS. 1A-1D illustrate schematic diagrams of a solid support suitable for fluidic coupling to a cartridge, comprised of subdivisions each subdivision comprising of micro-pores or micro-wells for subsequent qPCR, UniTaq, FRET, qLDR, or sequencing reactions and target identification. In FIG. 1A, each subdivision is 400-micron wide× 600-micron long (drawn as rectangular sections), comprising of 24 micro-pores or micro-wells with 50-micron diameter. Additional 100-micron wide ridges are used between subdivisions to provide separation of subdivisions and additional structural support. These are represented as the "white" areas between the rows and columns of rectangular subdivisions. In FIG. 1B, each subdivision is 600-micron wide×400-micron long (drawn as rectangular sections), comprising of 2,760 micro-pores or micro-wells with 5-micron diameter. Additional 100-micron wide ridges are used between subdivisions to provide separation of subdivisions and additional structural support. In FIG. 1C, each subdivision is 800-micron wide×1,200-micron long (drawn as rectangular sections), comprising of 96 micro-pores or micro-wells with 50-micron diameter. Additional 200-micron wide ridges are used between subdivisions to provide separation of subdivisions and additional structural support. In FIG. 1D, each subdivision is 400-micron wide×600-micron long (drawn as rectangular sections), comprising of 2,760 micro-pores or micro-wells with 5-micron diameter. Additional 100-micron wide ridges are used between subdivisions to provide separation of subdivisions and additional structural support.

FIG. 2 illustrates a schematic front view of an exemplary design for pre-chambers to allow for liquids to be fluidically moved to the chambers comprising of thousands of micro-wells or micro-pores. In this illustration, the input sample is fluidically connected to a large hexagonal chamber (bottom), which is fluidically connected to a first set of 12 diamond chambers (4 each containing large, medium, and small troughs, respectively), which are fluidically connected to a second set of 24 diamond chambers (2 each, containing large and small troughs, respectively), which are fluidically connected to 24 long narrower mixing chambers, which are fluidically connected to the chambers comprising of micro-wells or micro-pores (top of panel, with only 2 rows illustrated in the magnified front view).

FIG. 3 illustrates a schematic front view of another exemplary design for pre-chambers to allow for liquids to be fluidically moved to the chambers comprising of millions of micro-pores, suitable for Taqman™ or sequencing reactions. In this illustration, the input sample is fluidically connected to a large hexagonal chamber (bottom), which is fluidically connected to a first set of 8 hexagonal chambers (4 each containing large and small troughs, respectively), which are fluidically connected to a second set of 16 hexagonal chambers (2 each containing large and small troughs, respectively), which are fluidically connected to 16 long narrower mixing chambers, which are fluidically connected to the chambers comprising of micro-wells or micro-pores (top of panel, with only 2 rows illustrated in the magnified front view).

The back plate may be pressed against a heating element to allow for temperature control, heating, and/or thermocycling.

Figures 7A, 7B, 7C, 7D, 7E, 7F, 7G, 7H, 7I:
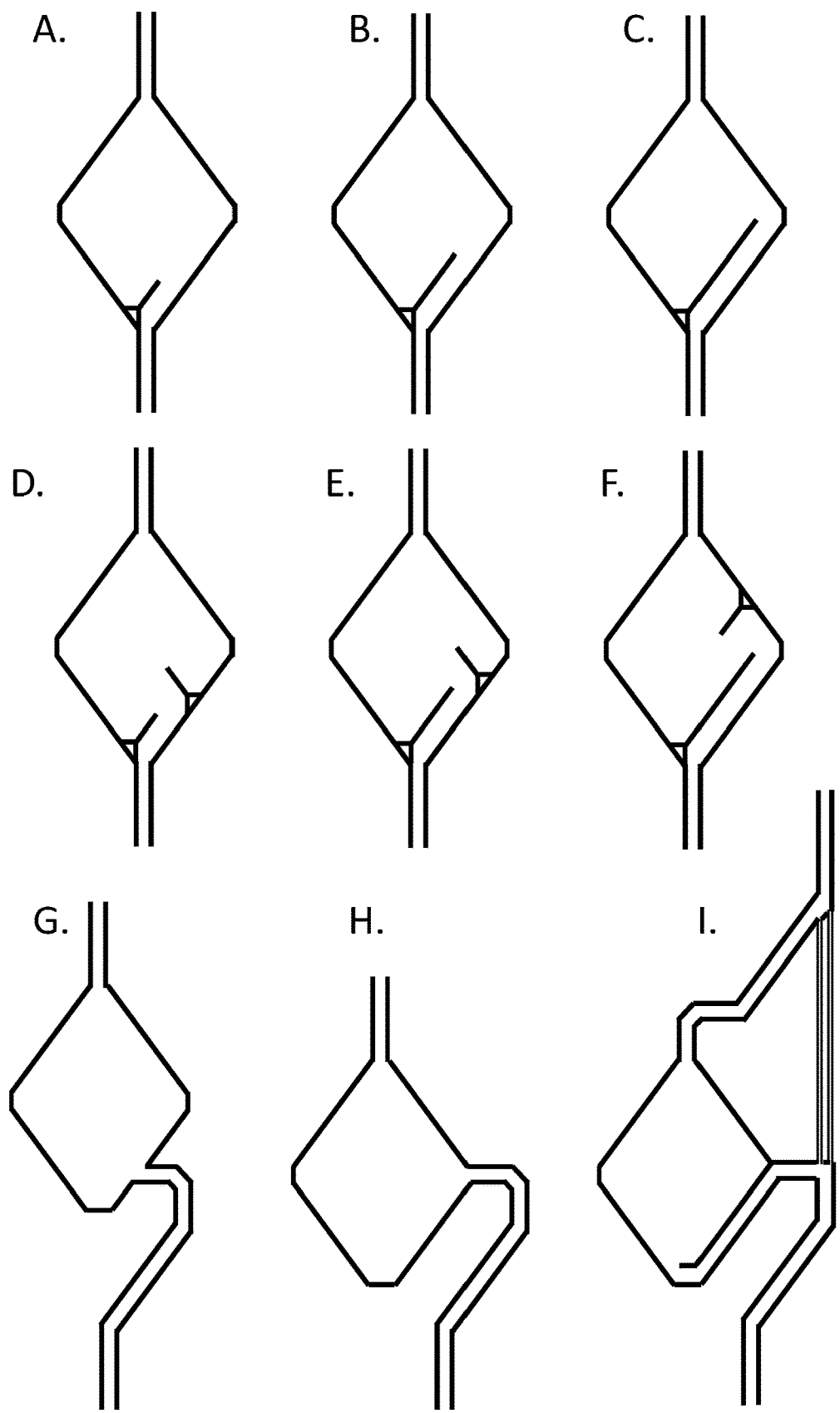

FIGS. 7A-7I illustrate schematic front views of various designs for pre-chambers that can undergo various tasks involving mixing different reagents, undergoing various amplification reactions, or saving a portion of said amplification reaction for subsequent use in the next reaction, or for fluidically moving liquids to the chambers comprising of micro-wells or micro-pores. FIG. 7A shows a chamber with trough for retaining a small portion of the reactants after draining. FIG. 7B shows a chamber with trough for retaining a medium portion of the reactants after draining. FIG. 7C shows a chamber with trough for retaining a large portion of the reactants after draining. FIG. 7D depicts a chamber with two troughs for retaining one or two small portions of the reactants after draining. FIG. 7E shows a chamber with two troughs for retaining one medium and/or one small portion of the reactants after draining. FIG. 7F depicts a chamber with trough for retaining a large portion of the reactants after draining, and additional barrier assures that the second reaction fluid is directed downward to fully mix with products previously remaining from the first reaction. FIG. 7G is like FIG. 7A, except the reagents are introduced from the side instead of the bottom of the chamber. FIG. 7H is similar to FIG. 7G; however, a greater amount of product is retained in the bottom of the chamber. FIG. 7I is like FIG. 7H, with some additions to allow for aqueous liquid and oil layers to move independently. In FIG. 7I, the chamber is like FIG. 7H, with some additions.

Figures 8A, 8B, 8C:
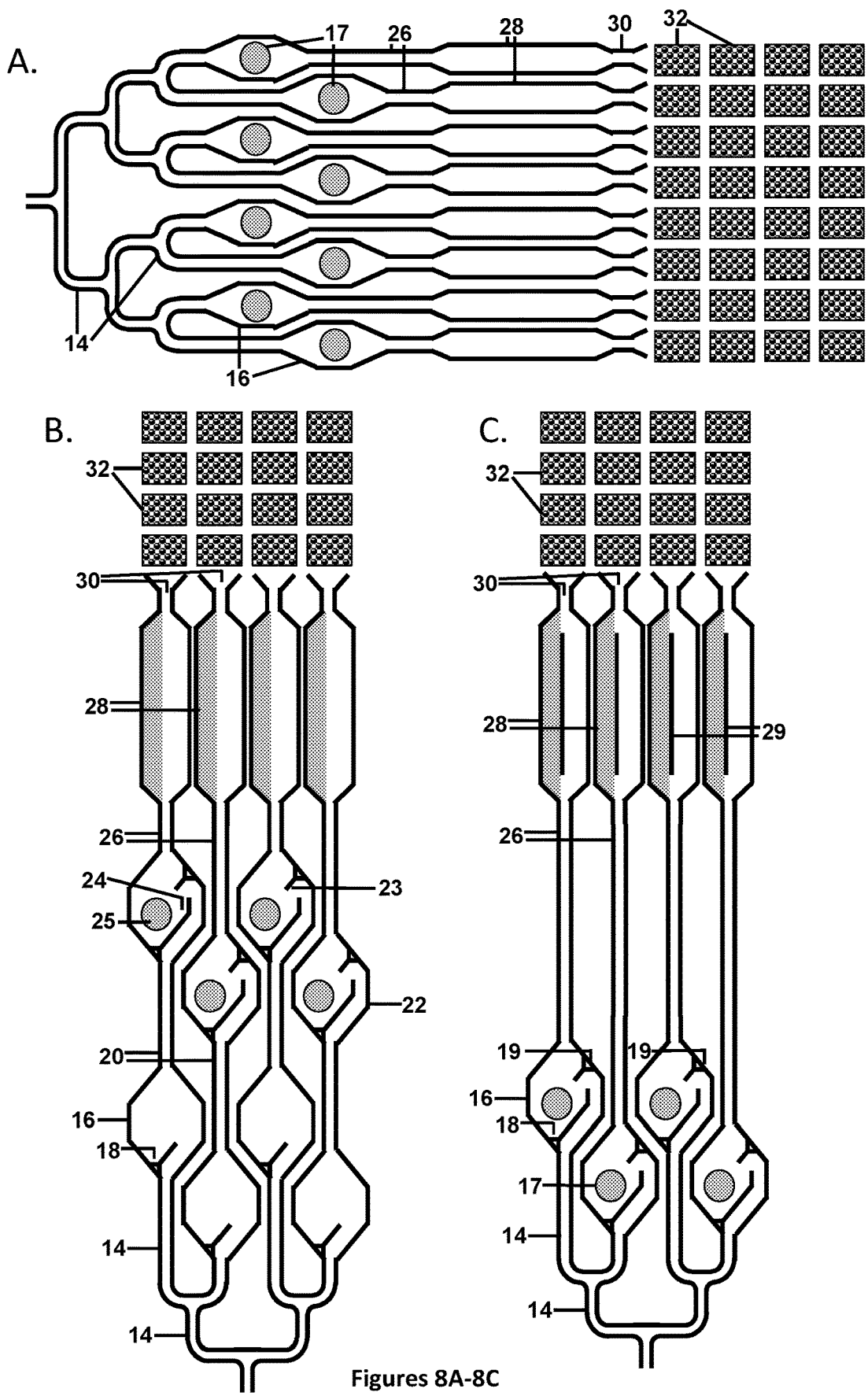

FIGS. 8A-8C illustrate schematic front views of various designs for pre-chambers to allow for liquids to be fluidically to the chambers comprising of micro-wells or micro-pores. FIG. 8A is an example of fluidically coupling primers and/or probes (gray circles) within 8 chambers that then empty into longer narrower chambers and into rows of micro-wells or micro-pores, for ultimately drying down within or covalently linking to the interior surfaces of micro-wells or micro-pores. FIG. 8B is an example of fluidically coupling reagents to 4+4 chambers that then empty into longer narrower chambers. The left side is coated, or made from plastic that is very hydrophobic, while the right side is either barely hydrophobic, or somewhat hydrophilic. FIG. 8C is like FIG. 8A, but with only 4 chambers, and with an extra plastic ridge or divider.

Figures 5A, 5B, 5C:
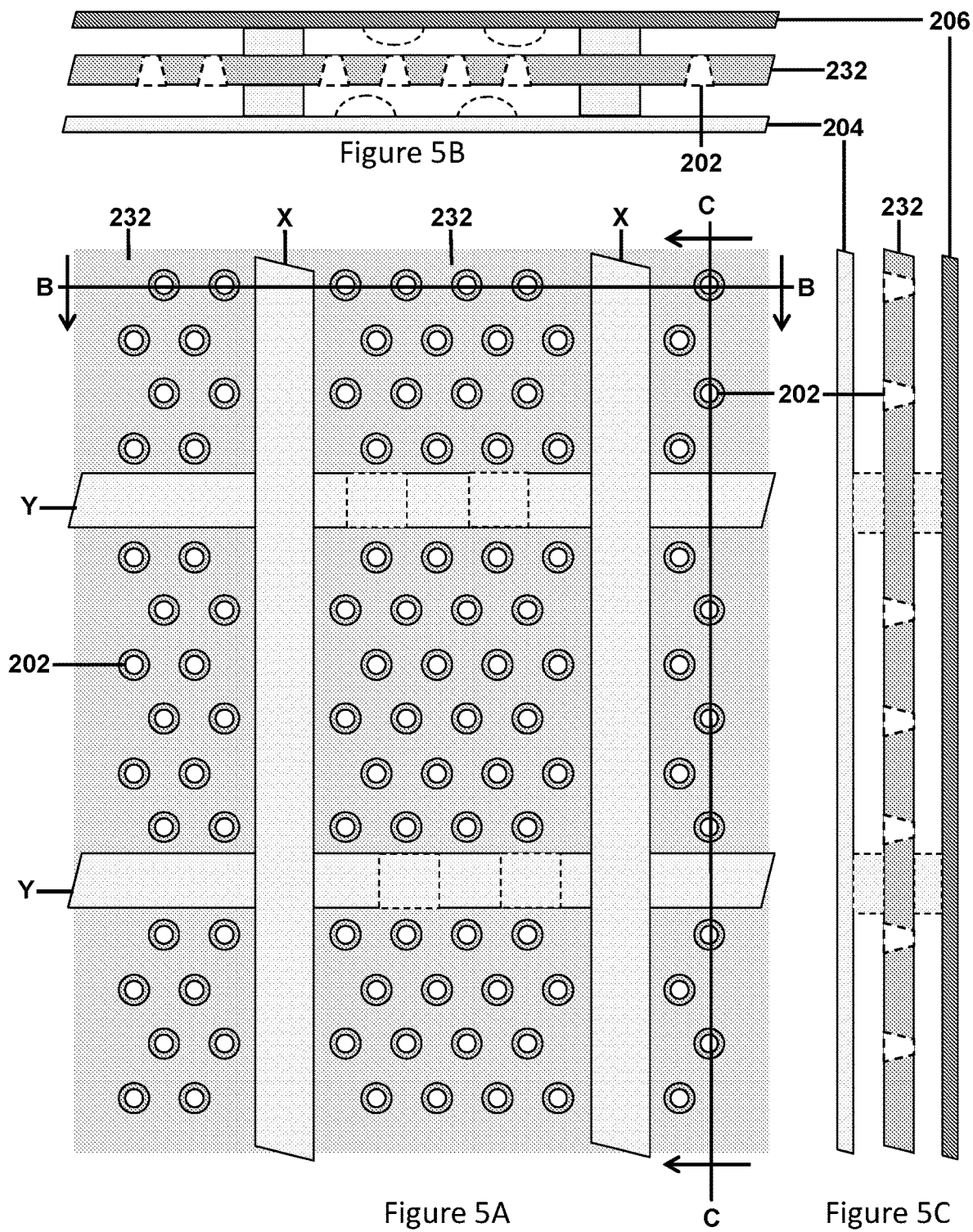
FIGS. 5A-5C illustrate schematic front view (FIG. 5A), a cross-sectional view taken along line B-B of FIG. 5A (FIG. 5B), and a cross-sectional view taken along line C-C of FIG. 5A (FIG. 5C) views of 50-micron micro-wells in a solid support, showing how ridges between the chambers are connected to the two plates to help direct fluidic flow and provide structural stability. The illustration also is relevant for 5 or 2.5-micron micro-pores, except there would be more micro-pores illustrated within each chamber. In this illustration, the front of the chambers is the area between the lighter plate and the micro-pores with the wider diameter, while the back of the chambers is the area between the darker plate and the micro-pores with the narrower diameter. The back plate may be pressed against a heating element to allow for temperature control, heating, and/or thermocycling. In one embodiment, the vertical ridges are flush with the top and bottom plates, while the horizontal ridges have indentations or channel enabling liquid to flow up the columns, but not from one column to the next.
Figures 6A, 6B, 6C:
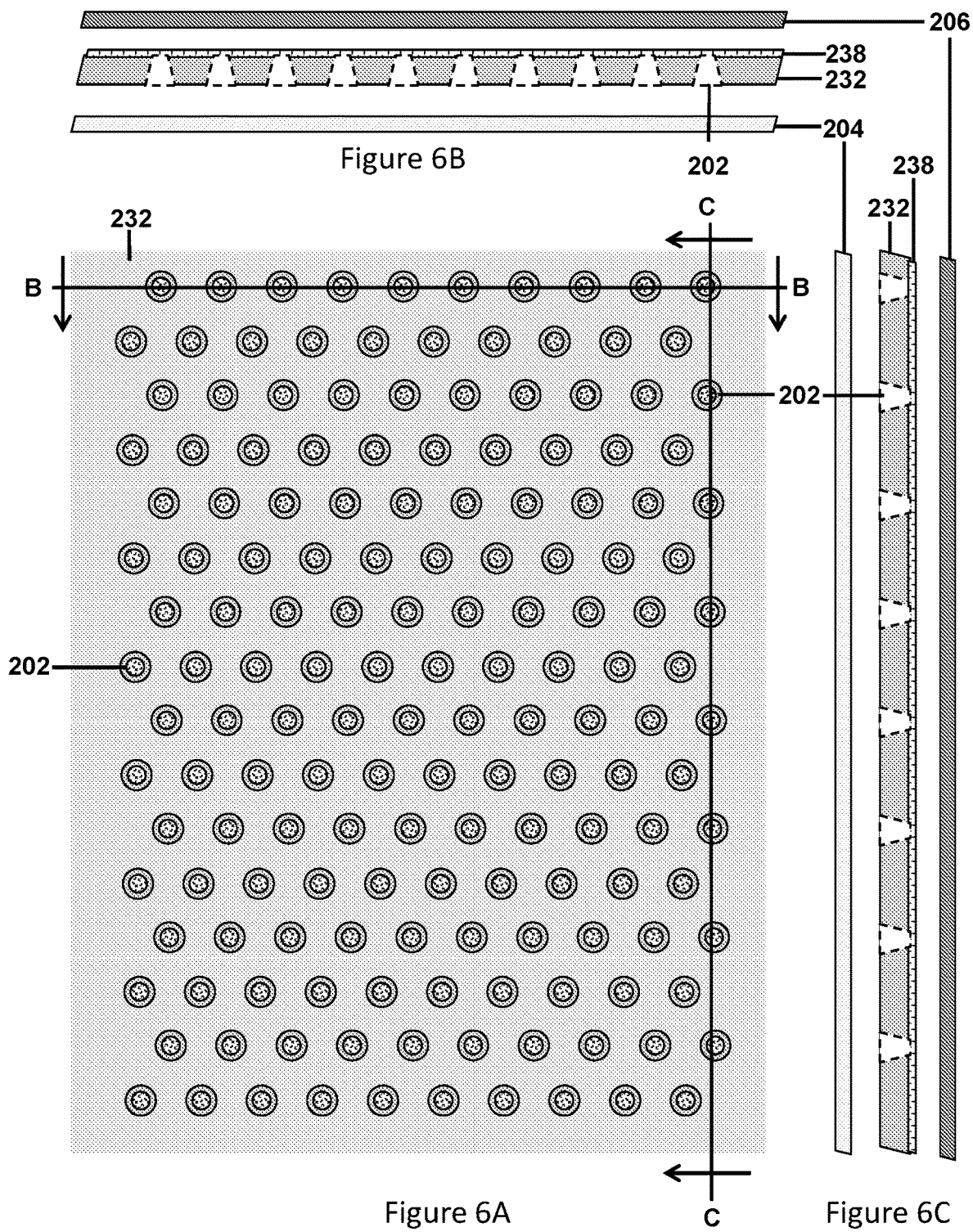
FIGS. 6A-6C illustrate schematic front view (FIG. 6A), a cross-sectional view taken along line B-B of FIG. 6A (FIG. 6B), and a cross-sectional view taken along line C-C of FIG. 6A (FIG. 6C) views of 50, 5 or 2.5-micron micro-pores in a solid support, which is like FIG. 13, but now illustrating how bottom of the 50, 5, or 2.5-micron micro-pores has another layer of 0.5-micron holes on silicon nitride 200 to 400 nanometers thick, enabling filling of the 5 or 2.5-micron micro-pores with liquid from the front, allowing air, but not liquid to escape through the 0.5-micron pores at the back. In this illustration, the front of the chambers is the area between the lighter plate and the micro-pores with the wider diameter, while the back of the chambers is the area between the darker plate and the micro-pores with the narrower diameter.
Figures 9A, 9B:
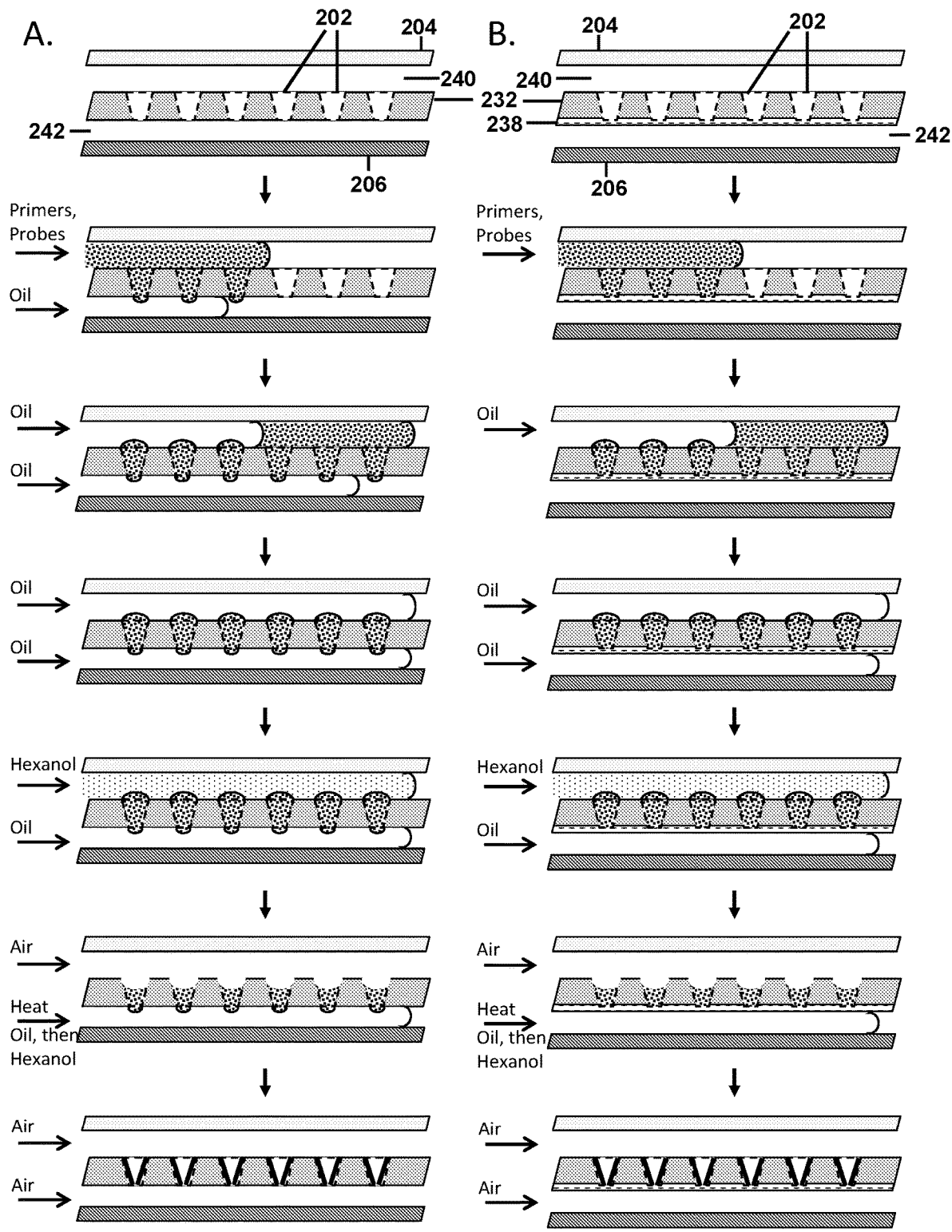

FIGS. 9A-9B illustrate schematic side views of embodiments for filling micro-pores, as illustrated from FIG. 5A and FIG. 6B. FIG. 9A shows micro-pores open from both the top and bottom. Primers (and probes) are fluidically introduced into the micro-pores from the top, while simultaneously oil is introduced from the bottom. Subsequently the aqueous solution is chased from the top region with oil, such that the primers/probes are fluidically isolated. The primers may be immobilized or dried down. FIG. 9B show micro-pores open from the top and with another layer of 0.5-micron holes on silicon nitride 200 to 400 nanometers thick, enabling filling of the 50, 5, or 2.5-micron micro-pores with liquid from the front, allowing air, but not liquid to escape through the 0.5-micron pores at the bottom.

Figure 10:
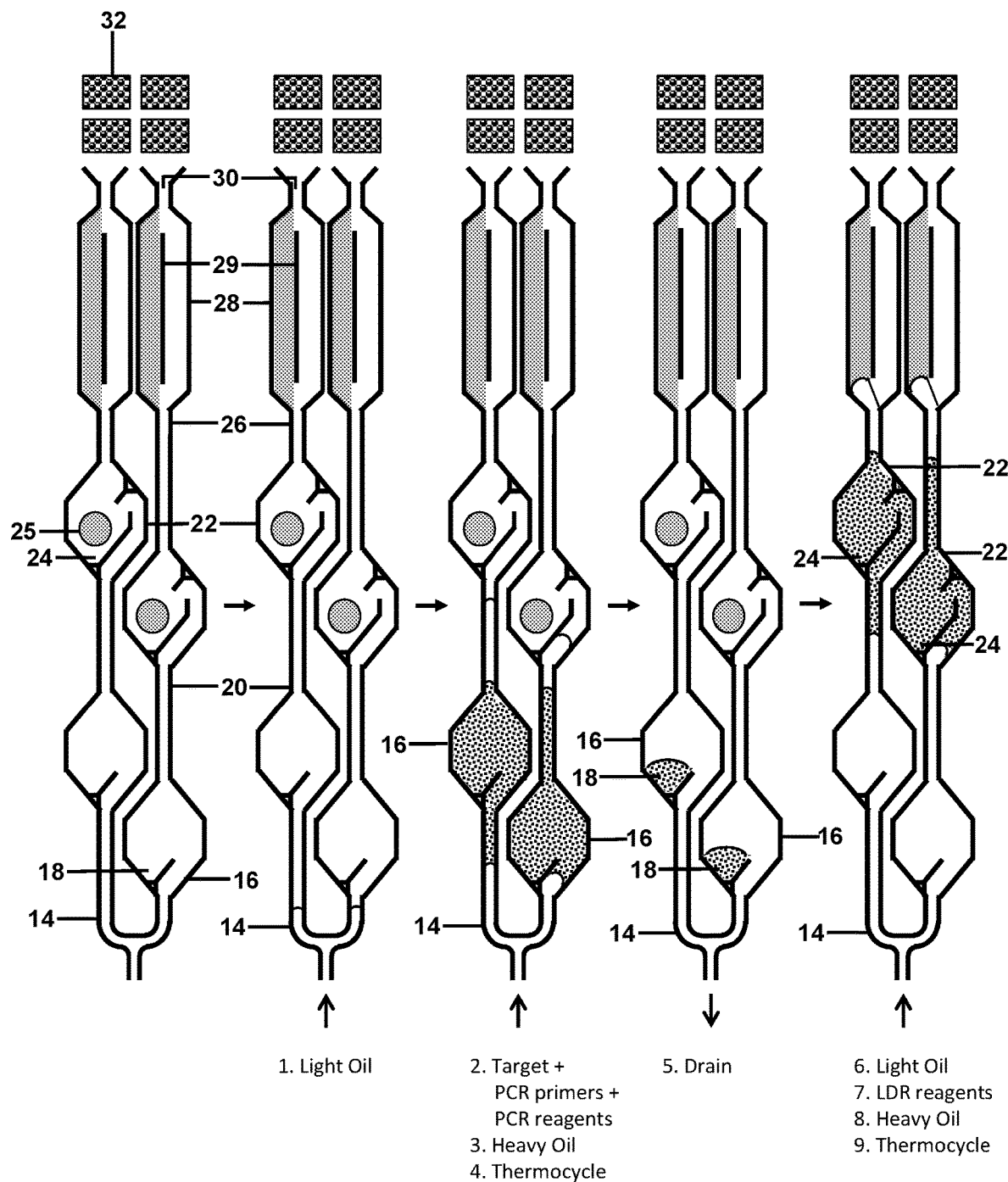

FIG. 10 illustrates a schematic front view of embodiments for filling reaction chambers prior to filling the micro-wells or micro-pores. The setup comprises of two sets of reaction chambers, each having a trough, and the second set is pre-spotted with appropriate ligation probe oligonucleotides (gray circle). A light-oil cap is introduced at the bottom, followed by an aqueous liquid comprising of target, PCR primers, and PCR reagents, which is then fluidically moved into the first set of reaction chambers using heavy oil. After the PCR step, the oils and most of the aqueous reaction are drained, leaving a portion of product in the troughs of the two initial chambers. The chambers are again filled with light oil, followed by LDR reagents and enzymes, and this aqueous reaction mixture is then fluidically moved into the second set of reaction chambers (where it mixes with the pre-spotted LDR primers) using heavy oil.

Figures 11A, 11B:
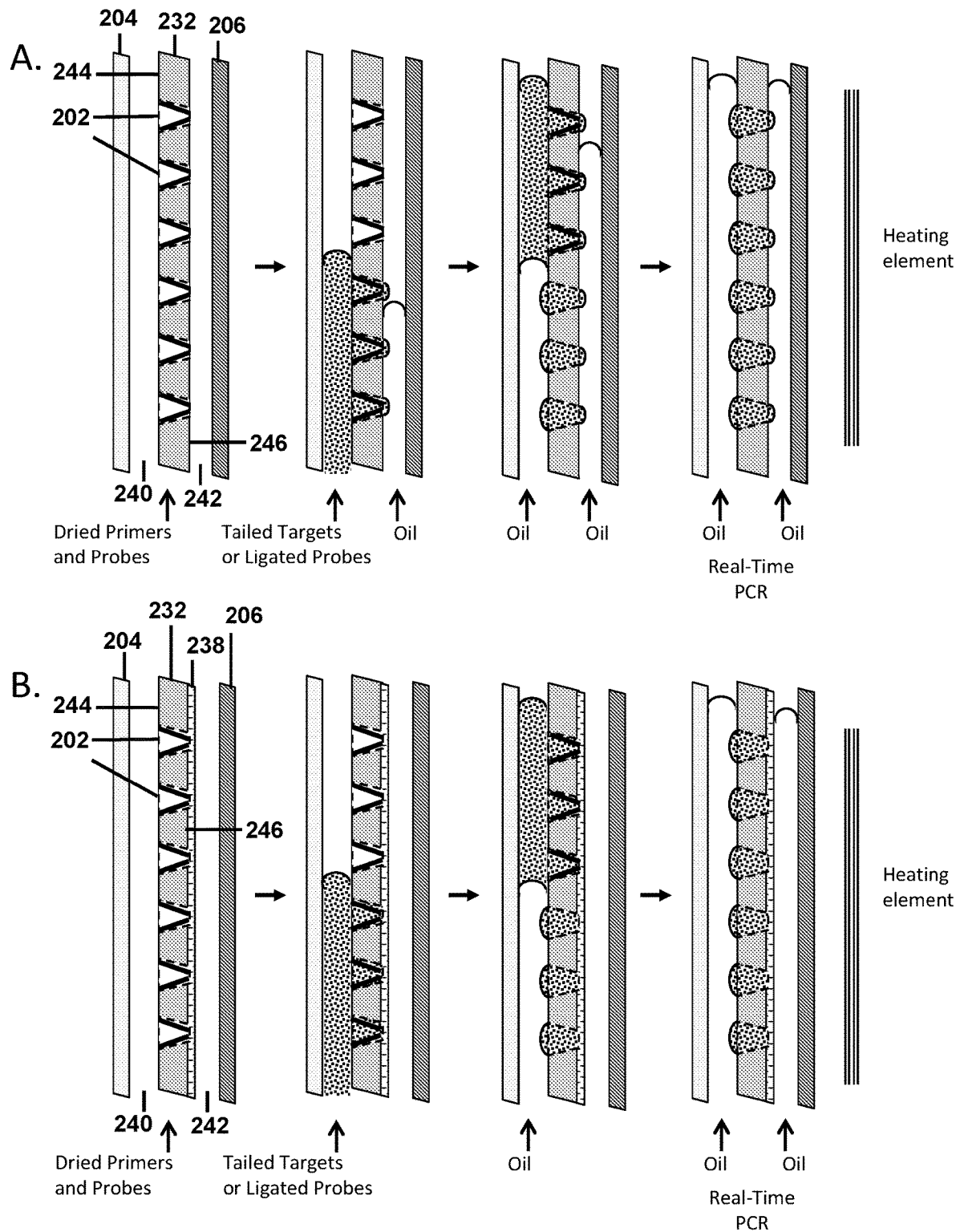

FIGS. 11A-11B illustrate schematic front views of embodiments for filling micro-pores, as illustrated from FIG. 5A and FIG. 6B), for performing real-time PCR reactions, such as Taqman™ or UniTaq reactions. The illustrations start with micro-pores that have been pre-filled with 1-4 UniTaq primer sets (or alternatively, 1-4 universal tag primer sets with target-specific Taqman™ probes), and dried down. The diagram is not to scale and is for illustrative purposes. In FIG. 11A, tailed targets or ligated probes are fluidically introduced into the micro-pores from the bottom front, while simultaneously oil is introduced from the bottom back. Subsequently oil is flowed in from the front, to chase the aqueous liquid out of the non-productive volume and into the micro-pores, while simultaneously covering each separate micro-pore on the front with oil. In FIG. 11B, all surfaces are hydrophobic, except the inside surfaces of the micro-pores, and the silicon nitride with the 0.5-micron holes. As aqueous fluid is pumped from the bottom front it enters the micro-pores from the front, displaces air out the back and does not push through the 0.5-micron silicon nitride pores. As the aqueous liquid fills the micro-pores from the front, oil is flowed in from the front, to chase the aqueous liquid out of the non-productive volume and into the micro-pores, while simultaneously covering each separate micro-pore on the front with oil. The back of the chambers may be filled with oil. Each micro-pore is fluidically isolated and suitable for subsequent independent amplification and thermal cycling reactions.

Figure 12:
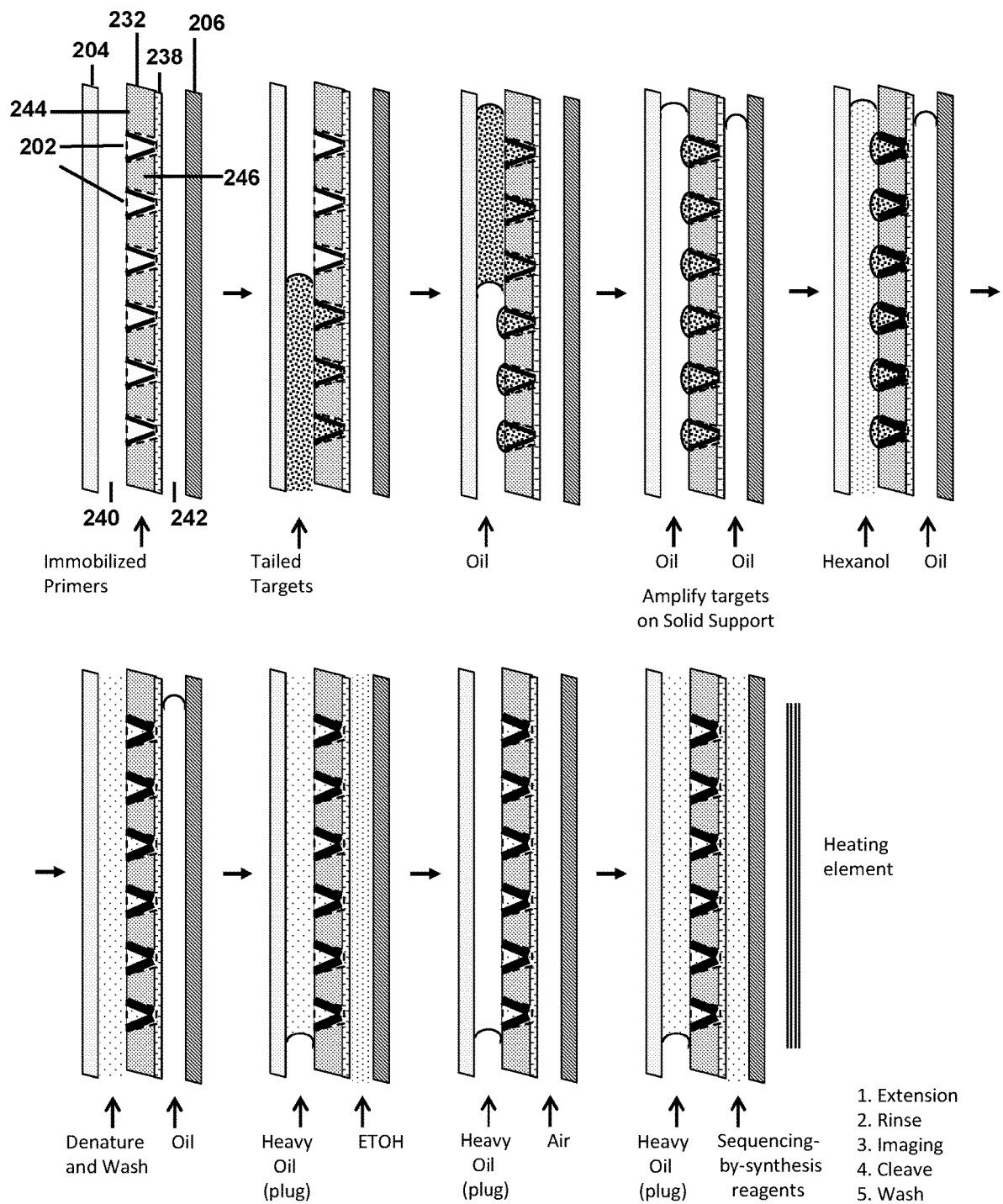

FIG. 12 illustrates a schematic side view of embodiments for filling micro-pores, as illustrated from FIG. 6, for performing sequencing reactions. In this example, all surfaces are hydrophobic, except the inside surfaces of the micro-pores, and the silicon nitride with the 0.5-micron holes. As aqueous fluid is pumped from the bottom front it enters the micro-pores from the front, displaces air out the back and does not push through the 0.5-micron silicon nitride pores. As the aqueous liquid fills the micro-pores from the front, oil is flowed in from the front, to chase the aqueous liquid out of the non-productive volume and into the micro-pores, while simultaneously covering each separate micro-pore on the front with oil. The back is also filled with oil. Each micro-pore is fluidically isolated and suitable for subsequent independent thermal cycling reactions to amplify and immobilize template strands onto the solid support on the interior surface of the pores. The oil is chased from the front chamber, while opposite strand product is denatured and with other products and primers washed away. A heavy oil plug is used to plug the bottom of the front chamber while the back is rinsed to provide an array with immobilized target strands clonally amplified within micro-pores suitable for sequencing.

Figures 13A, 13B:
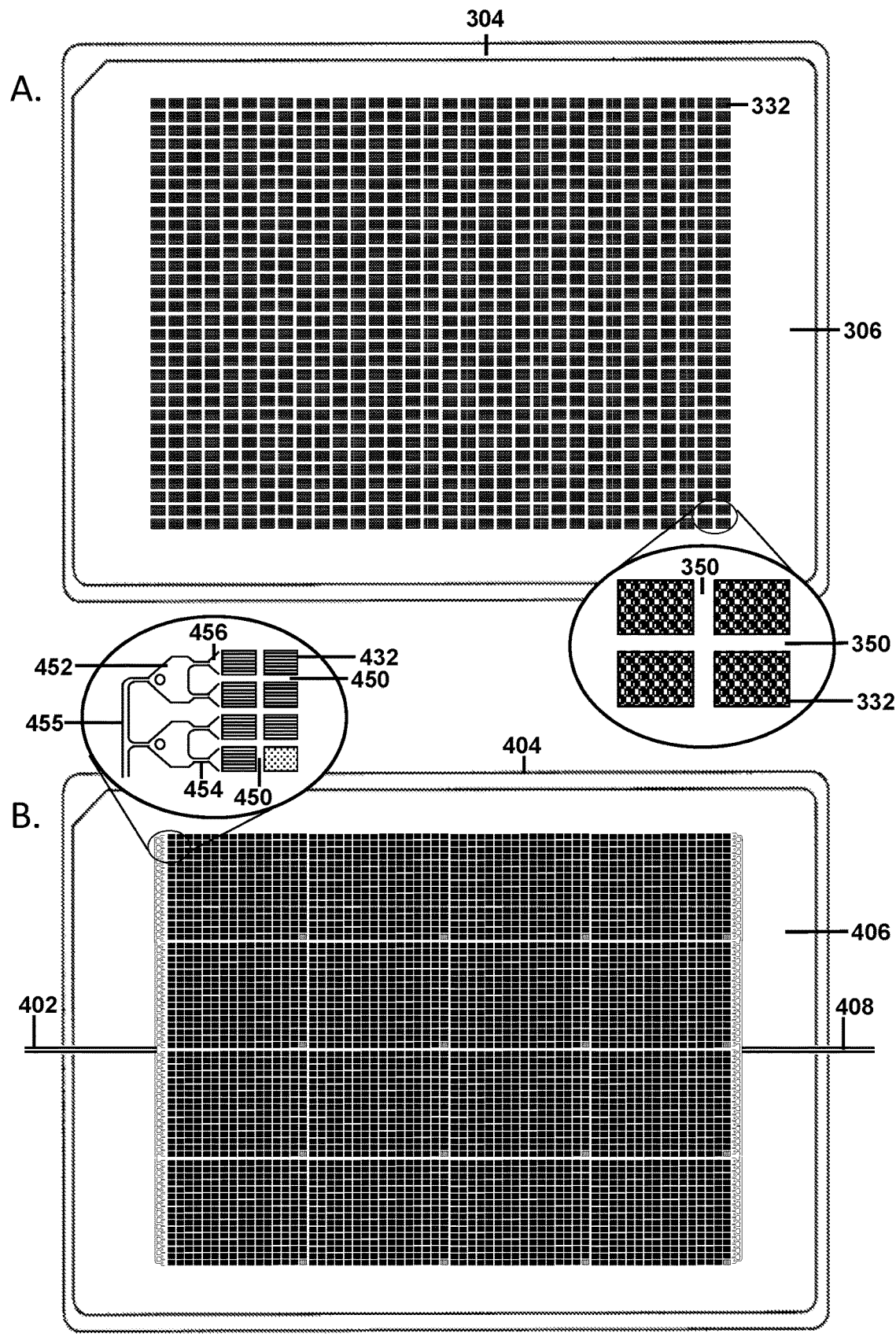

FIGS. 13A-13B illustrate a schematic front view of the chamber format using micro-wells or micro-pores as described in FIGS. 1 and 6. FIG. 13A is a micro-well format where the subdivisions are 800-micron wide×1200-micron long (drawn as rectangular sections), comprising of 96 micro-wells with 50-micron diameter. Additional 200-micron wide ridges are used between subdivisions to provide separation of subdivisions and additional structural support.

These are represented as the "white" areas between the rows and columns of rectangular subdivisions. FIG. 13B is an overview of microfluidic chambers for sequencing on an array of micro-pores in a microtiter plate format. In the magnification, only 2 double-columns and 1 double-row of subdivisions comprising 2,072 micro-pores each are shown. In one embodiment, feeding into the chambers containing the micro-pores are a series of individual openings that may be fluidically closed or open to entry of reagents, enzymes, targets or pre-amplified targets up all the chambers of a given column using acoustic droplet ejection. Entry of fluids into the individual openings when using acoustic droplet ejection may be facilitated by feeding the droplets into a series of hydrophilic input chambers, which subsequently feeds into the columns of micro-pores. In this schematic illustration, each individual opening is connected to a hydrophilic input chamber, which feeds into two columns of micro-pores. In addition, the chambers are also fluidically coupled to allow for entry of reagents from one entry port into all the chambers and exit on the other side into a single waste or exit port. Once the hydrophilic input chamber is properly filled with the reagents, enzymes, targets or pre-amplified targets, those openings are closed, and then oils or other reagents are added through the one entry port to fluidically move the input solutions into the micro-pores for further reactions.

FIG. 14 illustrates a schematic side view of the micro-titer plate format using micro-wells in chambers as described in FIG. 13A suitable for pre-filling with appropriate primers and probes. Step A shows the side view of one chamber within the hydrophobic plate, comprising of 50-micron hydrophilic wells with ridges on each side. In step B, the plate is flipped upside-down and filled with with 1-4 UniTaq primer sets (or alternatively, 1-4 universal tag primer sets with mutation or methylation-specific Taqman™ probes) using acoustic droplet ejection. In step C, the plate is centrifuged, spreading the aqueous liquid to the empty micro-wells, while step D illustrates that after centrifugation, droplets will form over the micro-wells as the aqueous solution avoids the hydrophobic surface. In step E, the aqueous solution is evaporated, leaving the dried primer/probe sets in the well (Illustrated in step F).

FIG. 15 illustrates a schematic side view of the micro-titer plate format using micro-wells in chambers as described in FIG. 13A, and pre-filled with the appropriate Taqman™ or UniTaq primers and probes. Step A shows the side view of one chamber within the hydrophobic plate, comprising of 50-micron hydrophilic wells with ridges on each side. In step B, the plate is flipped upside-down and filled with reagent suitable for real-time amplification (i.e. Taqman™ reaction) and target DNA, using acoustic droplet ejection. In step C, overlay the aqueous layer with hydrophobic mineral oil. In step D, the plate is transferred to a swinging bucket rotor for centrifugation. The denser aqueous liquid spreads to empty micro-wells. In step E, the plate is moved to the thermocycler. The droplets separate into individual micro-wells covered by mineral oil and suitable for amplification.

FIG. 16 illustrates an exemplary PCR-PCR-qPCR procedure with Taqman™ readout to identify or relatively quantify unknown pathogens.

FIG. 17 illustrates an exemplary PCR-PCR-qPCR procedure with UniTaq readout to identify or relatively quantify unknown pathogens.

FIG. 18 illustrates an exemplary PCR-PCR-qPCR procedure with Split probe UniTaq (UniRq) readout to identify or relatively quantify unknown pathogens.

FIG. 19 illustrates an exemplary PCR-LDR-qPCR procedure with Taqman™ readout to identify or relatively quantify unknown pathogens.

FIG. 20 illustrates an exemplary PCR-LDR-qPCR procedure with UniTaq readout to identify or relatively quantify unknown pathogens.

FIG. 21 illustrates an exemplary PCR-LDR-qPCR procedure with Split probe UniTaq (UniSpTq) readout to identify or relatively quantify unknown pathogens.

FIG. 22 illustrates an exemplary PCR-qLDR (UniLDq) procedure with universal split probe readout to identify or relatively quantify unknown pathogens.

FIG. 23 illustrates an exemplary PCR-qLDR (TsLDq) procedure with target-specific split probe readout to identify or relatively quantify unknown pathogens.

FIG. 24 illustrates a schematic front view of a portion of an exemplary design for pre-chamber loading to allow for liquids to be fluidically moved to the chambers comprising of micro-wells or micro-pores. This design illustrates the chamber architecture and micro-wells or micro-pores suitable for performing Multiplexed PCR-Nested PCR-UniTaq detection. (Alternatively, Multiplexed PCR-Nested PCR-Real-time-PCR with target-specific Taqman™ probes), for unknown pathogen identification and quantification. The gray circles symbolize areas of prefilling rows or columns with different primer or probe sets.

FIGS. 25A-25B illustrate schematic side views of cartridge, and valve, setup for running Multiplexed PCR-Nested PCR-Real-time-PCR with UniTaq or target-specific Taqman™ probes assays using a micro-pore plate composed of thousands of micro-pores. FIG. 25A is a schematic front view illustrating fluidic connection of micro-channels to the array of micro-wells or micro-pores, with 50-micron diameter. In FIG. 25B, the micro-pore plate is fluidically accessible from both sides of the pores: the first side (top of plate, illustrated on left side of plate) is in communication with Valves 1, 2, & 3 while the second side (bottom of plate, illustrated on right side of plate) is in communication with Valves 4 & 5.

FIG. 26 illustrates an exemplary PCR-PCR-qPCR procedure with Taqman™ readout to identify or relatively quantify unknown pathogens directly from blood.

FIG. 27 illustrates an exemplary PCR-PCR-qPCR procedure with UniTaq readout to identify or relatively quantify unknown pathogens directly from blood.

FIG. 28 illustrates an exemplary PCR-LDR-qPCR carryover prevention reaction with Taqman™ readout to identify or relatively quantify low-level mutations.

FIG. 29 illustrates an exemplary PCR-LDR-qPCR carryover prevention reaction with UniTaq readout to identify or relatively quantify low-level mutations.

FIG. 30 illustrates a front view of a portion of an exemplary design for pre-chamber loading to allow for liquids to be fluidically moved to the chambers comprising of micro-wells or micro-pores. This design illustrates the chamber architecture and micro-wells or micro-pores suitable for performing Multiplexed PCR-LDR-UniTaq detection, for identifying and quantifying unknown mutations at low-level in plasma. (Alternatively, use Multiplexed PCR-LDR-Real-time-PCR with mutation-specific Taqman™ probes). The gray circles symbolize areas of prefilling rows or columns with different primer or probe sets.

FIG. 31 illustrates an exemplary PCR-LDR-qPCR (with optional carryover prevention) reaction with Taqman™ readout to identify or relatively quantify low-level methylations.

FIG. 32 illustrates an exemplary PCR-LDR-qPCR (with optional carryover prevention) reaction with UniTaq readout to identify or relatively quantify low-level methylations.

FIG. 33 illustrates an exemplary RT-PCR-LDR-qPCR reaction with UniTaq readout to identify or relatively quantify wild-type and alternatively spliced mRNA transcripts.

FIG. 34 illustrates a front view of a portion of an exemplary design for pre-chamber loading to allow for liquids to be fluidically moved to the chambers comprising of micro-wells or micro-pores. This design illustrates the chamber architecture and micro-wells or micro-pores suitable for performing Multiplexed RT-PCR-LDR-UniTaq detection, for identifying and quantifying both rare and over-expressed lncRNA, mRNA, or splice variants. (Alternatively, use Multiplexed PCR-LDR-Real-time-PCR with target-specific Taqman™ probes). The gray circles symbolize areas of prefilling rows or columns with different primer or probe sets.

FIG. 35 illustrates an exemplary fragment identifier PCR method with sequencing-by-synthesis readout to identify mutations in one strand of unknown pathogens. In this example, products are distributed into micro-pores or beads into micro-pores containing immobilized second tag sequence primer.

FIG. 36 illustrates an embodiment of the fragment identifier PCR method where the first tag primer is present in larger amounts than both in solution and (longer) immobilized second tag primers, to maximize product yield per micro-pore.

FIG. 37 illustrates another embodiment of the fragment identifier PCR method where the in solution first tag primers comprise two different 5' portions, and with added 5' portion primers, which are present in larger amounts than both in solution, and (longer) immobilized second tag primer, to maximize product yield per micro-pore.

FIG. 38 illustrates another embodiment of the fragment identifier PCR method where the in solution first tag primer comprises dA35, and with added dA35 with GC rich toehold primer, are present in larger amounts than both in solution, and (longer) immobilized second tag primer, to maximize product yield per micro-pore.

FIG. 39 illustrates a front view of a portion of an exemplary design for pre-chamber loading to allow for liquids to be fluidically moved to the chambers comprising of micro-wells or micro-pores. This design illustrates the chamber architecture and micro-wells or micro-pores suitable for performing Multiplexed PCR-Nested PCR-sequencing, for unknown pathogen identification. The gray circles symbolize areas of prefilling rows or columns with different primer or probe sets. The diagram is not to scale and is for illustrative purposes.

FIG. 40 illustrates an exemplary fragment identifier PCR method with sequencing-by-synthesis readout to identify low-abundance mutations in one target strand of cfDNA. In this example, products are distributed into micro-pores or beads into micro-pores containing immobilized second tag sequence primer.

FIG. 41 illustrates an exemplary fragment identifier PCR method with sequencing-by-synthesis readout to identify low-abundance mutations in one target strand, across overlapping fragments of cfDNA. In this example, second tag sequence primers are biotinylated, and captured on streptavidin-coated beads to be distributed in micro-pores, or directly on streptavidin-coated micro-pores.

FIG. 42 illustrates an exemplary fragment identifier PCR method with sequencing-by-synthesis readout to identify low-abundance mutations in one target strand, across overlapping fragments of cfDNA. In this example, products are distributed into micro-pores or beads into micro-pores containing immobilized second tag sequence primer.

FIG. 43 illustrates additional detail of the PCR amplification with either biotinylated or immobilized second tag sequence primer, showing shorter amplicons form panhandles, which do not amplify, while the desired longer products amplify on the solid support.

FIG. 44 illustrates another embodiment of an exemplary fragment identifier PCR method with sequencing-by-synthesis readout to identify low-abundance mutations in one target strand, across overlapping fragments of cfDNA. In this drawing, two target-specific primers comprising the second tag sequence are illustrated. In this example, products are distributed into micro-pores or beads into micro-pores containing immobilized second tag sequence primer.

FIG. 45 illustrates another embodiment of an exemplary fragment identifier PCR method with sequencing-by-synthesis readout to identify low-abundance mutations in one target strand, across overlapping fragments of cfDNA. In this drawing, two target-specific primers comprising the first tag sequence are illustrated. In this example, products are distributed into micro-pores or beads into micro-pores containing immobilized second tag sequence primer.

FIG. 46 illustrates an exemplary fragment identifier PCR method with sequencing-by-synthesis readout to identify low-abundance mutations in both target strands, across overlapping fragments of cfDNA. In this example, products are distributed into micro-pores or beads into micro-pores containing immobilized first tag sequence primer. By using different nested primers containing the second tag sequence, the region amplified from the top strand differs from the region amplified from the bottom strand, and thus readout arising from the top and bottom strand sequences can be distinguished.

FIG. 47 illustrates an exemplary fragment identifier PCR method with sequencing-by-synthesis readout to identify SNPs and enumerate copy number of both locus-specific strands of cfDNA. In this example, products are distributed into micro-pores or beads into micro-pores containing immobilized first tag sequence primer. By using different nested primers containing the second tag sequence, the region amplified from the top strand differs from the region amplified from the bottom strand, and thus readout arising from the top and bottom strand sequences can be distinguished.

FIG. 48 illustrates a front view of a portion of an exemplary design for pre-chamber loading to allow for liquids to be fluidically moved to the chambers comprising of micro-wells or micro-pores. This design illustrates the chamber architecture and micro-wells or micro-pores suitable for performing Multiplexed PCR-Nested PCR-sequencing, for identifying unknown mutations at low-abundance in plasma, or for non-invasive prenatal testing of trisomy in plasma. The gray circles symbolize areas of prefilling rows or columns with different primer or probe sets.

Figures 49A, 49B:
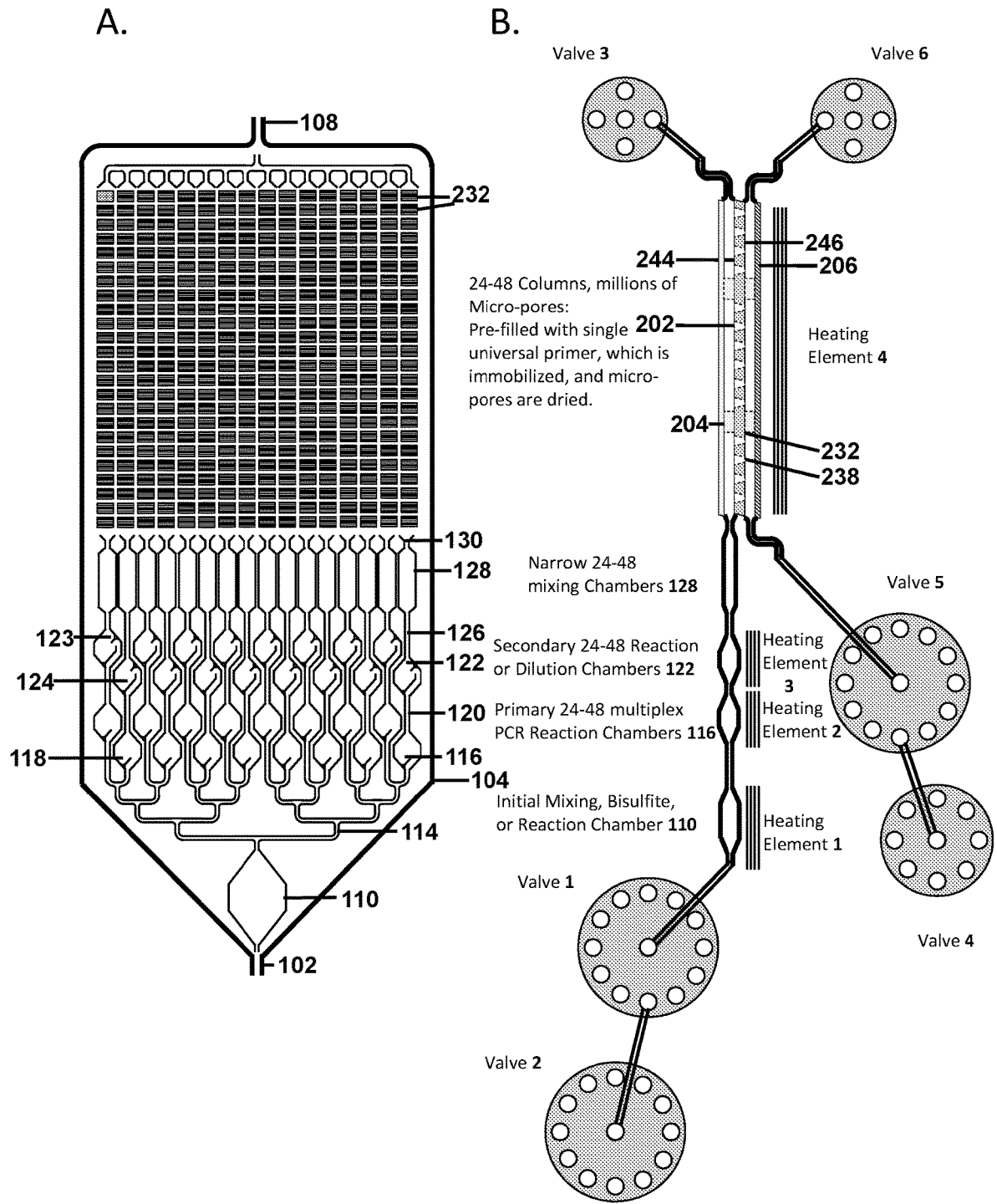

FIGS. 49A-49B illustrate a schematic side view of cartridge and valve setup for identifying unknown mutations at low-abundance in plasma, using Fragment identifier PCR-sequencing. FIG. 49A is a schematic front view illustrating fluidic connection of micro-channels to the array of micro-pores, with 5-micron diameter. FIG. 49B is a fluidics system for Fragment Identifier PCR-sequencing using a micro-pore plate composed of millions of micro-pores. The micro-pore plate is fluidically accessible from both sides of the pores: the first side (top of plate, illustrated on left side of plate) is in communication with Valves 1, 2, & 3 while the second side (bottom of plate, illustrated on right side of plate) is in communication with Valves 4, 5, & 6.

Figure 50:
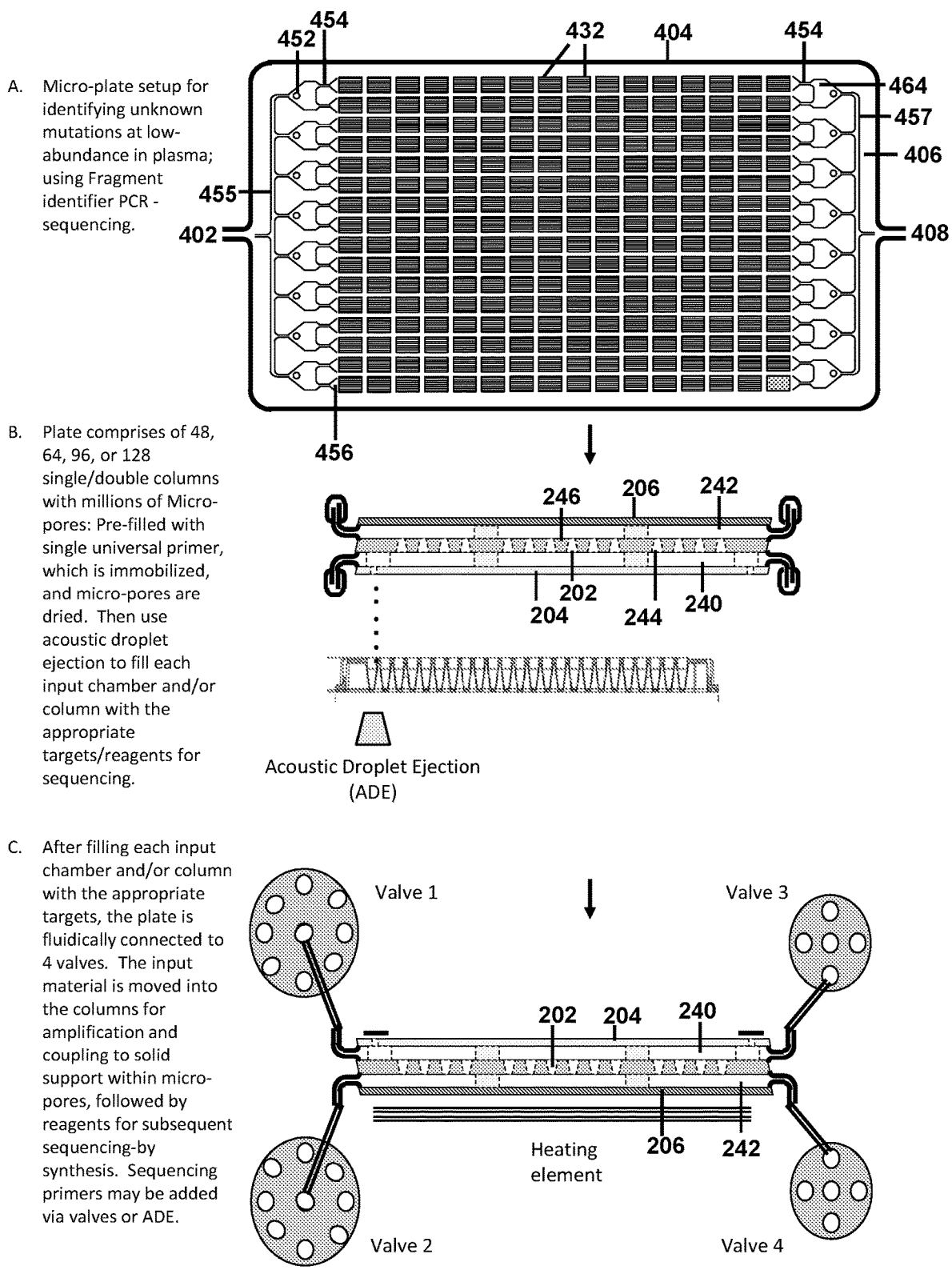

FIG. 50 illustrates a schematic side view of cartridge and valve setup for identifying unknown mutations at low-abundance in plasma, using Fragment Identifier PCR-sequencing. Step A involves providing a micro plate fluidic connection of micro-channels to the array of micro-pores, with 5-micron diameter. Step B shows initial reactions are performed in separate wells, and then acoustic droplet ejection is used to push the appropriate reagents, enzymes, buffers, targets and/or pre-amplified targets into openings that lead to input chambers and columns comprising millions of micro-pores. Step C shows the plate fluidically coupled to 4 valves. The micro-pore plate is fluidically accessible from both sides of the pores: the first side (illustrated as top of plate) is in communication with Valves 1 & 3 while the second side (illustrated as bottom of plate) is in communication with Valves 2 & 4.

FIG. 51 illustrates an exemplary Bsh1236I—Bisulfite—Fragment Identifier PCR method with sequencing-by-synthesis readout to identify low-abundance methylations in one target strand of cfDNA. In this example, products are distributed into micro-pores or beads into micro-pores containing immobilized second tag sequence primer.

FIG. 52 illustrates a front view of a portion of an exemplary design for pre-chamber loading to allow for liquids to be fluidically moved to the chambers comprising of micro-wells or micro-pores. This design illustrates the chamber architecture and micro-wells or micro-pores suitable for performing Multiplexed PCR-Nested PCR-sequencing and Bsh1236I—Bisulfite—Multiplexed PCR—Nested PCR—sequencing for identifying unknown mutations and methylations at low-abundance in plasma.

FIG. 53 illustrates an exemplary fragment identifier RT-PCR method with sequencing-by-synthesis readout to identify low- and medium-abundance lncRNA, mRNA, and splice-site variants, isolated from CTC's or exosomes. In this example, products are distributed into micro-pores or beads into micro-pores containing immobilized second tag sequence primer.

FIG. 54 illustrates a front view of a portion of an exemplary design for pre-chamber loading to allow for liquids to be fluidically moved to the chambers comprising of micro-wells or micro-pores. This design illustrates the chamber architecture and micro-wells or micro-pores suitable for performing Multiplexed RT-PCR-Nested PCR-Uni-Taq detection for identifying low- and medium-abundance lncRNA, mRNA, and splice-site variants, isolated from CTC's or exosomes. (Alternatively, Multiplexed PCR-Nested PCR-Real-time-PCR with transcript-specific Taqman™ probes.) The gray circles symbolize areas of prefilling rows or columns with different primer or probe sets.

DETAILED DESCRIPTION OF THE INVENTION

One aspect of the present invention relates to a system for identifying a plurality of nucleic acid molecules in a sample. This system comprises an inlet port and a cartridge. The cartridge defines a space containing multiple primary reaction chambers fluidically coupled to the inlet port to receive material from the inlet port and produce primary reaction chamber products from the material. The space also contains a product capture housing enclosing a solid support with a plurality of separate columns of a plurality of product capture subunits with each separate product capture subunit comprising an array of a plurality of individual hydrophilic micro-pores or micro-wells separated by hydrophobic surfaces where primary reaction products are further reacted to create array products. The array products are detected in the micro-pores or micro-wells, where one or more of the columns of separate product capture subunits receive material which has passed through one of the multiple primary reaction chambers.

In one embodiment, the system for identifying a plurality of nucleic acid molecules in a sample of the present invention further comprises an outlet for discharging material from the product capture housing.

In another embodiment of the system for identifying a plurality of nucleic acid molecules in a sample of the present invention, the space defined by the cartridge further contains one or more initial reaction chambers into which the inlet port discharges material and from which material is discharged into the multiple primary reaction chambers.

In yet another embodiment of the system for identifying a plurality of nucleic acid molecules in a sample of the present invention, the space defined by the cartridge further contains multiple secondary reaction chambers, one or more of which are fluidically coupled to one of the multiple primary reaction chambers to receive material from one of the multiple primary reaction chambers. The space also contains multiple mixing chambers each fluidically coupled to one of the multiple secondary reactions chambers to receive material from one of the multiple secondary reaction chambers and to discharge material to the product capture housing so that each column of separate product capture subunits is fluidically coupled to one of the one or more mixing chambers to receive material from one of the one or more mixing chambers.

In accordance with this embodiment of the system for identifying a plurality of nucleic acid molecules in a sample of the present invention, at least some of the multiple primary and secondary reaction chambers are configured to maintain a trough of liquid in the multiple primary and secondary reaction chambers.

In another embodiment of the system for identifying a plurality of nucleic acid molecules in a sample of the present invention, where the space defined by the cartridge further contains multiple secondary reaction chambers and multiple mixing chambers, the multiple primary and/or secondary reaction chambers each have an internal baffle to maintain a trough of liquid in the multiple primary and secondary reaction chambers.

In yet another embodiment of the system for identifying a plurality of nucleic acid molecules in a sample of the present invention, where the space defined by the cartridge further contains multiple secondary reaction chambers and multiple mixing chambers, the multiple primary and/or secondary reaction chambers each have one or more of internal baffles to maintain a plurality of troughs of liquid in the multiple primary and secondary reaction chambers.

In a further embodiment of the system for identifying a plurality of nucleic acid molecules in a sample of the present invention, where the space defined by the cartridge further contains multiple secondary reaction chambers and multiple mixing chambers, each of the mixing chambers includes a divider extending from proximate to where material enters the mixing chamber to proximate to where material leaves the mixing chambers.

In another embodiment of the system for identifying a plurality of nucleic acid molecules in a sample of the present invention, where the space defined by the cartridge further contains multiple secondary reaction chambers and multiple mixing chambers, each of the mixing chambers includes a first surface which is highly hydrophobic and a second surface spaced from, and less hydrophobic than, the first surface, where the first and second surfaces extend from proximate to where material enters the mixing chamber to proximate to where material leaves the mixing chambers.

In yet another embodiment of the system for identifying a plurality of nucleic acid molecules in a sample of the present invention, where the space defined by the cartridge further contains multiple secondary reaction chambers and multiple mixing chambers, the primary reaction chambers and/or the secondary reaction chambers comprise an internal surface on to which oligonucleotide primers or probes can be spotted.

In another embodiment of the system for identifying a plurality of nucleic acid molecules in a sample according to the invention, the product capture subunits comprise an array of a plurality of individual micro-pores each having opposed first and second open ends with the first end having a large diameter and the second end having a diameter which is smaller than that of the first end.

This system may further comprise a mesh screen covering the second ends of the micro-pores in the product capture housing or a bead placed in the individual micro-pores.

In a further embodiment of the system for identifying a plurality of nucleic acid molecules in a sample of the invention, the product capture subunits comprise an array of a plurality of individual micro-wells each having an open end and a closed end.

In another embodiment of the system for identifying a plurality of nucleic acid molecules in a sample of the present invention, where the space defined by the cartridge further contains multiple secondary reaction chambers and multiple mixing chambers, the product capture housing comprises a plurality of fluid channels to permit material to pass from the multiple mixing chambers, through a column of the product capture subunits into contact with the array of micro-pores or micro-wells in those subunits.

The plurality of fluid channels may be located above and/or below the solid support.

In another embodiment of the system for identifying a plurality of nucleic acid molecules in a sample of the present invention, the system may further comprise one or more valves for selectively introducing or removing reagents or reactants into or out of the cartridge through the inlet.

In a further embodiment of the system for identifying a plurality of nucleic acid molecules in a sample of the present invention, the system further comprises one or more valves for selectively introducing or removing reagents or reactants into or out of the product capture housing through the outlet port and/or through a location in the product capture housing distal from the outlet port.

In yet another embodiment of the system for identifying a plurality of nucleic acid molecules in a sample of the present invention, the system further comprises one or more heating elements in the cartridge proximate to the primary reaction chamber and/or the product capture housing.

In another embodiment of the system for identifying a plurality of nucleic acid molecules in sample of the present invention, when the space defined by the cartridge further contains one or more initial reaction chambers into which the inlet port discharges material and from which material is discharged into the multiple primary reaction chambers, the system may further comprise one or more heating elements in the cartridge proximate to the initial reaction chambers.

In another embodiment of the system for identifying a plurality of nucleic acid molecules in sample of the present invention, when the space defined by the cartridge further contains multiple secondary reaction chambers and multiple mixing chambers, the system may further comprise one or more heating elements in the cartridge proximate to one of the secondary reaction chamber and/or the one or more of the mixing chambers.

Another aspect of the present invention relates to a system for identifying a plurality of nucleic acid molecules in a sample. The system includes: an inlet port; an outlet port; and a cartridge comprising an array of micro-pores or micro-wells, with the cartridge fluidically coupling the inlet port and the outlet port. The cartridge defines a space containing multiple primary reaction chambers fluidically coupled to the inlet port to receive material from the inlet port and produce primary reaction chamber products from the material. The space also contains multiple secondary reaction chambers, one or more of which are fluidically coupled to one of the multiple primary reaction chambers to receive material from one of the multiple primary reaction chambers, and to produce secondary reaction chamber products. At least some of the multiple primary and secondary reaction chambers are configured to maintain a trough of liquid in the multiple primary and secondary reaction chambers to facilitate mixing of sample, reagents, and/or product reactants for generating subsequent reaction chamber or array products. The space also contains multiple mixing chambers each fluidically coupled to one of the multiple secondary reaction chambers to receive material from one of the multiple secondary reaction chambers and to discharge material to the product capture housing so that each column of separate product capture subunits is fluidically coupled to one of the one or more mixing chamber to receive material from one of the one or more mixing chambers. The space also contains a product capture housing enclosing a solid support with a plurality of separate columns of a plurality of product capture subunits with each separate product capture subunit comprising an array of a plurality of individual hydrophilic micro-pores or micro-wells separated by hydrophobic surfaces where secondary reaction products are further reacted to create array products. The array products are detected in the micro-pores or micro-wells, where one or more of the columns of separate product capture subunits receive material which has passed through one of the multiple primary reaction chambers.

Another aspect of the present invention relates to a system for identifying a plurality of nucleic acid molecules in a sample. The system includes: an inlet port; a second inlet location; an outlet port; and a cartridge fluidically coupling the inlet port, the second inlet location, and the outlet port. The cartridge defines a space containing a product capture housing enclosing a solid support with a plurality of separate columns of product capture subunits with each separate product capture subunit comprising an array of a plurality of individual micro-pores. The product capture housing comprises a plurality of fluid channels to permit material to pass from the inlet port and/or the second inlet location through a column of the product capture subunits into contact with the array of micro-pores in those subunits, and to the outlet port, where the plurality of fluid channels are located above and below the solid support. One or more valves are used to selectively introduce or remove reagents or reactants into or out of the product capture housing through the inlet port, the outlet port and/or through the second inlet location in the product capture housing distal from the outlet port.

A further aspect of the present invention relates to a method for preparing a system for identifying a plurality of nucleic acid molecules in a sample. The method comprises providing the system of the present invention and applying universal tag or capture oligonucleotide primers or probes to the micro-pores or micro-wells of the product capture subunits on the solid support within the product capture housing. As a result, the universal tag or capture oligonucleotide primers or probes are retained within the micro-pores or micro-wells.

The method for preparing a system for identifying a plurality of nucleic acid molecules in a sample of the present invention may further involve filling the one or more primary reaction chambers with primary reaction oligonucleotide probes or primers each having a first portion comprising a nucleotide sequence complementary to a portion of target nucleic acids in the sample. In accordance with this embodiment, the primary reaction oligonucleotide probes or primers may further comprise a second portion comprising a nucleotide sequence the same as or complementary to a portion of a universal tag or capture oligonucleotide primers, retained within the mirco-pores or micro-wells.

A further aspect of the present invention relates to a method for preparing a system for identifying a plurality of nucleic acid molecules in a sample. The method involves providing a system of the present invention, where the system comprises an inlet port and a cartridge. The cartridge defines a space containing multiple primary reaction chambers fluidically coupled to the inlet port to receive material from the inlet port and produce primary reaction chamber products from the material; a product capture housing enclosing a solid support with a plurality of separate columns of a plurality of product capture subunits with each separate product capture subunit comprising an array of a plurality of individual hydrophilic micro-pores or micro-wells separated by hydrophobic surfaces where primary reaction products are further reacted to create array products which are detected in the micro-pores or micro-wells, where one or more of the columns of separate product capture subunits receive material which has passed through one of the multiple primary reaction chambers; multiple secondary reaction chambers, one or more of which are fluidically coupled to one of the multiple primary reaction chambers to receive material from one of the multiple primary reaction chambers; and multiple mixing chambers each fluidically coupled to one of said multiple secondary reaction chambers to receive material from one of said multiple secondary reaction chambers and to discharge material to said product capture housing so that each column of separate product capture subunits is fluidically coupled to one of said one or more mixing chamber to receive material from one of said one or more mixing chambers. This method further involves applying universal tag or capture oligonucleotide primers or probes to the micro-pores or micro-wells of the product capture subunits on the solid support within the product capture housing. As a result, the universal tag or capture oligonucleotide primers or probes are retained within the micro-pores or micro-wells.

This method may further involve filling the one or more primary reaction chambers and/or secondary reaction chambers with primary or secondary reaction oligonucleotide probes or primers each having a first portion comprising a nucleotide sequence complementary to a portion of target nucleic acids in the sample. In accordance with this embodiment, the primary or secondary reaction oligonucleotide probes or primers may further comprise a second portion comprising a nucleotide sequence which is the same as or complementary to a portion of a universal tag or capture oligonucleotide primers, retained within the micro-pores or micro-wells.

In one embodiment of the methods for preparing a system for identifying a plurality of nucleic acid molecules in a sample of the present invention, the product capture subunit comprises an array of individual micro-pores each having opposed first and second open ends with the first end having a large diameter and the second end having a diameter which is smaller than that of the first end with a first passage in fluid communication with first end of the micro-pores and a second passage in fluid communication with the second end of the micro-pores, where the universal tag or capture oligonucleotide primers or probes are applied to the micro-pores by a method comprising the following steps in the sequence set forth as follows: passing the universal tag or capture oligonucleotide primers or probes through the first passage into the micro-pores through their first open ends while hydrophobic liquid is passed through the second passage; passing a hydrophobic liquid through the first passage while the hydrophobic liquid is passed through the second passage; passing a volatile solvent through the first passage while the hydrophobic liquid is passed through the second passage; and passing air through the first passage while heat, a hydrophobic liquid, a volatile solvent, and then air is passed through the second passage.

In another embodiment of the methods for preparing a system for identifying a plurality of nucleic acid molecules in a sample of the present invention, the product capture subunit comprises an array of individual micro-pores each having opposed first and second open ends with the first end having a large diameter and the second end having a diameter which is smaller than that of the first end with a first passage in fluid communication with first end of the micro-pores and a second passage separated from the second end of the micro-pores by a mesh screen covering the second ends, in fluid communication with a second passage, where the detection or capture oligonucleotide primers or probes are applied to the micro-pores by a method comprising the following steps in the sequence set forth as follows: passing the universal tag or capture oligonucleotide primers or probes through the first passage into the micro-pores through their first open ends; passing a hydrophobic liquid through the first passage to expel the universal tag or capture oligonucleotide primers or probes from the first passage; passing a hydrophobic liquid through the first passage while a hydrophobic liquid is passed through the second passage; passing a volatile solvent through the first passage while a hydrophobic liquid is passed through the second passage; and passing air through the first passage while heat, a hydrophobic liquid, a volatile solvent, and then air is passed through the second passage.

Another embodiment of the present invention relates to a process of identifying a plurality of nucleic acid molecules in a sample using the system of the present invention. Following filling of the one or more primary reaction chambers and/or the one or more secondary reaction chambers, (if present), the process comprises conducting the primary and/or secondary reactions in the system and detecting the presence of target nucleic acid molecules in the sample in the micro-wells or micro-pores based on carrying out the primary and/or secondary reactions.

Another embodiment of the present invention relates to a process of identifying a plurality of nucleic acid molecules in a sample using the system of the present invention. Following the carrying out the primary and/or secondary reactions, the products of such reactions are amplified in the micro-wells or micro-pores under conditions where a polymerase, exonuclease, endonuclease, or ribonuclease cleaves one or more probes comprising a quencher and fluorescent group in a target-specific manner, such that fluorescent groups are liberated to generate signal if the target nucleic acid molecules are present in the sample.

Another embodiment of the present invention relates to a process of identifying a plurality of nucleic acid molecules in a sample using the system of the present invention. The process of conducting the primary and/or secondary reactions involves providing a sample containing a plurality of target nucleic acid molecules and contacting the sample with a set of primary oligonucleotide primers having a first portion complementary to a portion of the target nucleic acid molecule or a complement of the target nucleic acid molecule, and a polymerase to form a first polymerase extension or chain reaction mixture. This mixture is subjected to a first polymerase extension or chain reaction in the one or more initial or primary reaction chambers to produce a first set of extension or amplification products. These products are then contacted with a set of secondary oligonucleotide primers having a first portion complementary to a portion of a primary extension or amplification product and a polymerase to form a second polymerase chain reaction mixture. This second mixture is subjected to a second polymerase chain reaction in the primary or secondary reaction chambers to produce a second set of amplification products, where each secondary amplification product comprises a 5' second portion sequence, a target nucleotide sequence-specific portion or its complement, and a 3' second portion complementary sequence.

Another embodiment of the present invention relates to a process of identifying a plurality of nucleic acid molecules in a sample using the system of the present invention. The process of conducting the primary and/or secondary reactions involves providing a sample containing a plurality of target nucleic acid molecules and contacting the sample with a set of primary oligonucleotide primers having a portion complementary to a portion of the target nucleic acid molecule or its extension product and a polymerase to form a first polymerase extension or chain reaction mixture. This mixture is subjected to a first polymerase chain reaction in the one or more initial or primary reaction chambers to produce a first set of extension or amplification products. These products are then contacted with a set of oligonucleotide probes having a first portion complementary to a portion of the first set of amplification products and a second portion and a ligase to form a ligase detection reaction mixture. This second mixture is subjected to a ligase detection reaction in the primary or secondary reaction chambers to produce a set of ligation products, where each ligation product comprises a 5' second portion sequence, a target nucleotide sequence-specific portion or its complement, and a 3' second portion sequence.

Yet another embodiment of the present invention relates to a process of identifying a plurality of nucleic acid molecules in a sample using the system of the present invention. The process of filling the one or more primary reaction chambers, if present, and the process of conducting the primary and/or secondary reactions in the system are carried out by a process involving the following steps in the sequence set forth as follows. Hydrophobic liquid is passed into the system through the inlet port. Primary reaction oligonucleotide probes or primers and reverse-transcription and/or polymerase chain reaction reagents and then hydrophobic liquid are passed into the system through the inlet port. A polymerase extension or chain reaction is carried out in the system and material is drained from the system through the inlet port. Hydrophobic liquid, polymerase chain reaction or ligase detection reaction reagents, and then hydrophobic liquid are passed into the system through the inlet port and a polymerase chain reaction or ligase detection reaction is carried out in the system.

Another embodiment of the present invention relates to a process of identifying a plurality of nucleic acid molecules in a sample using the system of the present invention, where the product capture subunit comprises an array of individual micro-pores. The micro-pores each have opposed first and second open ends with the first end having a large diameter and the second end having a diameter which is smaller than that of the first end with a first passage in fluid communication with first end of the micro-pores and a second passage in fluid communication with the second end of the micro-pores and where said conducting the secondary reaction in the system is carried out by a process involving the following steps in the sequence set forth as follows. The products of a polymerase chain reaction or a ligase detection reaction are passed into the product capture housing through the first passage while passing hydrophobic liquid through the second passage. Hydrophobic liquid is then passed through the first and second passages. The products of the polymerase chain reaction or a ligase detection reaction are then subjected to a polymerase chain reaction with universal tag primers and probes within the micro-pores in the product capture subunit.

Another embodiment of the present invention relates to a process of identifying a plurality of nucleic acid molecules in a sample using the system of the present invention, where the product capture subunit comprises an array of individual micro-pores. The micro-pores each have opposed first and second open ends with the first end having a large diameter and the second end having a diameter which is smaller than that of the first end with a first passage in fluid communication with first end of the micro-pores and a second passage in fluid communication with, and separated from, the second end of the micro-pores by a mesh screen covering the second ends of the micro-pores and where the process of conducting the secondary reactions in the system are carried out by a process involving the following steps in the sequence set forth as follows. The products of a polymerase chain reaction or a ligase detection reaction are passed into the product capture housing through the first passage. Hydrophobic liquid is passed through the first passage. Then, hydrophobic liquid is passed through the first and second passages. The products of the polymerase chain reaction or the ligase detection reaction are subjected to a polymerase chain reaction with universal tag primers and probes within the micro-pores in the product capture subunit.

Another embodiment of the present invention relates to a process of identifying a plurality of nucleic acid molecules in a sample using the system of the present invention, where in a sample, a plurality of nucleic acid molecules containing a target nucleotide sequence differing from nucleotide sequences in other nucleic acid molecules in the sample, or other samples, by one or more nucleotides, one or more nucleotide insertions or deletions, one or more copy numbers, one or more transcript sequences, one or more translocations, and/or one or more methylated residues are identified.

Another embodiment of the present invention relates to a process of identifying a plurality of nucleic acid molecules in a sample using the system of the present invention, where preparing the system involves filling the one or more primary reaction chambers with primary reaction oligonucleotide probes or primers each having a first portion comprising a nucleotide sequence complementary to a portion of target nucleic acids in the sample. Following the process of filling the one or more primary reaction chambers, the process further involves conducting the primary reaction in the system and obtaining the nucleotide sequence of target nucleic acid molecules in the sample following the process of conducting the primary reaction.

Another embodiment of the present invention relates to a process of identifying a plurality of nucleic acid molecules in a sample using the system of the present invention. The process comprises providing a sample containing a plurality of target nucleic acid molecules and contacting the sample with a set of primary oligonucleotide primers having a first portion complementary to a portion of the target nucleic acid molecules and a second portion and a polymerase to form a polymerase chain reaction mixture. This mixture is subjected to a polymerase chain reaction in the primary reaction chambers to produce a set of amplification products. The amplification products are passed to the product capture housing enclosing a solid support with a plurality of separate columns of a plurality of capture subunits with each separate product capture subunit comprising an array of a plurality of individual micro-pores containing immobilized capture probes complementary to the second portion. The target nucleic acid molecules are captured and copied onto the immobilized capture probes. The nucleotide sequence of the immobilized target nucleic acid molecules is obtained by carrying out sequencing reactions in the micro-pores.

In accordance with this embodiment, the product capture subunits may comprise an array of a plurality of individual micro-pores each having opposed first and second open ends with the first end having a large diameter and the second end having a diameter which is smaller than that of the first end. The process may further involve a mesh screen covering the second ends of the micro-pores in the product capture housing.

In another embodiment, the process of identifying a plurality of nucleic acid molecules in a sample using the system of the present invention further involves a bead containing the immobilized capture probes placed in the individual micro-pores.

In a further embodiment, the process of identifying a plurality of nucleic acid molecules in a sample using the system of the present invention further involves removing at least one second portion from the amplification product before the process of obtaining the nucleotide sequence and after the subjecting the polymerase chain reaction mixture to a polymerase chain reaction. The process of removing at least one second portion may be carried out with uracil DNA glycosylases, apurinic/apyrimidinic endonuclease, endonuclease III, endonuclease IV, endonuclease V, alkyladenine DNA glycosylase, formamidopyrimidine DNA glycosylase, or 8-oxyguanine DNA glycosylase, or combinations thereof.

Another embodiment relates to a process of identifying a plurality of nucleic acid molecules in a sample using the system of the present invention. The process involves providing a system of the present invention and applying universal tag or capture oligonucleotide primers or probes to the micro-pores or micro-wells of the product capture subunits on the solid support within the product capture housing, where the universal tag or capture oligonucleotide primers or probes are retained within the micro-pores or micro-wells. The process further involves filling the one or more primary reaction chambers with primary reaction oligonucleotide probes or primers each having a first portion comprising a nucleotide sequence complementary to a portion of target nucleic acids in the sample and conducting the primary reaction in the system. The process further involves obtaining the nucleotide sequence of target nucleic acid molecules in the sample following the process of conducting the primary reaction. The product capture subunit comprises an array of individual micro-pores each having opposed first and second open ends with the first end having a large diameter and the second end having a diameter which is smaller than that of the first end with a first passage in fluid communication with first end of the micro-pores and a second passage in fluid communication with, and separated from, the second end of the micro-pores by a mesh screen covering the second ends of the micro-pores and where the process of obtaining the nucleotide sequence is carried by a process comprising the following steps in the sequence set forth as follows. The products of a polymerase chain reaction are passed into the product capture housing through said first passage. Hydrophobic liquid is then passed through the first passage, such that the products are distributed into individual micro-wells. Next, hydrophobic liquid is passed through the first and second passages. The products are amplified in a polymerase chain reaction and/or isothermal reaction using the capture oligonucleotide primers under conditions to generate amplification products that are immobilized to the interior surface of the micro-wells. A volatile solvent is then passed through the first passage while hydrophobic liquid is passed through the second passage. The products of the polymerase chain reaction and/or isothermal reaction are denatured, and non-anchored nucleic acid molecules are washed away through the first passage while hydrophobic liquid is passed through the second passages, such that the products are isolated in individual micro-wells. Hydrophobic liquid with a higher density than water is passed through the first passages while volatile solvent, air, and then sequencing reagents are passed through the second passages. A sequencing reaction is then carried out in the product capture subunit.

The present invention also relates to a process for preparing a microtiter plate for identifying a plurality of nucleic acid molecules in a sample. This involves providing a microtiter plate with a plurality of separate rows and columns of product capture subunits with each separate product capture subunit comprising an array of a plurality of individual hydrophilic micro-wells separated by hydrophobic surfaces. The micro-wells of the microtiter plate are filled with an aqueous liquid containing oligonucleotide primers and/or probes. The microtiter plate is centrifuged to spread the aqueous liquid to unfilled micro-wells in each separate product capture subunit in the microtiter plates. Centrifuging is then terminated to urge the aqueous liquid out of contact with the hydrophobic surfaces. The aqueous liquid is evaporated, and the micro-wells are dried so that the oligonucleotide primers are left in the micro-wells.

Another embodiment of the present invention relates to a process of identifying a plurality of nucleic acid molecules in a sample using the process of the present invention for preparing dried oligonucleotide primers within micro-wells of a microtiter plate. This involves charging an aqueous sample into the microtiter plate, followed by charging a hydrophobic liquid into the microtiter plate so that the hydrophobic liquid is over the aqueous sample. The microtiter plate is centrifuged to spread the aqueous liquid to unfilled micro-wells in the microtiter plate. Centrifuging is then terminated to urge the aqueous liquid out of contact with the hydrophobic surfaces. A nucleic acid molecule amplification reaction is carried out under conditions where a polymerase, exonuclease, endonuclease, or ribonuclease cleaves one or more probes comprising a quencher and fluorescent group in a target-specific manner, such that fluorescent groups are liberated to generate signal if the target nucleic acid molecules are present in the sample.

In accordance with this embodiment, a plurality of nucleic acid molecules containing a target nucleotide sequence differing from nucleotide sequences in other nucleic acid molecules in the sample, or other samples, by one or more nucleotides, one or more nucleotide insertions or deletions, one or more copy numbers, one or more transcript sequences, one or more translocations, and/or one or more methylated residues are identified.

Another aspect of the present invention relates to a system for identifying a plurality of nucleic acid molecules in a sample. This system comprises an inlet port; an outlet port; and a cartridge fluidically coupled to the inlet port and the outlet port. The cartridge defines a space containing a product capture housing enclosing a solid support with a plurality of separate columns of product capture subunits. Each separate product capture subunit comprises an array of a plurality of individual hydrophilic micro-pores separated by hydrophobic surfaces each having opposed first and second open ends with the first end having a large diameter and the second end having a diameter which is smaller than that of the first end. The product capture housing comprises a plurality of fluid channels to permit material to pass from the inlet port through a column of the product capture subunits into contact with the array of micro-pores in those subunits, and to the outlet port, where the plurality of fluid channels are located above and below the solid support.

In one embodiment, the system for identifying a plurality of nucleic acid molecules in a sample further comprises one or more valves for selectively introducing or removing reagents and/or reactants into or out of the product capture housing through the inlet port or through the outlet port.

In another embodiment for identifying a plurality of nucleic acid molecules in a sample, the system further comprises one or more heating elements in the cartridge proximate to the product capture housing.

The present invention relates to a method for preparing a system for identifying a plurality of nucleic acid molecules in a sample. This method involves providing a system of the presented invention, where the system comprises an inlet port, an outlet port, and a cartridge fluidically coupling the inlet port and the outlet port and defining a space, as described above. This method further involves applying capture oligonucleotide primers or probes to the micro-pores of the product capture subunits on the solid support within the product capture housing, where the capture oligonucleotide primers or probes are retained within the micro-pores or micro-wells. In one embodiment, this method further involves conducting the reactions in the system and detecting the presence of target nucleic acid molecules in the sample in the micro-pores based on the conducting the reactions.

The present invention provides a set of devices, chambers, and assays for determining the cause of disease directly from a blood sample. Nucleic acids are purified from the clinical sample, targeted regions are subjected to a series of amplification reactions, and targets are identified or enumerated using either real-time PCR or sequencing as a readout. An overview of the urgent clinical needs that may be addressed by these devices is presented in Table 1.

TABLE 1

Overview of Clinical Need in Determining Cause of Disease Directly from a Blood Sample.

| Type | Clinical Need: i.e. disease identified directly from blood or plasma | Initial Reaction Chamber | Primary 24-96 PCR Multiplex Reaction Chambers | Secondary 24-96 Multiplex Reaction Chambers | Readout: Identify and enumerate targets using Taqman™ or Sequencing |
|---|---|---|---|---|---|
| 1 | Unknown pathogen(s) | Multiplexed PCR or RT-PCR (e.g. 9 cycles) | Multiplexed nested PCR (e.g. 5 cycles) | | Real-time Taqman™, UniTaq, or UniRq. Poisson Dist. & Ct values |
| 2 | Unknown pathogen(s) | Multiplexed PCR or RT-PCR (e.g. 30 cycles) | Multiplexed LDR (e.g. 20 cycles) | | Real-time Taqman™, UniTaq, or UniSpTq. Ct values |
| 3 | Identify and genotype unknown pathogen(s) | Multiplexed PCR or RT-PCR (e.g. 30 - 40 cycles) | | | LDR (e.g. 50 cycles) with UniLDq or TsLDq readout. Ct values |
| 4 | Unknown bacterial pathogen directly from blood | | Multiplexed PCR (e.g. 20 cycles) | Multiplexed nested PCR (e.g. 10 cycles) | Real-time Taqman™, UniTaq, or UniRq. Poisson Dist. from chambers |
| 5 | Mutation at low-level in plasma | | Multiplexed locus-specific PCR (e.g. 10 - 40 cycles) | Multiplexed LDR (e.g. 20 cycles) | Real-time Taqman™ or UniTaq. Poisson Dist. from chambers |
| 6 | Methylation at low-level in plasma | Bsh1236I, then treat with bisulfite | Multiplexed locus-specific PCR (e.g. 10 - 40 cycles) | Multiplexed LDR (e.g. 20 cycles) | Real-time Taqman™ or UniTaq. Poisson Dist. from chambers |

TABLE 1-continued

Overview of Clinical Need in Determining Cause of Disease Directly from a Blood Sample.

| Type | Clinical Need: i.e. disease identified directly from blood or plasma | Initial Reaction Chamber | Primary 24-96 PCR Multiplex Reaction Chambers | Secondary 24-96 Multiplex Reaction Chambers | Readout: Identify and enumerate targets using Taqman™ or Sequencing |
|---|---|---|---|---|---|
| 7 | lncRNA, mRNA, or splice variants. | Multiplexed RT-PCR (e.g. 7-9 cycles). | Multiplexed nested PCR (e.g. 10 cycles) | Differential dilutions | Real-time Taqman™ or UniTaq. Poisson Dist. from micro-pores. |
| 8 | Identify, quantify and genotype unknown pathogen(s) | Multiplexed PCR or RT-PCR (e.g. 10 cycles) | Multiplexed nested PCR (e.g. 5 cycles) | Micro-pores contain tag-specific primers | Target-specific, or universal tag-specific sequencing. Poisson Dist. from micro-pores. |
| 9 | Identify, quantify and genotype unknown pathogen(s) | Multiplexed PCR or RT-PCR (e.g. 10 cycles) | Multiplexed nested PCR (e.g. 5 cycles) | Micro-pores contain one or more immobilized universal primer(s) | Target-specific, or universal tag-specific sequencing. Poisson Dist. from micro-pores. |
| 10 | Unknown mutation at low-level in plasma | | Multiplexed Frag. ID PCR (e.g. 3 cycles) | Micro-pores contain one or more immobilized universal primer(s) | Target-specific, or universal tag-specific sequencing. Frag. ID enumerates each mutation; verify on both strands. |
| 11 | Non-invasive prenatal testing of trisomy | | Multiplexed Frag. ID PCR (e.g. 3 cycles) | Micro-pores contain one or more immobilized universal primer(s) | Target-specific, or universal tag-specific sequencing. Frag. ID enumerates each SNP, chromosomal copy; verify on both strands. |
| 12 | Unknown methylation at low-level in plasma | Bsh1236I, then treat with bisulfite | Multiplexed Frag. ID PCR (e.g. 3 cycles) | Micro-pores contain one or more immobilized universal primer(s) | Target-specific, or universal tag-specific sequencing. Frag. ID enumerates each methylation; verify on both strands. |

One of the primary challenges for detecting multiple unknown pathogens or mutations is to amplify all potential and desired fragments simultaneously while avoiding PCR dropout in a multiplexed reaction. Multiplexed PCR reactions may be difficult to optimize, and fragment dropout has been a nagging problem. Often initial PCR cycles in the range of 8-12 cycles can maintain relative copy number, but when some fragments amplify more efficiently, they tend to out-amplify and overwhelm less efficient fragments resulting in fragment dropout at later cycles. One solution to this problem is to perform an initial limited cycle multiplexed amplification, and then divide the products into 24 to 48 reaction chambers for subsequent amplification reactions at far lower complexity. An additional solution is to dilute the initial amplification products into subdivisions comprising tens, hundreds, or thousands of micro-pores or micro-wells. A given micro-pore or micro-well may then be used for 1 to 4 qPCR or individual sequencing reactions, thus allowing for accurate target enumeration or quantification, while minimizing the risks of PCR dropout.

One aspect of the invention is a set of subdivisions, preferably arranged in rows and columns, each subdivision comprising of single digits, tens, hundreds, or thousands of micro-pores or micro-wells for subsequent qPCR, UniTaq, FRET, qLDR, or sequencing reactions and target identification. In the preferred embodiments, the presence of target results in a fluorescence readout. In some embodiments, the target is amplified and immobilized or coupled to a solid support within the micro-pores or micro-wells. Such immobilization may occur directly on the interior surface on the micro-pores or micro-wells, on dendrimeric primers immobilized to the surface of the micro-pores or micro-wells, or on micro-beads that are either already distributed within micro-pores or micro-wells prior to amplification or are distributed into micro-pores or micro-wells after the initial amplification. Immobilization or coupling to the solid support enables interrogating the amplified target one or more times to determine the presence or absence of mutations, SNPs, or sequence variations within the target. This includes multiple rounds of ligation detection reactions (LDR), sequencing by synthesis, or sequencing by ligation.

Arrangement of subdivisions in rows and columns facilitates filling such rows and columns with either universal or target-specific primers, enzymes, reagents, buffers, targets, or pre-amplified targets. Filling may be accomplished by flowing liquids across all subdivisions in given rows or columns through fluidically coupled or connected channels, or alternatively by accurately dispensing liquids to individual subdivisions, e.g. using acoustic droplet ejection (ADE) technology. One manufacturer of ADE equipment is Labcyte (Sunnyvale Calif.).

In one embodiment of the current invention, this flexible design architecture enables identification, genotyping, and/or quantification of viral, bacterial, protozoal, malarial, or other pathogenic nucleic acids representing potentially 384, 768, or 1536 targets, mutations, resistance genes, pathogenesis genes and/or strain or serotype variants. Detecting bacterial DNA directly from blood is a particularly difficult challenge, since yields are typically on the order of 1-2 colony forming units per ml of blood; however, the spatial multiplexing approach may still enable identification of 32, 64, or 128 potential targets. When using the sequencing module as described below, the design enables determining about 150 base reads for 1,536 potential pathogenic targets.

Another embodiment of the design uses spatial dilution (e.g. into 48 sections) to enable accurate enumeration of copy number directly from plasma for non-invasive prenatal testing for trisomy (NIPT). Since the Watson strands should match the Crick strands in each of the 48 sections, i.e. columns (since they are generated from a given fragment with one of each strand), this is an internal control for loss of strands or other errors. Multiple unique loci on Chromosomes 2 (control), 13, 18, 21, X, and Y are used to establish copy number and discern trisomy or other chromosomal copy changes. In one embodiment, 184 locus regions could be interrogated on both strands, but this could be increased to 368 or 736 locus regions.

Another embodiment of the design enables PCR-LDR-qPCR single-molecule mutation detection directly from plasma for up to 64 or 128 potential targets, with additional flexibility when multiple mutations in a gene (i.e. the mutations in K-ras codons 12 & 13) are scored by a single signal. A similar level of flexibility may be applied for identifying and enumerating methylation of CpG sites in the promoter region of selected genes. The ability to perform serial dilutions within the chambers enables exact enumeration of 384 RNA targets, including rare and overexpressed lncRNA, mRNA, or splice variants, for example isolated from exosomes or platelets.

Another embodiment of the design enables determining low abundance mutations in 144 target regions, providing about 150 base reads for both strands, with accurate enumeration of each mutation. Sequencing methylated regions allows for pre-enrichment of these areas, such that over 2,000 methylated CpG promoter regions could be interrogated, even if present at low abundance.

In one embodiment of the invention (see FIG. 1A), the subdivisions Z are present in columns $A_1$ to $A_{ii}$ and rows $B_1$ to $B_v$ and are 400-micron wide×600-micron long. Additional 100-micron wide ridges X and Y are used between subdivisions Z to provide separation of subdivisions and additional structural support. Such ridges may be designed to have indentations or channels enabling fluid motion between subdivisions. The micro-pores or micro-wells are made in the solid support, which may comprise composites, plastics, metal, glass, silicon, silicon nitride, or mixtures thereof. The dimensions of the micro-pores or micro-wells may be 50-micron diameter, ranging from about 50-micron deep to 400-micron deep, and may be opened (i.e. micro-pores) or closed (i.e. micro-wells) at the bottom. The bottom of the 50-micron micro-pores may have another layer of 0.5-micron holes on silicon nitride 200 to 400-nanometers thick, enabling filling of the 50-micron micro-pores with liquid from the top, allowing air, but not liquid to escape through the 0.5-micron pores at the bottom. Microporous silicon nitride membranes can be fabricated by well-recognized methods, such as photolithography patterning and reactive ion etching of silicon nitride layers disposed on silicon wafer substrates (DesOrmeaux J P et al., "Nanoporous Silicon Nitride Membranes Fabricated from Porous Nanocrystalline Silicon Templates," *Nanoscale* 6(18):10798-805 (2014), which is hereby incorporated by reference in its entirety). In one embodiment, each subdivision comprises 6×4=24 micro-pores or micro-wells of 50-micron diameter, generated in Cartesian or hexagonal packing. Such an embodiment is ideally suited for subsequent qPCR, UniTaq, FRET, or qLDR detection.

TABLE 2

Different Embodiments of Micro-Wells or Micro-Pores in Cartridge or Micro-Titer Plate Format.

| Columns | Rows | Total sub-divisions | Width (cm) | Height (cm) | Total micro-pores | Micro-pores per column |
|---|---|---|---|---|---|---|
| For Real-time PCR readout in cartridge format: 50-micron micro-pores or micro-wells. Subdivisions are 400-micron wide × 600-micron long (high) Additional 100-micron wide ridges between subdivisions A given subdivision will contain 6 × 4 = 24 micro-pores or micro-wells. | | | | | | |
| 24 | 16 | 384 | 1.20 | 1.12 | 9,216 | 384 |
| 48 | 32 | 1,536 | 2.40 | 2.24 | 36,864 | 768 |
| 96 | 64 | 6,144 | 4.80 | 4.48 | 147,456 | 1,536 |
| For Real-time PCR readout in micro-titer plate format: 50-micron micro-wells. Subdivisions are 800-micron wide × 1,200-micron long Additional 200-micron wide ridges between subdivisions A given subdivision will contain 12 × 8 = 96 micro-wells. | | | | | | |
| 48 | 48 | 2,304 | 4.80 | 6.72 | 221,184 | 4,608 |
| 64 | 64 | 4,096 | 6.40 | 8.96 | 393,216 | 6,144 |
| For Sequencing readout in cartridge & micro-titer plate format: 5-micron micro-pores. Subdivisions are 400-micron × 600-micron - both orientations Additional 100-micron wide ridges between subdivisions A given subdivision will contain 60 × 46 = 2,760 micro-pores or micro-pores. | | | | | | |
| 24 | 16 | 384 | 1.20 | 1.12 | 1,059,840 | 44,160 |
| 48 | 32 | 1,536 | 2.40 | 2.24 | 4,239,360 | 88,320 |
| 96 | 64 | 6,144 | 4.80 | 4.48 | 16,957,440 | 176,640 |
| 24 | 32 | 768 | 1.68 | 1.60 | 2,119,680 | 88,320 |
| 48 | 64 | 3,072 | 3.36 | 3.20 | 8,478,720 | 176,640 |
| 96 | 128 | 12,888 | 6.72 | 6.40 | 33,914,880 | 353,280 |
| 96 | 96 | 9,216 | 4.80 | 6.72 | 25,436,160 | 264,960 |
| Double 48 | Double 48 | 2,304 | 4.80 | 6.72 | 25,436,160 | 529,920 |
| 128 | 128 | 16,384 | 6.40 | 8.96 | 45,219,840 | 353,280 |
| Double 64 | Double 64 | 4,096 | 6.40 | 8.96 | 45,219,840 | 706,560 |

In another embodiment of the invention (FIG. 1B), the subdivisions Z are present in columns $A_1$ to $A_i$ and rows $B_1$ to $B_{ix}$ and are 400-micron wide×600-micron long. Additional 100-micron wide ridges X and Y are used between subdivisions Z to provide separation of subdivisions and additional structural support. Such ridges may be designed to have indentations or channels enabling fluid motion between subdivisions. The micro-pores or micro-wells are made in the solid support, which may comprise composites, plastics, metal, glass, silicon, silicon nitride, or mixtures thereof. The dimensions of the micro-pores or micro-wells may be 5-micron diameter, ranging from about 5-micron deep to 40-micron deep, and may be open (i.e. micro-pores) or closed (i.e. micro-wells) at the bottom. The bottom of the 5 micron micro-pores may have another layer of 0.5-micron holes on silicon nitride 200 to 400-nanometers thick, enabling filling of the 5-micron micro-pores with liquid from the top, allowing air, but not liquid to escape through the 0.5-micron pores at the bottom. In one embodiment, each subdivision comprises 60×46=2,760 micro-pores or micro-wells of 5-micron diameter, generated in hexagonal packing. Such an embodiment is ideally suited for subsequent sequencing by synthesis, or sequencing by ligation.

In another variation of the above embodiment, the subdivisions Z are 400-micron wide×600-micron long, with 100-micron wide ridges X and Y between subdivisions. The dimensions of the micro-pores or micro-wells may be 2.5-micron diameter, ranging from about 2.5-micron deep to 20-micron deep, and may be open (i.e. micro-pores) or closed (i.e. micro-wells) at the bottom. The bottom of the 2.5-micron micro-pores may have another layer of 0.5-micron holes on silicon nitride 200 to 400-nanometers thick, enabling filling of the 2.5-micron micro-pores with liquid from the top, allowing air, but not liquid to escape through the 0.5-micron pores at the bottom. In one embodiment, each subdivision comprises 100×92=11,040 micro-pores or micro-wells of 2.5-micron diameter, generated in hexagonal packing. Such an embodiment is ideally suited for subsequent sequencing by synthesis, or sequencing by ligation.

In another embodiment of the invention (see FIG. 1C), the subdivisions Z are present in columns $A_1$ to $A_i$ and rows $B_1$ to $B_{ii}$ and are 800-micron wide×1200-micron long. Additional 200-micron wide ridges X and Y are used between subdivisions Z to provide separation of subdivisions and additional structural support. Such ridges may be designed to have indentations or channels enabling fluid motion between subdivisions. The micro-wells are made in the solid support, which may comprise composites, plastics, metal, glass, silicon, silicon nitride, or mixtures thereof. The dimensions of the micro-wells may be 50-micron diameter, ranging from about 50-micron deep to 400-micron deep. In one embodiment, each subdivision comprises 12×8=96 micro-pores or micro-wells of 50-micron diameter, generated in Cartesian or hexagonal packing. Such an embodiment is ideally suited for subsequent qPCR, UniTaq, FRET, or qLDR detection.

In another embodiment of the invention (See FIG. 1D), the subdivisions Z are present in columns $A_1$ to $A_{ii}$ and rows $B_1$ to $B_v$ and are 400-micron wide×600-micron long. Additional 100-micron wide ridges X and Y are used between subdivisions Z to provide separation of subdivisions and additional structural support. Such ridges may be designed to have indentations or channels enabling fluid motion between subdivisions. The micro-pores are made in the solid support, which may comprise composites, plastics, metal, glass, silicon, silicon nitride, or mixtures thereof. The dimensions of the micro-pores may be 5-micron diameter, ranging from about 5-micron deep to 40-micron deep. The bottom of the 5-micron micro-pores may have another layer of 0.5-micron holes on silicon nitride 200 to 400-nanometers thick, enabling filling of the 5-micron micro-pores with liquid from the top, allowing air, but not liquid to escape through the 0.5-micron pores at the bottom. In one embodiment, each subdivision comprises 60×46=2,760 micro-pores or micro-wells of 5 micron diameter, generated in hexagonal packing. Such an embodiment is ideally suited for subsequent sequencing by synthesis, or sequencing by ligation.

In another variation of the above embodiment, the subdivisions are 400 micron wide×600-micron long, with 100-micron wide ridges between subdivisions. The dimensions of the micro-pores or micro-wells may be 2.5-micron diameter, ranging from about 2.5-micron deep to 20-micron deep. The bottom of the 2.5-micron micro-pores may have another layer of 0.5-micron holes on silicon nitride 200 to 400-nanometers thick, enabling filling of the 2.5-micron micro-pores with liquid from the top, allowing air, but not liquid to escape through the 0.5-micron pores at the bottom. In one embodiment, each subdivision comprises 100×92=11,040 micro-pores of 2.5-micron diameter, generated in hexagonal packing. Such an embodiment is ideally suited for subsequent sequencing by synthesis, or sequencing by ligation.

The devices are envisioned to comprise an array of micro-pores or micro-wells, that are fluidically connected to micro-fluidic channels. In one embodiment, the fluidically connected channels feed various reagents and enzymes into a series of reaction chambers to enable pre-amplification reactions prior to moving the products into the array of micro-pores or micro-wells, for subsequent Taqman™ or sequencing readout.

Figure 2:
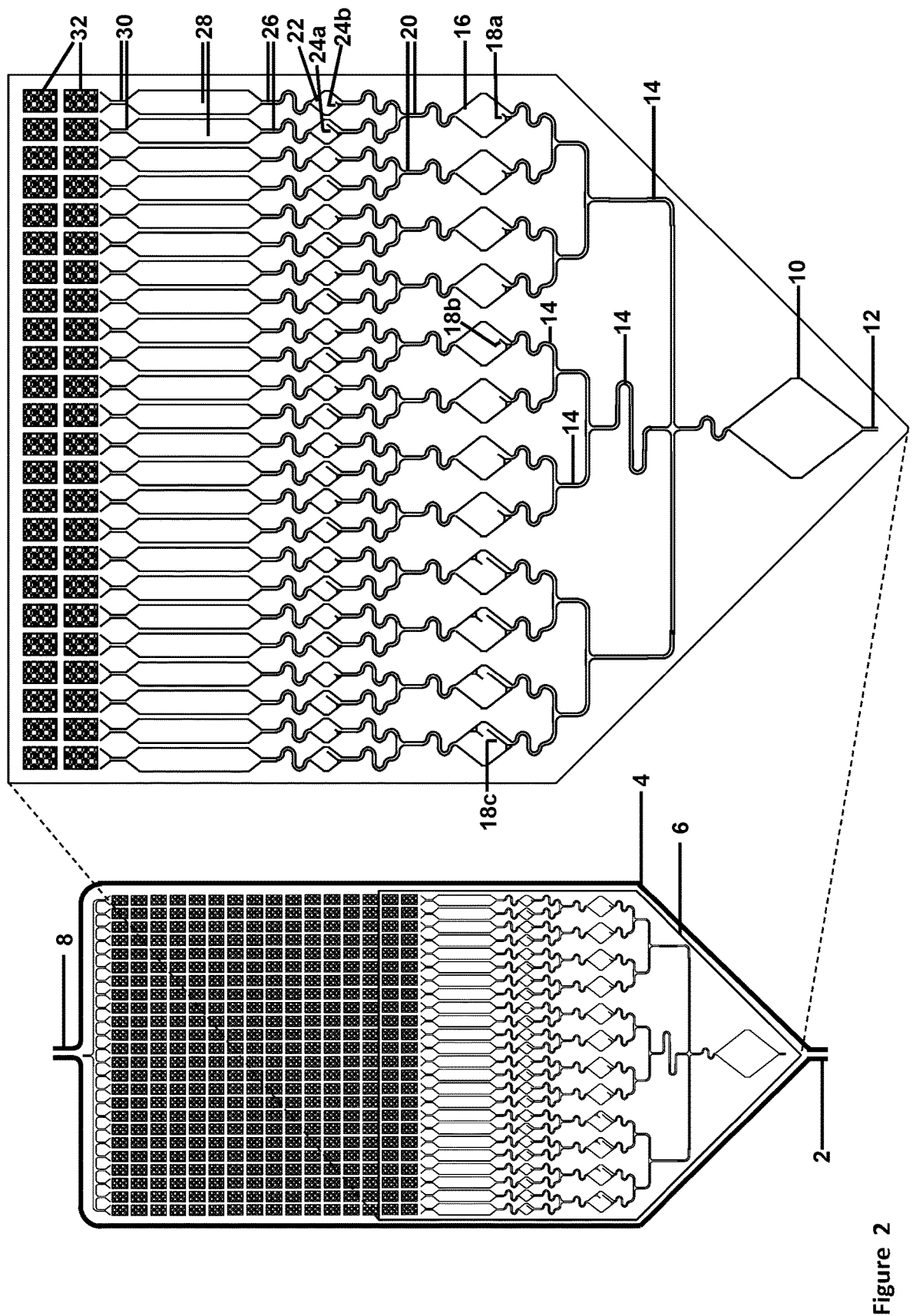
FIG. 2 illustrates a schematic front view of a fluidic connection of micro-channels to the array of micro-wells or micro-pores, with 50-micron diameter.

The left (bottom) portion of FIG. 2 is a schematic front view illustrating fluidic connection of micro-channels to the array of micro-wells or micro-pores, with 50-micron diameter. In this portion of FIG. 2, the microchannels are present in space 6 defined by cartridge 4 having inlet 2 and outlet 8. The right (top) portion of FIG. 2 provides a more detailed view of the components within the cartridge and illustrates a schematic front view of an exemplary design for pre-chambers to allow for liquids to be fluidically moved to the chambers comprising of thousands of micro-wells or micro-pores. This design illustrates chamber architecture suitable for performing Multiplexed RT-PCR-Nested PCR-UniTaq detection, for identifying low- and medium-abundance lncRNA, mRNA, and splice-site variants, isolated from CTC's or exosomes, as will be described below. In this illustration, the sample input is fluidically connected to a large hexagonal chamber 10 (bottom) through entrance 12, which is fluidically connected by conduits 14 to a first set of 12 diamond chambers 16 (4 each containing large troughs 18c, medium troughs 18b, and small troughs 18a, respectively), which are fluidically connected by conduits 20 to a second set of 24 diamond chambers 22 (2 each, containing large troughs 24a and small troughs 24b, respectively), which are fluidically connected by conduits 26 to 24 long narrower mixing chambers 28, which are fluidically connected by conduits 30 to subdivisions 32 comprising of micro-wells or micro-pores (top of panel, with only 2 rows illustrated). The serpentine pathways may be designed to restrict fluid flow, such that all chambers at a given level fill equally. The diagram is not to scale, and is for illustrative purposes.

Figure 3:
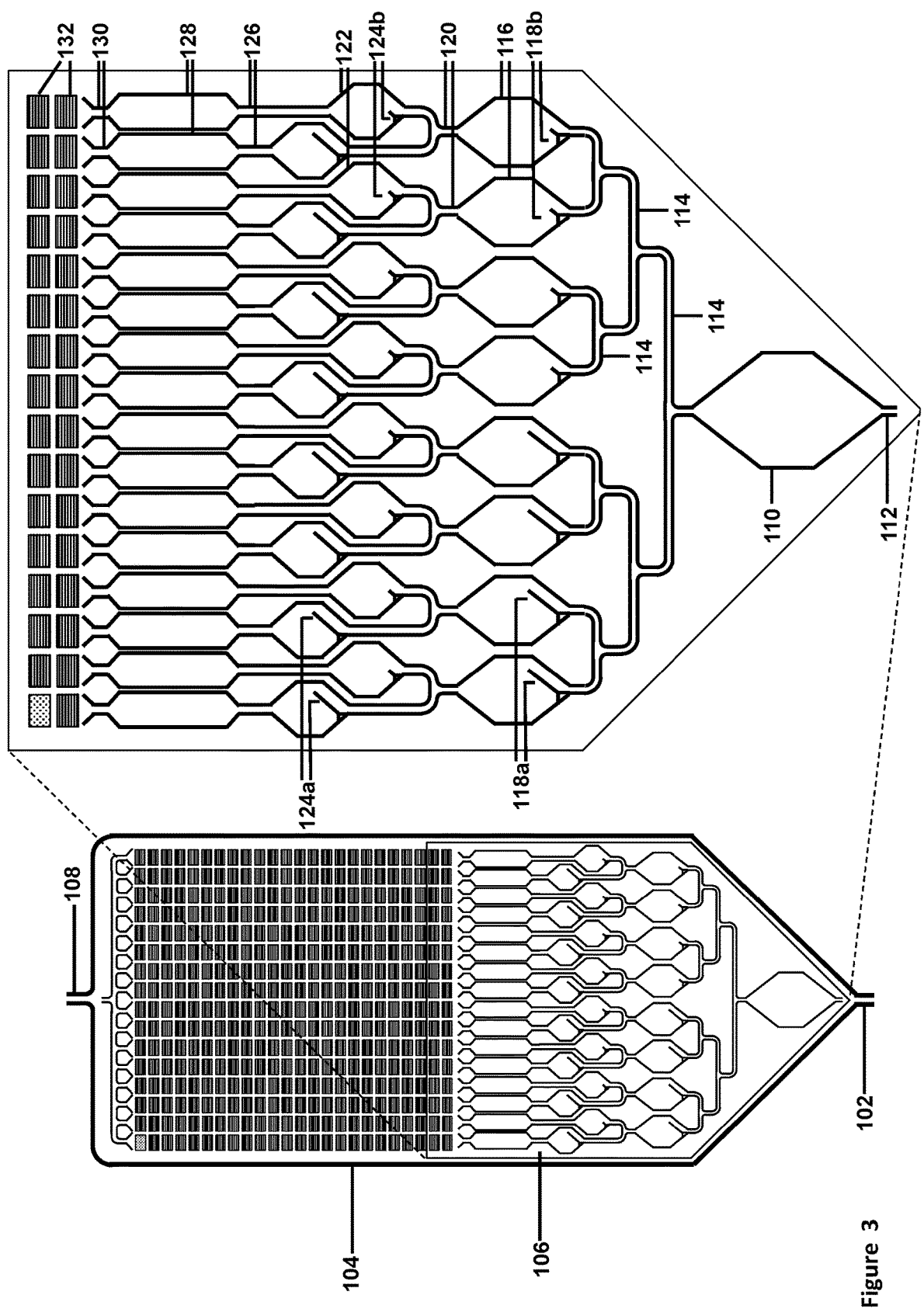
FIG. 3 illustrates a schematic front view of a fluidic connection of micro-channels to the array of micro-pores, with 5-micron diameter.

The left (bottom) portion of FIG. 3 is a schematic front view illustrating fluidic connection of micro-channels to the array of micro-pores, with 5-micron diameter. In this portion of FIG. 3, the microchannels are present in space 106 defined by cartridge 104 having inlet 102 and outlet 108. The right (top) portion of FIG. 3 provides a more detailed view of the components within the cartridge and illustrates a schematic front view of another exemplary design for pre-chambers to allow for liquids to be fluidically moved to the chambers comprising of millions of micro-pores, suitable for Taqman™ or sequencing reactions. In this illustration, the input sample is fluidically connected to a large hexagonal chamber 110 (bottom) through entrance 112, which is fluidically connected by conduit 114 to a first set of 8 hexagonal chambers 116 (4 each containing large troughs 118a and small troughs 118b, respectively), which are fluidically connected by conduits 120 to a second set of 16 hexagonal chambers 122 (2 each containing large through 124a and small troughs 124*b*, respectively), which are fluidically connected by conduit 126 to 16 long narrower mixing chambers 128, which are fluidically connected by conduits 130 to subdivisions 132 comprising of micro-pores (top of panel, with only 2 rows illustrated). The second set of 16 hexagonal chambers 122 are illustrated as slightly offset with each other, to allow for larger liquid volumes in each chamber, while maintaining a tight architecture. The fluidic pathways may be designed to restrict fluid flow, such that all chambers at a given level fill equally. The diagram is not to scale, and is for illustrative purposes.

Figures 4A, 4B, 4C:
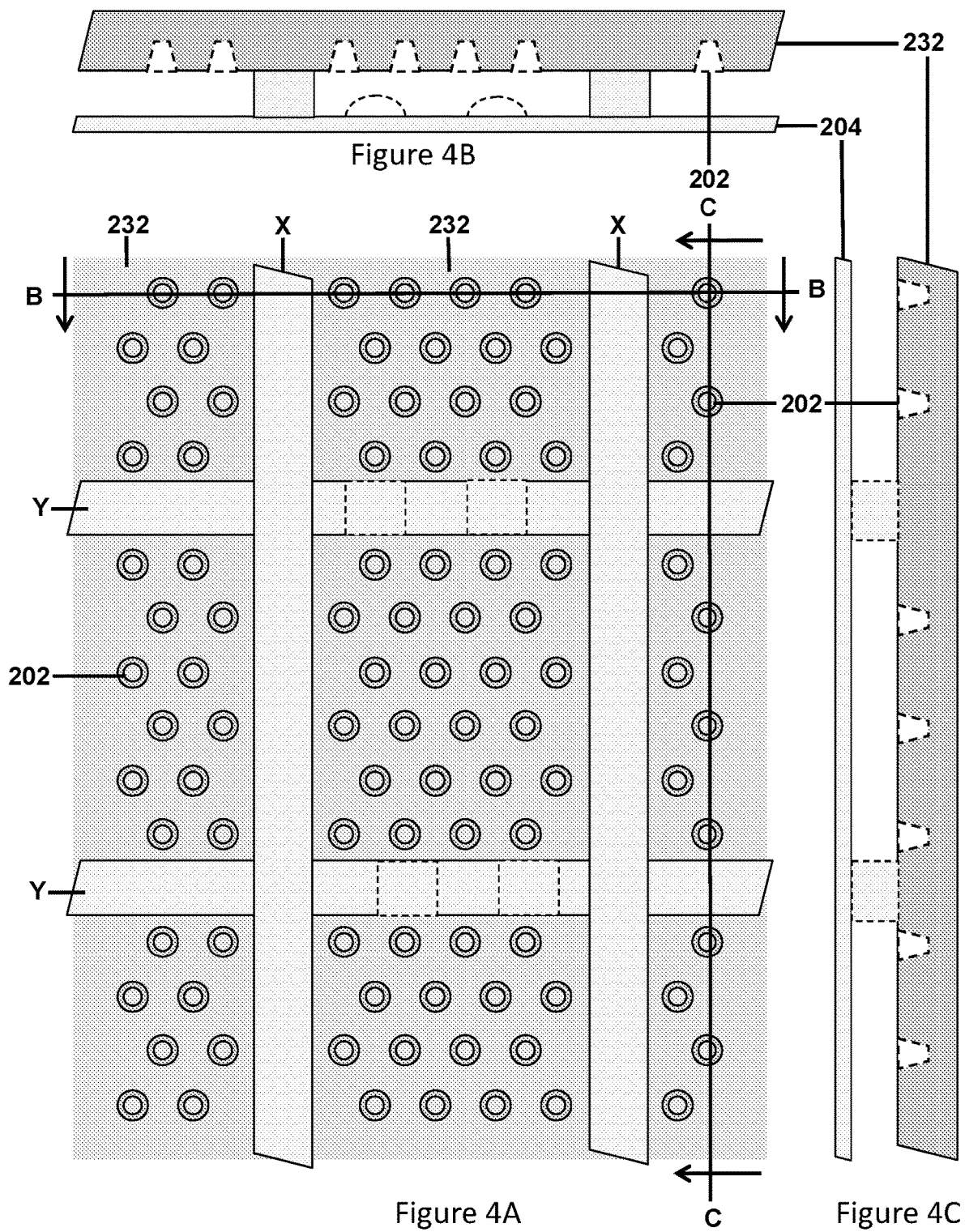
FIGS. 4A-4C illustrate a schematic front view (FIG. 4A), a cross-sectional view taken along line B-B of FIG. 4A (FIG. 4B), and a cross-sectional view taken along line C-C of FIG. 4A (FIG. 4C) views of 50-micron micro-wells in a solid support, showing how ridges between the chambers are connected to a plate to help direct fluidic flow and provide structural stability. The illustration also is relevant for 5 or 2.5-micron micro-pores, except there would be more micro-pores illustrated within each chamber. In one embodiment, the vertical ridges are flush with the top and bottom plates, while the horizontal ridges have indentations or channel enabling liquid to flow up the columns, but not from one column to the next.

FIGS. 4A-4C provide a schematic front (FIG. 4A), a schematic top cross-sectional view taken along line B-B in FIG. 4A (FIG. 4B), and a schematic side cross-sectional view taken along line C-C in FIG. 4A (FIG. 4C) of 50-micron micro-wells in subdivisions 232 of a solid support, with a plate 204 to help direct fluidic flow. The illustration also is relevant for 5 or 2.5-micron micro-pores 202, except there would be more micro-pores illustrated within each chamber. The diagram is not to scale and is for illustrative purposes. It provides an example of hexagonal spacing of the wells. In this embodiment, the interior surfaces of the micro-wells have a hydrophilic surface, while the exterior surface is hydrophobic, such that when flowing aqueous liquid containing target or pre-amplified target and/or primers over the micro-wells, (e.g. from bottom to top), the aqueous liquid fills each micro-well. When subsequently flowing a hydrophobic liquid, (i.e. mineral oil, silicone oil, fluorinated oil, or perfluorodecalin) over the wells, the aqueous liquid will remain in the separate wells covered by the hydrophobic liquid, allowing subsequent enzymatic or amplification reactions to proceed independently in each isolated well.

In one embodiment of FIG. 4, the surface of the plate is hydrophobic. In another embodiment, the surface of the plate is hydrophilic. In one embodiment, liquid is moved in from the bottom and out through the top, with one or more valves controlling input and output from the chambers. Flow of aqueous liquid into the micro-wells from bottom to top may be facilitated by applying positive pressure from the bottom, i.e. pumping the liquid into the chambers with the top part open to air, and/or by applying negative pressure (i.e. pulling a syringe, or partial vacuum) from the top. Flow rates may be adjusted by using different combinations of pressure.

FIGS. 5A-5C provide a schematic front view (FIG. 5A), a schematic top cross-sectional view taken along line B-B in FIG. 5A (FIG. 5B), and a schematic side cross-sectional view taken along line C-C in FIG. 5A (FIG. 5C) of 50-micron micro-pores 202 in subdivisions 232 a solid support, which is like FIGS. 4A-4C, but with front plate 204 and back plate 206. In this illustration, the front of the chambers is the area between the front plate and the micro-pores with the wider diameter, while the back of the chambers is the area between the back plate and the micro-pores with the narrower diameter. The back plate may be pressed against a heating element to allow for temperature control, heating, and/or thermocycling.

Both FIGS. 4A-4C & 5A-5C illustrate how ridges between the subdivisions are connected to plates 204 and 206 to help direct fluidic flow and provide structural stability. The illustration also is relevant for 5 or 2.5-micron micro-pores, except there would be more micro-pores illustrated within each chamber. The diagram is not to scale and is for illustrative purposes. In one embodiment, the vertical ridges are flush with the plates, while the horizontal ridges have indentations or channel enabling liquid to flow up the columns, but not from one column to the next. In another embodiment, suitable for initially pre-filling specific primers in rows, a temporary and complementary plate is used with horizontal ridges that have bumps to close the channels between columns, as well as provide extra height to enable liquid to flow across the rows and not from one row to the next. After filling the rows with desired primer sets, as the liquid evaporates, the primers concentrate onto the hydrophilic surface within the micro-pores, the plate may be removed to facilitate that evaporation, and then the final plate added back on, to enable flow up the columns, through the rows, but not from one column to the next. Ridges on the back of the solid support that contains the micro-pores also are of similar architecture in attaching to the back plate, such that liquid flows up the columns in the back as well. The position of the channels or indentations in the horizontal ridges may be offset to provide desired structural support. The exact dimensions of ridges, indentations, or channels in the horizontal ridges may be optimized to avoid dead-space with suboptimal fluid flow, i.e. in the corner of a given chamber.

FIGS. 6A-6C provide a schematic front view (FIG. 6A), a schematic top cross-sectional view taken along line B-B in FIG. 6A (FIG. 6B), and a schematic side cross-sectional view taken along line C-C in FIG. 6A (FIG. 6C) views of 50, 5, or 2.5-micron micro-pores 202 in a solid support 232, which is like FIGS. 5A-5C, but now illustrating how bottom of the 50, 5, or 2.5-micron micro-pores has another layer 238 of 0.5 micron holes on silicon nitride 200 to 400-nanometers thick, enabling filling of the 50, 5, or 2.5-micron micro-pores with liquid from the front, allowing air, but not liquid to escape through the 0.5-micron pores at the back. In these illustrations, the front of the chambers is the area between front plate 204 and the micro-pores with the wider diameter, while the back of the chambers is the area between the back plate 206 and the micro-pores with the narrower diameter. The back plate 206 may be pressed against a heating element to allow for temperature control, heating, and/or thermocycling. In one embodiment, the surfaces of both plates 204 and 206 are hydrophobic. In another embodiment, the surface of one plate is hydrophilic, while the other is hydrophobic. In another embodiment, the surfaces of both plates are hydrophilic. The diagrams are not to scale and are for illustrative purposes.

In the sections below, descriptions are provided of the different micro-fluidic chamber architecture, as well as illustrations of how the various chambers, micro-wells, and/or micro-pores are filled with liquids suitable for subsequent nucleic acid amplification, detection, and/or sequencing reactions.

FIGS. 7A-7I provide schematic front views of various designs for pre-chambers that can undergo various tasks involving mixing different reagents, undergoing various amplification reactions, or saving a portion of said amplification reaction for subsequent use in the next reaction, or for fluidically moving liquids to the chambers comprising of micro-wells or micro-pores. In general, the fluids enter from the bottom port and exit from the top port. In several follow-up examples, multiple chambers of the same size and type are filled simultaneously. In these examples, the chambers are made of generally hydrophobic material, the liquid is hydrophilic, and in the examples, a small amount of low-density hydrophobic oil (i.e. mineral oil) is used to seal the top of each chamber to allow for thermocycling without losing the aqueous portion of the liquid. Optionally, chasing behind the aqueous liquid may be a denser hydrophobic liquid such as fluorinated oil, or perfluorodecalin to seal the bottom of these chambers. Further, the density and viscosity of the aqueous layer may be adjusted using additives such as glycerol (which does influence enzymatic activity when used above 10% v/v), or other compounds that enhance enzyme stability or enhance amplification of GC-rich targets, such as betaine, ectoine, hydroxyectoine, mannosylglycerate, mannosylglyceramide, diglycerol phosphate, or other sugars or sugar derivatives. In FIG. 7A, a small plug of mineral oil leads the aqueous reaction components as the liquid is pumped into the chamber. The mineral oil reaches the top exit port and seals the chamber, the chamber is filled with aqueous liquid, and the bottom entry port is sealed with fluorinated oil. After thermal cycling (or other reaction), the liquids are withdrawn, leaving behind a small volume of aqueous liquid held in the shallow trough on the left of the entry port. When new reagents are introduced, they will mix with the amplification products of the previous reaction. FIG. 7B is the same as FIG. 7A; however, a greater amount of the product is retained in the trough. FIG. 7C is the same as FIG. 7A; however, almost half of the product is retained in the trough. FIG. 7D is a variation of FIG. 7A, where some primer sets may be printed in the second trough on the right. Under these conditions, products from a first reaction in a lower chamber may be fluidically pushed into this second chamber, such that they fill the first (left-side) trough, but do not go above the second trough. The fluids are removed leaving behind a small volume of aqueous liquid held in the shallow trough on the left of the entry port. When new reagents are introduced, they will mix with the amplification products of the previous reaction, as well as the primers deposited in the second trough. In this manner, a primary PCR may be followed by a secondary LDR or PCR reaction. Note that when withdrawing liquid from the secondary reaction, products are left behind in both the left and right-side troughs. FIG. 7E is a variation of FIG. 7D, with the first trough being larger to retain more of the first set of products. FIG. 7F is like FIG. 7C, except a second piece of plastic assures that the second reaction fluid is directed downward to fully mix with products previously remaining from the first reaction. FIG. 7G is like FIG. 7A, except for introducing the reagents from the side instead of the bottom so that the chamber can retain some product from the first reaction for subsequent mixing with a second reaction. FIG. 7H is like FIG. 7G; however, a greater amount of product is retained in the bottom of the chamber. In FIG. 7I, the chamber is like FIG. 7H, with some additions. When mineral oil is pushed up the entrance, some enters the two thin hydrophobic tubes, while the rest enters the side of the chamber. This is followed by aqueous liquid, which does not enter the thin hydrophobic openings, but completely pushes into the reaction chamber, with a small plug of mineral oil ahead of it. The mineral oil reaches the top exit port and seals the chamber, the chamber is filled with aqueous liquid, the two thin tubes are also filled with mineral oil, and the bottom entry port is sealed with fluorinated oil. After the reaction, when withdrawing liquid, the mineral oil empties from the two thin tubes, and air follows. Whatever products are created in the chamber stay there. These may be fluidically be pushed into the next chamber when sufficient aqueous fluid is added to push the liquid past the top air opening.

FIGS. 8A-8C provide schematic front views of various designs for pre-chambers to allow for liquids in conduits 14, 20, 26, and 30 to be fluidically moved to the chambers comprising of micro-wells or micro-pores. FIG. 8A is an example of fluidically coupling primers and/or probes (gray circles 17) within 8 chambers 16 that then empty by way of conduits 26 into longer narrower chambers 28 and subdivisions 32 of micro-wells or micro-pores, for ultimately drying down within or covalently linking to the interior surfaces of micro-wells or micro-pores. In one embodiment, during manufacture of the cartridge, rows are pre-filled with 1-4 UniTaq primer sets (or alternatively, 1-4 universal tag primer sets with target-specific Taqman™ probes). In one embodiment, a temporary plate is used to provide a fluidic pathway across the rows of micro-wells or micro-pores, while isolating each row from each other. The grey circles on the top of the drawing illustrate potential position for delivering or printing primer sets, for example by acoustic droplet ejection, capillary, inkjet, or quill printing. After printing, microfluidic channels may be used to distribute primer sets into each row and dried down into individual micro-wells or micro-pores. Once the primer sets are appropriately delivered and dried in place, the temporary plate is removed, and replaced with the permanent cover to provide a fluidic pathway up the columns of micro-wells or micro-pores, while isolating each column from its neighbor column. FIG. 8B is an example of fluidically coupling reagents to 4+4 chambers 16 and 22, with troughs 18 and 24 and baffles 23, that then empty into longer narrower chambers 28 and then to conduits 30 and subdivisions 32. In this illustration, the gray circles 25 represent specific primers suitable for polymerase and/or ligase-based DNA amplification reactions. The left side of the longer chambers are coated with, or made from, plastic that is very hydrophobic, while the right side is either barely hydrophobic, or somewhat hydrophilic. When a small plug of mineral oil is pushed out of the initial chambers it naturally migrates towards the left, allowing the aqueous reactants that follow it to sweep directly into the columns comprising of micro-wells or micro-pores (upper portion of figure). Thus, if filling the micro-wells or micro-pores is best served by first being exposed to aqueous liquid (to avoid trapped air bubbles occluding movement of liquid), then this trick removes the mineral oil out of the way. FIG. 8C is a schematic like FIG. 8B, where there of fluidically coupling reagents to 4 chambers 16, with troughs 18 and baffles 19 that then empty into longer narrower chambers 28 and then to subdivisions 32. In this illustration, the gray circles 17 represent specific primers suitable for polymerase and/or ligase-based DNA amplification reactions. FIG. 8C illustrates an extra plastic ridge or divider 29 helping keep the hydrophobic oil separate from and not mixing with the follow-on aqueous solution as it is pumped up through the chambers.

FIGS. 9A-9B provide schematic side views of embodiments for filling micro-pores, as illustrated from FIG. 5B and FIG. 6B. In these illustrations, the interior sides of the micro-pores 202 are hydrophilic, while the other surfaces are hydrophobic. In one embodiment, different primers and probes are printed, for example by acoustic droplet ejection, capillary, inkjet, or quill printing (see FIG. 8A), in pre-chambers suitable for fluidically moving into the array of micro-pores. Front plate 204 is shown above channel 240 in FIGS. 9A and 9B. FIG. 9A illustrates micro-pores 202 open from both the top and bottom within solid support 232. Primers (and probes) are fluidically introduced into the micro-pores from the top channel 240, while simultaneously oil (preferably with higher density than the aqueous solution) is introduced from the bottom channel 242 which is formed with back plate 206. Subsequently the aqueous solution is chased from the top channel 240 with oil (with lower density), such that the primers/probes are fluidically isolated. If the primers are to be covalently immobilized to the surface, that chemistry may take place when both the top channel 240 and bottom channel 242 are filled with oil.

Alternatively, the primers may be immobilized by capture, for example biotinylated primers may be captured by streptavidin-coated surfaces. If the primer-probes are for subsequent drying, then they may be formulated in a volatile salt, such as ammonium acetate, or alternatively, may have a stabilizing buffer, comprising of betaine, ectoine, hydroxyectoine, mannosylglycerate, mannosylglyceramide, diglycerol phosphate, or other sugars or sugar derivatives. Subsequently, the top oil may be chased with a volatile organic (i.e. hexanol) that is not miscible with aqueous solution in the micro-pores. The volatile organic may be chased with air, and in the presence of mild heat, the aqueous evaporates, leaving the desired primers and probes dried to the interior surface of the micro-pores. Oil on the bottom may also be chased with a volatile organic, followed by air to dry the array chamber. Alternatively, when the primers are immobilized to the interior surface of the micro-pores 202, excess primers are washed away before adding an optional volatile organic (i.e. ethanol) and drying down. FIG. 9B illustrates micro-pores 202 within the solid support 232 open from the top channel 240 (formed with plate 202) and have another layer 238 of 0.5-micron holes on silicon nitride 200 to 400-nanometers thick, enabling filling of the 50, 5, or 2.5-micron micro-pores with liquid from the front via channel 240, allowing air, but not liquid to escape through the 0.5-micron pores at the bottom channel 242 (formed with back plate 206). In this illustration, oil is added to the bottom channel 242 to enable subsequent heating of reactants within the micro-pores 202 if needed during the optional primer immobilization step. In other embodiments, e.g. adding primer/probes without immobilization, the use of oil in the bottom and/or top chamber may be optional.

FIG. 10 provides a schematic front view of embodiments for filling reaction chambers prior to filling the micro-wells or micro-pores of subdivisions 32. The setup comprises two sets of reaction chambers 16 and 22 fed by conduits 14 and 20, each having a trough 18 and 24, and the second set is pre-spotted with appropriate ligation probe oligonucleotides (gray circle 25). The left side illustrates a schematic diagram of a portion of the micro-fluidics and chambers for the initial multiplexed PCR pre-amplification, and a subsequent ligase detection reaction (LDR) prior to Taqman™ readout in the micro-pore array. In the next panel, a light-oil cap is introduced at the bottom into conduit 14, this is then followed by an aqueous liquid comprising of target, PCR primers, and PCR reagents, and this aqueous reaction mixture is then fluidically moved into the first set of reaction chambers 16 using heavy oil. After the PCR thermocycling step, the oils and most of the aqueous reaction are drained by way of conduit 14, but a small portion of the PCR product is retained in the trough 18 of each of the two initial chambers 16. The chambers are again filled through conduit 14 with light oil, followed by LDR reagents and enzymes, and this aqueous reaction mixture is then fluidically moved into the second set of reaction chambers 22 (where it mixes with the pre-spotted LDR primers) using heavy oil. Reaction chambers 22 empty by way of conduits 26 into reaction chambers 28 (which is divided by plastic ridge or divider 29) and by way of conduit 30 into subdivisions 32 of micro-wells or micro-pores. After the LDR thermocycling step, once again, the reagents are drained, but the LDR product is retained in the trough 24. This product is now suitable for fluidically combining with PCR mastermix and being moved into the micro-pore array for subsequent Taqman™ reactions, as explained in the FIGS. 11A-B.

FIGS. 11A-11B provide schematic side views of embodiments for filling micro-pores 202, as illustrated from FIG. 5C and FIG. 6C, for performing real-time PCR reactions, such as Taqman™ or UniTaq reactions. In FIGS. 11A-11B, front plate 204 is shown to the left of channel 240 and back plate 206 is shown to the right of channel 242. The illustrations start with micro-pores 202 in solid support 232 that have been pre-filled with 1-4 UniTaq primer sets (or alternatively, 1-4 universal tag primer sets with target-specific Taqman™ probes), and dried down. In one embodiment, the interior surfaces of the micro-pores 202 have a hydrophilic surface, while the exterior front 244 and back 246 surfaces are hydrophobic, such that when flowing aqueous liquid containing target or pre-amplified target and/or primers over the micro-pores, (e.g. from bottom through channel 242 to the top through channel 240 from the front side 244 where the pores have a wider diameter), the aqueous liquid fills each micro-pore. In one embodiment, liquid is moved in channel 240 or 242 from the bottom and out through the top in channel 240 or 242, respectively, with one or more valves controlling input and output from the chambers. In one embodiment, fluid input and output in the front and back of the chambers is modulated or controlled by separate valves or applying separate pressures. Flow of aqueous liquid into the micro-pores from bottom to top may be facilitated by applying positive pressure from the bottom through channel 240 or 242, i.e. pumping the liquid into the chambers with the top part open to air, and/or by applying negative pressure (i.e. pulling a syringe, or partial vacuum) from the top. Flow rates may be adjusted by using different combinations of pressure from top, bottom, front or back. For illustrative purposes, consider the task of filling the micro-pores 202 with aqueous liquid suitable for subsequent individualized amplification within the micro-pores 202. In FIG. 11A, all surfaces including front 244 and back 246 are hydrophobic, except the inside surfaces of the micro-pores 202. As aqueous fluid is pumped using positive pressure from the bottom front it enters the micro-pores 202 from the front 244 through channel 240, displaces air out the back 246 through channel 242 and forms a meniscus in the back of the pores 202. To avoid having the weight of the aqueous liquid build as it rises on the front to create sufficient pressure to push liquid out the back of micro-pores that are filled initially, hydrophobic liquid is pumped from the bottom back 246 through channel 242 so it covers the aqueous meniscus in the back of the pores 202 shortly after they are formed. Optimal pressure height differences can be experimentally determined, and will be a function of liquid viscosity, liquid density, difference in liquid volume, as well as hydrophobicity of the outside surfaces of the solid support with the micro-pores. As the aqueous liquid fills the micro-pores 202 from the front 244 through channel 240, a hydrophobic liquid (i.e. heavy oil) is flowed in from the front 244 through channel 240, to chase the aqueous liquid out of the non-productive volume and into the micro-pores 202, while simultaneously covering each separate micro-pore 202 on the front 244 with oil. Thus, the micro-pores are each filled with aqueous liquid, and sealed on the front 244 and back 246 with hydrophobic liquid. Each micro-pore 202 is fluidically isolated and suitable for subsequent independent amplification and thermal cycling reactions. In FIG. 11B, all surfaces are hydrophobic, except the inside surfaces of the micro-pores 202, and the silicon nitride 238 with the 0.5-micron holes. As aqueous fluid is pumped using positive pressure from the bottom front 244 through channel 240 it enters the micro-pores 202 from the front 244, displaces air out the back 246 through channel 242 and does not push liquid through the 0.5-micron silicon nitride pores. As the aqueous liquid fills the micro-pores 202 from the front 244, oil is flowed in from the front 244 through channel 240, to chase the aqueous liquid out of the non-productive volume and into the micro-pores 202, while simultaneously covering each separate micro-pore 202 on the front 244 with oil. The back of the chambers may be filled with humidified air and heated to eventually heat the aqueous liquid in the micro-pores. Alternatively, the back 246 through channel 242 of the chambers may also be filled with oil as illustrated. Thus, the micro-pores 202 are each filled with aqueous liquid, and sealed on the front and back with oil. Each micro-pore is fluidically isolated and suitable for subsequent independent amplification and thermal cycling reactions.

FIG. 12 provides a schematic side view of embodiments for filling micro-pores, as illustrated from FIGS. 6A-6C, for performing sequencing reactions. In FIG. 12, front plate 204 is shown to the left of channel 240 and back plate 206 is shown to the right of channel 242. In this example, all surfaces, including front 244 and back 246, are hydrophobic, except the inside surfaces of the micro-pores 202, and the silicon nitride 238 with the 0.5-micron holes. As aqueous fluid is pumped using positive pressure from the bottom front 244 through channel 240, it enters the micro-pores 202 from the front 244, displaces air out the back 246 through channel 242 and does not push through the 0.5-micron silicon nitride pores. As the aqueous liquid fills the micro-pores 202 from the front 244, oil is flowed in from the front 244, to chase the aqueous liquid out of the non-productive volume and into the micro-pores, while simultaneously covering each separate micro-pore on the front 244 with oil. The back 246 in channel 242 is also filled with oil. Thus, the micro-pores 202 are each filled with aqueous liquid and sealed on the front 244 and back 246 with oil. Each micro-pore 202 is fluidically isolated and suitable for subsequent independent thermal cycling reactions to amplify and immobilize template strands onto the solid support on the interior surface of the pores. The oil is chased from the front 244 through channel 240, while opposite strand product is denatured and with other products and primers washed away. A heavy oil plug is used to plug the bottom of the front 244 at channel 240 while the back 246 through channel 242 is rinsed (e.g. ethanol), optionally air-dried, and now the array has immobilized target strands clonally amplified within micro-pores 202 suitable for sequencing. Flow of aqueous liquid into the micro-pores from bottom at back 246 to top front 244 and back 246 may be facilitated by applying positive pressure from the bottom, i.e. pumping the liquid into channels 240 and 242 with the top part open to air, and/or by applying negative pressure (i.e. pulling a syringe, or partial vacuum) from the top. Flow rates may be adjusted by using different combinations of pressure, or restricting the opening at the top back, thus assuring that most of the sequencing reagents volume enters through the bottom back 246, but flows through the micro-pores 202 and out the top front 244. An additional advantage of using the silicon nitride layer 238 on the back-side of the micro-pores 202 is that aqueous liquid added from the front side 244 will not break the air interface on the back side 246, but if the back 246 at channel 242 is filled with aqueous liquid, they will flow freely through the 0.5 micron holes to the front 244 of the micro-pores 202. This provides increased flexibility in reagent addition and washing in or out different reagents in subsequent sequencing reactions.

FIGS. 13A-13B provide schematic front views of the chamber format using micro-wells or micro-pores as described in FIGS. 1 and 6A-6C. FIG. 13A shows an overview of the micro-well format where within cartridge 304 defining space 306 the subdivisions 332 are 800-micron wide×1200-micron long (drawn as rectangular sections), comprising of 96-micro-wells with 50-micron diameter. Additional 200-micron wide ridges 350 are used between subdivisions 332 to provide separation of subdivisions and additional structural support. These are represented as the "white" areas between the rows and columns of rectangular subdivisions 332. In this schematic illustration, for simplicity, 32 columns×32 rows are shown; other embodiments include 48 columns×48 rows, and 64 columns×64 rows. FIG. 13B shows an overview of microfluidic chambers for sequencing on an array of micro-pores in a microtiter plate format. In this schematic illustration, within cartridge 404 defining space 406, are 32 double-columns×32 double-rows are shown, and in the magnification, only 2 double-columns and 1 double-row of subdivisions 432 (spaced by white ridges 450) comprising 2,072 micro-pores each are shown; other embodiments include 48 double-columns×48 double-rows, 64 double-columns×64 double-rows; while still other embodiments include 96 columns×96 rows and 128 columns×128 rows. In one embodiment, feeding into the chambers through inlet containing the micro-pores are a series of individual openings that may be fluidically closed or open to entry of reagents, enzymes, targets or pre-amplified targets up all the chambers in a column using acoustic droplet ejection. Entry of fluids into the individual openings through inlet 402 when using acoustic droplet ejection may be facilitated by applying negative pressure from the other side (i.e. vacuum), and/or by feeding the droplets in conduit 455 into a series of hydrophilic input chambers 452 and conduits 454 and transitions 456, that subsequently feeds into subdivisions 432 having the columns of micro-pores. In this schematic illustration, each individual opening is connected to a hydrophilic input chamber 452, which feeds into two columns of subdivisions 432 containing micro-pores. In addition, the chambers are also fluidically coupled to allow for entry of reagents from one entry port into all the chambers and exit on the other side into a single waste or exit port 408. Once the hydrophilic input chamber 452 is properly filled with the reagents, enzymes, targets or pre-amplified targets, those openings are closed, and then oils or other reagents are added through the one entry port to fluidically move the input solutions into the micro-pores for further reactions.

Alternative configurations for micro-wells or micro-pores may also be considered. OpenArray technology is available through ThermoFisher (Carlsbad, Calif.). This technology uses a metal microscope slide-sized plate with 3,072 through-holes, which may be configured into a variety of different ways. For example, the plate may be divided into 48 subarrays with 64 through-holes or micro-pores (each subarray is in the same spacing as a traditional 384 well microtiter plate. As currently configured, each through-hole is 300-microns in diameter and 300-micron deep, wherein the through-hole is hydrophilic or has a hydrophilic coating, but the front and back surface of the plate has a hydrophobic coating. Thus, aqueous reagents are retained in the through-holes via surface tension. After filling the through holes with the appropriate amplification and detection primers, these primers may be dried onto the inner surface of the through-holes. Subsequently, addition of the sample, enzymes, and appropriate buffer solubilizes the primers, while use of hydrophobic liquid (i.e. mineral oil) on both sides seals the reactions in place in each through-hole. This technology could be extended by manufacturing the through-holes with 60-micron diameter, which would enable about 1,225 through-holes per subarray for a total of 58,800 through-holes or micro-pores per microscope slide-sized plate.

Another system, also developed by ThermoFisher is the QuantStudio 3D digital PCR 20K Chip, comprising of a silicon substrate that has been etched to contain 20,000 micro-wells of 60-micron diameter. Primers, reagents, and enzyme are added, the plate is sealed to distribute the liquid into the micro-wells, and the reaction is run—the limitation being that only a single reaction may be performed on the chip. Another system is being developed by Formulatrix (Bedford, Mass.) and is known as the Constellation Digital PCR system. In this system, a standard microtiter plate is divided into either 24 chambers comprising 32,000 micro-wells (of about 50-micron diameter) or 96 chambers comprising 8,000 micro-wells. This design is also compatible with use of 24 chambers comprising 200,000 micro-wells (of about 20-micron diameter), 96 chambers comprising 50,000 micro-wells, or 384 chambers comprising 12,500 micro-wells. Each chamber has an input well that is fluidically coupled to an input channel, which is fluidically coupled to numerous connecting channels comprising of individual partitions, and then all the connecting channels are fluidically coupled to an output channel, which has a vent or air-hole. At the bottom of the channel is a clear plastic suitable for sealing to the plate. Primers, reagents, and enzyme are added to the input well and fluidically pumped through the input channel, and the connecting channels, with excess moving into the output channel and vent. Subsequently, a roller is used to compress the bottom seal, which blocks off the channels, such that each partition becomes an isolated micro-well suitable for thermocycling and digital PCR readout. This system may be modified, such that the bottom plastic only forms a temporary seal, either by using pressure to temporarily block off the connecting channels and create the partitions (micro-wells) only during the amplification reaction, or a temporary sealant that may be subsequently dissolved. For subsequent sequencing reactions, after amplification and immobilization of targets in individual partitions (micro-wells), the bottom plastic may be unsealed, unreacted reagent and products that are not covalently immobilized may be denatured and washed away. The resulting clonally amplified single-stranded targets are suitable for subsequent sequencing-by-synthesis reactions, as described below or as known in the art.

FIG. 14 provides a schematic side view of the micro-titer plate format 500 using micro-wells 302 in solid support 332 as described in FIG. 13A, suitable for pre-filling with appropriate primers and probes. Step A shows the side view of one chamber within the hydrophobic plate, comprising of 50-micron hydrophilic wells with ridges 350 on each side. In step B, the plate is flipped upside-down and filled with with 1-4 UniTaq primer sets (or alternatively, 1-4 universal tag primer sets with mutation or methylation-specific Taqman™ probes) using acoustic droplet ejection. In step C, the plate is centrifuged, spreading the aqueous liquid to the empty micro-wells, while step D illustrates that after centrifugation, droplets will form over the micro-wells as the aqueous solution avoids the hydrophobic surface. In step E, the aqueous solution is evaporated, leaving the dried primer/probe sets in the well (Illustrated in Step F).

FIG. 15 provides a schematic side view of the micro-titer plate format using micro-wells 302 in solid support 332 and ridges 350 as described in FIG. 13, Panel A, and optionally pre-filled with the appropriate Taqman™ or UniTaq primers and probes (as Illustrated). Step A shows the side view of one chamber within the hydrophobic plate, comprising of 50-micron hydrophilic wells with ridges on each side. In step B, the plate is flipped upside-down and filled with reagent suitable for real-time amplification (i.e. Taqman™ reaction) and target DNA, using acoustic droplet ejection. The PCR primers and Taqman™ probe(s) may have been previously added to the chambers and dried down (as illustrated in FIG. 14), or alternatively are added along with the target, enzyme, and reagents. In step C, overlay the aqueous layer with hydrophobic mineral oil. In step D, the plate is transferred to a swinging bucket rotor for centrifugation. The denser aqueous liquid spreads to empty micro-wells. In step E, the plate is moved to the thermocycler. The droplets separate into individual micro-wells covered by mineral oil and suitable for amplification.

One aspect of the present invention is directed to a method for identifying, in a sample, a plurality of nucleic acid molecules containing a target nucleotide sequence differing from nucleotide sequences in other nucleic acid molecules in the sample, or other samples, by one or more nucleotides, one or more copy numbers, one or more transcript sequences, and/or one or more methylated residues. This method involves providing a sample potentially containing one or more nucleic acid molecules containing the target nucleotide sequence differing from the nucleotide sequences in other nucleic acid molecules by one or more nucleotides, one or more copy numbers, one or more transcript sequences, and/or one or more methylated residues. One or more primary oligonucleotide primer sets are provided, each primary oligonucleotide primer set comprising (a) a first primary oligonucleotide primer that comprises a nucleotide sequence that is complementary to a sequence adjacent to the target nucleotide sequence, and (b) a second primary oligonucleotide primer that comprises a nucleotide sequence that is complementary to a portion of an extension product formed from the first primary oligonucleotide primer. The contacted sample is blended with the one or more primary oligonucleotide primer sets, a deoxynucleotide mix, and a DNA polymerase to form a polymerase chain reaction mixture, and the polymerase chain reaction mixture is subjected to one or more polymerase chain reaction cycles comprising a denaturation treatment, a hybridization treatment, and an extension treatment, thereby forming primary extension products comprising the target nucleotide sequence or a complement thereof. The initial PCR products are distributed into 24, 36, or 48 Primary PCR Reaction Chambers. The method further involves blending the primary extension products with a polymerase, and one or more secondary oligonucleotide primer sets to form a secondary polymerase reaction mixture. Each secondary oligonucleotide primer set comprising (a) a first secondary oligonucleotide primer that comprises a 5' primer-specific portion and a nucleotide sequence that is complementary to a sequence adjacent to and/or comprising the target nucleotide sequence, and (b) a second secondary oligonucleotide primer that comprises a 5' primer-specific portion and a nucleotide sequence that is complementary to a portion of an extension product formed from the first secondary oligonucleotide primer. The contacted sample is blended with the one or more secondary oligonucleotide primer sets, a deoxynucleotide mix, and a DNA polymerase to form a polymerase chain reaction mixture, and the polymerase chain reaction mixture is subjected to one or more polymerase chain reaction cycles comprising a denaturation treatment, a hybridization treatment, and an extension treatment, thereby forming primary extension products comprising the target nucleotide sequence or a complement thereof. The secondary extension product sequences in the sample are detected and distinguished to identify the presence of one or more nucleic acid molecules containing target nucleotide sequences differing from nucleotide sequences in other nucleic acid molecules in the sample by one or more nucleotides, one or more copy numbers, one or more transcript sequences, and/or one or more methylated residues.

FIGS. 16-18 illustrate various embodiments of this aspect of the present invention.

FIG. 16 (steps A-F) illustrates an exemplary PCR-PCR-qPCR for unknown pathogen identification. This method starts by isolating pathogen genomic DNA as shown in step A. If the pathogen is an RNA virus, an initial reverse-transcriptase step is used to generate cDNA. As shown in FIG. 16 (step B), the sample is subject to an amplification reaction, e.g., a polymerase chain reaction (PCR) to amplify target-containing regions of interest in an Initial Reaction Chamber. The multiplexed PCR amplification reaction is carried out using locus specific primers and a deoxynucleotide mix. In one embodiment, limited cycle amplification (12-20 cycles) is performed to maintain relative ratios of different amplicons being produced. In another embodiment, primers contain identical 8-11 base tails on their 5' ends to prevent primer dimers from amplifying. Distribute initial PCR products into 24, 36, or 48 Primary PCR Reaction Chambers.

As shown in FIG. 16 step C, target-specific oligonucleotide secondary primers are hybridized to the primary amplified products and polymerase (filled diamond) is used to amplify target-containing regions of interest. As illustrated in step C of this figure, another layer of specificity can be incorporated into the method by including a 3' cleavable blocking group (Blk 3', e.g. C3 spacer), and an RNA base (r), in the secondary primers. Upon target-specific hybridization, RNase H (star symbol) removes the RNA base to generate a polymerase extension competent 3'OH group (FIG. 16, step C). The first secondary oligonucleotide primer contains a 5' primer-specific portion (Ai) and the second secondary oligonucleotide primer contains a 5' primer-specific portion (Ci) that permits subsequent amplification of the secondary amplification products. Following the secondary amplification reaction, the extension products from each Primary PCR Reaction Chamber are distributed into 384 or 768 micro-wells or micro-pores containing one or more tag-specific primer pairs, each pair comprising of matched primers Ai and Ci, PCR amplified, and detected. As shown in FIG. 16, steps E & F, detection of the PCR product can be carried out using traditional TaqMan™ detection assay (see U.S. Pat. No. 6,270,967 to Whitcombe et al., and U.S. Pat. No. 7,601,821 to Anderson et al., which are hereby incorporated by reference in their entirety). For detection using TaqMan™ an oligonucleotide probe spanning the target region is used in conjunction with primers suitable for hybridization on the primer-specific portions of the secondary PCR products for amplification and detection. The TaqMan™ probe contains a fluorescent reporter group on one end (F1) and a quencher molecule (Q) on the other end that are in close enough proximity to each other in the intact probe that the quencher molecule quenches fluorescence of the reporter group. During amplification, the TaqMan™ probe and upstream primer hybridize to their complementary regions of the ligation product. The 5'→3' nuclease activity of the polymerase extends the hybridized primer and liberates the fluorescent group of the TaqMan™ probe to generate a detectable signal (FIG. 16, step F).

FIG. 17 (steps A-F) illustrates an exemplary PCR-PCR-qPCR for unknown pathogen identification. This method starts by isolating pathogen genomic DNA as shown in step A. If the pathogen is an RNA virus, an initial reverse-transcriptase step is used to generate cDNA. As shown in FIG. 17 (step B), the sample is subject to an amplification reaction, e.g., a polymerase chain reaction (PCR) to amplify target-containing regions of interest in an Initial Reaction Chamber. The multiplexed PCR amplification reaction is carried out using locus specific primers and a deoxynucleotide mix. In one embodiment, limited cycle amplification (12-20 cycles) is performed to maintain relative ratios of different amplicons being produced. In another embodiment, primers contain identical 8-11 base tails on their 5' ends to prevent primer dimers from amplifying. Distribute initial PCR products into 24, 36, or 48 Primary PCR Reaction Chambers.

The UniTaq system is fully described in U.S. Patent Application Publication No. 2011/0212846 to Spier, which is hereby incorporated by reference in its entirety. The UniTaq system involves the use of three unique "tag" sequences, where at least one of the unique tag sequences (Ai) is present in the first oligonucleotide primer, and the second and third unique tag portions (Bi and Ci) are in the second oligonucleotide primer sequence as shown in FIG. 17, step C. Upon PCR amplification of the oligonucleotide primers in a primer set, the resulting extension product will contain the Ai sequence—target specific sequences—Bi' sequence—Ci' sequence. The essence of the UniTaq approach is that both secondary oligonucleotide primers of a PCR primer set need to be the correct matched set to generate a positive signal, which allows for highly multiplexed nucleic acid detection. For example, and as described herein, this is achieved by requiring hybridization of two parts, i.e., two of the tags, to each other.

As shown in FIG. 17 step C, target-specific oligonucleotide secondary primers are hybridized to the primary amplified products and polymerase (filled diamond) is used to amplify target-containing regions of interest. As illustrated in step C of this Figure, another layer of specificity can be incorporated into the method by including a 3' cleavable blocking group (Blk 3', e.g. C3 spacer), and an RNA base (r), in the secondary primers. Upon target-specific hybridization, RNase H (star symbol) removes the RNA base to generate a polymerase extension competent 3'OH group (FIG. 17, step C). The first secondary oligonucleotide primer contains a 5' primer-specific portion (Ai) and the second secondary oligonucleotide primer contains a 5' primer-specific portion (Bi, Ci) that permits subsequent amplification and detection of the secondary amplification products. Following the secondary amplification reaction, the extension products from each Primary PCR Reaction Chamber are distributed into 384 or 768 micro-wells or micro-pores containing one or more tag-specific primer pairs, each pair comprising of matched primers (F1-Bi-Q-Ai and Ci). For detection, the secondary PCR product containing Ai (a first primer-specific portion), Bi' (a UniTaq detection portion), and Ci' (a second primer-specific portion) is primed on both strands using a first oligonucleotide primer having the same nucleotide sequence as Ai, and a second oligonucleotide primer that is complementary to Ci' (i.e., Ci). The first oligonucleotide primer also includes a UniTaq detection probe (Bi) that has a detectable label F1 on one end and a quencher molecule (Q) on the other end (F1-Bi-Q-Ai). Optionally positioned proximal to the quencher is a polymerase-blocking unit, e.g., HEG, THF, Sp-18, ZEN, or any other blocker known in the art that is sufficient to stop polymerase extension. PCR amplification results in the formation of double stranded products as shown in FIG. 17, step F). In this example, a polymerase-blocking unit prevents a polymerase from copying the 5' portion (Bi) of the first universal primer, such that the bottom strand of product cannot form a hairpin when it becomes single-stranded.

Formation of such a hairpin would result in the 3' end of the stem annealing to the amplicon such that polymerase extension of this 3' end would terminate the PCR reaction.

The double stranded PCR products are denatured, and when the temperature is subsequently decreased, the upper strand of product forms a hairpin having a stem between the 5' portion (Bi) of the first oligonucleotide primer and portion Bi' at the opposite end of the strand (FIG. 17, step G). Also during this step, the second oligonucleotide primer anneals to the 5'-primer specific portion (Ci') of the hairpinned product. Upon extension of the second universal primer in step G, 5' nuclease activity of the polymerase cleaves the detectable label D1 or the quencher molecule from the 5' end of the amplicon, thereby increasing the distance between the label and the quencher and permitting detection of the label.

FIG. 18 (steps A-F) illustrates an exemplary PCR-PCR-qPCR (UniRq) for unknown pathogen identification. This method starts by isolating pathogen genomic DNA as shown in step A. If the pathogen is an RNA virus, an initial reverse-transcriptase step is used to generate cDNA. As shown in FIG. 18 (step B), the sample is subject to an amplification reaction, e.g., a polymerase chain reaction (PCR) to amplify target-containing regions of interest in an Initial Reaction Chamber. The multiplexed PCR amplification reaction is carried out using locus specific primers and a deoxynucleotide mix. In one embodiment, limited cycle amplification (12-20 cycles) is performed to maintain relative ratios of different amplicons being produced. In another embodiment primers contain identical 8-11 base tails on their 5' ends to prevent primer dimers from amplifying. Distribute initial PCR products into 24, 36, or 48 Primary PCR Reaction Chambers.

The split probe system is fully described in U.S. Pat. No. 9,598,728 to Barany et al., which is hereby incorporated by reference in its entirety. Herein, a split probe system designed for PCR amplification that involves the use of four unique "tag" sequences, where the first unique tag sequence (Ai) and split portions of the second and third unique tag portions (Bi', ti'), are present in the first secondary oligonucleotide primer, and the other split portions of second and third unique tag portions (tj and Bj), as well as the fourth unique tag sequence (Ci) are in the second secondary oligonucleotide primer sequence as shown in FIG. 18, step C. Upon PCR amplification of the oligonucleotide primers in a primer set, the resulting extension product will contain the Ai sequence-Bi', and ti' sequence—target specific sequences—ti', Bj' sequences—Ci' sequence. The essence of the split probe approach is that both secondary oligonucleotide primers of a PCR primer set need to be correct to obtain a positive signal, which allows for highly multiplexed nucleic acid detection. For example, and as described herein, this is achieved by requiring hybridization of two parts, i.e., two of the tags, to each other.

As shown in FIG. 18 step C, target-specific oligonucleotide secondary primers are hybridized to the primary amplified products and polymerase (filled diamond) is used to amplify target-containing regions of interest. As illustrated in step C of this figure, another layer of specificity can be incorporated into the method by including a 3' cleavable blocking group (Blk 3', e.g. C3 spacer), and an RNA base (r), in the secondary primers. Upon target-specific hybridization, RNase H (star symbol) removes the RNA base to generate a polymerase extension competent 3'OH group (FIG. 18, step C). The first secondary oligonucleotide primer contains a 5' primer-specific portion (Ai, Bi', ti') and the second secondary oligonucleotide primer contains a 5' primer-specific portion (tj, Bj, Ci) that permits subsequent amplification and detection of the secondary amplification products. Following the secondary amplification reaction, the extension products from each Primary PCR Reaction Chamber are distributed into 384 or 768 micro-wells or micro-pores containing one or more tag-specific primer pairs, each pair comprising of matched primers (F1-r-Bj, Bi-Q-Ai and Ci). For detection, the secondary PCR product containing Ai (a first primer-specific portion), Bi' (a split UniTaq detection portion), ti' (a region complementary to the target sequence), the target sequence including internal ti, tj sequences, tj' (a region complementary to the target sequence), Bi' (a split UniTaq detection portion), and Ci' (a second primer-specific portion) is primed on both strands using a first oligonucleotide primer having the same nucleotide sequence as Ai, and a second oligonucleotide primer that is complementary to Ci' (i.e., Ci). The first oligonucleotide primer also includes a UniTaq detection probe (Bj, Bi, with an internal ribose base) that has a detectable label F1 on one end and a quencher molecule (Q) on the other end (F1-r-Bj, Bi-Q-Ai). Optionally positioned proximal to the quencher is a polymerase-blocking unit, e.g., HEG, THF, Sp-18, ZEN, or any other blocker known in the art that is sufficient to stop polymerase extension. PCR amplification results in the formation of double stranded products as shown in FIG. 18, step F). In this example, a polymerase-blocking unit prevents a polymerase from copying the 5' portion (Bj, Bi) of the first universal primer, such that the bottom strand of product cannot form a hairpin when it becomes single-stranded. Formation of such a hairpin would result in the 3' end of the stem annealing to the amplicon such that polymerase extension of this 3' end would terminate the PCR reaction.

The double stranded PCR products are denatured, and when the temperature is subsequently decreased, the upper strand of product forms 4 hairpins form between pathogen-specific sequences (ti & ti'; tj & tj'), Bi & Bi', and Bj & Bj'. This renders the ribose base in the Bj sequence double-stranded, enabling RNaseH2 to liberate the fluorescent group F1 label from the product, thereby increasing the distance between the label and the quencher and permitting detection of the label (FIG. 18, step G). One advantage of the split probe design is that a false product resulting from primer dimer formation, i.e. (F1-r-Bj, Bi-Q-Ai-Bi'-ti'-primer dimer-tj', Bj'-Ci') would not give a false-positive signal since it would not form the ti & ti'; tj & tj' hairpins, leaving only the Bi & Bi' stem, and then the r-Bj and Bj' sequences which would not form a stem at the hybridization temperature used in the amplification reaction.

Another aspect of the present invention is directed to a method for identifying, in a sample, a plurality of nucleic acid molecules containing a target nucleotide sequence differing from nucleotide sequences in other nucleic acid molecules in the sample, or other samples, by one or more nucleotides, one or more copy numbers, one or more transcript sequences, and/or one or more methylated residues. This method involves providing a sample potentially containing one or more nucleic acid molecules containing the target nucleotide sequence differing from the nucleotide sequences in other nucleic acid molecules by one or more nucleotides, one or more copy numbers, one or more transcript sequences, and/or one or more methylated residues. One or more primary oligonucleotide primer sets are provided, each primary oligonucleotide primer set comprising (a) a first primary oligonucleotide primer that comprises a nucleotide sequence that is complementary to a sequence adjacent to the target nucleotide sequence, and (b) a second primary oligonucleotide primer that comprises a nucleotide sequence that is complementary to a portion of an extension product formed from the first primary oligonucleotide primer. The contacted sample is blended with the one or more primary oligonucleotide primer sets, a deoxynucleotide mix, and a DNA polymerase to form a polymerase chain reaction mixture in an Initial Reaction Chamber, and the polymerase chain reaction mixture is subjected to one or more polymerase chain reaction cycles comprising a denaturation treatment, a hybridization treatment, and an extension treatment, thereby forming primary extension products comprising the target nucleotide sequence or a complement thereof. The initial PCR products are distributed into 24, 36, or 48 Primary LDR Reaction Chambers. The method further involves blending the primary extension products with a ligase and one or more oligonucleotide probe sets to form a ligation reaction mixture. Each oligonucleotide probe set comprises (a) a first oligonucleotide probe having a target nucleotide sequence-specific portion, and (b) a second oligonucleotide probe having a target nucleotide sequence-specific portion, wherein the first and second oligonucleotide probes of a probe set are configured to hybridize, in a base specific manner, adjacent to one another on a complementary target nucleotide sequence of a primary extension product with a junction between them. The first and second oligonucleotide probes of the one or more oligonucleotide probe sets are ligated together to form ligated product sequences in the ligation reaction mixture, and the ligated product sequences in the sample are detected and distinguished to identify the presence of one or more nucleic acid molecules containing target nucleotide sequences differing from nucleotide sequences in other nucleic acid molecules in the sample by one or more nucleotides, one or more copy numbers, one or more transcript sequences, and/or one or more methylated residues.

FIGS. 19-23 illustrate various embodiments of this aspect of the present invention.

FIG. 19 (steps A-F) illustrates an exemplary PCR-LDR-qPCR (Taqman™) for unknown pathogen identification. This method starts by isolating pathogen genomic DNA as shown in step A. If the pathogen is an RNA virus, an initial reverse-transcriptase step is used to generate cDNA. As shown in FIG. 19 (step B), the sample is subject to an amplification reaction, e.g., a polymerase chain reaction (PCR) to amplify target-containing regions of interest in an Initial PCR Reaction Chamber. The multiplexed PCR amplification reaction is carried out using locus specific primers and a deoxynucleotide mix. In one embodiment, limited cycle amplification (12-20 cycles) is performed to maintain relative ratios of different amplicons being produced. In another embodiment, the regions of interest are amplified using 20-40 cycles. In another embodiment primers contain identical 8-11 base tails on their 5' ends to prevent primer dimers from amplifying. Distribute initial PCR products into 24, 36, or 48 Primary LDR Reaction Chambers (Step C).

As shown in FIG. 19 step D, target-specific oligonucleotide probes are hybridized to the amplified products and ligase (filled circle) covalently seals the two oligonucleotides together when hybridized to their complementary sequence. The upstream oligonucleotide probe contains a 5' primer-specific portion (Ai) and the downstream oligonucleotide probe contains a 3' primer-specific portion (Ci') that permits subsequent amplification of the ligation product. Following ligation, the ligation products from each Primary LDR Reaction Chamber are distributed into 384 or 768 micro-wells or micro-pores containing one or more tag-specific primer pairs, each pair comprising of matched primers Ai and Ci, PCR amplified, and detected. As shown in FIG. 19, steps E & F, detection of the ligation product can be carried out using traditional TaqMan™ detection assay (see U.S. Pat. No. 6,270,967 to Whitcombe et al., and U.S. Pat. No. 7,601,821 to Anderson et al., which are hereby incorporated by reference in their entirety). For detection using TaqMan™ an oligonucleotide probe spanning the ligation junction is used in conjunction with primers suitable for hybridization on the primer-specific portions of the ligation products for amplification and detection. The TaqMan™ probe contains a fluorescent reporter group on one end (F1) and a quencher molecule (Q) on the other end that are in close enough proximity to each other in the intact probe that the quencher molecule quenches fluorescence of the reporter group. During amplification, the TaqMan™ probe and upstream primer hybridize to their complementary regions of the ligation product. The 5'→3' nuclease activity of the polymerase extends the hybridized primer and liberates the fluorescent group of the TaqMan™ probe to generate a detectable signal (FIG. 19, step F).

FIG. 20 illustrates another exemplary PCR-LDR-qPCR (UniTaq) for unknown pathogen identification. This method starts by isolating pathogen genomic DNA as shown in step A. If the pathogen is an RNA virus, an initial reverse-transcriptase step is used to generate cDNA. As shown in FIG. 20 (step B), the sample is subject to an amplification reaction, e.g., a polymerase chain reaction (PCR) to amplify target-containing regions of interest in an Initial Reaction Chamber. In this embodiment, the ligation probes are designed to contain UniTaq primer and tag sequences to facilitate detections. In another embodiment primers contain identical 8-11 base tails on their 5' ends to prevent primer dimers from amplifying. Distribute initial PCR products into 24, 36, or 48 Primary LDR Reaction Chambers (Step C).

The UniTaq system is fully described in U.S. Patent Application Publication No. 2011/0212846 to Spier, which is hereby incorporated by reference in its entirety. The UniTaq system involves the use of three unique "tag" sequences, where at least one of the unique tag sequences (Ai) is present in the first oligonucleotide probe, and the second and third unique tag portions (Bi' and Ci') are in the second oligonucleotide probe sequence as shown in FIG. 20, step D. Upon ligation of oligonucleotide probes in a probe set, the resulting ligation product will contain the Ai sequence-target specific sequences-Bi' sequence-Ci' sequence. The essence of the UniTaq approach is that both oligonucleotide probes of a ligation probe set need to be correct in order to get a positive signal, which allows for highly multiplexed nucleic acid detection. For example, and as described herein, this is achieved by requiring hybridization of two parts, i.e., two of the tags, to each other.

After ligation, the ligation products of each Primary LDR Reaction Chamber are distributed into 384 or 768 micro-wells or micro-pores that contain the appropriate UniTaq primer pairs (FIG. 20, step E). For detection, the ligation product containing Ai (a first primer-specific portion), Bi' (a UniTaq detection portion), and Ci' (a second primer-specific portion) is primed on both strands using a first oligonucleotide primer having the same nucleotide sequence as Ai, and a second oligonucleotide primer that is complementary to Ci' (i.e., Ci). The first oligonucleotide primer also includes a UniTaq detection probe (Bi) that has a detectable label F1 on one end and a quencher molecule (Q) on the other end (F1-Bi-Q-Ai). Optionally positioned proximal to the quencher is a polymerase-blocking unit, e.g., HEG, THF, Sp-18, ZEN, or any other blocker known in the art that is sufficient to stop polymerase extension. PCR amplification results in the formation of double stranded products as shown in FIG. 20, step F). In this example, a polymerase-blocking unit prevents a polymerase from copying the 5' portion (Bi) of the first universal primer, such that the bottom strand of product cannot form a hairpin when it becomes single-stranded. Formation of such a hairpin would result in the 3' end of the stem annealing to the amplicon such that polymerase extension of this 3' end would terminate the PCR reaction.

The double stranded PCR products are denatured, and when the temperature is subsequently decreased, the upper strand of product forms a hairpin having a stem between the 5' portion (Bi) of the first oligonucleotide primer and portion Bi' at the opposite end of the strand (FIG. 20, step G). Also, during this step, the second oligonucleotide primer anneals to the 5'-primer specific portion (Ci') of the hairpinned product. Upon extension of the second universal primer in step G, 5' nuclease activity of the polymerase cleaves the detectable label D1 or the quencher molecule from the 5' end of the amplicon, thereby increasing the distance between the label and the quencher and permitting detection of the label.

FIG. 21 illustrates another exemplary PCR-LDR-qPCR (UniSpTq) for unknown pathogen identification. This method starts by isolating pathogen genomic DNA as shown in step A. If the pathogen is an RNA virus, an initial reverse-transcriptase step is used to generate cDNA. As shown in FIG. 20 (step B), the sample is subject to an amplification reaction, e.g., a polymerase chain reaction (PCR) to amplify target-containing regions of interest in an Initial Reaction Chamber. In this embodiment, the ligation probes are designed to contain split probe and tag sequences to facilitate detections. In another embodiment primers contain identical 8-11 base tails on their 5' ends to prevent primer dimers from amplifying. Distribute initial PCR products into 24, 36, or 48 Primary LDR Reaction Chambers (Step C).

The split probe system is fully described in U.S. Pat. No. 9,598,728 to Barany et al., which is hereby incorporated by reference in its entirety. The split probe system involves the use of four unique "tag" sequences, where the first unique tag sequence (Ai) and split portions of the second and third unique tag portions (Bi', zi), are present in the first oligonucleotide probe, and the other split portions of second and third unique tag portions (zi', Bj'), as well as the fourth unique tag sequence (Ci') are in the second oligonucleotide probe sequence as shown in FIG. 21, step D. Upon ligation of oligonucleotide probes in a probe set, the resulting ligation product will contain the Ai sequence-Bi', and zi sequence-target specific sequences-zi', Bj' sequences-Ci' sequence. The essence of the split probe approach is that both oligonucleotide probes of a ligation probe set need to be correct to obtain a positive signal, which allows for highly multiplexed nucleic acid detection. For example, and as described herein, this is achieved by requiring hybridization of two parts, i.e., two of the tags, to each other.

After ligation, the ligation products of each Primary LDR Reaction Chamber are distributed into 384 or 768 microwells or micro-pores that contain the appropriate UniTaq primer pairs (FIG. 21, step E). For detection, the ligation product containing Ai (a first primer-specific portion), Bi' (a first split probe detection portion), Bj' (a second split probe detection portion), and Ci' (a second primer-specific portion) is primed on both strands using a first oligonucleotide primer having the same nucleotide sequence as Ai, and a second oligonucleotide primer that is complementary to Ci' (i.e., Ci). The first oligonucleotide primer also includes a UniTaq detection probe (Bj, Bi) that has a detectable label F1 on one end and a quencher molecule (Q) on the other end (F1-Bj, Bi-Q-Ai). Optionally positioned proximal to the quencher is a polymerase-blocking unit, e.g., HEG, THF, Sp-18, ZEN, or any other blocker known in the art that is sufficient to stop polymerase extension. PCR amplification results in the formation of double stranded products as shown in FIG. 21, step F). In this example, a polymerase-blocking unit prevents a polymerase from copying the 5' portion (Bj, Bi) of the first universal primer, such that the bottom strand of product cannot form a hairpin when it becomes single-stranded. Formation of such a hairpin would result in the 3' end of the stem annealing to the amplicon such that polymerase extension of this 3' end would terminate the PCR reaction.

The double stranded PCR products are denatured, and when the temperature is subsequently decreased, the upper strand of product forms 3 hairpins between Bi & Bi', zi & zi', and Bj & Bj' (FIG. 21, step G). Also, during this step, the second oligonucleotide primer anneals to the 5'-primer specific portion (Ci') of the hairpinned product. Upon extension of the second universal primer in step G, 5' nuclease activity of the polymerase cleaves the detectable label D1 or the quencher molecule from the 5' end of the amplicon, thereby increasing the distance between the label and the quencher and permitting detection of the label. As soon as polymerase has traversed Bj', the short zi-zi' stem falls apart and polymerase continues extending to create the dsDNA product.

Both the UniTaq probe and the split probe approach provide the advantage of allowing a standard set of primers/probes to be printed in the appropriate micro-pores or micro-wells. Note that the Ci primer will make copies of the downstream LDR probe, independent of whether it was ligated to form a product or remained unligated. If that extension product forms a primer dimer with the upstream probe/primer in the absence of target using the UniTaq probe design, such a product (F1-Bi-Q-Ai-partial target-Bi'-Ci') would allow for the Bi & Bi' hairpin to form at the hybridization temperature, and then give a false-positive signal. One advantage of the split probe design is that such a false product (F1-Bj, Bi-Q-Ai-partial target-zi', Bj'-Ci') would not give a false-positive signal since it would not form the Bi & Bi', zi & zi' hairpins, leaving only the Bj & Bj' sequences, which would not form a stem at the hybridization temperature used in the amplification reaction.

The ligation products may also be used to generate signal directly in a process termed PCR-qLDR, as exemplified below in FIGS. 22 and 23. One such approach is described in WO/2016/057832 to Barany et al., which is hereby incorporated by reference in its entirety, uses ligation detection probes that generate a FRET or fluorescent signal after ligation.

In one embodiment, the first ligation probe contains a 3' target specific region and a 5' tail sequence with a donor or acceptor moiety and the second ligation probe in a probe set contains a 5' target specific region and 3' tail sequence with an acceptor or donor moiety, respectively. The 5' and 3' tail sequences of the ligation probes in a probe set are complementary to each other and the acceptor and donor groups generate a detectable signal via Førster Resonance Energy Transfer (FRET) when brought in close proximity to each other. Following ligation, unligated oligonucleotide probes are washed away, and the ligation product is denatured from the immobilized amplification products. Upon denaturation, the complementary 5' and 3' tail sequences of the ligation products hybridize to each other bringing the donor and acceptor groups in close proximity to each other to generate a detectable FRET signal.

In another embodiment, the upstream probe may contain a fluorescent reporter group on the 5' end followed by the tail sequence portion, a quenching group (e.g., ZEN), and the target-specific portion. In the single-stranded form, the fluorescent group is quenched by the Zen group. Upon ligation of the upstream and downstream ligation probes and denaturation of the resulting the ligation product, the complementary 5' and 3' tail portions of the ligation product hybridize to form a short double stranded portion. Under these conditions, the reporter group is no longer quenched by the quenching group and a detectable signal is produced. This is referred to as a hybridization unquenching probe (HuQP).

An approach for qLDR that does not require PCR is termed "Multiple Ligase Reactions and Probe Cleavages for SNP Detection"—(Kim, "PCR Free Multiple Ligase Reactions and Probe Cleavages for the SNP Detection of KRAS Mutation with Attomole Sensitivity," *Analyst* 141(16):6381-6386 (2016), which is hereby incorporated by reference in its entirety). In this approach, two primers are hybridized to, and ligated on a target if there is perfect complementarity with the target at the junction. The two primers also contain non-complementary sequences on their non-ligating 3' and 5' ends. After ligation, the ligation products (LP's) are complexed with a strand displacing hairpin (SDH) due to the higher melting temperature (Tm) of the LP with the SDH than with the target. The free target then can be recycled for a new ligation with the two primers. The addition of the SDH to the ligase reaction allows multiple enzymatic ligations of the two primers for each single target during the isothermal condition. To generate a detectable signal, the SNP-specific ligation is followed by a modified cycling probe assay with gold nanoparticles (AuNPs). In the cycling probe assay, the target-bound chimeric probe with a fluorescent donor and quencher at either end is digested with RNase H. RNase H cleaves RNA phosphodiester bonds only when they present in an RNA-DNA heteroduplex; it does not digest the DNA in the heteroduplex, nor does it digest single- or double-stranded RNA or DNA. The cycling probe assay is designed to utilize these properties of RNase H. When the target DNA strand becomes free upon RNA degradation, another intact RNA molecule can hybridize with the DNA, leading to linear signal amplification.

FIG. 22 illustrates another exemplary PCR-qLDR (Uni-LDq) for unknown pathogen identification. This method starts by isolating pathogen genomic DNA as shown in step A. If the pathogen is an RNA virus, an initial reverse-transcriptase step is used to generate cDNA. As shown in FIG. 22 (step B), the sample is subject to an amplification reaction, e.g., a polymerase chain reaction (PCR) to amplify target-containing regions of interest in an Initial Reaction Chamber. In this embodiment, the ligation probes are designed to contain tag sequences to facilitate detections. In another embodiment primers contain identical 8-11 base tails on their 5' ends to prevent primer dimers from amplifying. Distribute initial PCR products into 384 or 768 micro-wells or micro-pores (Step C).

Pathogen-specific ligation oligonucleotides have tags (Bi'-ti'-upstream target sequence; downstream target sequence-tj'-Bj') for subsequent detection. The ti' and tj' sequences are complementary to sequences ti, tj in the target at the ligation junction. When detecting specific SNPs or mutations, blocking LNA or PNA wild-type probes suppress ligation to wild-type sequence. As illustrated in step D of this figure, another layer of specificity can be incorporated into the method by including a 3' cleavable blocking group (Blk 3', e.g. C3 spacer), and an RNA base (r), in the upstream ligation probe. Upon target-specific hybridization, RNase H (star symbol) removes the RNA base to generate a ligation competent 3'OH group (FIG. 22, step D). Once the target-specific oligonucleotide probes are hybridized to the amplified products, and the optional RNaseH step liberates the 3'OH group, ligase (filled circle) covalently seals the two oligonucleotides together when hybridized to their complementary sequence (FIG. 22, step E).

In the presence of probe (F1-r-Bj, Bi-Q), and after the denaturation step, as the temperature decreases, 4 double-stranded stems form between probe and pathogen-specific sequences (ti & ti'; tj & tj'), Bi & Bi', and Bj & Bj'. This renders the ribose base in the Bj sequence double-stranded, enabling RNaseH2 to liberate the fluorescent group and generate signal (FIG. 22, step F). The cleaved probe dissociates from the product and new probe can hybridize to generate additional signal. Unligated LDR primers would not form all hairpins, and thus RNaseH2 would not liberate signal. In one embodiment of this approach, after the PCR reaction, products are distributed into micro-wells or micro-pores, which already contain the target-specific LDR primers, as well as the universal probe(s).

FIG. 23 illustrates another exemplary PCR-qLDR (TsLDG) for unknown pathogen identification. This method starts by isolating pathogen genomic DNA as shown in step A. If the pathogen is an RNA virus, an initial reverse-transcriptase step is used to generate cDNA. As shown in FIG. 23 (step B), the sample is subject to an amplification reaction, e.g., a polymerase chain reaction (PCR) to amplify target-containing regions of interest in an Initial Reaction Chamber. In this embodiment, the ligation probes are designed to contain tag sequences to facilitate detections. In another embodiment primers contain identical 8-11 base tails on their 5' ends to prevent primer dimers from amplifying. Distribute initial PCR products into 384 or 768 micro-wells or micro-pores (Step C).

Pathogen-specific ligation oligonucleotides have tags (Bi'-upstream target sequence; downstream target sequence-tj') for subsequent detection. The tj' sequence is complementary to the tj sequence in the target at the ligation junction. When detecting specific SNPs or mutations, blocking LNA or PNA wild-type probes suppress ligation to wild-type sequence. As illustrated in step D of this figure, another layer of specificity can be incorporated into the method by including a 3' cleavable blocking group (Blk 3', e.g. C3 spacer), and an RNA base (r), in the upstream ligation probe. Upon target-specific hybridization, RNase H (star symbol) removes the RNA base to generate a ligation competent 3'OH group (FIG. 23, step D). Once the target-specific oligonucleotide probes are hybridized to the amplified products, and the optional RNaseH step liberates the 3'OH group, ligase (filled circle) covalently seals the two oligonucleotides together when hybridized to their complementary sequence (FIG. 23, step E).

In the presence of probe (F1-r-pathogen sequence-Bi-Q), and after the denaturation step, as the temperature decreases, 2 double-stranded stems form between pathogen-specific sequences (ti,tj & ti',tj'), and Bi & Bi'. This renders the ribose base in the pathogen sequence double-stranded, enabling RNaseH2 to liberate the fluorescent group and generate signal. The cleaved probe dissociates from the product and new probe can hybridize to generate additional signal. Unligated LDR primers would not form both stems, and thus RNaseH2 would not liberate signal. In one embodiment of this approach, after the PCR reaction, products are distributed into micro-wells or micro-pores, which already contain the target-specific LDR primers, as well as the pathogen sequence specific probe(s).

To what extent does qLDR with a cleavable probe (cP) generate more signal than when using LDR with either a FRET probe, or hybridization unquenching (HuQP) probe. The latter generates a linear signal as a function of cycle, i.e. if running "X" cycles of LDR, then amount of fluorescent signal generated "F" is proportional to X; i.e. $F=f(X)$. When using the cleavable probe as in FIGS. 22 and 23, the amount of signal generated is a function of both the number of times the probe is cleaved "C" during a single LDR cycle, and the number of cycles X; i.e. $F=f(X)(X-1)C$. On a practical level, 50 cycles of LDR-FRET or LDR-HuQP will give a dynamic range of 50-fold signal change, while 50 cycles of LDR-cP will give a dynamic range of 1,225-fold signal change.

FIG. 24 is a schematic front view of a portion of an exemplary design for pre-chamber loading to allow for liquids to be fluidically moved to the chambers comprising of micro-wells or micro-pores. This design illustrates the chamber architecture and micro-wells or micro-pores suitable for performing Multiplexed PCR-Nested PCR-UniTaq detection. (Alternatively, Multiplexed PCR-Nested PCR-Real-time-PCR with target-specific Taqman™ probes), for unknown pathogen identification and quantification. In FIG. 24, the input sample is fluidically connected to a large hexagonal chamber 16 (containing trough 18; bottom, Initial Reaction Chamber), which is fluidically connected by conduit 20 to hexagonal chambers 22 (containing large troughs 24 and baffles 23, Primary PCR Reaction Chambers), which are fluidically connected by conduit 26 to long narrower mixing chambers 28, which are fluidically connected by conduit 30 to the chambers comprising subdivisions 32 of micro-wells or micro-pores (top of panel, with only 4 rows illustrated). The diagram is not to scale and is for illustrative purposes. During manufacture of the cartridge, subdivision rows are pre-filled with 1-4 UniTaq primer sets (or alternatively, 1-4 universal tag primer sets with target-specific Taqman™ probes). During manufacture of the cartridge, Primary PCR Reaction Chambers leading up to the columns of micro-wells or micro-pores are pre-filled with nested PCR primer sets with either UniTaq or universal tag sequences on their 5' ends. The grey circles 25 on the right side of the drawing illustrate potential position for delivering or printing probe sets, for example by acoustic droplet ejection, capillary, inkjet, or quill printing. In this illustrative example, showing 4 each of the planned 24 columns 32 rows equaling 768 subdivisions, each subdivision comprising 24 micro-wells or micro-pores, the initial multiplexed PCR amplification (or reverse-transcription-PCR for RNA targets) is for 9 cycles to generate up to 512 copies of each original target in an Initial Reaction Chamber. If needed, fresh PCR reagents are added, and the initial multiplexed reaction is divided into the Primary PCR Reaction Chambers (pre-filled with nested PCR primers as described above), with average distribution of 20 copies of each original pathogen in each Primary PCR Reaction Chamber. Optionally, primers containing an RNA base and 3' blocking group are unblocked with RNaseH2 only when bound to the correct target, providing additional specificity and avoiding false products. Perform 5 cycles of nested PCR using target-specific primers with UniTaq or universal tags in groups of 16, 32, or 64 primer sets, to generate an average of 640 copies of each pathogen-specific target per Primary PCR Reaction Chamber. If needed, fresh PCR reagents are added, mixed with the nested PCR products of each Primary PCR Reaction Chambers, and distributed into mixing chambers and then into micro-pores of each column. Universal or UniTaq primers in each subdivision of each row will amplify only those products from each column with the correct tags. Poisson distribution in micro-pores will enumerate pathogen-specific targets initially present at low abundance, while Ct values across micro-pores in each subdivision will provide approximate copy information for pathogen-specific targets initially present at high abundance.

The cartridge design of FIG. 24 may also be used to perform Multiplexed PCR-LDR-UniTaq detection. (Alternatively, Multiplexed PCR-LDR-Real-time-PCR with target-specific Taqman™ probes), for unknown pathogen identification and quantification. During manufacture of the cartridge, Primary LDR Reaction Chambers leading up to the columns of micro-wells or micro-pores are pre-filled with LDR probe sets with either UniTaq or universal tag sequences on their non-ligating 5' (upstream) and 3' (downstream) ends. The grey circles 25 on the right side of the drawing illustrate potential position for delivering or printing probe sets, for example by acoustic droplet ejection, capillary, inkjet, or quill printing. The probes are dried down, and the cover part of the cartridge assembled to seal the probe sets in their appropriate positions. During use of the cartridge, reactions are fluidically moved from the Initial Reaction Chamber of the cartridge up through the Primary LDR Reaction Chambers, the Mixing Chamber, and eventually up the columns of micro-wells or micro-pores, where each column is isolated from its neighbor column. In this illustrative example, showing 4 of the planned 24 columns and 8 of the 32 rows equaling 768 subdivisions, each subdivision comprising 24 micro-wells or micro-pores, the initial multiplexed PCR amplification (or reverse-transcription-PCR for RNA targets) is for 30 cycles to amplify original target in an Initial Reaction Chamber. Polymerase is inactivated (e.g. by heat killing or protease digestion), multiplexed products are diluted 10-fold into a ligase reaction mixture comprising of ligase, ATP, or NAD, and distributed into the Primary LDR Reaction Chambers (pre-filled with LDR probes as described above). Optionally, either PCR primers and/or LDR upstream probes containing an RNA base and 3' blocking group are unblocked with RNaseH2 only when bound to the correct target, providing additional specificity and avoiding false products. Perform 20 cycles of LDR using allele-specific probes with UniTaq or universal tags in groups of 16, 32, or 64 primer sets. Fresh PCR reagents are added, mixed with the LDR products of each Primary LDR Reaction Chambers, and distributed into the Mixing Chambers and then the micro-pores of each column. Universal or UniTaq primers in each subdivision of each row will amplify only those products from each column with the correct tags. Ct values across the 24 micro-pores in each subdivision will provide approximate copy information for pathogen-specific targets initially present at high abundance.

In an alternative embodiment using 48 columns and 48 rows equaling 2,304 subdivisions, each subdivision comprising 96 micro-wells, 1-4 UniTaq primer sets (or alternatively, 1-4 universal tag primer sets with target-specific Taqman™ probes) are delivered directly to the appropriate subdivision in each row by acoustic droplet ejection, capillary, inkjet, or quill printing, and then dried down into individual micro-wells. The initial multiplexed PCR amplification (or reverse-transcription-PCR for RNA targets) is for 10 cycles to generate up to 1,024 copies of each original target in an Initial Reaction Chamber or well. If needed, use "tandem" PCR primers. Fresh PCR reagents are added, and the initial multiplexed reaction is distributed into 48 wells or Primary PCR Reaction Chambers (with nested PCR primers added using acoustic droplet ejection), with average distribution of 20 copies of each original pathogen per well or Primary PCR Reaction Chamber. Optionally, primers containing an RNA base and 3' blocking group are unblocked with RNaseH2 only when bound to the correct target, providing additional specificity and avoiding false products. Perform 3-4 cycles of nested PCR using target-specific primers with UniTaq or universal tags in groups of 24, or 48 primer sets, to generate an average of 160-320 copies of each pathogen-specific target per well or Primary PCR Reaction Chamber. Fresh PCR reagents are added, mixed with the nested PCR products of each well or Primary PCR Reaction Chamber, and distribute products of each well or Primary PCR Reaction Chamber into 2 or 4 sets of 24 or 12 subdivisions respectively containing 96 micro-wells. When using 2 sets, the second set is a 100/1 dilution of the first. When using 4 sets, each set is a 20/1 dilution of the previous set. This allows coverage of pathogens present across many orders of magnitude. On average, each initial subdivision will get 12 copies of each original pathogen, with a given micro-well getting one or zero copies of original pathogen. If pathogen is present in higher numbers, each subdivision will get additional copies. Universal or UniTaq primers in each subdivision of each row will amplify only those products from each column with the correct tags. Poisson distribution in 96 micro-wells will enumerate pathogen-specific targets initially present at low abundance, while Ct values across micro-wells in a subdivision will provide approximate copy information for pathogen-specific targets initially present at high abundance.

FIGS. 25A-25B are schematic side views of cartridge 4, valve, and reagent setup for identifying and quantifying unknown pathogen using Multiplexed PCR-Nested PCR-Real-time-PCR with UniTaq or target-specific Taqman™ probes; identifying and quantifying unknown mutations at low-level in plasma using Multiplexed PCR-LDR-Real-time-PCR with UniTaq or mutation-specific Taqman™ probes; and identifying and quantifying methylations and unknown mutations at low-level in plasma using Multiplexed PCR-LDR-Real-time-PCR with UniTaq or target-specific Taqman™ probes. FIG. 25A is a schematic front view illustrating fluidic connection of micro-channels to the array of micro-wells or micro-pores, with 50-micron diameter. For simplicity, the figure illustrates one Initial Multiplex Reaction Chamber 10, 16 Primary multiplex PCR Reaction Chambers 16 with troughs 18, 16 Secondary multiplex Reaction Chambers 22 with troughs 24 and baffles 23, 16 Narrow Mixing Chambers 28, and one main Chamber comprising subdivisions 32 of 16 columns and thousands of micro-pores or micro-wells. These are coupled together by conduits 14, 20, 26, and 30 as shown. Fluid enters cartridge 4 through inlet 2 and leaves through outlet 8. However, other configurations of the chambers may also be used, for example the multiplexed PCR-Nested PCR-Real-time PCR for pathogen detection described in FIG. 24 would not require the Secondary multiplex Reaction Chambers. FIG. 25B illustrates the fluidics system for multiplexed PCR-Nested PCR-Real-time PCR with UniTaq or target specific Taqman™ probes using a micro-pore plate system (as generally described in FIGS. 11-12) composed of thousands of micro-pores 202. The micro-pore plate is fluidically accessible from both sides of the pores: the first side (top of plate, illustrated on left side of plate) is in communication with Valves 1, 2, & 3 while the second side (bottom of plate, illustrated on right side of plate) is in communication with Valves 4 & 5. Valve 1 dispenses a lysis/protease buffer, enzymes, wash buffer, elute buffer, buffer, EtOH, Light Oil, and Heavy Oil, as needed through the Initial Multiplex Reaction Chamber, the primary PCR Reaction Chambers, and additional chambers across the first side of the micro-pore plate through Valve 3 to Waste. In addition, Valve 1 can select a Waste port, which can be used to vacate the first side of micro-pore plate, other chambers, PCR Reaction Chambers, and initial multiplex Reaction Chambers by the introduction of Air through Valve 3 in a reverse direction. Valve 1 can also select Valve 2. Valve 2 dispenses Initial multiplex PCR primers, Master PCR Mix, initial reverse-transcription primers, Master reverse transcription mix, Wash, EtOH, & Air through Initial Multiplex Reaction Chamber, the PCR Reaction Chambers, and additional chambers across the first side of the micro-pore plate through Valve 3 to Waste. Valve 4 dispenses Air, Light Oil, Heavy Oil and Waste across the second side of the micro-pore plate through Valve 5 to Waste. In addition, Valve 1 can select a Waste port, which can be used to vacate the second side micro-pore plate by introduction of Air through Valve 5 in a reverse direction.

TABLE 3

Reagent Setup for Multiplexed PCR - Nested PCR - Real-Time-PCR

| Port | Valve 1 | Valve 2 | Valve 4 | Valves 3/5 |
|---|---|---|---|---|
| 1 | Lysis/Protease Buf. | Initial PCR primers | Air | Waste |
| 2 | Wash | Master PCR mix | Light Oil | Air |
| 3 | Elute Buffer | Initial RT primers | Heavy Oil | Or connect with |
| 4 | Enz/Prim. from V2 | Master RT mix | Empty | Air/waste of |
| 5 | Empty (Pre-mix) | Buffer | | Valve 1/4 |
| 6 | Waste | Wash | | |
| 7 | Buffer | ETOH | | |
| 8 | ETOH | Air | | |
| 9 | Air | Empty | | |
| 10 | Light Oil | Empty | | |
| 11 | Heavy Oil | Empty | | |
| 12 | Hexanol | Empty | | |

FIG. 25B illustrates several heating elements 1-4 that would be designed to provide independent heating/cooling to the Initial Multiplex Reaction Chamber 10, the Primary 24-48 multiplex PCR reaction Chambers 16, the Secondary 24-48 multiplex Reaction Chambers 22, and the main Chamber 28 comprising of 24-48 columns and thousands of micro-pores or micro-wells 202 of subdivisions 32. The back plate 206 (opposite front plate 204), or one or more flat surface(s) 244 and 246 of the micro-pore or micro-well channel(s) 240 and 242, and the reaction chambers may be pressed against these heating elements to allow for temperature control, heating, and/or thermocycling. As illustrated in FIG. 25, the two heating elements behind the Primary 24-48 multiplex PCR reaction Chambers 16, the Secondary 24-48 multiplex Reaction Chambers 22 would be designed as two rectangular (horizontal) strips to control all the Primary Chambers independently of all the Secondary Chambers. Alternative configurations may also be used, for example having independent heating elements for each Primary Chamber, having additional rows of chambers (i.e. Primary, Secondary, Tertiary, etc.) having additional rows or heating elements, and/or having the 24-48 spatial multiplexing arranged in a different geometry than rows or columns, for either/or the Initial Reaction Chamber 10, the Primary Chambers 16, the Secondary Chambers 22, the Mixing Chambers 28, and the main chamber comprising subdivisions of the thousands of micro-wells or micro-pores. For example, a plate may comprise 24 separate input wells, each fluidically connect to an individual Primary multiplex PCR reaction Chamber 16, an individual Secondary multiplex Reaction Chamber 22, an individual Mixing chamber 28, and an individual Chamber comprising subdivisions of hundreds to thousands of micro-pores or micro-wells. Samples may undergo an optional initial multiplexed reaction, and then imported into the 24 individual input wells via acoustic droplet ejection or other fluidic means.

FIG. 26 (steps A-F) illustrates an exemplary PCR-PCR-qPCR for unknown bacterial pathogen identification directly from blood. This method starts by isolating pathogen genomic DNA as shown in step A. Any pre-capture of bacteria directly from the blood, i.e. by using aptamers or antibodies will facilitate detection. The challenge is to amplify out the rare bacterial DNA from the massive excess of WBC DNA. As shown in FIG. 26 (step B), the sample is distributed into 24, 36, or 48 Primary PCR Reaction Chambers, each of which is subject to an amplification reaction, e.g., a polymerase chain reaction (PCR) to amplify target-containing regions of interest. The multiplexed PCR amplification reaction is carried out using target-specific primers and a deoxynucleotide mix. Optionally, a strand-displacing polymerase is used, with tandem or multiple primers for each target. In one embodiment, limited cycle amplification (12-20 cycles) is performed. In another embodiment, primers contain identical 8-11 base tails on their 5' ends to prevent primer dimers from amplifying.

As shown in FIG. 26 step C, target-specific oligonucleotide secondary primers are hybridized to the primary amplified products and polymerase (filled diamond) is used to amplify target-containing regions of interest in Secondary PCR Reaction Chambers. As illustrated in step C of this figure, another layer of specificity can be incorporated into the method by including a 3' cleavable blocking group (Blk 3', e.g. C3 spacer), and an RNA base (r), in the secondary primers. Upon target-specific hybridization, RNase H (star symbol) removes the RNA base to generate a polymerase extension competent 3'OH group (FIG. 26, step C). Following the nested primer amplification, products of each Secondary PCR Reaction Chamber are distributed into 384 or 768 micro-wells or micro-pores. The PCR products can be detected using pairs of matched primers Ai and Ci, and TaqMan™ probes that span the ligation junction as described supra for FIG. 16 (see FIG. 26, steps D-F), or using other suitable means known in the art.

FIG. 27 (steps A-F) illustrates another exemplary PCR-PCR-qPCR for unknown bacterial pathogen identification directly from blood. This method starts the same as illustrated in FIG. 26 with initial distribution of target nucleic acids into Primary PCR Reaction Chambers and multiplexed PCR amplifications, except it uses the UniTaq readout.

As shown in FIG. 27 step C, target-specific oligonucleotide secondary primers are hybridized to the primary amplified products and polymerase (filled diamond) is used to amplify target-containing regions of interest in the Secondary PCR Reaction Chambers. As illustrated in step C of this figure, another layer of specificity can be incorporated into the method by including a 3' cleavable blocking group (Blk 3', e.g. C3 spacer), and an RNA base (r), in the secondary primers. Upon target-specific hybridization, RNase H (star symbol) removes the RNA base to generate a polymerase extension competent 3'OH group (FIG. 27, step C). Following the nested primer amplification, products of each Secondary PCR Reaction Chamber are distributed into 384 or 768 micro-wells or micro-pores. The PCR products are amplified using UniTaq-specific primers (i.e., F1-Bi-Q-Ai, Ci) and detected as described supra for FIG. 17 (see FIG. 27, steps D-G), or using other suitable means known in the art.

The cartridge design of FIG. 24 may also be used to perform Multiplexed PCR-Nested PCR-UniTaq detection of unknown bacterial pathogen, directly from blood. (Alternatively, Multiplexed PCR-Nested PCR-Real-time-PCR with target-specific Taqman™ probes). During manufacture of the cartridge, rows are pre-filled with 1-4 UniTaq primer sets (or alternatively, 1-4 universal tag primer sets with target-specific Taqman™ probes). During use of the cartridge, reactions are fluidically moved from the Initial Reaction chambers of the cartridge up through the Primary PCR Reaction Chambers, the Mixing Chambers and eventually up the columns of micro-wells or micro-pores, where each column is isolated from its neighbor column. In this illustrative example, with 24 columns and 32 rows equaling 768 subdivisions, each subdivision comprising 24 micro-wells or micro-pores, the sample is divided into the 24 columns, and the initial multiplexed PCR amplification is with strand-displacing polymerase and large sets of tandem or more primer sets with 10-12 bp tails, for 20 cycles to generate 1,000,000 copies of each original target, if present. Nested primers containing an RNA base and 3' blocking group are unblocked with RNaseH2 only when bound to the correct target, providing additional specificity and avoiding false products. 10 cycles of nested PCR are performed using target-specific primers with UniTaq or universal tags in groups of 16, 32, or 64 primer sets in each Primary PCR Reaction Chamber. If needed, fresh PCR reagents are added, mixed with the nested PCR products of each Primary PCR Reaction Chamber, and distributed into Mixing Chambers and then into micro-wells or micro-pores of each column. Universal or UniTaq primers in each subdivision of each row will amplify only those products from each column with the correct tags. Pre-amplification of target and use of tails to prevent primer dimer formation will allow identification of bacterial pathogens at the single cell level.

In an alternative embodiment using 48 columns and 48 rows equaling 2,304 subdivisions, each subdivision comprising 96 micro-wells, 1-4 UniTaq primer sets (or alternatively, 1-4 universal tag primer sets with target-specific Taqman™ probes) are delivered directly to the appropriate subdivisions in each row by acoustic droplet ejection, capillary, inkjet, or quill printing, and then dried down into individual micro-wells. Initial sample is distributed into 48 wells. 9 cycles of multiplexed PCR are performed in a well or an Initial Reaction Chamber, maximum of 512 copies of each original pathogen, if present. Use "tandem" or more PCR primer sets. Also, all PCR primers include identical 5' tail sequences, preferably 10-12 bases to suppress amplification of primer dimers. On average, each initial subdivision will get 10 copies of each original pathogen, with a given micro-well getting one or zero copies of original pathogen. If pathogen is present in higher numbers, each subdivision will get additional copies. Universal or UniTaq primers in each subdivision of each row will amplify only those products from each column with the correct tags. Poisson distribution in 96 micro-wells will enumerate pathogen-specific targets initially present at low abundance, while Ct values across micro-wells will provide approximate copy information for pathogen-specific targets initially present at high abundance.

FIG. 28 illustrates another exemplary PCR-LDR-qPCR reaction (with optional carryover prevention) to detect low-level mutations. Genomic or cfDNA is isolated (FIG. 28, step A), and distributed into 24, 36, 48, or 64 wells or Primary PCR Reaction Chambers prior to PCR. The isolated DNA sample is optionally treated with UDG to digest dU containing nucleic acid molecules that may be present in the sample (FIG. 28, step B). The region of interest is selectively amplified using locus-specific upstream primers, locus-specific downstream primers, a blocking LNA or PNA probe comprising wild-type sequence, and a deoxynucleotide mix that optionally includes dUTP. In this embodiment, another layer of selectivity can be incorporated into the method by including a 3' cleavable blocking group (Blk 3', e.g. C3 spacer), and an RNA base (r), in the upstream primer. Upon target-specific hybridization, RNase H (star symbol) removes the RNA base to liberate a 3'OH group which is a few bases upstream of the mutation, and suitable for polymerase extension (FIG. 28, step B). A blocking LNA or PNA probe comprising wild-type sequence that partially overlaps with the upstream PCR primer will preferentially compete in binding to wild-type sequence over the upstream primer, but not as much to mutant DNA, and thus suppresses amplification of wild-type DNA during each round of PCR. The amplified products optionally contain dU as shown in FIG. 28, step C, which allows for subsequent treatment with UDG or a similar enzyme for carryover prevention. Distribute products from each Primary PCR Reaction Chamber into corresponding Secondary LDR Reaction Chambers.

As shown in FIG. 28 step D, target-specific oligonucleotide probes are hybridized to the amplified products and ligase (filled circle) covalently seals the two oligonucleotides together when hybridized to their complementary sequence. In this embodiment, the upstream oligonucleotide probe having a sequence specific for detecting the mutation of interest further contains a 5' primer-specific portion (Ai) to facilitate subsequent detection of the ligation product. Once again, the presence of blocking LNA or PNA probe comprising wild-type sequence suppresses ligation to wild-type target sequence if present after the enrichment of mutant sequence during the PCR amplification step. The downstream oligonucleotide probe, having a sequence common to both mutant and wild-type sequences contains a 3' primer-specific portion (Ci') that, together with the 5' primer specific portion (Ai) of the upstream probe having a sequence specific for detecting the mutation, permit subsequent amplification and detection of only mutant ligation products. As illustrated in step D of this Figure, another layer of specificity can be incorporated into the method by including a 3' cleavable blocking group (Blk 3', e.g. C3 spacer), and an RNA base (r), in the upstream ligation probe. Upon target-specific hybridization, RNase H (star symbol) removes the RNA base to generate a ligation competent 3'OH group (FIG. 28, step D). Following ligation, products of each Secondary LDR Reaction Chamber are distributed into 384 or 768 micro-wells or micro-pores. The ligation products can be detected using pairs of matched primers Ai and Ci, and TaqMan™ probes that span the ligation junction as described supra for FIG. 19 (see FIG. 28, steps E-G), or using other suitable means known in the art.

FIG. 29 illustrates another exemplary PCR-LDR-qPCR reaction (with optional carryover prevention) to detect low-level mutations. Genomic or cfDNA is isolated (FIG. 29, step A), and distributed into 24, 36, 48, or 64 wells or Primary PCR Reaction Chambers prior to PCR. The isolated DNA sample is optionally treated with UDG to digest dU containing nucleic acid molecules that may be present in the sample (FIG. 29, step B). Upstream locus-specific primers are designed a few bases upstream of the mutation, and include a 3' cleavable blocking group (Blk 3', e.g. C3 spacer), and an RNA base (r). Upon target-specific hybridization, RNase H (star symbol) removes the RNA base to liberate a 3'OH that is suitable for polymerase extension (FIG. 29, step B). A blocking LNA or PNA probe comprising wild-type sequence that partially overlaps with the upstream PCR primer will preferentially compete in binding to wild-type sequence over the upstream primer, but not as much to mutant DNA, and thus suppresses amplification of wild-type DNA during each round of PCR. The amplified products optionally contain dU as shown in FIG. 29, step C, which allows for subsequent treatment with UDG or a similar enzyme for carryover prevention. Distribute products from each Primary PCR Reaction Chamber into corresponding Secondary LDR Reaction Chambers.

As shown in FIG. 29 step D, target-specific oligonucleotide probes are hybridized to the amplified products and ligase (filled circle) covalently seals the two oligonucleotides together when hybridized to their complementary sequence. In this embodiment, the upstream oligonucleotide probe having a sequence specific for detecting the mutation of interest further contains a 5' primer-specific portion (Ai) to facilitate subsequent detection of the ligation product. Once again, the presence of blocking LNA or PNA probe comprising wild-type sequence suppresses ligation to wild-type target sequence if present after the enrichment of mutant sequence during the PCR amplification step. The downstream oligonucleotide probe, having a sequence common to both mutant and wild-type sequences contains a 3' primer-specific portion (Bi'-Ci') that, together with the 5' primer specific portion (Ai) of the upstream probe having a sequence specific for detecting the mutation, permit subsequent amplification and detection of only mutant ligation products. As illustrated in step D of this Figure, another layer of specificity can be incorporated into the method by including a 3' cleavable blocking group (Blk 3', e.g. C3 spacer), and an RNA base (r), in the upstream ligation probe. Upon target-specific hybridization, RNase H (star symbol) removes the RNA base to generate a ligation competent 3'OH group (FIG. 29, step D). Following ligation, products of each Secondary LDR Reaction Chamber are distributed into 384 or 768 micro-wells or micro-pores. The ligation products are amplified using UniTaq-specific primers (i.e., F1-Bi-Q-Ai, Ci) and detected as described supra for FIG. 20 (see FIG. 29, steps E-H), or using other suitable means known in the art.

FIG. 30 is a schematic front view of a portion of an exemplary design for pre-chamber loading to allow for liquids to be fluidically moved to the chambers comprising of micro-wells or micro-pores. This design illustrates the chamber architecture and micro-wells or micro-pores suitable for performing Multiplexed PCR-LDR-UniTaq detection, for identifying and quantifying unknown mutations at low-level in plasma. (Alternatively, use Multiplexed PCR-LDR-Real-time-PCR with mutation-specific Taqman™ probes). In FIG. 30, the input sample is fluidically connected to and mixed with appropriate reagents in the Initial Reaction Chamber 10 (bottom) through entrance 12. Initial Reaction Chamber 10 (bottom) is fluidically connected by conduit 14 to a first set of hexagonal chambers 16 (containing small troughs 18, Primary PCR Reaction Chambers), which are fluidically connected by conduit 20 to a second set of hexagonal chambers 22 (containing large troughs 24 and baffles 23, Secondary LDR Reaction Chambers), which are fluidically connected by conduit 26 to long narrower mixing chambers 28, which are fluidically connected by conduit 30 to the chambers comprising subdivisions 32 of micro-wells or micro-pores (top of panel, with only 4 rows illustrated). The diagram is not to scale and is for illustrative purposes. During manufacture of the cartridge, rows are pre-filled with 1-4 UniTaq primer sets (or alternatively, 1-4 universal tag primer sets with target-specific Taqman™ probes). During manufacture of the cartridge, Secondary LDR Reaction Chambers 22 leading up to the columns of subdivisions of micro-wells or micro-pores are optionally pre-filled with LDR probe sets with either UniTaq or universal tag sequences on their non-ligating 5' (upstream) and 3' (downstream) ends. The grey circles 25 on the left side of the drawing illustrate potential position for delivering or printing probe sets, for example by acoustic droplet ejection, capillary, inkjet, or quill printing. The probes are dried down, and the cover part of the cartridge assembled to seal the probe sets in their appropriate positions. Alternatively, when using identical LDR primer sets in each pre-chamber, they may be added after the PCR step, without the need to initially print them in the cartridge. During use of the cartridge, reactions are fluidically moved from the Initial Reaction Chamber 10 of the cartridge up through the Primary PCR Reaction Chambers 16, through the Secondary LDR Reaction Chambers 22, and eventually up the Mixing Chambers 28 and through the columns of subdivisions 32 of micro-wells or micro-pores, where each column is isolated from its neighbor column. In this illustrative example, showing 4 each of the planned 24 columns and 32 rows equaling 768 subdivisions, each subdivision comprising 24 micro-wells or micro-pores, the initial multiplexed PCR amplification is repeated in each of the initial Primary PCR Reaction Chambers 16 for 10-40 cycles in the presence of PNA or LNA to suppress amplification of wild-type sequence, but not mutant sequence. In another embodiment, to minimize dropout of fragments during multiplexed PCR, an initial "pre-amplification" multiplexed PCR is performed for 8-20 cycles in the initial reaction chamber 10. These products are then distributed into the Primary PCR Reaction Chambers 16. In one variation, each of the primary reaction chambers contains from 1-4 PCR primer sets with PNA or LNA to suppress amplification of wild-type sequence, and single or multiplexed PCR is performed for an additional 10-30 cycles to enable amplification of 1-4 different fragments containing potential mutations in a single primary reaction chamber. In another variation, 6 sets of 4 primary reaction chambers contains from 4-16 PCR primer sets with PNA or LNA to suppress amplification of wild-type sequence, and multiplexed PCR is performed for an additional 10-30 cycles to enable amplification of 4-16 different fragments containing potential mutations in a single primary reaction chamber. Polymerase is inactivated (e.g. by heat killing or protease digestion), each chamber of multiplexed products is diluted 10-fold into a ligase reaction mixture comprising of ligase, ATP, or NAD, and distributed into the corresponding Secondary LDR Reaction Chambers 22 (pre-filled with LDR probes as described above). Optionally, either PCR primers and/or LDR upstream probes containing an RNA base and 3' blocking group are unblocked with RNaseH2 only when bound to the correct target, providing additional specificity and avoiding false products. Perform 20 cycles of LDR using allele-specific probes with UniTaq or universal tags in groups of 16, 32, or 64 primer sets. LDR primers for different mutations of the same gene may be designed to give the same signal in the same subdivision. Fresh PCR reagents are added, mixed with the LDR products of each Secondary LDR Reaction Chamber 22, and distributed through the Mixing Chambers 28 and then into micro-pores of each column. Universal or UniTaq primers in each subdivision of each row will amplify only those products from each column with the correct tags. Presence or absence of specific mutations in each of the columns allows for enumerating the number of low-level mutations in plasma.

In an alternative embodiment using 48 columns and 48 rows equaling 2,304 subdivisions, each subdivision comprising 96 micro-wells, 1-4 UniTaq primer sets (or alternatively, 1-4 universal tag primer sets with target-specific Taqman™ probes) are delivered directly to the appropriate subdivisions in each row by acoustic droplet ejection, capillary, inkjet, or quill printing, and then dried down into individual micro-wells. Distribute initial sample into 48 wells or Primary PCR Reaction Chambers 16. Highest level of DNA in plasma=10,000 genome equivalents. On average, 200 copies of each target per Primary PCR Reaction Chamber 16, with at most 1 mutation. Perform 10-40 cycles of locus-specific PCR with blocking PNA or LNA to reduce amplification of wild-type DNA. Optional: Use dUTP during PCR reaction (and pre-treat with UDG to avoid carry-over contamination of initial sample). Optionally, either PCR primers and/or LDR upstream probes containing an RNA base and 3' blocking group are unblocked with RNaseH2 only when bound to the correct target, providing additional specificity and avoiding false products. Also, all downstream PCR primers include identical 5' tail sequences, preferably 8-11 bases to suppress amplification of primer dimers. In another embodiment, to minimize dropout of fragments during multiplexed PCR, an initial "pre-amplification" multiplexed PCR is performed for 8-20 cycles in an initial well or reaction chamber. These products are then distributed into 48 wells or Primary PCR Reaction Chambers 16. In one variation, each of the 48 wells or primary reaction chambers contains from 1-4 PCR primer sets with PNA or LNA to suppress amplification of wild-type sequence, and single or multiplexed PCR is performed for an additional 10-30 cycles to enable amplification of 1-4 different fragments containing potential mutations in a single well or primary reaction chamber. In another variation, 12 sets of 4 primary reaction chambers contains from 4-16 PCR primer sets with PNA or LNA to suppress amplification of wild-type sequence, and multiplexed PCR is performed for an additional 10-30 cycles to enable amplification of 4-16 different fragments containing potential mutations in a single well or primary reaction chamber. Dilute products of each well with LDR primers and buffers. Perform 20 cycles of LDR using allele-specific primers with UniTaq tails, in groups of 16, 32, or 64 primer sets in wells or Secondary LDR Reaction Chamber 22. LDR primers for different mutations of the same gene may be designed to give the same signal in the same subdivision. LDR reactions may be performed in the same reaction chamber, or in 2 separate reaction chambers, and then re-combined. Add UniTaq master mix and UDG and distribute products of each well or Secondary LDR Reaction Chamber 22 into 48 subdivisions respectively containing 96 micro-pores. The subdivisions have been pre-spotted with appropriate UniTaq primers, and/or probes; (see FIGS. 28, and 29). PCR amplify 1, 2, or 4 potential products in each micro-pore using the pre-spotted primer sets and determine Ct value in each micro-pore of each subdivision. Use one, two, or four different fluorescent dyes on the UniTaq primers.

The cartridge and valve setup of FIG. 25 may also be used for quantifying unknown mutations at low-level in plasma using Multiplexed PCR-LDR-Real-time-PCR with UniTaq or mutation-specific Taqman™ probes. This figure also illustrates the fluidics system for multiplexed PCR-LDR-Real-time PCR with UniTaq or mutation-specific Taqman™ probes using a micro-pore plate composed of thousands of micro-pores. The micro-pore plate is fluidically accessible from both sides of the pores: the first side (top of plate, illustrated on left side of plate) is in communication with Valves 1, 2, & 3 while the second side (bottom of plate, illustrated on right side of plate) is in communication with Valves 4 & 5. Valve 1 dispenses a lysis/protease buffer, enzymes, wash buffer, elute buffer, buffer, EtOH, Light Oil, and Heavy Oil, as needed through the Initial 24-48 multiplex PCR Reaction Chambers, the 24-48 LDR Reaction Chambers, and additional chambers across the first side of the micro-pore plate through Valve 3 to Waste. In addition, Valve 1 can select a Waste port, which can be used to vacate the first side of micro-pore plate, other chambers, LDR Reaction Chambers, and initial multiplex PCR Reaction Chambers by the introduction of Air through Valve 3 in a reverse direction. Valve 1 can also select Valve 2. Valve 2 dispenses Initial multiplex PCR primers, optional LDR primers, Master PCR Mix, Master LDR Mix, Master UDG Mix, buffer, Wash, EtOH, & Air through Initial 24-48 multiplex PCR Reaction Chambers, the 24-48 LDR Reaction Chambers, and additional chambers across the first side of the micro-pore plate through Valve 3 to Waste. Valve 4 dispenses Air, Light Oil, Heavy Oil and Waste across the second side of the micro-pore plate through Valve 5 to Waste. In addition, Valve 1 can select a Waste port, which can be used to vacate the second side micro-pore plate by introduction of Air through Valve 5 in a reverse direction.

TABLE 4

Reagent Setup for Multiplexed PCR - LDR - Real-Time-PCR

| Port | Valve 1 | Valve 2 | Valve 4 | Valves 3/5 |
|---|---|---|---|---|
| 1 | Lysis/Protease Buf. | Initial PCR primers | Air | Waste |
| 2 | Wash | Optional LDR probes | Light Oil | Air |
| 3 | Elute Buffer | Master PCR mix | Heavy Oil | Or connect with |
| 4 | Enz/Prim. from V2 | Master LDR mix | Empty | Air/waste of |
| 5 | Empty (Pre-mix) | Master UDG mix | | Valve 1/4 |
| 6 | Waste | Buffer | | |
| 7 | Buffer | Wash | | |
| 8 | ETOH | ETOH | | |
| 9 | Air | Air | | |
| 10 | Light Oil | Empty | | |
| 11 | Heavy Oil | Empty | | |
| 12 | Hexanol | Empty | | |

FIG. 25B illustrates several heating elements that would be designed to provide independent heating/cooling to the Initial Multiplex Reaction Chamber 10, the Primary 24-48 Multiplex PCR reaction Chambers 16, the Secondary 24-48 Multiplex Reaction Chambers 22, and the main Chamber comprising subdivisions of 24-48 columns and thousands of micro-pores or micro-wells. The back plate, or one or more flat surface(s) of the micro-pore or micro-well chamber, and the reaction chambers may be pressed against these heating elements to allow for temperature control, heating, and/or thermocycling. As illustrated in FIG. 25, the two heating elements behind the Primary 24-48 Multiplex PCR reaction Chambers 10, the Secondary 24-48 Multiplex Reaction Chambers 22 would be designed as two rectangular (horizontal) strips to control all the Primary Chambers independently of all the Secondary Chambers. Alternative configurations may also be used, for example the initial multiplexed PCR may be divided into two steps (i) Single-sided multiplexed primer linear extension with or without blocking primer to suppress extension of wild-type DNA, and (ii) Addition of the complementary primers for limited or extended PCR amplification of the initial extension products. Such a configuration would require at least four independently controlled heating elements behind the (i) Primary 24-48 multiplex polymerase extension reaction Chambers, (ii) the Secondary 24-48 multiplex Reaction Chambers, (iii) the Tertiary 24-48 multiplex Reaction Chambers, and (iv) the main Chamber comprising of 24-48 columns and thousands of micro-pores or micro-wells.

FIG. 31 illustrates another exemplary PCR-LDR-qPCR reaction (with optional carryover prevention) to detect methylation. Genomic or cfDNA is isolated (FIG. 31, step A), and treated with Bsh1236I (CG^CG) in the Initial Reaction Chamber to completely digest unmethylated DNA. The isolated DNA sample is optionally treated with UDG to digest dU containing nucleic acid molecules that may be present in the sample (FIG. 31, step B). The enzymatically treated DNA is treated with bisulfite, which converts C but not 5 meC to U, and renders the strands non-complementary. The bisulfite treated DNA is then distributed into 24, 36, 48, or 64 wells or Primary PCR Reaction Chambers and locus-specific regions containing the methylated CpG of interest are amplified using PCR (FIG. 31, step B). In this embodiment, another layer of selectivity can be incorporated into the method by including a 3' cleavable blocking group (Blk 3', e.g. C3 spacer), and an RNA base (r), in the upstream primer. Upon target-specific hybridization, RNase H (star symbol) removes the RNA base to liberate a 3'OH group which is a few bases upstream of the mutation, and suitable for polymerase extension (FIG. 31, step B). Downstream primers contain identical 8-11 base tails on their 5' ends to prevent primer dimers. The amplified products optionally contain dU as shown in FIG. 31, step C, which allows for subsequent treatment with UDG or a similar enzyme for carryover prevention.

As shown in FIG. 31 step D, target-specific oligonucleotide probes are hybridized to the amplified products and ligase (filled circle) covalently seals the two oligonucleotides together when hybridized to their complementary sequence in the Secondary LDR Reaction Chambers. In this embodiment, the upstream oligonucleotide probe having a sequence specific for detecting the methylation status of the CpG of interest further contains a 5' primer-specific portion (Ai) to facilitate subsequent detection of the ligation product. The downstream oligonucleotide probe contains a 3' primer-specific portion (Ci') that, together with the 5' primer specific portion (Ai) of the upstream probe having a sequence specific for detecting the mutation, permit subsequent amplification and detection of only methylation-specific ligation products. As illustrated in step D of this Figure, another layer of specificity can be incorporated into the method by including a 3' cleavable blocking group (Blk 3', e.g. C3 spacer), and an RNA base (r), in the upstream ligation probe. Upon target-specific hybridization, RNase H (star symbol) removes the RNA base to generate a ligation competent 3'OH group (FIG. 31, step D). Following ligation, the ligation products can be detected using pairs of matched primers Ai and Ci, and TaqMan™ probes that span the ligation junction as described supra for FIG. 19 (see FIG. 31, steps E-G), or using other suitable means known in the art.

FIG. 32 illustrates another exemplary PCR-LDR-qPCR reaction (with optional carryover prevention) to detect methylation, with the same initial steps as in FIG. 31, steps A-C. As shown in FIG. 32 step D, target-specific oligonucleotide probes are hybridized to the amplified products and ligase (filled circle) covalently seals the two oligonucleotides together when hybridized to their complementary sequence.

In this embodiment, the upstream oligonucleotide probe having a sequence specific for detecting the methylation status of the CpG of interest further contains a 5' primer-specific portion (Ai) to facilitate subsequent detection of the ligation product. The downstream oligonucleotide probe contains a 3' primer-specific portion (Bi'-Ci') that, together with the 5' primer specific portion (Ai) of the upstream probe having a sequence specific for detecting the mutation, permit subsequent amplification and detection of only methylation-specific ligation products. As illustrated in step D of this figure, another layer of specificity can be incorporated into the method by including a 3' cleavable blocking group (Blk 3', e.g. C3 spacer), and an RNA base (r), in the upstream ligation probe. Upon target-specific hybridization, RNase H (star symbol) removes the RNA base to generate a ligation competent 3'OH group (FIG. 32, step D). Following ligation, the ligation products are amplified using UniTaq-specific primers (i.e., F1-Bi-Q-Ai, Ci) and detected as described supra for FIG. 20 (see FIG. 32, steps E-H), or using other suitable means known in the art.

The cartridge design of FIG. 30 may also be used for performing Multiplexed PCR-LDR-UniTaq detection, for identifying and quantifying methylations and unknown mutations at low-level in plasma. (Alternatively, use Multiplexed PCR-LDR-Real-time-PCR with mutation or methylation-specific Taqman™ probes).

The cartridge and valve setup of FIG. 25 may also be used for quantifying methylations and unknown mutations at low-level in plasma using Multiplexed PCR-LDR-Real-time-PCR with UniTaq or target-specific Taqman™ probes. This figure illustrates the fluidics system for multiplexed PCR-LDR-Real-time PCR with UniTaq or target specific Taqman™ probes using a micro-pore plate composed of thousands of micro-pores. The micro-pore plate is fluidically accessible from both sides of the pores: the first side (top of plate, illustrated on left side of plate) is in communication with Valves 1, 2, & 3 while the second side (bottom of plate, illustrated on right side of plate) is in communication with Valves 4 & 5. Valve 1 dispenses a lysis/protease buffer, enzymes, wash buffer, elute buffer, buffer, EtOH, Light Oil, and Heavy Oil, as needed through the bisulfite reaction chamber, the initial 24-48 multiplex PCR Reaction Chambers, the 24-48 LDR Reaction Chambers, and additional chambers across the first side of the micro-pore plate through Valve 3 to Waste. In addition, Valve 1 can select a Waste port, which can be used to vacate the first side of micro-pore plate, other chambers, LDR Reaction Chambers, initial multiplex PCR Reaction Chambers, and the bisulfite reaction chamber by the introduction of Air through Valve 3 in a reverse direction. Valve 1 can also select Valve 2. Valve 2 dispenses initial multiplex PCR primers for the methylation targets, initial multiplex PCR primers for the mutation targets, optional LDR primers, Master PCR Mix, Master LDR Mix, Master UDG Mix, Bsh1236I, bisulfite, buffer, Wash, EtOH, & Air through the bisulfite reaction chamber, initial 24-48 multiplex PCR Reaction Chambers, the 24-48 LDR Reaction Chambers, and additional chambers across the first side of the micro-pore plate through Valve 3 to Waste. Valve 4 dispenses Air, Light Oil, Heavy Oil and Waste across the second side of the micro-pore plate through Valve 5 to Waste. In addition, Valve 1 can select a Waste port, which can be used to vacate the second side micro-pore plate by introduction of Air through Valve 5 in a reverse direction.

TABLE 5

Reagent Setup for Multiplexed PCR-LDR-Real-Time-PCR (with Bisulfite).

| Port | Valve 1 | Valve 2 | Valve 4 | Valves 3/5 |
|---|---|---|---|---|
| 1 | Lysis/Protease Buf. | PCR primers—Meth. | Air | Waste |
| 2 | Wash | PCR primer—Mut. | Light Oil | Air |
| 3 | Elute Buffer | Optional LDR probes | Heavy Oil | Or connect with |
| 4 | Enz/Prim. from V2 | Master PCR mix | Empty | Air/waste of |
| 5 | Empty (Pre-mix) | Master LDR mix | | Valve 1/4 |
| 6 | Waste | Master UDG mix | | |
| 7 | Buffer | Bsh1236I | | |
| 8 | ETOH | Bisulfite | | |
| 9 | Air | Buffer | | |
| 10 | Light Oil | Wash | | |
| 11 | Heavy Oil | ETOH | | |
| 12 | Hexanol | Air | | |

FIG. 25B illustrates several heating elements that would be designed to provide independent heating/cooling to the Initial Multiplex Reaction Chamber 10, the Primary 24-48 Multiplex PCR reaction Chambers 16, the Secondary 24-48 Multiplex Reaction Chambers 22, and the main Chamber comprising subdivisions of 24-48 columns and thousands of micro-pores or micro-wells. The back plate, or one or more flat surface(s) of the micro-pore or micro-well chamber, and the reaction chambers may be pressed against these heating elements to allow for temperature control, heating, and/or thermocycling. As illustrated in FIG. 25, the two heating elements behind the Primary 24-48 Multiplex PCR reaction Chambers 10, the Secondary 24-48 Multiplex Reaction Chambers 22 would be designed as two rectangular (horizontal) strips to control all the Primary Chambers independently of all the Secondary Chambers. Alternative configurations may also be used. For example, the methylated DNA may be enriched for using methyl-specific binding protein or antibody to methylated DNA instead of the Bsh1236I selection process. This step may take place either within the cartridge, or prior to entering the methyl-enriched DNA into the cartridge. After bisulfate treatment, the initial multiplexed PCR may be divided into two steps (i) Single-sided multiplexed primer linear extension with or without blocking primer to suppress extension of unmethylated DNA DNA, and (ii) Addition of the complementary primers for limited or extended PCR amplification of the initial extension products. Such a configuration would require at least four independently controlled heating elements behind the (i) Primary 24-48 multiplex polymerase extension reaction Chambers, (ii) the Secondary 24-48 multiplex Reaction Chambers, (iii) the Tertiary 24-48 multiplex Reaction Chambers, and (iv) the main Chamber comprising of 24-48 columns and thousands of micro-pores or micro-wells.

FIG. 33 illustrates a RT-PCR-PCR-qPCR reaction to detect low-level alternatively spliced transcripts. FIG. 33, step A illustrates the wild-type transcript containing exon 3a (top) and the low level alternatively spliced transcript containing exon 3b (bottom) to be detected. This method involves isolating mRNA and generating a cDNA copy with reverse-transcriptase using 3' transcript-specific primers (i.e. to exon 4) in the Initial Reaction Chamber. Taq polymerase is activated to perform limited cycle PCR amplification (i.e. 7 cycles) to maintain relative ratios of different amplicons (FIG. 33, step B). In one embodiment, the initial multiplex reaction is distributed into 6 Primary PCR Reaction Chambers, with average distribution of 20 copies of each original transcript in each Primary PCR Reaction Chamber.

As shown in FIG. 33 step C, target-specific oligonucleotide secondary primers are hybridized to the primary amplified products and polymerase (filled diamond) is used to PCR amplify target-containing regions of interest (i.e. 10 cycles) in the Primary PCR Reaction Chambers. In this embodiment, a primer specific for the alternative splice variant (i.e., exon 3b), and which does not hybridize to the wild-type variant (i.e., exon 3a), is utilized to only generate amplification products corresponding to the alternative splice variant. Differentially dilute products from each of the 6 chambers into 4 smaller Secondary Reaction/Dilution Chambers for a total of 24 chambers. Following the nested primer amplification, the PCR products from each Secondary Reaction/Dilution Chamber are differentially diluted and distributed into 384 or 768 micro-pores. The products are amplified using UniTaq-specific primers (i.e., F1-Bi-Q-Ai, Ci) and detected as described supra for FIG. 20 (see FIG. 33, steps D-F), or using other suitable means known in the art.

FIG. 34 is a schematic front view of a portion of an exemplary design for pre-chamber loading to allow for liquids to be fluidically moved to the chambers comprising of micro-wells or micro-pores. This design illustrates the chamber architecture and micro-wells or micro-pores suitable for performing Multiplexed RT-PCR-Nested PCR-UniTaq detection, for enumeration of both rare and overexpressed lncRNA, mRNA, or splice variants. (Alternatively, Multiplexed RT-PCR-Nested PCR-Real-time-PCR with target-specific Taqman™ probes). In FIG. 34, the input sample is fluidically connected to the Initial Reaction Chamber 10 (bottom) through entrance 12. Initial Reaction Chamber 10 is fluidically coupled to hexagonal chamber 16 (containing large trough 18, comprising the Primary PCR Reaction Chamber) by conduit 14. The Primary PCR Reaction Chamber 16 is fluidically connected by conduit 20 to a second set of hexagonal chambers 22 (each initial chamber connecting to 4 chambers, containing a large trough 24a, medium trough 24c, small trough 24b, and very small trough 24d, respectively, comprising the Secondary Reaction/dilution Chambers 22), which are fluidically connected by conduits 26 to long narrower mixing chambers 28, which are fluidically connected by conduits 30 to the chambers of subdivisions 32 comprising micro-wells or micro-pores (top of panel, with only 4 rows illustrated). The diagram is not to scale and is for illustrative purposes. During manufacture of the cartridge, rows are pre-filled with 1-4 UniTaq primer sets (or alternatively, 1-4 universal tag primer sets with target-specific Taqman™ probes). During manufacture of the cartridge, chambers leading up to the columns of micro-wells or micro-pores are pre-filled with Nested PCR primer sets with either UniTaq or universal tag sequences on their 5' ends. The grey circle 17 on the left side of the drawing illustrates a potential position for delivering or printing primer sets, for example by acoustic droplet ejection, capillary, inkjet, or quill printing. The primers are dried down, and the cover part of the cartridge assembled to seal the probe sets in their appropriate positions. During use of the cartridge, reactions are fluidically moved from the initial chambers of the cartridge up the cartridge, and eventually up the columns of micro-wells or micro-pores, where each column is isolated from its neighbor column. In this illustrative example, showing 4 each of the planned 24 columns and 32 rows equaling 768 subdivisions, each subdivision comprising 24 micro-wells or micro-pores, the initial multiplexed reverse-transcription-PCR is for 7 cycles to amplify original target in the Initial Reaction Chamber. Distribute initial multiplex products into the Primary PCR Reaction Chambers, with average distribution of 20 copies of each original transcript in each Primary PCR Reaction Chamber. Perform 10 cycles of nested PCR using target-specific primers with UniTaq or universal tags in groups of 16, 32, or 64 primer sets. Each Primary PCR Reaction Chamber is designed to retain a certain percentage of liquid volume after draining. Perform 3 cycles of filling and draining to differentially dilute products. Distribute products from each of the Primary PCR Reaction Chamber into the Secondary Reaction/Dilution Chambers. Each Secondary Reaction/Dilution Chamber is designed to retain a certain percentage of liquid volume after draining. Perform 3 cycles of filling and draining to differentially dilute products. Distribute nested PCR products the mixing chambers and then into micro-pores of each column. Universal or UniTaq primers in each row will amplify only those products from each column with the correct tags. Poisson distribution in micro-pores will enumerate low-copy, medium-copy, and high-copy lncRNA, mRNA, or splice variants.

In an alternative embodiment using 48 columns and 48 rows equaling 2,304 subdivisions, each subdivision comprising 96 micro-wells, 1-4 UniTaq primer sets (or alternatively, 1-4 universal tag primer sets with target-specific Taqman™ probes) are delivered directly to the appropriate subdivisions in each row by acoustic droplet ejection, capillary, inkjet, or quill printing, and then dried down into individual micro-wells. Perform 10 cycles of multiplexed RT-PCR, maximum of 1,024 copies of each original RNA molecule in the Initial Reaction Chamber or well. If needed, use "tandem" PCR primers. Also, all PCR primers may include identical 5' tail sequences, preferably 10-11 bases to suppress amplification of primer dimers. Distribute initial multiplexed products into 48 wells or Primary PCR Reaction Chambers. Average distribution in each well is 20 copies of each original RNA target. Perform 3-4 cycles of nested PCR using primers with UniTaq tails, in groups of 24, or 48 primer sets, for a maximum of 160-320 copies of each original pathogen. Distribute products of each well into 2 or 4 sets of 24 or 12 subdivisions respectively containing 96 micro-pores. When using 2 sets, the second set is a 100/1 dilution of the first. When using 4 sets, each set is a 20/1 dilution of the previous set. This allows coverage of RNA molecules present across many orders of magnitude. On average, each initial subdivision will get 12 copies of each original RNA molecule, with a given micro-pore getting one or zero copies of original RNA. If RNA is present in higher numbers, each subdivision will get additional copies. PCR amplify 1, 2, or 4 potential products in each micro-pore using the pre-spotted UniTaq primer sets and determine Ct value in each micro-pore of each subdivision. Use one, two, or four different fluorescent dyes on the UniTaq primers. Poisson distribution in 96 micro-pores across 2 or 4 dilution sets will provide some degree of enumeration for very low copy RNA, as well as higher copy RNA in sample.

Another embodiment of the present invention is a system for sequencing by synthesis or by ligation of target molecules on a solid support. One or more target molecules are amplified within a 5-micron diameter micro-pore, for example as described in FIG. 1. The target is amplified and immobilized or coupled to a solid support within the micro-pores or micro-wells. Such immobilization may occur directly on the interior surface on the micro-pores or micro-wells, on dendrimeric primers immobilized to the surface of the micro-pores or micro-wells, or on micro-beads that are either already distributed within micro-pores or micro-wells prior to amplification or are distributed into micro-pores or micro-wells after amplification. The micro-beads may be porous with considerably more surface area for higher levels of amplification than could be achieved on the inside surface of a micro-pore alone. Immobilization or coupling to the solid support enables interrogating the amplified target one or more times to determine the presence or absence of mutations, SNps or sequence variations within the target.

Standard approaches for detecting sequencing-by-synthesis fluorescent product depend on amplifying only one target per well and using a single universal primer to generate sequencing reads. One approach for amplifying single target molecules is to immobilize both forward and reverse primers on a solid support, known as cluster amplification. However this approach limits total yield of strands within a cluster, since extension products tend to re-hybridize with each other rather than with fresh primers. An alternative approach is to amplify DNA on beads within aqueous droplets, surrounded by oil. Herein, a simpler approach is proposed, wherein the amplification takes place in solution, and products are then captured on the solid support, or on immobilized primers, that are then extended to make copies of the amplified products. This allows for the reactions to take place in larger volumes, resulting in higher yields of multiple amplified products, that may then be sequenced using selected target-specific primers, or alternatively, different sets of sequencing primers comprising of common and variable regions. For each round of sequencing, with appropriate loading and primer selection, about 30%-35% of the micro-pores will provide a unique sequencing read.

The micro-pores and micro-wells are constructed to have hydrophilic surfaces within and hydrophobic surfaces on the outside. This architecture is suitable for drawing the sample fluids into discrete isolated volumes of liquids, enabling amplification without cross-talk between micro-pores or micro-wells. Further, the hydrophilic surface can be functionalized for attachment/immobilization of primers within the micro-pores or micro-wells, but not outside so there can be no cross-talk.

When the solid support is comprised of Poly(methyl methacrylate)—(a.k.a. PMMA, Plexiglass, Lucite)—, cyclic olefin copolymer (COC), polyethylene, or polypropylene sheeting one approach is to create the micro-pores or micro-wells via UV laser ablation. Alternatively, the micro-pores and micro-wells are created via injection molding, imprinting, hot embossing, or etching, and those specific surfaces exposed to UV light using a masking approach. These processes generate a carboxylate surface, suitable for EDC/NHS mediated covalently linkage of 5' amino-terminated oligonucleotides to generate micro-arrays (Situma et al., "Fabrication of DNA Microarrays onto Poly(methyl Methacrylate) with Ultraviolet Patterning and Microfluidics for the Detection of Low-abundant Point Mutations," *Anal Biochem* 340(1):123-35 (2005); McCarley et al., "Resist-free Patterning of Surface Architectures in Polymer-based Microanalytical Devices," *J Am Chem Soc.* 127(3):842-3 (2005); Soper et al., "Fabrication of DNA Microarrays onto Polymer Substrates Using UV Modification Protocols With Integration Into Microfluidic Platforms for the Sensing of Low-abundant DNA Point Mutations," *Methods* 37(1):103-13 (2005); Wang et al., "Microarrays Assembled in Microfluidic Chips Fabricated From Poly(Methyl Methacrylate) for the Detection of Low-Abundant DNA Mutations," *Anal Chem.* 75(5):1130-40 (2003), which are hereby incorporated by reference in their entirety).

In an alternative embodiment, covalently attached polymer brushes are grown on the surface of PMMA by atom transfer radical polymerization (ATRP) (Balamurugan et al., "Aqueous-based Initiator Attachment and ATRP Grafting of Polymer Brushes from Poly(Methyl Methacrylate) Substrates," *Langmuir* 28(40):14254-60 (2012), which is hereby incorporated by reference in its entirety). This approach is based on the covalent immobilization of an ATRP initiator on PMMA surfaces and subsequent surface-initiated aqueous ATRP formation of Poly(N isopropylacrylamide) PNIPAAm. Briefly, selected regions of PMMA are UV modified to introduce carboxylic acid functional groups, which are subsequently converted to amino groups by reacting with ethylenediamine in EDC/NHS. These amine-functionalized PMMA surfaces are then reacted with the activated ester of the ATRP initiator; N-hydroxysuccinimidyl-2-bromo-2-methylpropionate. From the covalently attached initiator surfaces, atom-transfer polymerization in water is carried out to grow PNIPAAm brushes. This aqueous-based route to grafting polymers from surfaces can be adaptable to a variety of substrates and water-soluble ATRP monomers.

In an alternative embodiment, COC surfaces were photografted with poly(ethylene glycol) methacrylate (PEGMA) using a two-step sequential approach: covalently-bound surface initiators are formed in the first step and graft polymerization of PEGMA is then carried out from these sites in the second step. (Stachowiak et al., "Hydrophilic Surface Modification of Cyclic Olefin Copolymer Microfluidic Chips Using Sequential Photografting," *J Sep Sci.* 30(7):1088-93 (2007), which is hereby incorporated by reference in its entirety). A similar approach is also used for low-density polyethylene films. (Wang et al., "Surface Modification of Low-Density Polyethylene Films by UV-Induced Graft Copolymerization and Its Relevance to Photolamination," *Langmuir* 14(4):921-927 (1998), which is hereby incorporated by reference in its entirety).

In an alternative embodiment, hydrophobic surfaces are converted to hydrophilic ones using a hydrophilic coating (Zilio et al., "Universal Hydrophilic Coating of Thermoplastic Polymers Currently Used in Microfluidics," *Biomed Microdevice.* 16(1):107-14 (2014), which is hereby incorporated by reference in its entirety). In another variation, the wettability of a device is spatially controlled using a photoreactive coating to generate the hydrophilic surface (Abate et al., "Photoreactive Coating for High-Contrast Spatial Patterning of Microfluidic Device Wettability," *Lab Chip* 8(12):2157-60 (2008), which is hereby incorporated by reference in its entirety).

As described in U.S. Patent Application Publication No. 2015/0099642 to Barany et al., which is hereby incorporated by reference in its entirety, the surfaces of the solid support may also contain a layer of linker molecules that couple the oligonucleotides to the solid support, although it will be understood that the linker molecules are not required elements of the present invention. The linker molecules are preferably of sufficient length to permit polymers in a completed substrate to interact freely with molecules exposed to the substrate. The linker molecules should be 6-50 atoms long to provide sufficient exposure. Suitable linker molecules can be selected based upon their hydrophilic/hydrophobic properties. The linker molecules may be, for example, aryl acetylene, ethylene glycol oligomers containing 2-10 monomer units, diamines, diacids, amino acids, or combinations thereof.

The linker molecules can be attached to the substrate via carbon-carbon bonds using, for example, (poly)tri-fluoro-chloroethylene surfaces. The linker molecules may optionally be attached in an ordered array, i.e., as parts of the head groups in a polymerized monolayer. In alternative embodiments, the linker molecules are adsorbed to the surface of the substrate.

The device of the present invention can comprise various types of oligonucleotides depending on the application. In one embodiment of the present invention, the oligonucleotides of the device are capture oligonucleotide probes as described in U.S. Pat. Nos. 6,852,487 and 7,455,965 to Barany et al., which are hereby incorporated by reference in their entirety. Accordingly, the present invention also encompasses a method of capturing a plurality of target nucleotide sequence on a solid support.

Other suitable methods of solid-phase amplification that can be carried out using the device of the present invention are described in U.S. Pat. No. 6,017,738 to Morris et al., U.S. Pat. No. 7,741,463 to Gormley et al., U.S. Pat. No. 7,754,429 to Rigatti et al., and U.S. Pat. No. 6,355,431 to Chee et al., and U.S. Patent Publication No. 2009/0226975 to Sabot et al., U.S. Patent Publication No. 2001/0036632 to Yu et al., 2008/0108149 to Sundararaj an et al., and U.S. Patent Publication No. 2005/0053980 to Gunderson et al., which are hereby incorporated by reference in their entirety. The device of the present invention is also suitable for carrying out other multiplex nucleic acid reactions including, without limitation, single-base or multi-base extension reactions, primer extension assays, solid-phase sequencing, solid phase oligonucleotide ligation assay, pair end reads, RNA sequencing, copy number analysis, ChIP sequencing, and others as described in U.S. Patent Application Publication No. 2010/0015626 to Oliphant et al., which is hereby incorporated by reference in its entirety.

As described in U.S. Patent Application Publication No. 2015/0099642 to Barany et al., which is hereby incorporated by reference in its entirety, one aspect of the present invention relates to methods of attaching oligonucleotides within micro-wells or micro-pores on a solid support. The first of these methods involves providing a solid support having a base surface, a top surface, and a plurality of side surfaces extending between the base and top surfaces. The base surface, top surface, and plurality of side surfaces collectively form a plurality of micro-wells or micro-pores on the solid support. A mask is applied to cover the base surface of the solid support and the masked device is exposed to an activating agent to activate the unmasked surfaces of the solid support, while the masked surfaces of the solid support are non-activated. The mask is removed from the solid support and the exposed solid support is contacted with a plurality of oligonucleotides under conditions effective for the oligonucleotides to attach to the activated surfaces of the solid support, but not to the non-activated surfaces of the solid support, thereby attaching oligonucleotides within micro-wells or micro-pores on a solid support.

As described in U.S. Patent Application Publication No. 2015/0099642 to Barany et al., which is hereby incorporated by reference in its entirety, in accordance with this aspect of the present invention, the solid support preferably comprises a polymer material. Suitable polymers include, without limitation, poly(methyl methacrylate), polycarbonates, polysulfones, elastomers, and polymeric organosilicones. The solid support having a base surface, top surface and plurality of side surfaces extending between the base and top surfaces is formed from a solid support having a planar surface where the planar surface has been treated to form base, top, and a plurality of side surfaces to generate micro-wells or micro-pores on a solid support. In one embodiment, the planar surface is subjected to hot embossing as described in U.S. Pat. No. 8,758,974 to Soper et al., which is hereby incorporated by reference in its entirety. This approach is preferred when the solid support comprises a polymeric material. In an alternative embodiment of this aspect of the present invention, the planar surface is subjected to photolithography to generate micro-wells or micro-pores on a solid support.

Methods of modifying surfaces of polymers for the attachment of biological molecules, including oligonucleotides is described in U.S. Pat. No. 8,758,974 to Soper et al., which is hereby incorporated by reference in its entirety. To achieve selective activation and attachment of oligonucleotides within micro-wells or micro-pores on a solid support, the plurality of patterned positions on the solid support are selectively masked and exposed to an activating agent, e.g., UV light. In one embodiment of this aspect of the present invention, the activating agent is actinic light. Preferably, exposure to actinic light is carried out in an oxidizing atmosphere. In many applications, ordinary air is suitable, although it is also possible to use an atmosphere with a higher or lower concentration of oxygen (or other oxidizing agent) to modify the patterning if desired. Other oxidizing agents known in the art may be used in lieu of, or in addition to, oxygen, for example SO2, NO2, or CNBr (see e.g., Kavc et al., "Surface Modification of Polyethylene by Photochemical Introduction of Sulfonic Acid Groups," *Chem. Mater.* 12:1053-1059 (2000); Meyer et al, "Surface Modification of Polystyrene by Photoinitiated Introduction of Cyano Groups," *Macromol. Rapid Commun.* 20:515-520 (1999), which are hereby incorporated by reference in their entirety). Actinic light exposure activates polymer surfaces, promoting photooxidation and generating carboxyl groups on the exposed surfaces. Suitable surfaces for actinic light activation include, without limitation, acrylate polymers (e.g., PMMA), aromatic polymers (e.g., polystyrene, phenoxy resins), polyamides, polysulfones, and copolymers.

Activation of the array surface using actinic light as the activating agent can be achieved via exposure to broadband ultraviolet light, narrow band UV lamps (e.g., 254 nm), or UV lasers at frequencies absorbed by the polymers being used. Alternatively, activation of the array surface can be achieved using an oxygen plasma as the activating agent. Cyclic olefin copolymer (COC) is a preferred polymer due to its extraordinarily low autofluorescence levels and its ability to generate a high density of functional groups following UV or oxygen plasma exposure.

As described in U.S. Pat. No. 8,758,974 to Soper et al., which is hereby incorporated by reference in its entirety, oligonucleotides, preferably, amine-terminated oligonucleotides are attached to the activated areas of the surface using methods well known in the art, e.g., click chemistry using ethyl-3-(3-dimethylaminopropyl) carbodiimide hydrochloride (EDC) as a crosslinker and N-hydroxysuccinimide (NETS) an intermediate ester. However, other attachment chemistries can be used as well, such as disulfides, maleimides, or siloxanes. When forming an array containing a plurality of micro-wells or micro-pores, oligonucleotides are attached to activated side surfaces of the wells and bottom surfaces, if present, but not the masked top surfaces.

As described in U.S. Patent Application Publication No. 2015/0099642 to Barany et al., which is hereby incorporated by reference in its entirety, another method of forming arrays of oligonucleotides on a solid support involves providing a solid support having a planar substrate and a photosensitive layer over a surface of the substrate. The solid support is subjected to a photolithography process under conditions effective to form micro-wells or micro-pores on the solid support. The solid support is contacted with oligonucleotides under conditions effective for the oligonucleotides to attach to portions of the photosensitive layer which are either exposed or left unexposed by the photolithography process but not portions of the photosensitive layer which are left unexposed or exposed, respectively, thereby attaching oligonucleotides within micro-wells or micro-pores on the solid support.

Various methods of generating functional groups on photosensitive surfaces (i.e., SU-8 or one of its variants) to allow for the covalent attachment of oligonucleotides to the solid support are known in the art. Suitable functional groups include, without limitation, a carboxyl group, a carbonyl group, a hydroxyl group, an amino group, an epoxy group, and a silanol group.

As described in U.S. Patent Application Publication No. 2015/0099642 to Barany et al., which is hereby incorporated by reference in its entirety, SU-8 is a preferred surface material that comprises epoxide rings suitable for covalent attachment of oligonucleotides without additional activation or modification (See also Wang et al., "Surface Graft Polymerization of SU-8 for Bio-MEMS Applications," *J. Micromech. Microeng.* 17:1371-1380 (2007), which is hereby incorporated by referenced in its entirety). In one embodiment, amine-terminated oligonucleotides can be added to the SU-8 surface using alkaline solutions (pH~12) that hydrolyze surface epoxide groups and form secondary amines with the oligonucleotides carrying a primary amine. Alternatively, SU-8 micro-wells or micro-pores are treated with nitric acid to generate surface confined hydroxyl groups that are subsequently reacted with primary amine containing oligonucleotides (FIG. 24; Wang et al., "Surface Graft Polymerization of SU-8 for Bio-MEMS Applications," *J. Micromech. Microeng.* 17:1371-1380 (2007), which is hereby incorporated by referenced in its entirety). In yet another embodiment, SU-8 polymer micro-wells or micro-pores are exposed to UV radiation (254 nm) to generate surface hydroxyls and carboxylic acid groups. These approaches do not require a contact optical mask because the solid support substrate comprises a material that does not change its surface chemistry following exposure to the activating agent.

Alternative attachment chemistries compatible with epoxy-based resists, such as SU-8, are also suitable for use to attach oligonucleotides to the internal surface of micro-wells or micro-pores. For example, in one embodiment a cross-linking reagent is used to modify the functional group present on the surface of the support. Suitable crosslinking reagents include, without limitation, glycine, glutaraldehyde, and aminopropyltriethoxysilane (APTES), as described in U.S. Patent Application Publication No. 2015/0099642 to Barany et al., which is hereby incorporated by reference in its entirety.

In one embodiment for immobilizing dendrimers on a solid support, multiple primers are attached to the solid surface through a series of branched oligodeoxyribonucleotides, known as bDNA. (Horn et al., "An Improved Divergent Synthesis of Comb-type Branched Oligodeoxyribonucleotides (bDNA) Containing Multiple Secondary Sequences," *Nucleic Acids Res.* 25(23):4835-41 (1997), which is hereby incorporated by reference in its entirety). In this approach, bDNA contains one unique oligonucleotide, the primary sequence, covalently attached through a comb-like branch network to many identical copies of a different oligonucleotide, the secondary sequence. Multiple copies of a composite oligonucleotide, suitable for target amplification, are hybridized to, and then covalently cross-linked to the bDNA network. Suitable nucleotide analogues for inter-strand cross-linking are provided below. Alternatively, strands may be linked using enzymatic processes such as a DNA ligase. The 5' end of the composite oligonucleotide is designed to be complementary to the secondary sequences and suitable for crosslinking, while the 3' end is suitable for use as a tag sequence for amplification of the desired target.

A versatile and creative embodiment for controlled assembly of dendrimer-like DNA uses Y-shaped DNA molecules created by hybridization. (Li et al., "Controlled Assembly of Dendrimer-like DNA," *Nat Mater.* 3(1):38-42 (2004); Um et al., "Dendrimer-like DNA-based Fluorescence Nanobarcodes," *Nat Protoc.* 1(2):995-1000 (2006); Campolongo et al., "DNA Nanomedicine: Engineering DNA as a Polymer for Therapeutic and Diagnostic Applications," *Adv Drug Deliv Rev.* 62(6):606-16 (2010), which are hereby incorporated by reference in their entirety). Such molecules can be assembled by controlled hybridization, with ligation of smaller Y-shaped molecules to each other to create multi-armed dendrimer structures, and then made more permanent by crosslinking the DNA strands to each other. Use of a portion of terminal DNA molecules with an amino group, biotin group or other moiety at a 5' or 3' end such that it is suitable for covalent or non-covalent immobilization of the dendrimer complex to the solid support. Multiple copies of a composite oligonucleotide, suitable for target amplification, are hybridized to, and then covalently cross-linked or ligated to the bDNA network. The 5' end of the composite oligonucleotide is designed to be complementary to the secondary sequences and suitable for crosslinking or ligation, while the 3' end is suitable for use as a tag sequence for amplification of the desired target.

In another embodiment, branched DNA is synthesized from tripropargylated oligonucleotides by cycloaddition using "stepwise and double click" chemistry. (Xiong et al., "Construction and Assembly of Branched Y-shaped DNA: "click" Chemistry Performed on Dendronized 8-aza-7-deazaguanine Oligonucleotides," *Bioconjug Chem.* 23(4):856-70 (2012), which is hereby incorporated by reference in its entirety). Dendronized oligonucleotides decorated with 7-tripropargylamine side chains carrying two terminal triple bonds are further functionalized with bis-azides to give derivatives with two terminal azido groups. Subsequently, the branched side chains with two azido groups or two triple bonds are combined with DNA-fragments providing the corresponding clickable function. Likewise, oligonucleotides comprising the commercially available azide, alkyne, or DBCO moiety may be used. These approaches yield branched (Y shaped) three-armed DNA. Annealing of branched DNA with a first set of complementary oligonucleotides yields supramolecular assemblies, which may be rendered heat stable by using the crosslinking approaches described herein. A second set of complementary composite oligonucleotides a hybridized to, and then covalently cross-linked or ligated to the supramolecular bDNA network. The 5' end of the composite oligonucleotide is designed to be complementary to the first set of complementary oligonucleotides and suitable for crosslinking or ligation, while the 3' end is suitable for use as a tag sequence for amplification of the desired target.

In another embodiment, the dendrimer is assembled directly on the solid support (Benters et al., "DNA Microarrays with PAMAM Dendritic Linker Systems," *Nucleic Acids Res.* 30(2):E10 (2002), which is hereby incorporated by reference in its entirety). This approach uses pre-fabricated polyamidoamine (PAMAM) starburst dendrimers as mediator moieties between the solid support and the desired oligonucleotides suitable for use as a tag sequence for amplification of the desired target. Dendrimers containing 64 primary amino groups in their outer sphere are covalently attached to silylated glass supports and, subsequently, the dendritic macromolecules are modified with glutaric anhydride and activated with N-hydroxysuccinimide. The activated surface may now be decorated with amino-modified DNA-oligomers, yielding a highly stable surface with high loading density of the desired oligonucleotide primer.

In another embodiment, the primer may be covalently attached to the solid surface, another oligonucleotide, or to a dendrimer oligonucleotide using Dibenzocyclooctyl (DBCO) for copper-free click chemistry (to an azide); 5-Octadiynyl dU for click chemistry (to an azide); Amino Modifier C6 dT (for peptide linkage); or Azide, for click chemistry to an alkyne or DBCO. Oligonucleotides comprising modified bases suitable for crosslinking either to other oligonucleotides or to a solid support are commercially available, for example from IDT (Integrated DNA technologies, Coralville, Iowa 52241, USA).

In another embodiment, oligonucleotides are synthesized with a modified base containing a furan moiety. Upon exposure to visible light in the presence of methylene blue, this induces singlet oxygen formation, which triggers furan oxidation, and the resulting aldehyde then rapidly reacts with complementary A or C to form stable interstrand adducts. (Op de Beeck et al., "Sequence Specific DNA Cross-linking Triggered by Visible Light," *J Am Chem Soc.* 134(26):10737-40 (2012), which is hereby incorporated by reference in its entirety).

Another approach to stabilize dendrimer structures is to use photo-crosslinking. (Rajendran et al., "Photo-cross-linking-assisted Thermal Stability of DNA Origami Structures and its Application for Higher-temperature Self-assembly," *J Am Chem Soc.* 133(37):14488-91 (2011), which is hereby incorporated by reference in its entirety). In this approach 8-methoxypsoralen is used to crosslink pyrimidine bases to each other upon exposure to UV light.

In another embodiment, nucleotide analogs of abasic sites are used to facilitate interstrand crosslinking (Ghosh et al., "Synthesis of Cross-linked DNA Containing Oxidized Abasic Site Analogues," *J Org Chem.* 79(13):5948-57 (2014), which is hereby incorporated by reference in its entirety).

In another embodiment, 4-vinyl substituted pyrimidine and 6-vinyl purine nucleotide analogs are used to form interstrand crosslinks (Nishimoto et al., "4-vinyl-substituted pyrimidine Nucleosides Exhibit the Efficient and Selective Formation of Interstrand Cross-links with RNA and Duplex DNA," *Nucleic Acids Res.* 41(13):6774-81 (2013), which is hereby incorporated by reference in its entirety). These analogues include a 2-amino-6-vinylpurine derivative, for cross-linking with cytosine as well as 4-vinyl substituted pyrimidine derivatives, T-vinyl and U-vinyl.

As described in WO 2016/057832 to Barany et al., which is hereby incorporated by reference in its entirety, the oligonucleotide may be covalently attached to the solid surface using Dibenzocyclooctyl (DBCO) for copper-free click chemistry (to an azide); 5-Octadiynyl dU for click chemistry (to an azide); Amino Modifier C6 dT (for peptide linkage); or Azide, for click chemistry to an alkene or DBCO. Alternatively, the oligonucleotide may comprise a capture moiety such as a biotin group or a His-Tag, which would be captured by immobilized streptavidin or NTA matrix respectively present within the micro-wells or micropores on the solid support.

Alternative means of forming surfaces with covalently attached identical copies of the limited (short) RCA amplicon includes Sequoia amplification (WO2013/012440 to Barany et al., which is hereby incorporated by reference in its entirety) and wildfire amplification (Ma et al., "Isothermal Amplification Method for Next-Generation Sequencing," *Proc Natl Acad Sci USA* 10(35):14320-3 (2013), which is hereby incorporated by reference in its entirety).

As described in WO 2015/188192 to Barany et al., which is hereby incorporated by reference in its entirety, the solid support can be made from a wide variety of materials. The substrate may be biological, nonbiological, organic, inorganic, or a combination of any of these, existing as particles, strands, precipitates, gels, sheets, tubing, spheres, beads, containers, capillaries, pads, slices, films, plates, slides, discs, membranes, etc. The substrate may have any convenient shape, such as a disc, square, circle, etc. The substrate is preferably flat but may take on a variety of alternative surface configurations. For example, the substrate may contain raised or depressed regions on which the hybridization takes place. The substrate and its surface preferably form a rigid support on which to carry out sequencing reactions described herein.

Commercially available next generation sequencing solid support platforms used for template preparation can be utilized in the system and methods of the present invention. For example, the Illumina® Flow Cell, Life Technologies® IonSphere™ and emulsion PCR beads, and 454 emulsion PCR beads can be used in the system and methods of the present invention. Accordingly, the first solid support primer-specific portion of the circular chimeric single stranded nucleic acid constructs is designed to be the same as the primers immobilized on a commercially available NGS solid support. Therefore, the extension products containing the complement of the first solid support primer-specific portion are capable of hybridizing to primers on the NGS solid support surface.

FIG. 35 provides an embodiment of primer design for sequencing and identifying pathogens in one target strand. Isolate genomic DNA, while for RNA viruses an initial reverse-transcriptase step generates cDNA. The target DNA may be pre-amplified using PCR in the Initial Reaction Chamber (FIG. 35, step A). In one variation, the PCR amplified DNA or cDNA is distributed into 24, 36, or 48 Primary PCR Reaction Chambers. Nested, locus-specific primer pairs are provided to amplify target sequences, each primer pair comprising of: (i) a first locus-specific primer, said primer comprising of a first 5' universal or tag sequence portion, a locus-specific 3' portion, a cleavable base such as a ribo-nucleotide and a blocking group on the 3' end; and (ii) a second locus-specific primer with two or more dU bases throughout the primer sequence, said primer comprising of a second 5' universal or tag sequence portion, a fragment identifier sequence, and a locus-specific 3' portion, a cleavable base such as a ribo-nucleotide and a blocking group on the 3' end. The locus-specific primers are unblocked with RNaseH2 only when bound to target, liberating a 3'OH suitable for polymerase-mediated extension (FIG. 35, step B). Two or three cycles of PCR amplification are performed using a thermostable polymerase, preferably a strand-displacement polymerase. These amplification cycles generate product containing the first 5' universal or tag sequence portion, the target sequence between the two locus-specific primer portions, the internal fragment identifier, and the second 5' universal or tag sequence. The original primers and portion of primers in products are destroyed using UDG (uracil DNA glycosylase) and optionally, APE1 (human apurinic endonuclease; FIG. 35, step C). This renders a portion of one of the ends of each double-stranded amplification product single-stranded. Distribute products into micro-pores or beads into micro-pores containing immobilized second tag sequence primers. In the presence of both first and second tag primers, products are PCR amplified in micro-pores such that a given micro-pore generally contains zero or one clonal amplification of a given region, but the micro-pore may contain multiple clonal amplicons from different regions. After denaturation, and removal of unbound fragments, remaining tethered single-stranded target DNA is suitable for primer-directed sequencing. (FIG. 35, step D).

For best sequencing signal, especially if amplifying multiple products in a micro-pore or bead, it is desirable to amplify products such that most of the immobilized primers are extended, converting them to target-comprising strands suitable for sequencing. FIGS. 36, 37, and 38 provide three different embodiments, which may be used individually or in combinations, or with other approaches.

FIG. 36 illustrates an embodiment where the first tag primer is present in larger amounts than both in solution and immobilized second tag primers. Immobilized primer is longer than in solution second tag primer. Optionally, at the end of the PCR or other amplification cycles, hybridization temperature is above Tm of shorter tag primer to favor synthesis of single stranded products to hybridize to immobilized primer and drive extension of such primers to completion.

FIG. 37 illustrates another embodiment where the in solution first tag primers comprise two different 5' portions, and with added 5' portion primers, which are present in larger amounts than both second tag primers. Immobilized primer is longer than in solution second tag primer. Using strand-displacement polymerase lacking 5'-3' nuclease activity, perform combined isothermal and thermo-cycling amplification. Re-annealing of products with different 5' portions generates a Y shaped structure at the end and enables strand displacement amplification. This helps drive extension of immobilized primers to completion.

FIG. 38 illustrates another embodiment where the in solution first tag primer comprises dA35, and with added dA35 with GC rich toehold primer, are present in larger amounts than both second tag primers. Immobilized primer is longer than in solution second tag primer. Using strand-displacement polymerase lacking 5'-3' nuclease activity, perform isothermal and/or thermo-cycling amplification. Primer toehold is released with RNaseH2 only when bound to target. Excess single-stranded product hybridizes to immobilized primer and helps drive extension of immobilized primers to completion.

Sequencing of the immobilized extension products can be achieved using sequence-by-synthesis as described and depicted herein. Sequence-by-synthesis includes fluorescence-based sequencing-by-synthesis and ion-based sequencing-by-synthesis. Other suitable sequencing methods can also be employed, including, for example and without limitation, fluorescent primer hybridization, molecular beacon hybridization, primer extension, exonuclease-based sequencing, ligase detection reaction, ligase chain reaction, pyrosequencing, fluorescence-based sequencing-by-ligation, nanopore and nanotube based sequencing, and ion-based sequencing-by-ligation.

As described more fully in WO 2016/154337 to Barany et al., which is hereby incorporated by reference in its entirety, suitable capture molecules and methods for immobilizing target nucleic acid molecules on the solid support are described supra. Similarly, methods of generating immobilized extension products that are complementary to the target nucleic acid molecule using solid phase amplification are also described supra.

In accordance with this aspect of the present invention, the immobilized target nucleic acid molecule or immobilized extension product thereof is subject to a nucleotide extension reaction process. The nucleotide extension reaction mixture comprises a collection of nucleotide triphosphates where each type of nucleotide triphosphate in the collection has (i) a different cleavable fluorescently labeled group, and (ii) a cleavable blocking moiety that inhibits addition of a subsequent nucleotide triphosphate.

The blocking moiety of the nucleotide triphosphate may directly block the addition of a subsequent nucleotide triphosphate at its 3'OH group. In this embodiment, the blocking moiety is appended to the nucleoside triphosphate at the 2'-O of a ribose, or the 3'-O of a deoxyribose. These nucleotide triphosphates are the same as or analogous to fluorescent sequencing-by-synthesis (Ju et al., "Four-color DNA Sequencing by Synthesis Using Cleavable Fluorescent Nucleotide Reversible Terminators," *Proc Natl Acad Sci USA* 103(52):19635-40 (2006), which is hereby incorporated by reference in its entirety). In the case of 3'-O blocking groups, there are several well-demonstrated examples in the literature such as but not limited to amino, azidomethyl, and cyanoethyl groups. The specific nature of the group should be chosen for a combination of efficiency of enzymatic incorporation and ease of removal during the deblocking step. Removal of the blocking group is specific to the chemical nature of the blocking group but examples would be the use of mild aqueous reagents (i.e., reducing agents) at temperatures that preserve the primer-template duplex and do not cause loss of signal due to melting of the primer-template duplex.

Alternatively, the blocking moiety of the nucleotide triphosphate reversibly inhibits the addition of a subsequent nucleotide triphosphate at its 3'OH group. These blocking moieties can be appended to a nucleotide triphosphate at the C5 or C7 position of the nucleoside, i.e., the pyrimidine or purine, respectively. These nucleotide triphosphates are the same as or similar to Lightning Terminators™ (LaserGen, Inc.) (Gardner et al., "Rapid Incorporation Kinetics and Improved Fidelity of a Novel Class of 3'OH Unblocked Reversible Terminators," *Nucleic Acids Research* 40(15): 7404-15 (May 2012) and Litosh et al., "Improved Nucleotide Selectivity and Termination of 3'-OH Unblocked Reversible Terminators by Molecular Tuning of 2 nitrobenzyl Alkylated HOMedU Triphosphates," *Nucleic Acids Research* 39(6):e39 (2011), which are hereby incorporated by reference in their entirety) and Virtual Terminator™ (Helicos BioSciences) (Bowers et al., "Virtual Terminator Nucleotides for Next-Generation DNA Sequencing," *Nat. Methods* 6:593-595 (2003), U.S. Pat. No. 8,071,755 to Efcavitch et al, U.S. Pat. No. 8,114,973 to Siddiqi et al, WO 2008/0169077 to Siddiqi et al, which are hereby incorporated by reference in their entirety). Chemical moieties which interfere with incorporation of dNTPs by a template dependent DNA polymerase that utilize steric bulk or charged inhibition or combinations of both can be used. Examples of inhibitory moieties are dipeptides of Glu-Glu or Asp-Asp.

In all these embodiments, a gene-specific primer may be used to initiate sequencing-by-synthesis to determine the unique sequence of the target. In one embodiment, the upstream locus-specific primers used in the initial nested amplification may double as sequencing primers. Since these primers are unblocked with RNaseH2 only when bound to the target, essentially eliminating potential false-reads from primer binding incorrectly.

Alternatively, the locus-specific primers are designed to comprise of variable regions. Individual targets will contain distinct variable regions and are then sequenced by using individual primers. In one embodiment, a first set of 8-16 sequencing primers comprises a common 5' sequence (16 bases), and variable 3' sequences (8 bases). Or, a second set of 64-256 sequencing primers comprises a common 5' sequence (8 bases), a variable middle sequence (8 bases, 8-16 variants) and hyper-variable 3' sequences (8 bases, 64-256 variants). One approach is to use split & pool synthesis strategies. By way of example, synthesis of a family of 16 variant primers would comprise synthesis of the locus-specific 3' region, splitting into 4 aliquots, each getting an additional four bases, pooling, and splitting again into 4 aliquots, each getting an additional four bases, and then pooling and finishing synthesis with 16 bases of common sequence on the 5' end. Consider the initial 4 bases on the 3' side being GTCA, ACTG, TGAC, and CAGT, the next four bases being GCTA, ATCG, TAGC, and CGAT, followed by 16 bases on the 5' side. Then a set of 16 sequencing primers could be used to sequence each amplicon uniquely, while minimizing mis-priming from one primer binding to a mismatched complement.

```
                                                (SEQ ID No: 1)
 1. (16 base common sequence)-GTCA-GCTA (SEQ ID No: 2)
 2. (16 base common sequence)-GTCA-ATCG (SEQ ID No: 3)
 3. (16 base common sequence)-GTCA-TAGC (SEQ ID No: 4)
 4. (16 base common sequence)-GTCA-CGAT (SEQ ID No: 5)
 5. (16 base common sequence)-ACTG-GCTA (SEQ ID No: 6)
 6. (16 base common sequence)-ACTG-ATCG (SEQ ID No: 7)
 7. (16 base common sequence)-ACTG-TAGC (SEQ ID No: 8)
 8. (16 base common sequence)-ACTG-CGAT (SEQ ID No: 9)
 9. (16 base common sequence)-TGAC-GCTA (SEQ ID No: 10)
10. (16 base common sequence)-TGAC-ATCG (SEQ ID No: 11)
11. (16 base common sequence)-TGAC-TAGC (SEQ ID No: 12)
12. (16 base common sequence)-TGAC-CGAT (SEQ ID No: 13)
13. (16 base common sequence)-CAGT-GCTA (SEQ ID No: 14)
14. (16 base common sequence)-CAGT-ATCG (SEQ ID No: 15)
15. (16 base common sequence)-CAGT-TAGC (SEQ ID No: 16)
16. (16 base common sequence)-CAGT-CGAT
```

FIG. 39 is a schematic front view of a portion of an exemplary design for pre-chamber loading to allow for liquids to be fluidically moved to the chambers comprising of micro-wells or micro-pores. This design illustrates the chamber architecture and micro-wells or micro-pores suitable for performing Multiplexed PCR-Nested PCR-sequencing, for unknown pathogen identification. In FIG. 39, the input sample is fluidically connected to a large hexagonal chamber 116 (bottom, Initial Reaction Chamber), which is fluidically connected by conduits 120 to a set of hexagonal chambers 122 (containing large troughs 124 and baffles 123, Primary PCR Reaction Chambers), which are fluidically connected by conduit 126 to long narrower mixing chambers 128, which are fluidically connected by conduits 130 to the chambers of subdivisions 132 comprising micro-pores (top of panel, with only 4 rows illustrated). The diagram is not to scale and is for illustrative purposes. During manufacture of the cartridge, rows are pre-filled with one or more universal tag primer sets, where one primer is immobilized to the solid support and the other primer is bound, but that primer is released at higher temperature. During manufacture of the cartridge, chambers leading up to the columns of micro-wells or micro-pores are pre-filled with nested PCR primer sets with universal tag sequences on their 5' ends. The grey circles 125 on the left side of the drawing illustrate potential position for delivering or printing primer sets, for example by acoustic droplet ejection, capillary, inkjet, or quill printing. The primers are dried down, and the cover part of the cartridge assembled to seal the primer sets in their appropriate positions. During use of the cartridge, reactions are fluidically moved from the initial chambers of the cartridge up the cartridge, and eventually up the columns of micro-wells or micro-pores, where each column is isolated from its neighbor column. In this illustrative example, showing 4 each of planned 48 columns and 64 rows equaling 3,072 subdivisions, each subdivision comprising 2,760 micro-pores, for a total of 8,478,720 micro-pores in the array, the initial multiplexed PCR amplification (or reverse-transcription-PCR for RNA targets) is for 10 cycles to generate up to 1,024 copies of each original target in the Initial Reaction Chamber. If needed, fresh PCR reagents are added, and the initial multiplexed reaction is distributed into the Primary PCR Reaction Chambers (pre-filled with nested PCR primers as described above), with average distribution of 20 copies of each original pathogen target in each Primary PCR Reaction Chamber. Optionally, primers containing an RNA base and 3' blocking group are unblocked with RNaseH2 only when bound to the correct target, providing additional specificity and avoiding false products. Perform 5 cycles of nested PCR using target-specific primers with universal tags in groups of 32, or 64 primer sets, to generate an average of 640 copies of each pathogen-specific target per Primary PCR Reaction Chamber. Remove universal primer sequence from product with UDG/APE1 to generate single-stranded tails on one side of the PCR products, which facilitates hybridization to immobilized primer in micro-pore. If needed, fresh PCR reagents are added, mixed with the nested PCR products of each Primary PCR Reaction Chamber, and distributed into the Mixing Chambers and then into the micro-pores of each column. PCR amplify one or more products in each micro-pore and melt off non-anchored strand. Universal primers in each subdivision of each row will amplify only those products from each column with the correct tags. Add either target-specific, or universal tag-specific sequencing primers. Perform sequencing-by-synthesis. Poisson distribution in micro-pores will enumerate target sequences, while direct sequence information will identify variant pathogens.

The cartridge design of FIG. 39 may also be used in a different embodiment to perform Multiplexed PCR-Nested PCR-sequencing, for unknown pathogen identification. In this embodiment, all micro-pores are pre-filled with a single universal primer, which is immobilized, and micro-pores are dried. Since all subdivisions contain the identical primer, they may be added through the columns, or by other means. In this illustrative example, showing 4 each of the planned 48 columns and 64 rows equaling 3,072 subdivisions, each subdivision comprising 2,760 micro-pores, for a total of 8,478,720 micro-pores in the array, the initial multiplexed PCR amplification (or reverse-transcription-PCR for RNA targets) is for 10 cycles to generate up to 1,024 copies of each original target in the Initial Reaction Chamber. If needed, fresh PCR reagents are added, and the initial multiplexed reaction is divided into the Primary PCR Reaction Chambers (pre-filled with nested PCR primers as described above), with average distribution of 20 copies of each original pathogen target in each Primary PCR Reaction Chamber. Optionally, primers containing an RNA base and 3' blocking group are unblocked with RNaseH2 only when bound to the correct target, providing additional specificity and avoiding false products. Perform 5 cycles of nested PCR using target-specific primers with 8-12 unique tag sequence on one primer of the set, and universal sequences on their 5' ends, to generate an average of 640 copies of each pathogen-specific target per Primary PCR Reaction Chamber. Remove universal primer sequence from product with UDG/APE1 to generate single-stranded tails on one side of the PCR products, which facilitates hybridization to immobilized primer in micro-pore. If needed, fresh PCR reagents are added, mixed with the nested PCR products of each Primary PCR Reaction Chambers, and distributed into the Mixing Chambers and then into the micro-pores of each column. PCR amplify one or more products in each micro-pore and melt off non-anchored strand. Universal primers in each subdivision of each row will amplify only those products from each column with the correct tags. Add either target-specific, or universal primers with unique tag-specific portions as sequencing primers. Perform sequencing-by-synthesis. Poisson distribution in micro-pores will enumerate target sequences, while direct sequence information will identify variant pathogens.

In an alternative embodiment using 48 double-columns and 48 double-rows equaling 2,304 subdivisions, each subdivision comprising 11,040 micro-pores, with 529,920 micro-pores per double-column. Initial multiplexed amplification of the sample for 10 cycles of PCR, provides a maximum of 1,024 copies of each original pathogen in a well or Initial Reaction Chamber. Distribute initial multiplexed products into 48 wells or Primary PCR Reaction Chambers, mixed with locus-specific primers, buffer, and polymerase into the Primary PCR Reaction Chambers, for example by using acoustic droplet ejection as illustrated in FIG. 50. Average distribution in each well or Primary PCR Reaction Chamber is 20 copies of each original pathogen. Perform 2-3 cycles of nested PCR in groups of 32, maximum of 80 to 160 copies of each original pathogen target. Optional, remove universal primer sequence from product with UDG/APE1 to improve hybridization of product to immobilized primer in micro-pores. Distribute products of each well or Primary PCR Reaction Chamber into 529,920 micro-pores. PCR amplify multiple products in each micro-pore and melt off non-anchored strand. Perform sequencing-by-synthesis. Poisson distribution in micro-pores will enumerate target sequences, while direct sequence information will identify variant pathogens.

FIG. 40 provides one embodiment of primer design for sequencing and identifying mutations in one target strand. In this and the following embodiments, the original genomic segments comprise segments of cfDNA (~160 bp) or segments of sheared genomic DNA (~160 bp) containing, e.g., tumor specific mutations (FIG. 40, step A). Distribute the sample into 48 Primary PCR Reaction Chambers. The spatial distribution will assure that for low abundance mutations, each mutant fragment is in a different Primary PCR Reaction Chamber. Thus, when a mutation is present in two or more Primary PCR Reaction Chambers, it is most likely a true mutation and not a polymerase error. Nested, locus-specific primer pairs are provided to amplify target sequences, each primer pair comprising of: (i) a first locus-specific primer, said primer comprising of a first 5' universal or tag sequence portion, a locus-specific 3' portion, a cleavable base such as a ribo-nucleotide and a blocking group on the 3' end; and (ii) a second locus-specific primer with two or more dU bases throughout the primer sequence, said primer comprising of a second 5' universal or tag sequence portion, a fragment identifier sequence, and a locus-specific 3' portion, a cleavable base such as a ribo-nucleotide and a blocking group on the 3' end. The locus-specific primers are unblocked with RNaseH2 only when bound to target, liberating a 3'OH suitable for polymerase-mediated extension (FIG. 40, step B). Two or three cycles of PCR amplification are performed using a thermostable polymerase, preferably a strand-displacement polymerase. These amplification cycles generate product containing the first 5' universal or tag sequence portion, the target sequence between the two locus-specific primer portions, the internal fragment identifier, and the complement of the second 5' universal or tag sequence. The original primers and portion of primers in products are destroyed using UDG (uracil DNA glycosylase) and optionally, APE1 (human apurinic endonuclease; FIG. 40, step C). This renders a portion of one of the ends of each double-stranded amplification product single-stranded. In one variation, distribute products into micro-pores or beads into micro-pores containing immobilized second tag sequence primers. In the presence of both first and second tag primers, products are PCR amplified in micro-pores such that a given micro-pore generally contains zero or one clonal amplification of a given region, but that micro-pore may contain multiple clonal amplicons from different regions. After denaturation, and removal of unbound fragments, remaining tethered single-stranded target DNA is suitable for primer-directed sequencing. (FIG. 40, step D). In another variation, anneal biotinylated primer containing second tag sequence to the single-stranded region. Strand displacement polymerase extends to form full-length double-stranded copy of fragment. Both extended and free biotinylated primers are captured on streptavidin coated beads to be distributed in micro-pores, or directly on streptavidin coated micro-pores. In the presence of both first and second tag primers, products are PCR amplified in micro-pores such that a given micro-pore generally contains zero or one clonal amplification of a given region, but that micro-pore may contain multiple clonal amplicons from different regions. After denaturation, and removal of unbound fragments, remaining tethered single-stranded target DNA is suitable for primer-directed sequencing (Not shown, but like FIG. 41, below).

FIGS. 41 and 42 provide embodiments of primer design for sequencing and identifying mutations in one target strand across overlapping fragments. Distribute the sample into 48 Primary PCR Reaction Chambers. The spatial distribution will assure that for low abundance mutations, each mutant fragment is in a different Primary PCR Reaction Chamber. Nested, locus-specific primer pairs, across overlapping regions (i.e. one or more exons for a cancer-specific gene) are provided to amplify overlapping target sequences, each primer pair comprising of: (i) a first locus-specific primer, said primer comprising of a first 5' universal or tag sequence portion, a locus-specific 3' portion, a cleavable base such as a ribo-nucleotide and a blocking group on the 3' end; and (ii) a second locus-specific primer with two or more dU bases throughout the primer sequence, said primer comprising of a second 5' universal or tag sequence portion, which differs slightly from the first universal or tag sequence, a fragment identifier sequence, and a locus-specific 3' portion, a cleavable base such as a ribo-nucleotide and a blocking group on the 3' end. The locus-specific primers are unblocked with RNaseH2 only when bound to target, liberating a 3'OH suitable for polymerase-mediated extension (FIG. 41, step B). Two or three cycles of PCR amplification are performed using a thermostable polymerase, preferably a strand-displacement polymerase. These amplification cycles generate overlapping products, both shorter (slightly longer than primer dimer), and longer products (comprising 100 or more bases of target sequences), containing the first 5' universal or tag sequence portion, the target sequence between the two locus-specific primer portions, the internal fragment identifier, and the complement of the second 5' universal or tag sequence. The original primers and portion of primers in products are destroyed using UDG (uracil DNA glycosylase) and optionally, APE1 (human apurinic endonuclease; FIG. 41, step C). This renders a portion of one of the ends of each double-stranded amplification product single-stranded. In one variation, anneal biotinylated primer containing second tag sequence to the single-stranded region. Strand displacement polymerase extends to form full-length double-stranded copy of fragment (FIG. 41, step D). Both extended and free biotinylated primers are captured on streptavidin coated beads to be distributed in micro-pores, or directly on streptavidin coated micro-pores. In the presence of both first and second tag primers, longer products are PCR amplified in micro-pores such that a given micro-pore generally contains zero or one clonal amplification of a given region, but that micro-pore may contain multiple clonal amplicons from different regions. Shorter products form panhandles and do not amplify. After denaturation, and removal of unbound fragments, remaining tethered single-stranded target DNA is suitable for primer-directed sequencing (FIG. 41, step E). FIG. 43, step A illustrates in close-up how the longer products, but not the shorter products amplify. In another variation, distribute products into micro-pores or beads into micro-pores containing immobilized second tag sequence primers. In the presence of both first and second tag primers, longer products are PCR amplified in micro-pores such that a given micro-pore generally contains zero or one clonal amplification of a given region, but that micro-pore may contain multiple clonal amplicons from different regions. Shorter products form panhandles and do not amplify. After denaturation, and removal of unbound fragments, remaining tethered single-stranded target DNA is suitable for primer-directed sequencing. (FIG. 42, step D). FIG. 43, step B illustrates in close-up how the longer products, but not the shorter products amplify, when one primer is immobilized.

FIGS. 44 and 45 provide one embodiment of primer design for sequencing and identifying mutations in one target strand across overlapping fragments. Distribute the sample into 48 Primary PCR Reaction Chambers. The spatial distribution will assure that for low abundance mutations, each mutant fragment is in a different Primary PCR Reaction Chamber. Nested, locus-specific primer pairs, across overlapping regions (i.e. one or more exons for a cancer-specific gene) are provided to amplify overlapping target sequences, each primer pair comprising of: (i) a first locus-specific primer, said primer comprising of a first 5' universal or tag sequence portion, a locus-specific 3' portion, a cleavable base such as a ribo-nucleotide and a blocking group on the 3' end; and (ii) a second locus-specific primer with two or more dU bases throughout the primer sequence, said primer comprising of a second 5' universal or tag sequence portion, a fragment identifier sequence, and a locus-specific 3' portion, a cleavable base such as a ribo-nucleotide and a blocking group on the 3' end. The primer pairs are designed such that overlapping sets are in opposite orientation, i.e. the shorter product (about the size of a primers dimer) would arise from primers with the same tag sequence, while the longer product would arise from primers with the two different tag sequences. The locus-specific primers are unblocked with RNaseH2 only when bound to target, liberating a 3'OH suitable for polymerase-mediated extension (FIGS. 44, 45, step B). Two or three cycles of PCR amplification are performed using a thermostable polymerase, preferably a strand-displacement polymerase. These amplification cycles generate overlapping products, both shorter (slightly longer than primer dimer, with identical tags), and longer products comprising 100 or more bases of target sequences, containing the first 5' universal or tag sequence portion, the target sequence between the two locus-specific primer portions, the internal fragment identifier, and the complement of the second 5' universal or tag sequence. The original primers and portion of primers in products are destroyed using UDG (uracil DNA glycosylase) and optionally, APE1 (human apurinic endonuclease; FIGS. 44, 45, step C). This renders a portion of one of the ends of each double-stranded amplification product single-stranded. In one variation, distribute products into micro-pores or beads into micro-pores containing immobilized second tag sequence primers. In the presence of both first and second tag primers, longer products are PCR amplified in micro-pores such that a given micro-pore generally contains zero or one clonal amplification of a given region, but that micro-pore may contain multiple clonal amplicons from different regions. Shorter products are either missing second tag sequences (FIG. 44, step D), or form panhandles, that do not amplify, and further are not attached to the solid support (FIG. 45, step D). After denaturation, and removal of unbound fragments, remaining tethered single-stranded target DNA is suitable for primer-directed sequencing. (FIGS. 44 & 45, step D). In another variation, anneal biotinylated primer containing second tag sequence to the single-stranded region. Strand displacement polymerase extends to form full-length double-stranded copy of fragment. Both extended and free biotinylated primers are captured on streptavidin coated beads to be distributed in micro-pores, or directly on streptavidin coated micro-pores. In the presence of both first and second tag primers, longer products are PCR amplified in micro-pores such that a given micro-pore generally contains zero or one clonal amplification of a given region, but that micro-pore may contain multiple clonal amplicons from different regions. Shorter products are either missing second tag sequences, or form panhandles, that do not amplify, and further are not attached to the solid support. After denaturation, and removal of unbound fragments, remaining tethered single-stranded target DNA is suitable for primer-directed sequencing (Not shown, but like FIG. 41).

FIG. 46 provides one embodiment of primer design for sequencing and identifying mutations in both target strands across overlapping fragments. Distribute the sample into 48 Primary PCR Reaction Chambers. The spatial distribution will assure that for low abundance mutations, each mutant fragment is in a different Primary PCR Reaction Chamber. Nested, locus-specific primer pairs, across overlapping regions (i.e. one or more exons for a cancer-specific gene) are provided to amplify overlapping target sequences, each primer pair comprising of: (i) a first locus-specific primer with two or more dU bases throughout the primer sequence, said primer comprising of a first 5' universal or tag sequence portion, a fragment identifier sequence, a locus-specific 3' portion, a cleavable base such as a ribo-nucleotide and a blocking group on the 3' end; and (ii) a second locus-specific primer with two or more dU bases throughout the primer sequence, said primer comprising of the same or slightly different first 5' universal or tag sequence portion, a fragment identifier sequence, and a locus-specific 3' portion, a cleavable base such as a ribo-nucleotide and a blocking group on the 3' end. The locus-specific primers are unblocked with RNaseH2 only when bound to target, liberating a 3'OH suitable for polymerase-mediated extension (FIG. 46, step B). Two or three cycles of PCR amplification are performed using a thermostable polymerase, preferably Taq DNA polymerase. These amplification cycles generate overlapping products, both shorter product (but mostly destroyed by the 5'→3' exonuclease activity of Taq polymerase, as extension from upstream primers will run into shorter extension products), and longer products (comprising 100 or more bases of target sequences), containing the first 5' universal or tag sequence portion, an internal fragment identifier, the target sequence between the two locus-specific primer portions, another internal fragment identifier, and the complement of the identical or slightly different first 5' universal or tag sequence. The original primers and portion of primers in products are destroyed using UDG (uracil DNA glycosylase) and optionally, APE1 (human apurinic endonuclease; FIG. 46, step C). This renders a portion of both ends of each double-stranded amplification product single-stranded. In one variation, distribute products into micro-pores or beads into micro-pores containing immobilized second tag sequence primers. In the presence of both first and second tag primers, longer products are PCR amplified in micro-pores such that a given micro-pore generally contains zero or one clonal amplification of a given region, but may contain multiple clonal amplicons from different regions. After denaturation, and removal of unbound fragments, remaining tethered single-stranded target DNA is suitable for primer-directed sequencing. (FIG. 46, step E). In another variation, anneal biotinylated primer containing first tag sequence to the single-stranded region. Strand displacement polymerase extends to form full-length double-stranded copy of both strands of each fragment. Add a third set of nested, locus-specific primers comprising a first 5' universal or tag sequence portion, a locus-specific 3' portion, a cleavable base such as a ribo-nucleotide and a blocking group on the 3' end. The third set of locus-specific primers are unblocked with RNaseH2 only when bound to target, liberating a 3'OH suitable for polymerase-mediated extension, preferable for 1-2 PCR cycles using a strand-displacement polymerase. Both extended and free biotinylated primers are captured on streptavidin coated beads to be distributed in micro-pores, or directly on streptavidin coated micro-pores. In the presence of both first and second tag primers, longer products are PCR amplified in micro-pores such that a given micro-pore generally contains zero or one clonal amplification of a given region, but that micro-pore may contain multiple clonal amplicons from different regions. After denaturation, and removal of unbound fragments, remaining tethered single-stranded target DNA is suitable for primer-directed sequencing.

FIG. 47 provides one embodiment of primer design for sequencing and identifying SNPs and enumerating copy number of both locus strands. Distribute the sample into 48 Primary PCR Reaction Chambers. The spatial distribution will assure that for low abundance mutations, each mutant fragment is in a different Primary PCR Reaction Chamber. Locus-specific primer pairs, are provided to amplify target sequences containing SNPs, each primer pair comprising of: (i) a first locus-specific primer with two or more dU bases throughout the primer sequence, said primer comprising of a first 5' universal or tag sequence portion, a fragment identifier sequence, a locus-specific 3' portion, a cleavable base such as a ribo-nucleotide and a blocking group on the 3' end; and (ii) a second locus-specific primer with two or more dU bases throughout the primer sequence, said primer comprising of the same or slightly different first 5' universal or tag sequence portion, a fragment identifier sequence, and a locus-specific 3' portion, a cleavable base such as a ribo-nucleotide and a blocking group on the 3' end. The locus-specific primers are unblocked with RNaseH2 only when bound to target, liberating a 3'OH suitable for polymerase-mediated extension (FIG. 47, step B). Three cycles of PCR amplification are performed using a thermostable polymerase, preferably a strand-displacement polymerase. These amplification cycles generate products containing the first 5' universal or tag sequence portion, an internal fragment identifier, the target sequence between the two locus-specific primer portions, another internal fragment identifier, and the complement of the identical or slightly different first 5' universal or tag sequence. The original primers and portion of primers in products are destroyed using UDG (uracil DNA glycosylase) and optionally, APE1 (human apurinic endonuclease; FIG. 47, step C). This renders a portion of both ends of each double-stranded amplification product single-stranded. In one variation, distribute products into micro-pores or beads into micro-pores containing immobilized second tag sequence primers. In the presence of both first and second tag primers, products are PCR amplified in micro-pores such that a given micro-pore generally contains zero or one clonal amplification of a given region, but that micro-pore may contain multiple clonal amplicons from different regions. After denaturation, and removal of unbound fragments, remaining tethered single-stranded target DNA is suitable for primer-directed sequencing. (FIG. 47, step E). In another variation, anneal biotinylated primer containing first tag sequence to the single-stranded region. Strand displacement polymerase extends to form full-length double-stranded copy of both strands of each fragment. Add a third set of nested, locus-specific primers comprising a first 5' universal or tag sequence portion, a locus-specific 3' portion, a cleavable base such as a ribo-nucleotide and a blocking group on the 3' end. The third set of locus-specific primers are unblocked with RNaseH2 only when bound to target, liberating a 3'OH suitable for polymerase-mediated extension, preferable for 1-2 PCR cycles using a strand-displacement polymerase. Both extended and free biotinylated primers are captured on streptavidin coated beads to be distributed in micro-pores, or directly on streptavidin coated micro-pores. In the presence of both first and second tag primers, products are PCR amplified in micro-pores such that a given micro-pore generally contains zero or one clonal amplification of a given region, but that micro-pore may contain multiple clonal amplicons from different regions. After denaturation, and removal of unbound fragments, remaining tethered single-stranded target DNA is suitable for primer-directed sequencing (Not shown, but like FIG. 41).

FIG. 48 is a schematic front view of a portion of an exemplary design for pre-chamber loading to allow for liquids to be fluidically moved to the chambers comprising of micro-wells or micro-pores. This design illustrates the chamber architecture and micro-wells or micro-pores suitable for identifying unknown mutations at low-abundance in plasma; using Fragment identifier PCR-sequencing. In FIG. 48, the input sample is fluidically connected by conduits 120 to a set of hexagonal chambers 122 (containing large troughs 124 and baffles 123, the Primary PCR Reaction Chambers), which are fluidically connected by conduits 126 to long narrower mixing chambers 128, which are fluidically connected by conduits 130 to the chambers comprising subdivisions 232 of micro-pores (top of panel, with only 4 rows illustrated). The diagram is not to scale and is for illustrative purposes. During manufacture of the cartridge, micro-pores are pre-filled with a single universal primer, which is immobilized, and micro-pores are dried. Since all subdivisions contain the identical primer, they may be added through the columns, or by other means. During use of the cartridge, reactions are fluidically moved up the cartridge, and eventually up the columns of micro-wells or micro-pores, where each column is isolated from its neighbor column. In this illustrative example, showing 4 each of the planned 48 columns and 64 rows equaling 3,072 subdivisions, each subdivision comprising 2,760 micro-pores, for a total of 8,478,720 micro-pores in the array, the initial plasma DNA (highest level of 10,000 genome equivalents) is combined with buffer, enzymes, fragment identifier primers, equally split, and fluidically moved into the set of diamond chambers is distributed into the Primary PCR Reaction Chambers, with average distribution of 200 copies of each target per Primary PCR Reaction Chamber, with at most 1 mutation. Optionally, primers containing an RNA base and 3' blocking group are unblocked with RNaseH2 only when bound to the correct target, providing additional specificity and avoiding false products. Perform 3 cycles of fragment identifier PCR for both strands, each strand covering slightly different sequences. Yields 4 copies of top strand, and 4 copies of bottom strand. Remove universal primer sequence from product with UDG/APE1 to generate single-stranded tails on one or both sides of the PCR products, which facilitates hybridization to immobilized primer in micro-pore. If needed, fresh PCR reagents are added, mixed with the PCR products of each Primary PCR Reaction Chamber, and distributed into the Mixing Chambers and then into the micro-pores of each column. PCR amplify one or more products in each micro-pore using nested target-specific primer and universal primer and melt off non-anchored strand. Add either target-specific, or universal primers with unique tag-specific portions as sequencing primers. Perform sequencing-by-synthesis. Generate about 80 bases of sequence information, plus 10 bases of unique fragment identifier barcode, for accurate enumeration of each mutation, with verification on both strands. In one embodiment, 72 sequencing primers are used to cover 36 target regions, for both Watson and Crick strand, including overlapping regions when needed. If needed, an additional 72 sequencing primers may be used. In another embodiment, the cartridge is designed with room for 4 rounds of sequencing=288 primers—covers 144 target regions, both strands, with accurate enumeration of each mutation. In another embodiment, the original nested primers may also be used as sequencing primers. Also, the nested primers may be designed to contain different sets of universal sequences comprising the master universal sequence and then 8-12 bases on the 3' end to uniquely sequence different fragments, such that on average, 72 products are sequenced per individual sequencing primer. Optionally, repeat with next sequencing primer to sequence next 72 fragments.

In an alternative embodiment, low-abundance mutations are identified and enumerated using 48 double-columns and 48 double-rows equaling 2,304 subdivisions, each subdivision comprising 11,040 micro-pores, with 529,920 micro-pores per double-column. Distribute initial sample into 48 wells or Primary PCR Reaction Chambers, mixed with locus-specific primers, buffer, and polymerase into 48 Primary PCR Reaction Chamber, for example by using acoustic droplet ejection as illustrated in FIG. 50. Highest level of DNA in plasma=10,000 genome equivalents. On average, 200 copies of each target per subdivision, with at most 1 mutation. Perform 3 cycles of fragment identifier PCR for both strands, each strand covering slightly different sequences. Yields 4 copies of top strand, and 4 copies of bottom strand. Treat with UDG/APE1, and distribute products into sections (columns) with 529,920 micro-pores. Assuming 75% capture, a given target will have about 1200 copies per section (column), and if a mutation is present, there should be about 3 copies of the "Watson strand" and about 3 copies of the "Crick strand". PCR amplify multiple products in each micro-pore using nested target-specific primers and universal primers, and subsequently melt off non-anchored strand. In one embodiment, add 256 sequencing primers—covers 128 target regions, for both Watson and Crick strand, including overlapping regions when needed. Generate about 80 bases of sequence information, plus 10 bases of unique fragment identifier barcode. Approximately 307,200 micro-pores out of the 529,920 micro-pores will generate sequence information, with about 75% of these providing reads from a single PCR product per sequencing round. Add an additional 256 sequencing primers as often as needed to sequence as many targeted regions as needed. In one embodiment, the original nested primers may also be used as sequencing primers. In another embodiment, the nested primers may be designed to contain different sets of universal sequences comprising the master universal sequence and then 8-16 bases on the 3' end to uniquely sequence different fragments, such that on average, 256 products are sequenced per individual sequencing primer. Optionally, repeat with next sequencing primer to sequence next 256 fragments.

The design illustrated in FIG. 48 is also suitable for non-invasive prenatal testing (NIPT) of trisomy in plasma; using Fragment identifier PCR-sequencing. The basic idea is to enumerate how many copies of each strand are present. Since the Watson strands should match the Crick strands in each of the Primary PCR Reaction Chambers (since they are generated from a given fragment with one of each strand), this is an internal control for loss of strands or other errors. Multiple unique loci on Chromosomes 2 (control), 13, 18, 21, X, and Y are used to establish copy number as well as discern trisomy or other chromosomal copy changes.

During manufacture of the cartridge, micro-pores are pre-filled with a single universal primer, which is immobilized, and micro-pores are dried. Since all subdivisions contain the identical primer, they may be added through the columns, or by other means. During use of the cartridge, reactions are fluidically moved up the cartridge, and eventually up the columns of micro-wells or micro-pores, where each column is isolated from its neighbor column. In this illustrative example, showing 4 each of the planned 48 columns 64 rows equaling 3,072 subdivisions, each subdivision comprising 2,760 micro-pores, for a total of 8,478,720 micro-pores in the array, the initial plasma DNA (adjusted to 2,000 genome equivalents) is combined with buffer, enzymes, fragment identifier primers, equally split, and fluidically moved into the set of diamond chambers is divided into 48 Primary PCR Reaction Chambers, with average distribution of 40 copies of each locus per Primary PCR Reaction Chamber, with different SNPs. Optionally, primers containing an RNA base and 3' blocking group are unblocked with RNaseH2 only when bound to the correct target, providing additional specificity and avoiding false products. Perform 3 cycles of fragment identifier PCR for both strands, each strand covering slightly different sequences. Yields 4 copies of top strand, and 4 copies of bottom strand. Remove universal primer sequence from product with UDG/APE1 to generate single-stranded tails on both sides of the PCR products, which facilitates hybridization to immobilized primer in micro-pore. If needed, fresh PCR reagents are added, mixed with the PCR products of each Primary PCR Reaction Chamber, and distributed into the Mixing Chambers and then into the micro-pores of each column. PCR amplify one or more products in each micro-pore using nested target-specific primer and universal primer and melt off non-anchored strand. Add either target-specific, or universal primers with unique tag-specific portions as sequencing primers. Perform sequencing-by-synthesis. Generate about 50 bases of sequence information, plus 10 bases of unique fragment identifier barcode, for accurate enumeration of each SNP and chromosomal copy number, with verification on both strands.

In an alternative embodiment, for identifying chromosomal copy changes in NIPT, using 48 double-columns and 48 double-rows equaling 2,304 subdivisions, each subdivision comprising 11,040 micro-pores, with 529,920 micro-pores per double-column. Distribute initial sample into 48 wells or Primary PCR Reaction Chambers. Adjust DNA in plasma/sample to 2,000 genome equivalents. Distribute initial sample mixed with locus-specific primers, buffer, and polymerase into 48 wells or Primary PCR Reaction Chambers, for example by using acoustic droplet ejection as illustrated in FIG. 50. On average, 40 copies of each locus per Primary PCR Reaction Chamber, with different SNPs. Perform 3 cycles of fragment identifier PCR for both strands, each strand covering slightly different sequences. Yields 4 copies of top strand, and 4 copies of bottom strand. Treat with UDG/APE1, and distribute products of each Primary PCR Reaction Chamber into 529,920 micro-pores. Assuming 75% capture, a given locus will have about 240 copies per subdivision (120 for Watson strand and 120 for Crick strand). PCR amplify multiple products in each well using nested locus-specific primers and universal primers, and melt off non-anchored strand. In one embodiment, add 2,208 sequencing primers (or one primer, see below)—covers 1,104 locus regions, for both Watson and Crick strand. Generate about 50 bases of sequence information, plus 10 bases of unique fragment identifier barcode. Optionally add an additional 2,208 (or one primer, see below) sequencing primers. The above calculations are based on filling on average about 50% of the micro-pores. (Poisson distribution: mean lambda=0.4; Initial percentage x=0). Under such conditions, approximately 60% of the micro-pores will not give any sequencing reads, about 30% are unique (i.e. single reads), about 7.5% will give double reads, and about 1.3% will give triple reads. On a practical level, the single reads are unambiguous for distinguishing SNPs. The double reads may be used to determine loci, but double reads should not be used to distinguish SNPs. Between the single and double reads, over 90% of the strands are covered, and since that distribution is essentially random, this approach should provide highly accurate enumeration of each strand present in the initial sample. In one embodiment, the original nested primers may also be used as sequencing primers. In another embodiment, the nested primers may be designed to contain different sets of universal sequences comprising the master universal sequence and then 8-16 bases on the 3' end to uniquely sequence different fragments, such that on average, 368 products are sequenced per individual sequencing primer. Repeat with next sequencing primer to sequence next 1,104 fragments.

The ability to accurately enumerate copy number in a clinical sample has additional uses as well. In the field of NIPT, there may be an opportunity to detect de novo Duchenne's muscular dystrophy (DMD). This disease may arise sporadically due to deletion of a portion of the DMD gene. Coverage of both SNPs and all exons across the DMD would allow for accurate assessment of copy loss.

Another embodiment of the ability to accurately enumerate both copy number and SNPs would be to identify LOH or gene amplification, initially in circulating tumor cells (CTC's), but ultimately in cfDNA as well. This approach would be facilitated by determining the haplotype of the diploid genome in normal cells for that patient, which may be accomplished by standard approaches from DNA isolated from the buffy coat fraction (polymorphonuclear leukocytes, PMN's). Sufficient DNA would be required to achieve statistical significance, but briefly if there is a consistent undercount or over count of all the SNPs on a given chromosomal arm (i.e. 8p, often lost in cancers; or 20q, often gained in cancers) then that would suggest loss or gain of that arm respectively in the clinical sample. Depending on the percent of tumor derived cfDNA in the plasma sample, this technique may be sensitive enough for detection of cancer (i.e. when trying to identify LOH in cfDNA), and it may assist in guiding treatment decisions, or monitoring efficacy of therapy (i.e. when scoring for copy changes directly from CTC's).

FIGS. 49A-49B are schematic side views of cartridge 104 and valve setup for identifying unknown mutations at low-abundance in plasma; using Fragment identifier PCR-sequencing; identifying unknown pathogen using Multiplexed PCR-Nested PCR-sequencing; and identifying methylations and unknown mutations at low-abundance in plasma; using Fragment identifier PCR-sequencing. FIG. 49A is a schematic front view illustrating fluidic connection of micro-channels to subdivisions of arrays of micro-pores 202, with 5-micron diameter. The bottom of the array of micro-pores has another layer 238. For simplicity, the figure illustrates one Initial Multiplex Reaction Chamber 110, 16 Primary multiplex PCR reaction Chambers 116 (containing troughs 118), 16 Secondary multiplex Reaction Chambers 122 (containing troughs 124 and baffles 123), 16 Narrow Mixing Chambers 128, and one main Chamber comprising subdivisions 232 of 16 columns and millions of micro-pores or micro-wells. These are coupled together by conduits 114, 120, 126, and 130 as shown. Fluid enters cartridge 104 through inlet 102 and leaves through outlet 108. However, other configurations of the chambers may also be used, for example the multiplexed PCR-Nested PCR-sequencing for pathogen detection described in FIG. 48 would not require the Secondary multiplex Reaction Chambers. FIG. 49B shows the fluidics system for Fragment identifier PCR-sequencing using a micro-pore plate composed of millions of micro-pores 202. The micro-pore plate is fluidically accessible from both sides of the pores: the first side 244 (top of plate, illustrated on left side of plate) is in communication with Valves 1, 2, & 3 while the second side 246 (bottom of plate, illustrated on right side of plate) is in communication with Valves 4, 5, & 6. Valve 1 dispenses a lysis/protease buffer, enzymes, wash buffer, elute buffer, buffer, EtOH, Light Oil, and Heavy Oil, as needed through the Initial Reaction Chamber 110, the 48 Primary PCR Reaction Chambers 116, and additional chambers across the first side of the micro-pore plate through Valve 3 to Waste. In addition, Valve 1 can select a Waste port, which can be used to vacate the first side of micro-pore plate, other chambers, Primary PCR Reaction Chambers 116, and Initial Reaction Chamber 110 by the introduction of Air through Valve 3 in a reverse direction. Valve 1 can also select Valve 2. Valve 2 dispenses Fragment ID PCR primers, Master PCR Mix, Master UDG/APE1 Buffer, Nested & Universal Primers, Wash, EtOH, & Air through Initial Multiplex Reaction Chamber, the PCR Reaction Chambers, and additional chambers across the first side of the micro-pore plate through Valve 3 to Waste. Valve 5 dispenses Sequencing primer sets 1, 2, &, 3, buffer, ETOH, Air, Light Oil, Heavy Oil and Waste across the second side of the micro-pore plate through Valve 6 to Waste. Valve 5 can also select Valve 4. Valve 4 dispenses Extension mix including polymerase and appropriate fluorescently labeled nucleotides for sequencing-by-synthesis, Rinse buffer, Imaging buffer, Cleavage buffer, and Wash. In addition, Valve 1 can select a Waste port, which can be used to vacate the second side micro-pore plate by introduction of Air through Valve 6 in a reverse direction.

TABLE 6

Reagent Setup for Fragment Identifier PCR-Sequencing (Mutation)

| Port | Valve 1 | Valve 2 | Valve 4 | Valves 5 | V 3/6 |
|---|---|---|---|---|---|
| 1 | Lysis/Protease Buf. | Frag. ID PCR primers | Extension | Reagents from V4 | Waste |
| 2 | Wash | Master PCR mix | Rinse | Seq. primers 1 | Air |
| 3 | Elute Buffer | Master UDG/APE1 | Imaging | Seq. primers 2 | or connect |
| 4 | Enz/Prim. from V2 | Nested & Univ. prim. | Cleave | Seq. primers 3 | with air/ |
| 5 | Empty (Pre-mix) | Buffer | Wash | Empty (Pre-mix) | waste of |
| 6 | Waste | Wash | Empty | Waste | V 1/5 |
| 7 | Buffer | ETOH | Empty | Buffer | |
| 8 | ETOH | Air | Empty | ETOH | |
| 9 | Air | Empty | | Air | |
| 10 | Light Oil | Empty | | Light Oil | |
| 11 | Heavy Oil | Empty | | Heavy Oil | |
| 12 | Hexanol | Empty | | Hexanol | |

FIG. 49B illustrates several heating elements that would be designed to provide independent heating/cooling to the Initial Multiplex Reaction Chamber 110, the Primary 24-48 Multiplex PCR reaction Chambers 116, the Secondary 24-48 Multiplex Reaction Chambers 122, and the main Chamber comprising subdivisions 232 of 24-48 columns and thousands of micro-pores or micro-wells. The back plate 206 (opposite front plate 204) or one or more flat surface(s) of the micro-pore or micro-well chamber, and the reaction chambers may be pressed against these heating elements to allow for temperature control, heating, and/or thermocycling. As illustrated in FIG. 49, the two heating elements behind the Primary 24-48 Multiplex PCR reaction Chambers 116, the Secondary 24-48 Multiplex Reaction Chambers 122 would be designed as two rectangular (horizontal) strips to control all the Primary Chambers independently of all the Secondary Chambers. Alternative configurations may also be used. For example, having independent heating elements for each Primary Chamber, having additional rows of chambers (i.e. Primary, Secondary, Tertiary, etc.) having additional rows or heating elements, and/or having the 24-48 spatial multiplexing arranged in a different geometry than rows or columns, for either/or the Initial Reaction Chamber 110, the Primary Chambers 116, the Secondary Chambers 118, the Mixing Chambers 120, and the main chamber comprising subdivisions 232 of the thousands of micro-wells or micro-pores. Alternative configurations may also be used, for example the initial limited cycle PCR may be divided into two steps (i) Single-sided multiplexed primer linear extension with or without blocking primer to suppress extension of wild-type DNA, and (ii) Addition of the complementary primers for one or two PCR amplification cycles of the initial extension products. As another example, a plate may comprise 24 separate input wells, each fluidically connect to an individual Primary multiplex PCR reaction Chamber 116, an individual Secondary multiplex Reaction Chamber 122, an individual Mixing chamber 128, and an individual Chamber comprising subdivisions 232 of thousands to millions of micro-pores or micro-wells. Samples may undergo an optional initial multiplexed reaction, and then imported into the 24 individual input wells via acoustic droplet ejection or other fluidic means.

The cartridge and valve setup of FIG. 49 may also be used for identifying unknown pathogen using Multiplexed PCR-Nested PCR-sequencing. This figure illustrates the fluidics system for multiplexed PCR-Nested PCR-sequencing using a micro-pore plate composed of millions of micro-pores. The micro-pore plate is fluidically accessible from both sides of the pores: the first side (top of plate 244, illustrated on left side of plate) is in communication with Valves 1, 2, & 3 while the second side (bottom of plate 246, illustrated on right side of plate) is in communication with Valves 4, 5, & 6. Valve 1 dispenses a lysis/protease buffer, enzymes, wash buffer, elute buffer, buffer, EtOH, Light Oil, and Heavy Oil, as needed through the Initial Multiplex Reaction Chamber 110, the 48 PCR Reaction Chambers 116, and additional chambers across the first side of the micro-pore plate through Valve 3 to Waste. In addition, Valve 1 can select a Waste port, which can be used to vacate the first side of micro-pore plate, other chambers, Primary PCR Reaction Chambers 116, and Initial Reaction Chambers 110 by the introduction of Air through Valve 3 in a reverse direction. Valve 1 can also select Valve 2. Valve 2 dispenses Initial multiplex PCR primers, Master PCR Mix, initial reverse-transcription primers, Master reverse transcription mix, Master UDG/APE1 Buffer, Nested & Universal Primers, Wash, EtOH, & Air through Initial Reaction Chamber 110, the Primary PCR Reaction Chambers 116, and additional chambers across the first side of the micro-pore plate through Valve 3 to Waste. Valve 5 dispenses Sequencing primer sets 1, 2, &, 3, buffer, ETOH, Air, Light Oil, Heavy Oil and Waste across the second side of the micro-pore plate through Valve 6 to Waste. Valve 5 can also select Valve 4. Valve 4 dispenses Extension mix including polymerase and appropriate fluorescently labeled nucleotides for sequencing-by-synthesis, Rinse buffer, Imaging buffer, Cleavage buffer, and Wash. In addition, Valve 1 can select a Waste port, which can be used to vacate the second side micro-pore plate by introduction of Air through Valve 6 in a reverse direction.

TABLE 7

Reagent Setup for PCR-Sequencing (Unknown Pathogens)

| Port | Valve 1 | Valve 2 | Valve 4 | Valves 5 | V 3/6 |
|---|---|---|---|---|---|
| 1 | Lysis/Protease Buf. | Initial PCR primers | Extension | Reagents from V4 | Waste |
| 2 | Wash | Master PCR mix | Rinse | Seq. primers 1 | Air |
| 3 | Elute Buffer | Initial RT primers | Imaging | Seq. primers 2 | or connect |
| 4 | Enz/Prim. from V2 | Master RT mix | Cleave | Seq. primers 3 | with air/ |
| 5 | Empty (Pre-mix) | Master UDG/APE1 | Wash | Empty (Pre-mix) | waste of |
| 6 | Waste | Nested & Univ. prim. | Empty | Waste | V 1/5 |
| 7 | Buffer | Buffer | Empty | Buffer | |
| 8 | ETOH | Wash | Empty | ETOH | |
| 9 | Air | ETOH | | Air | |
| 10 | Light Oil | Air | | Light Oil | |
| 11 | Heavy Oil | Empty | | Heavy Oil | |
| 12 | Hexanol | Empty | | Hexanol | |

FIG. 50 are schematic views of an alternative cartridge 404 with inlet 402 and outlet 408 and valve setup for identifying unknown mutations at low-abundance in plasma; using Fragment identifier PCR-sequencing. Panel A shows a schematic front view illustrating fluidic connection of micro-channels to the array of micro-pores, with 5-micron diameter. This setup is for the alternative embodiments described above, i.e. when using 48 double-columns and 48 double-rows equaling 2,304 subdivisions, each subdivision comprising 11,040 micro-pores, with 529,920 micro-pores per double-column. In these embodiments, initial reactions are performed in separate wells or Reaction Chambers 452, and then acoustic droplet ejection through conduits 455 is used to push the appropriate reagents, enzymes, buffers, targets and/or pre-amplified targets through conduits 454 into openings 456 that lead to input chambers and subdivisions 432 having columns comprising micro-pores. Subsequently, the plate is fluidically coupled to 4 valves (Panel C). Liquid leaving subdivisions 432 pass through conduits 454, chambers 467, and conduits 457 leading to outlet 405. The micro-pore plate is fluidically accessible from both sides of the pores through channels 240 and 242: the first side 206 (illustrated as top of plate) is in communication with Valves 1 & 3 while the second side 204 (illustrated as bottom of plate) is in communication with Valves 2 & 4. Valve 1 dispenses Extension mix including polymerase and appropriate fluorescently labeled nucleotides for sequencing-by-synthesis, Rinse buffer, Imaging buffer, Cleavage buffer, Wash, Light Oil and ETOH. Valve 2 dispenses Wash, Rinse buffer, Cleavage buffer, ETOH, Heavy Oil, and Air. In addition, Valve 1 can select a Waste port, which can be used to vacate the second side micro-pore plate by introduction of Air through Valve 4 in a reverse direction.

FIG. 51 provides one embodiment of primer design for sequencing and identifying methylations in one target strand. cfDNA is treated with Bsh1236I (CG^CG) to completely digest unmethylated DNA in the Initial Reaction Chamber. Treat with bisulfite, which converts C but not 5 meC to dU, and renders the strands non-complementary. Distribute the sample into 48 Primary PCR Reaction Chambers. The spatial distribution will assure that for low abundance methylations, each methylated fragment is in a different Primary PCR Reaction Chamber. Thus, when a methylation is present in two or more Primary PCR Reaction Chambers, it is most likely a true methylation and not due to incomplete cleavage or bisulfite conversion. Nested, locus-specific primer pairs are provided to amplify target sequences, each primer pair comprising of: (i) a first locus-specific primer, said primer comprising of a first 5' universal or tag sequence portion, a locus-specific 3' portion, a cleavable base such as a ribo-nucleotide and a blocking group on the 3' end; and (ii) a second locus-specific primer with two or more dU bases throughout the primer sequence, said primer comprising of a second 5' universal or tag sequence portion, a fragment identifier sequence, and a locus-specific 3' portion, a cleavable base such as a ribo-nucleotide and a blocking group on the 3' end. The locus-specific primers are unblocked with RNaseH2 only when bound to target, liberating a 3'OH suitable for polymerase-mediated extension (FIG. 51, step B). Two or three cycles of PCR amplification are performed using a thermostable polymerase, preferably a strand-displacement polymerase. These amplification cycles generate product containing the first 5' universal or tag sequence portion, the target sequence between the two locus-specific primer portions, the internal fragment identifier, and the complement of the second 5' universal or tag sequence. The original bisulfite-converted DNA, primers and portion of primers in products are destroyed using UDG (uracil DNA glycosylase) and optionally, APE1 (human apurinic endonuclease; FIG. 51, step C). This renders a portion of one of the ends of each double-stranded amplification product single-stranded. In one variation, distribute products into micro-pores or beads into micro-pores containing immobilized second tag sequence primers. In the presence of both first and second tag primers, products are PCR amplified in micro-pores such that a given micro-pore generally contains zero or one clonal amplification of a given region, but may contain multiple clonal amplicons from different regions. After denaturation, and removal of unbound fragments, remaining tethered single-stranded target DNA is suitable for primer-directed sequencing (FIG. 51, step D). In another variation, anneal biotinylated primer containing second tag sequence to the single-stranded region. Strand displacement polymerase extends to form full-length double-stranded copy of fragment. Both extended and free biotinylated primers are captured on streptavidin coated beads to be distributed in micro-pores, or directly on streptavidin coated micro-pores. In the presence of both first and second tag primers, products are PCR amplified in micro-pores such that a given micro-pore generally contains zero or one clonal amplification of a given region, but that micro-pore may contain multiple clonal amplicons from different regions. After denaturation, and removal of unbound fragments, remaining tethered single-stranded target DNA is suitable for primer-directed sequencing (Not shown, but like FIG. 41).

FIG. 52 is a schematic front view of a portion of an exemplary design for pre-chamber loading to allow for liquids to be fluidically moved to the chambers comprising of micro-wells or micro-pores. This design illustrates the chamber architecture and micro-wells or micro-pores suitable for identifying methylation and unknown mutations at low-abundance in plasma; using Fragment identifier PCR-sequencing. In FIG. 52, the input sample is fluidically connected to a large hexagonal chamber 110 (bottom, Initial Reaction Chambers) through inlet 112, which is fluidically connected by conduits 114 to a first set of hexagonal chambers 116 (containing small troughs 118, Primary PCR Reaction Chambers), which are fluidically connected by conduits 120 to a second set of hexagonal chambers 122 (containing large troughs 124 and baffles 123, Secondary Reaction Chambers), which are fluidically connected by conduits 126 to long narrower mixing chambers 128, which are fluidically connected by conduits 130 to the chambers comprising subdivisions 232 of micro-pores (top of panel, with only 4 rows illustrated). The diagram is not to scale and is for illustrative purposes. During manufacture of the cartridge, micro-pores are pre-filled with a single universal primer, which is immobilized, and micro-pores are dried. Since all subdivisions contain the identical primer, they may be added through the columns, or by other means. During use of the cartridge, reactions are fluidically moved up the cartridge, and eventually up the columns of micro-wells or micro-pores, where each column is isolated from its neighbor column. In this illustrative example, showing 4 each of the planned 48 columns and 64 rows equaling 3,072 subdivisions, each subdivision comprising 2,760 micro-pores, for a total of 8,478,720 micro-pores in the array, the initial plasma DNA (highest level of 10,000 genome equivalents) is divided in half, with the second half temporarily stored. The first half is combined with buffer, enzymes, fragment identifier primers, equally split, and fluidically moved into the first set of diamond chambers is distributed into 48 Primary PCR Reaction Chambers, with average distribution of 200 copies of each target per Primary PCR Reaction Chamber, with at most 1 mutation. Optionally, primers containing an RNA base and 3' blocking group are unblocked with RNaseH2 only when bound to the correct target, providing additional specificity and avoiding false products. Perform 3 cycles of fragment identifier PCR for both strands, each strand covering slightly different sequences. Yields 4 copies of top strand, and 4 copies of bottom strand. Remove universal primer sequence from product with UDG/APE1 to generate single-stranded tails on one or both sides of the PCR products, which facilitates hybridization to immobilized primer in micro-pore. The products are fluidically moved to the Secondary Reaction Chambers, and the earlier chambers are drained and washed. Digest second half of sample with Bsh1236I in the Initial Reaction Chamber. Treat digested DNA with bisulfite, and re-purify DNA strands. Mix bisulfite treated DNA with primers, reagents, and polymerase, and distribute into first set of 48 Primary PCR Reaction Chambers. Highest level of DNA in plasma after restriction endonuclease cleavage is about 200 genome equivalents. On average, after endonuclease treatment, 4 copies of each target per Primary PCR Reaction Chamber, with at most 1 is methylated. Perform 3 cycles of fragment identifier PCR for both strands, each strand covering slightly different sequences. Yields 4 copies of top strand, and 4 copies of bottom strand of originally methylated DNA. Remove universal primer sequence from product with UDG/APE1 to generate single-stranded tails on one or both sides of the PCR products. These methylation-specific primary PCR products are combined with the earlier mutation-specific products in the Secondary Reaction Chambers, then moved up into the long (narrower) Mixing Chambers while mixing with the fresh buffer, primers and polymerase, and then finally the products are distributed into the chambers comprising of micro-pores of each column. PCR amplify one or more products in each micro-pore using nested target-specific primer and universal primer and melt off non-anchored strand. Add either target-specific, or universal primers with unique tag-specific portions as sequencing primers. Perform sequencing-by-synthesis. Generate about 80 bases of sequence information, plus 10 bases of unique fragment identifier barcode, for accurate enumeration of each mutation, with verification on both strands. In one embodiment, 72 sequencing primers are used to cover 36 target regions, for identifying and verifying mutations in both Watson and Crick strands, including overlapping regions when needed. If needed, an additional 72 sequencing primers may be used. In another embodiment, the cartridge is designed with room for 4 rounds of sequencing=288 primers—covers 144 target regions, both strands, with accurate enumeration of each mutation. In another embodiment, the original nested primers may also be used as sequencing primers. Also, the nested primers may be designed to contain different sets of universal sequences comprising the master universal sequence and then 8-12 bases on the 3' end to uniquely sequence different fragments, such that on average, 72 products are sequenced per individual sequencing primer. Optionally, repeat with next sequencing primer to sequence next 72 fragments. In one embodiment, the methylated regions are sequenced in the same round as the regions containing potential mutations. In another embodiment, the methylated regions are covered in one of the independent sequencing runs, which theoretically could cover 2,760 methylated regions, with accurate enumeration of every methylated region.

In an alternative embodiment, low-abundance methylation and mutations are identified and enumerated using 48 double-columns and 48 double-rows equaling 2,304 subdivisions, each subdivision comprising 11,040 micro-pores, with 529,920 micro-pores per double-column. Divide initial plasma sample in half, and then distribute half into 48 wells or Primary PCR Reaction Chambers, mixed with locus-specific primers, buffer, and polymerase into 48 subdivisions, for example by using acoustic droplet ejection as illustrated in FIG. 50. Highest level of DNA in plasma=10,000 genome equivalents. On average, 200 copies of each target per Primary PCR Reaction Chamber, with at most 1 mutation. Perform 3 cycles of fragment identifier PCR for both strands, each strand covering slightly different sequences. Yields 4 copies of top strand, and 4 copies of bottom strand. Treat with UDG/APE1 to remove universal primer sequence from product. Digest second half of sample with Bsh1236I in a well or Initial Reaction Chamber. Treat digested DNA with bisulfite, and re-purify DNA strands. Mix bisulfite treated DNA with primers, reagents, and polymerase, and distribute into 48 wells or Primary PCR Reaction Chambers. Highest level of DNA in plasma after restriction endonuclease cleavage is about 200 genome equivalents. On average, after endonuclease treatment, 4 copies of each target per Primary PCR Reaction Chamber, with at most 1 is methylated. Perform 3 cycles of fragment identifier PCR for both strands, each strand covering slightly different sequences. Yields 4 copies of top strand, and 4 copies of bottom strand of originally methylated DNA. Treat with UDG/APE1 to remove universal primer sequence from product. Combine and distribute methylation and mutation target products from each Primary PCR Reaction Chamber into 529,920 micro-pores. Assuming 75% capture, a given mutation target will have about 1200 copies per section (column), and if a mutation is present, there should be about 3 copies of the "Watson strand" and about 3 copies of the "Crick strand". Assuming 75% capture, a given methylation target will have about 16 copies per section (column), and if a methylated region is present, there should be about 3 copies of the "Watson strand" and about 3 copies of the "Crick strand". PCR amplify multiple products in each micro-pore using nested target-specific primers and universal primers, and melt off non-anchored strand. In one embodiment, add 256 sequencing primers—covers 128 target regions, for both Watson and Crick strand, including overlapping regions when needed. Generate about 80 bases of sequence information, plus 10 bases of unique fragment identifier barcode. Approximately 307,200 micro-pores out of the 529,920 micro-pores will generate sequence information, with about 75% of these providing reads from a single PCR product per sequencing round. Add an additional 256 sequencing primers as often as needed to sequence as many targeted regions as needed. In one embodiment, the original nested primers may also be used as sequencing primers. In another embodiment, the nested primers may be designed to contain different sets of universal sequences comprising the master universal sequence and then 8-16 bases on the 3' end to uniquely sequence different fragments, such that on average, 256 products are sequenced per individual sequencing primer. Optionally, repeat with next sequencing primer to sequence next 256 fragments. In one embodiment, the methylated regions are sequenced in the same round as the regions containing potential mutations. In another embodiment, the methylated regions are covered in one of the independent sequencing runs, which theoretically could cover 19,200 methylated regions, with accurate enumeration of every methylated region. Thus, if a master universal sequence is used just for the methylated regions, this single primer could cover all the methylated regions in a single run.

The cartridge and valve setup of FIG. 49 may also be used for identifying methylations and unknown mutations at low-abundance in plasma; using Fragment identifier PCR-sequencing. This figure illustrates the fluidics system for Fragment identifier PCR-sequencing using a micro-pore plate composed of millions of micro-pores. The micro-pore plate is fluidically accessible from both sides of the pores: the first side (top of plate, illustrated on left side of plate) is in communication with Valves 1, 2, & 3 while the second side (bottom of plate, illustrated on right side of plate) is in communication with Valves 4, 5, & 6. Valve 1 dispenses a lysis/protease buffer, enzymes, wash buffer, elute buffer, buffer, EtOH, Light Oil, and Heavy Oil, as needed through the Initial Reaction Chamber, the 48 Primary PCR Reaction Chambers, and additional chambers across the first side of the micro-pore plate through Valve 3 to Waste. In addition, Valve 1 can select a Waste port, which can be used to vacate the first side of micro-pore plate, other chambers, Primary PCR Reaction Chambers, and Initial Reaction Chamber by the introduction of Air through Valve 3 in a reverse direction. Valve 1 can also select Valve 2. Valve 2 dispenses Fragment ID PCR primers 1, Master PCR Mix, Master UDG/APE1 Buffer, Nested & Universal Primers 1, Bsh1236I, Bisulfite, Fragment ID PCR primers 2, Nested & Universal Primers 2, Wash, EtOH, & Air through Initial Multiplex Reaction Chamber, the PCR Reaction Chambers, and additional chambers across the first side of the micro-pore plate through Valve 3 to Waste. Valve 5 dispenses Sequencing primer sets 1, 2, &, 3, buffer, ETOH, Air, Light Oil, Heavy Oil and Waste across the second side of the micro-pore plate through Valve 6 to Waste. Valve 5 can also select Valve 4. Valve 4 dispenses Extension mix including polymerase and appropriate fluorescently labeled nucleotides for sequencing-by-synthesis, Rinse buffer, Imaging buffer, Cleavage buffer, and Wash. In addition, Valve 1 can select a Waste port, which can be used to vacate the second side micro-pore plate by introduction of Air through Valve 6 in a reverse direction.

TABLE 8

Reagent Setup for Fragment Identifier PCR-Sequencing (Mutation and Methylation)

| Port | Valve 1 | Valve 2 | Valve 4 | Valves 5 | V 3/6 |
|---|---|---|---|---|---|
| 1 | Lysis/Protease Buf. | Frag. ID PCR prim. 1 | Extension | Reagents from V4 | Waste |
| 2 | Wash | Master PCR mix | Rinse | Seq. primers 1 | Air |
| 3 | Elute Buffer | Master UDG/APE1 | Imaging | Seq. primers 2 | or connect |
| 4 | Enz/Prim. from V2 | Nested, Univ. prim. 1 | Cleave | Seq. primers 3 | with air/ |
| 5 | Empty (Pre-mix) | Bsh1236I | Wash | Empty (Pre-mix) | waste of |
| 6 | Waste | Bisulfite | Empty | Waste | V 1/5 |
| 7 | Buffer | Frag. ID PCR prim. 2 | Empty | Buffer | |
| 8 | ETOH | Nested, Univ. prim. 2 | Empty | ETOH | |
| 9 | Air | Buffer | | Air | |
| 10 | Light Oil | Wash | | Light Oil | |
| 11 | Heavy Oil | ETOH | | Heavy Oil | |
| 12 | Hexanol | Air | | Hexanol | |

FIG. 49B illustrates several heating elements that would be designed to provide independent heating/cooling to the Initial Multiplex Reaction Chamber 110, the Primary 24-48 multiplex PCR reaction Chambers 116, the Secondary 24-48 multiplex Reaction Chambers 122, and the main Chamber comprising subdivisions 232 of 24-48 columns and thousands of micro-pores or micro-wells. The back plate, or one or more flat surface(s) of the micro-pore or micro-well chamber, and the reaction chambers may be pressed against these heating elements to allow for temperature control, heating, and/or thermocycling. As illustrated in FIG. 49, the two heating elements behind the Primary 24-48 multiplex PCR reaction Chambers 116, the Secondary 24-48 multiplex Reaction Chambers 122 would be designed as two rectangular (horizontal) strips to control all the Primary Chambers independently of all the Secondary Chambers. Alternative configurations may also be used, for example having independent heating elements for each Primary Chamber, having additional rows of chambers (i.e. Primary, Secondary, Tertiary, etc.) having additional rows or heating elements, and/or having the 24-48 spatial multiplexing arranged in a different geometry than rows or columns, for either/or the Initial Reaction Chamber 110, the Primary Chambers 116, the Secondary Chambers 122, the Mixing Chambers 128, and the main chamber comprising subdivisions 232 of the thousands of micro-wells or micro-pores. Alternative configurations may also be used, for example the methylated DNA may be enriched for using methyl-specific binding protein or antibody to methylated DNA instead of the Bsh1236I selection process. This step may take place either within the cartridge, or prior to entering the methyl-enriched DNA into the cartridge. After bisulfite treatment, the initial limited cycle multiplexed PCR may be divided into two steps (i) Single-sided multiplexed primer linear extension with or without blocking primer to suppress extension of unmethylated DNA DNA, and (ii) Addition of the complementary primers for one or two PCR amplification cycles of the initial extension products.

FIG. 53 provides one embodiment of primer design for sequencing low- and medium-abundance lncRNA, mRNA, and splice variants. Use reverse-transcriptase to make cDNA copies with 3' transcript-specific primers in the Initial Reaction Chamber (FIG. 53, step A). Distribute the sample into 24 Primary PCR Reaction Chambers. Nested, transcript-specific primer pairs are provided to amplify transcript sequences, each primer pair comprising of: (i) a first locus-specific primer, said primer comprising of a first 5' universal or tag sequence portion, a locus-specific 3' portion, a cleavable base such as a ribo-nucleotide and a blocking group on the 3' end; and (ii) a second locus-specific primer with two or more dU bases throughout the primer sequence, said primer comprising of a second 5' universal or tag sequence portion, a transcript identifier sequence, and a locus-specific 3' portion, a cleavable base such as a ribo-nucleotide and a blocking group on the 3' end. The locus-specific primers are unblocked with RNaseH2 only when bound to cDNA or complement, liberating a 3'OH suitable for polymerase-mediated extension (FIG. 53, step B). Two or three cycles of PCR amplification are performed using a thermostable polymerase, preferably a strand-displacement polymerase. These amplification cycles generate product containing the first 5' universal or tag sequence portion, the transcript sequence between the two locus-specific primer portions, the internal transcript identifier, and the complement of the second 5' universal or tag sequence. The original primers and portion of primers in products are destroyed using UDG (uracil DNA glycosylase) and optionally, APE1 (human apurinic endonuclease; FIG. 53, step C). This renders a portion of one of the ends of each double-stranded amplification product single-stranded. In one variation, distribute products into micro-pores or beads into micro-pores containing immobilized second tag sequence primers. In the presence of both first and second tag primers, products are PCR amplified in micro-pores such that a given well generally contains zero or one clonal amplification of a given region, but that pore may contain multiple clonal amplicons from different regions. After denaturation, and removal of unbound fragments, remaining tethered single-stranded target DNA is suitable for primer-directed sequencing (FIG. 53, step D). In another variation, anneal biotinylated primer containing second tag sequence to the single-stranded region. Strand displacement polymerase extends to form full-length double-stranded copy of fragment. Both extended and free biotinylated primers are captured on streptavidin coated beads to be distributed in micro-pores, or directly on streptavidin coated micro-pores. In the presence of both first and second tag primers, products are PCR amplified in micro-pores such that a given micro-pore generally contains zero or one clonal amplification of a given region, but may contain multiple clonal amplicons from different regions. After denaturation, and removal of unbound fragments, remaining tethered single-stranded target DNA is suitable for primer-directed sequencing (Not shown, but like FIG. 41).

FIG. 54 is a schematic front view of a portion of an exemplary design for pre-chamber loading to allow for liquids to be fluidically moved to the chambers comprising of micro-wells or micro-pores. This design illustrates the chamber architecture and micro-wells or micro-pores suitable for performing Multiplexed RT-PCR-Nested PCR-UniTaq detection, for enumeration of both rare and over-expressed lncRNA, mRNA, splice variants or gene-fusions. (Alternatively, Multiplexed RT-PCR-Nested PCR-Real-time-PCR with target-specific Taqman™ probes). The input sample is fluidically connected through inlet 12 to a large hexagonal chamber 10 (bottom, Initial Reaction Chamber), which is fluidically connected by conduits 14 to a first set of hexagonal chambers 16 (8 each containing large troughs 18c, medium troughs 18b, and small troughs 18a, respectively (with large trough 18a shown in FIG. 54), the Primary PCR Reaction Chambers), which are fluidically connected by conduits 20 to a second set of hexagonal chambers 22 (2 each containing large troughs 24a and small troughs 24b, respectively, the Secondary Reaction Chambers), which are fluidically connected by conduits 26 to long narrower Mixing Chambers 28, which are fluidically connected by conduits 30 to the chambers comprising subdivisions 32 of micro-wells or micro-pores (top of panel, with only 4 rows illustrated). The diagram is not to scale and is for illustrative purposes. During manufacture of the cartridge, rows are pre-filled with 1-4 UniTaq primer sets (or alternatively, 1-4 universal tag primer sets with target-specific Taqman™ probes). During manufacture of the cartridge, chambers leading up to the columns of micro-wells or micro-pores are pre-filled with Nested PCR primer sets with either UniTaq or universal tag sequences on their 5' ends. The grey circles 17 on the left side of the drawing illustrate potential position for delivering or printing primer sets, for example by acoustic droplet ejection, capillary, inkjet, or quill printing. The primers are dried down, and the cover part of the cartridge assembled to seal the probe sets in their appropriate positions. During use of the cartridge, reactions are fluidically moved from the initial chambers of the cartridge up the cartridge, and eventually up the columns of micro-wells or micro-pores, where each column is isolated from its neighbor column. In this illustrative example, showing 4 of the planned 48 columns and 8 of the 64 rows equaling 3,072 subdivisions, each subdivision comprising 2,760 micro-pores, for a total of 8,478,720 micro-pores in the array, the initial multiplexed reverse-transcription-PCR is for 9 cycles to generate 512 copies of each original transcript in the Initial Reaction Chamber. Distribute initial multiplex products into the Primary PCR Reaction Chambers, with average distribution of 20 copies of each original transcript in each Primary PCR Reaction Chamber. Perform 10 cycles of nested PCR using target-specific primers with UniTaq or universal tags in groups of 16, 32, or 64 primer sets. Each Primary PCR Reaction Chamber is designed to retain a certain percentage of liquid volume after draining. Perform 3 cycles of filling and draining to differentially dilute products. Dilute products from each of the Primary PCR Reaction Chambers into 2 Secondary Reaction Chambers. Each Secondary Reaction Chamber is designed to retain a certain percentage of liquid volume after draining. Perform 2 cycles of filling and draining to differentially dilute products. Distribute nested PCR products into Mixing Chambers and then into micro-pores of each column. Universal or UniTaq primers in each row will amplify only those products from each column with the correct tags. Poisson distribution in micro-pores will enumerate low-copy, medium-copy, and high-copy lncRNA, mRNA, splice variants, or gene-fusions.

EXAMPLES

Prophetic Example 1—Use of PCR-PCR-Taqman™ or PCR-PCR Unitaq Detection for Unknown Pathogen Identification and Quantification The assay described below would use a cartridge with 24×16=384 (or optional 768) subdivisions for 9,216 micro-well or micro-pore array format, with 24 micro-wells or micro-pores per subdivision, and 384 micro-wells or micro-pores per column (using pre-spotted array): Please see FIGS. 16, 17, 18, and 24.

The assay may be designed to detect and quantify 384, 768, or 1,536 potential targets. Preparation of the cartridge would require spotting 24× of either 16, 32, or 64 nested PCR primer pairs on the front side of the array, with adding UniTaq or Universal Tag primer and target-specific probe sets at right angles and drying them down before cartridge assembly.

1. Initial multiplexed amplification of the sample—384, 768, or 1536 potential targets. Perform 9 cycles of multiplexed PCR in the Initial Reaction chamber, yielding a maximum of 512 copies of each original pathogen. If needed, use "tandem" PCR primers. Also, all PCR primers may include identical 5' tail sequences, preferably 10-11 bases to suppress amplification of primer dimers.

2. Distribute initial multiplexed products into 24 Primary PCR Reaction Chambers. Average distribution in each Primary PCR Reaction Chamber is 20 copies of each original pathogen target. Perform 5 cycles of nested PCR using primers with UniTaq tails, in groups of 16, 32, or 64 primer sets, for a maximum of 640 copies of each original pathogen.

3. Distribute products of each Primary PCR Reaction Chamber into 384 micro-wells or micro-pores. On average, each subdivision (comprising 24 micro-wells or micro-pores) will get 40 copies of each original pathogen, with a given well getting one or two copies of original pathogen. If pathogen present in higher numbers, each subdivision will get additional copies. PCR amplify 1, 2, or 4 potential products in each well using the UniTaq primer sets and determine Ct value in each micro-pore of each subdivision. Use one, two, or four different fluorescent dyes on the UniTaq primers. Poisson distribution in 24 micro-wells or micro-pores (per subdivision) will enumerate pathogen-specific targets initially present at low abundance, while Ct values across 24 micro-wells or micro-pores (per subdivision) will provide approximate copy information for pathogen-specific targets initially present at high abundance.

Note 1: The success of this assay format depends on there being no primer dimers formed by the UniTaq primers, especially when using nested primers. Using 3'-blocked UniTaq primers and RNaseH2 to unblock at an RNA base would solve this problem (see FIG. 17). The same 3' block/RNase trick may also be used on the nested primer set, however there is a slight risk such primers would be less effective since sequence drift of the pathogen may prevent the primers from amplifying that particular target.

Note 2: An additional approach to avoid target-independent signal from primer dimers is to use nested primers that comprise partial target sequence in the tag region and amplify a complementary region within the target using a strand-displacing polymerase that lacks the 5'-3' nuclease activity. After the UniTaq amplification step, and denaturation of the double-stranded product, the labeled product forms a cloverleaf structure, bringing an RNA base in the probe into a double-stranded form and suitable for liberating the fluorescent group with RNaseH2 (See FIG. 18). However, should a primer dimer form in the absence of pathogen, it would lack the pathogen-specific sequences of the product, thus not form the clover-leaf structure, thus not be cleaved by RNaseH2. It is noted that for viral pathogens, there is a slight risk such primers may be less effective in identifying the target, since sequence drift of the target may interfere with formation of the desired cloverleaf structure.

Note 3: For RNA viruses, an initial Reverse-transcriptase step would be included—or one can use Tth DNA polymerase and Mn2+ in the amplification buffer for a single-step RT-PCR. Note also that the sample may be split, and one aliquot is used to amplify potential RNA targets, say for 10-cycles, while the second is used to amplify potential low-level bacterial targets, for example for 20 cycles. The two separate PCR amplification products are then mixed, diluted into PCR buffer, and distributed into the 24 subdivisions for the nested PCR reactions.

Note 4: One advantage of using the UniTaq primers is they may be placed very close to each other such that multiple nested products may be generated off a single initial target amplicon. This allows primer design with 2, 3, or 4 initial targets for each pathogen, followed by 2, 3, or 4 nested primer sets within each target fragment. A pathogen would then only be called positive if a minimum of 2 or 3 of the 4 to 16 possible signals are observed. Another advantage of this approach is it would limit the number of PCR primers in the initial multiplexed reaction. A further advantage is that primers can be designed such that those signals are displayed in different subdivisions to mitigate any target-independent (false) signals.

Prophetic Example 2—Use of PCR-PCR-Taqman™ or PCR-PCR Unitaq Detection for Unknown Pathogen Identification and Quantification The assay described below would use a cartridge with 48×48=2,304 subdivisions for 221, 1846 micro-well array format, with 96 micro-wells per subdivision, and 4,608 micro-wells per column (acoustic droplet ejection into microtiter array plate): Please see FIGS. 16, 17, and 18.

The assay may be designed to detect and quantify 576, or 1,152 potential targets. Preparation of the microtiter plate would require spotting UniTaq or Universal Tag primer and target-specific probe sets and drying them down before use of microtiter plate.

1. Initial multiplexed amplification of the sample—576, or 1,152 potential targets. Perform 10 cycles of multiplexed PCR in a well or Initial Reaction Chamber, maximum of 1,024 copies of each original pathogen. If needed, use "tandem" PCR primers. Also, all PCR primers may include identical 5' tail sequences, preferably 10-11 bases to suppress amplification of primer dimers.

2. Distribute initial multiplexed products into 48 wells or Primary PCR Reaction Chambers. Average distribution in each well or Primary PCR Reaction Chamber is 20 copies of each original pathogen target. Perform 3-4 cycles of nested PCR using primers with UniTaq tails, in groups of 24, or 48 primer sets, for a maximum of 160-320 copies of each original pathogen.

3. Distribute products of each well or Primary PCR Reaction Chamber into 2 or 4 sets of 24 or 12 subdivisions, respectively, containing 96 micro-wells. When using 2 sets, the second set is a 100/1 dilution of the first. When using 4 sets, each set is a 20/1 dilution of the previous set. This allows coverage of pathogens present across many orders of magnitude. On average, each initial subdivision will get 12 copies of each original pathogen, with a given micro-well getting one or zero copies of original pathogen. If pathogen is present in higher numbers, each subdivision will get additional copies. PCR amplify 1, 2, or 4 potential products in each micro-well using the pre-spotted UniTaq primer sets and determine Ct value in each micro-well of each subdivision. Use one, two, or four different fluorescent dyes on the UniTaq primers. Poisson distribution in 96 micro-wells across 2 or 4 dilution sets will provide some degree of enumeration for very low copy pathogen, as well as higher copy pathogen in sample.

See also, notes 1-4 in Example 1 above.

Prophetic Example 3—Use of PCR-LDR-Taqman™, PCR-LDR Unitaq, or PCR-LDR-Split UniTaq (UniSpTq) Detection for Unknown Pathogen Identification and Quantification The assay described below would use a cartridge with 24×16=384 (or optional 768) subdivisions for 9,216 microwell or micro-pore array format, with 24 micro-wells or micro-pores per subdivision, and 384 micro-wells or micro-pores per column (using pre-spotted array): Please see FIGS. 19, 20, 21, and 24.

The assay may be designed to detect and quantify 384, 768, or 1,536 potential targets. Preparation of the cartridge would require spotting 24× of either 16, 32, or 64 LDR primer pairs on the front side of the array, with adding UniTaq or Universal Tag primer and target-specific probe sets at right angles and drying them down before cartridge assembly.

1. Initial multiplexed amplification of the sample—384, 768, or 1536 potential targets. Perform 30 cycles of PCR in the Initial Reaction Chamber, to provide maximum amplification of each original pathogen. If needed, use "tandem" PCR primers. Also, all PCR primers should include identical 5' tail sequences, preferably 10-11 bases to suppress amplification of primer dimers.

2. Distribute initial multiplexed products into 24 Primary LDR Reaction Chambers, while diluting 10-fold. Average distribution in each Primary LDR Reaction Chamber will be millions of copies of each original pathogen target. Perform 20 cycles of LDR using allele-specific primers with UniTaq tails, in groups of 16, 32, or 64 primer sets.

3. Distribute LDR products of each Primary LDR Reaction Chamber into 384 micro-pores. PCR amplify 1, 2, or 4 potential products in each well using the UniTaq primer sets and determine Ct value in each micro-pore of each subdivision. Use one, two, or four different fluorescent dyes on the UniTaq primers. Ct values across 24 micro-wells or micro-pores (per subdivision) provide approximate copy information for pathogen-specific targets initially present at high abundance.

Note 1: The success of this assay format depends on there being no primer dimers formed by the UniTaq primers, e.g. with the downstream LDR primers. This problem has been solved as follows: The initial PCR reaction includes UDG to destroy any accidental carryover contamination in the original sample, and the PCR products incorporate dUTP. After LDR, the UniTaq master mix contains UDG, and will destroy any of the PCR products, such that the only amplification can come off the LDR product. (See also, FIGS. 19 & 20).

Note 2: When using the UniTaq primers for the last amplification step, it may be performed using either a simple probe design (FIG. 20), or a split probe design (FIG. 21). The original probe design has the potential for forming ligation-independent primer dimers if the extension product off the downstream ligation primer forms a primer dimer with the upstream F1-Bi-Q-Ai UniTaq tag primer (FIG. 20). The primer-dimer problem may be addressed by using the split probe design shown in FIG. 21. After the UniTaq amplification step, and denaturation of the double-stranded product, the labeled product forms a stem-loop structure, allowing the 5'-3' nuclease activity of Taq polymerase to extend primer Ci and liberate the fluorescent group to generate signal. As soon as the polymerase has traversed the first stem region, the second shorter (zi-zi') stem falls apart, and polymerase continues extending to create dsDNA products. If there is a ligation-independent primer dimer product that arose from the extension product off the downstream ligation primer with the upstream F1-Bi-Q-Ai UniTaq tag primer, that product will be missing the zi sequence, and consequently will not form the full stem loop structure, thus when Ci extends the Bj probe region will not be hybridized to the Bj' sequence, the fluorescent group (F1) will not be liberated from the quencher (Q).

Note 3: For RNA viruses, an initial Reverse-transcriptase step would be included—or one can use Tth DNA polymerase and Mn2+ in the amplification buffer for a single-step RT-PCR. Note also that the sample may be split, and one aliquot is used to amplify potential RNA targets, say for 30-cycles, while the second is used to amplify potential low-level bacterial targets, for example for 40 cycles. The two separate PCR amplification products are then mixed, diluted into LDR buffer, and distributed into the 24 Secondary LDR Reaction Chamber for the LDR reactions.

Note 4: One advantage of using LDR primers is they may be placed very close to each other such that multiple, even overlapping LDR products may be generated off a single initial target amplicon. This allows primer design with 2, 3, or 4 initial targets for each pathogen, followed by 2, 3, or 4 LDR primer sets within each target fragment. A pathogen would then only be called positive if a minimum of 2 or 3 of the 4 to 16 possible signals are observed. Another advantage of this approach is it would limit the number of PCR primers in the initial multiplexed reaction. A further advantage is that primers can be designed such that those signals are displayed in different subdivisions to mitigate any target-independent (false) signals.

Prophetic Example 4—Use of PCR-PCR-qLDR Detection or PCR-qLDR Detection with Either Universal or Target-Specific Probes, (e.g. UniLDq or TsLDq) for Unknown Pathogen Identification and Quantification The assay described below would use a cartridge with 24×16=384 (or optional 768) subdivisions for 9,216 micro-well or micro-pore array format, with 24 micro-wells or micro-pores per subdivision, and 384 micro-wells or micro-pores per column (using pre-spotted array): Please see FIGS. 22, and 23.

The assay may be designed to detect and quantify 384, 768, or 1,536 potential targets. Preparation of the cartridge would require spotting 24× of either 16, 32, or 64 nested PCR primer pairs on the front side of the array, with adding qLDR primer and probe sets at right angles, and drying them down before cartridge assembly.

1. Initial multiplexed amplification of the sample—384, 768, or 1536 potential targets. Perform 10-15 cycles of PCR in the Initial Reaction Chamber, to provide 1,000 to 32,000-fold amplification of each original pathogen target. If needed, use "tandem" PCR primers. Also, all PCR primers should include identical 5' tail sequences, preferably 10-11 bases to suppress amplification of primer dimers.

2. Distribute initial multiplexed products into 24 Primary PCR Reaction Chambers, while diluting 10-fold. Average distribution in each Primary PCR Reaction Chamber will be 4 to 130 copies of each original pathogen target. Perform 20-30 cycles of PCR using either a subset of the above primers, or nested primers, in groups of 16, 32, or 64 primer sets. Also, all PCR primers should include identical 5' tail sequences, preferably 10-11 bases to suppress amplification of primer dimers.

3. Distribute PCR products of each Primary PCR Reaction Chamber into 384 micro-wells or micro-pores. iLDR ("i" is for isothermal) amplify 1, 2, or 4 potential products in each well using the primer sets as described below, and determine Ct value in each micro-pore of each subdivision. Use one, two, or four different fluorescent dyes on the UniTaq primers.

Alternatively, for Unknown Bacterial Pathogen Identification Directly from Blood (Using PCR-qLDR Detection):

1. Distribute initial sample into 24 Primary PCR Reaction Chambers. Initial multiplexed amplification of the sample—32, 64, or 128 potential targets. Perform 30-40 cycles of multiplexed PCR, to provide billions of copies of each original target, if present. Use "tandem" or more PCR primer sets. Also, all PCR primers include identical 5' tail sequences, preferably 10-12 bases to suppress amplification of primer dimers.

2. Distribute PCR products of each Primary PCR Reaction Chamber into 384 micro-pores. iLDR (i is for isothermal) amplify 1, 2, or 4 potential products in each well using the primer sets as described below and determine Ct value in each micro-pore of each subdivision. Use one, two, or four different fluorescent dyes on the UniTaq primers.

Note 1: As an alternative to using UniTaq to generate fluorescent signal, a new approach is introduced; termed "iLDR" (i for isothermal), see FIGS. 22 and 23. The first version of this approach uses universal Tag and probe sequences (FIG. 22). Here, the LDR primers contain both tag sequences (Bi'; Bj'), as well as sequences complementary to the ligation junction region (ti', tj'). In the presence of PCR amplified product, the ligation probes hybridize adjacent to each other and are covalently linked using thermostable ligase. In the presence of probe (F1-r-Bj, Bi-Q), and after the denaturation step, as the temperature decreases, 4 double-stranded stems form between probe and pathogen-specific sequences (ti & ti'; tj & tj'), Bi & Bi', and Bj & Bj'. This renders the ribose base in the Bj sequence double-stranded, enabling RNaseH2 to liberate the fluorescent group (F1) and generate signal. The cleaved probe dissociates from the product and new probe can hybridize to generate additional signal. Unligated LDR primers would not form all hairpins, and thus RNaseH2 would not liberate signal. The amount of signal generated is a function of how many probes are cleaved during each hybridization step to the cumulative LDR product formed in the previous LDR steps. For example, if 10 fluorescent molecules are liberated for each LDR product formed, then after 5 cycles of LDR, there would be a 10-fold increase in signal, after 15 cycles, a 100-fold increase, and after 46 cycles, a 1,000-fold increase. The amount of product formed is about 4 to 5× (cycle #)^2. The potential advantage of using PCR-iLDR is that the procedure requires only 2 steps (instead of the 3 required by PCR-LDR-UniTaq). If sufficient signal is generated by the iLDR step for detection, it simplifies the overall protocol.

Note 2: The second version of iLDR uses probes that are sequence-specific. Here, the LDR primers contain one tag sequence (Bi'), and one sequence complementary to the ligation junction region (tj'). In the presence of probe (F1-r-pathogen sequence-Bi-Q), and after the denaturation step, as the temperature decreases, 2 double-stranded stems form between pathogen-specific sequences (ti,tj & ti',tj'), and Bi & Bi'. This renders the ribose base in the pathogen sequence double-stranded, enabling RNaseH2 to liberate the fluorescent group and generate signal. The cleaved probe dissociates from the product and new probe can hybridize to generate additional signal. Unligated LDR primers would not form both stems, and thus RNaseH2 would not liberate signal. As above, the amount of signal generated is a function of how many probes are cleaved during each hybridization step to the cumulative LDR product formed in the previous LDR steps.

Note 3: For RNA viruses, an initial Reverse-transcriptase step would be included—or one can use Tth DNA polymerase and Mn2+ in the amplification buffer for a single-step RT-PCR. Note also that the sample may be split, and one aliquot is used to amplify potential RNA targets, say for 30-cycles, while the second is used to amplify potential low-level bacterial targets, for example for 40 cycles. The two separate PCR amplification products are then mixed, diluted into LDR buffer, and distributed into the 24 Secondary LDR Reaction Chambers for the LDR reactions.

Note 4: One advantage of using LDR primers is they may be placed very close to each other such that multiple, even overlapping LDR products may be generated off a single initial target amplicon. This allows primer design with 2, 3, or 4 initial targets for each pathogen, followed by 2, 3, or 4 LDR primer sets within each target fragment. A pathogen would then only be called positive if a minimum of 2 or 3 of the 4 to 16 possible signals are observed. Another advantage of this approach is it would limit the number of PCR primers in the initial multiplexed reaction. A further advantage is that primers can be designed such that those signals are displayed in different subdivisions to mitigate any target-independent (false) signals.

Prophetic Example 5—Use of PCR-PCR-Taqman™ or PCR-PCR Unitaq Detection for Unknown Pathogen Identification and Quantification Directly from Blood The assay described below would use a cartridge with 24×16=384 (or optional 768) subdivisions for 9,216 micro-well or micro-pore array format, with 24 micro-wells or micro-pores per subdivision, and 384 micro-wells or micro-pores per column (using pre-spotted array): Please see FIGS. 26, and 27.

The assay may be designed to detect and quantify 32, 64, or 128 potential targets. Preparation of the cartridge would require spotting 16, 32, or 64 nested PCR primer pairs on the front side of the array, with adding UniTaq or Universal Tag and target-specific probe and primer sets at right angles and drying them down before cartridge assembly.

1. Distribute initial sample into 24 Primary PCR Reaction Chambers. Initial multiplexed amplification of the sample—32, 64, or 128 potential targets. Perform 20 cycles of multiplexed PCR, maximum of 1,000,000 copies of each original target, if present. Use "tandem" or more PCR primer sets. Also, all PCR primers include identical 5' tail sequences, preferably 10-12 bases to suppress amplification of primer dimers.

2. Perform 10 cycles of nested PCR in Secondary PCR Reaction Chambers using primers with UniTaq tails, in groups of 16, 32, or 64 primer sets. Primers are unblocked with RNaseH2 only when bound to correct target.

3. Distribute PCR products of each Secondary PCR Reaction Chamber into 384 micro-pores. Universal or UniTaq primers in each row will amplify only those products from each column with the correct tags. Pre-amplification of target and use of tails to prevent primer dimer formation will allow identification of bacterial pathogens at the single cell level.

Note 1: The success of this assay format depends on there being no primer dimers formed by the UniTaq primers, e.g. with the nested primers. Using 3'-blocked UniTaq primers and RNaseH2 to unblock at an RNA base would solve this problem. The same 3' block/RNase trick may also be used on the nested primer set; however, there is a slight risk such primers would be less effective since sequence drift of the pathogen may prevent the primers from amplifying that particular target.

Note 2: One advantage of using the UniTaq primers is they may be placed very close to each other such that multiple nested products may be generated off a single initial target amplicon. This allows primer design with 2, 3, or 4 initial targets for each pathogen, followed by 2, 3, or 4 nested primer sets within each target fragment. A pathogen would then only be called positive if a minimum of 2 or 3 of the 4 to 16 possible signals are observed.

Prophetic Example 6—Use of PCR-PCR-Taqman™ or PCR-PCR Unitaq Detection for Unknown Pathogen Identification and Quantification Directly from Blood The assay described below would use a cartridge with 48×48=2,304 subdivisions for 221, 1846 micro-well array format, with 96 micro-wells per subdivision, and 4,608 micro-wells per column (acoustic droplet ejection into microtiter array plate): Please see FIGS. 26 and 27.

The assay may be designed to detect and quantify 48, 96, or 192 potential targets. Preparation of the microtiter plate would require spotting UniTaq or Universal Tag primer and target-specific probe sets, and drying them down before use of microtiter plate.

1. Distribute initial sample into 48 wells or Primary PCR Reaction Chambers. Initial multiplexed amplification of the sample—48, 96, or 192 potential targets. Perform 9 cycles of multiplexed PCR, maximum of 512 copies of each original pathogen, if present. Use "tandem" or more PCR primer sets. Also, all PCR primers include identical 5' tail sequences, preferably 10-12 bases to suppress amplification of primer dimers.

2. Distribute products of each well or Primary PCR Reaction Chamber into 48 subdivisions respectively containing 96 micro-wells. The subdivisions have been pre-spotted with appropriate nested target-specific primers, UniTaq primers, and/or probes; (see FIGS. 16, 17, and 18). On average, each initial subdivision will get 10 copies of each original pathogen, with a given micro-well getting one or zero copies of original pathogen. If pathogen is present in higher numbers, each subdivision will get additional copies. PCR amplify 1, 2, or 4 potential products in each micro-pore using the pre-spotted primer sets and determine Ct value in each micro-well of each subdivision. Use one, two, or four different fluorescent dyes on the UniTaq primers. Poisson distribution in 96 micro-wells will provide some degree of enumeration for very low copy pathogen.

See notes 1-2 for Example 5 above.

Prophetic Example 7—Use of PCR-LDR-Taqman™ or PCR-LDR Unitaq Detection for Low Abundance Mutation and/or CpG Methylation Identification and Quantification Directly from Plasma The assay described below would use a cartridge with 24×16=384 (or optional 768) subdivisions for 9,216 micro-well or micro-pore array format, with 24 micro-wells or micro-pores per subdivision, and 384 micro-wells or micro-pores per column (using pre-spotted array): Please see FIGS. 28, 29, and 30.

The assay may be designed to detect and quantify 64, or 128 potential targets, allowing for multiple mutations to be scored by a single fluorescent color. Preparation of the cartridge would require spotting 16, 32, or 64 nested PCR primer pairs on the front side of the array, with adding UniTaq or Universal Tag and target-specific probe and primer sets at right angles, and drying them down before cartridge assembly.

1. Distribute initial sample into 24 Primary PCR Reaction Chambers. Highest level of DNA in plasma=10,000 genome equivalents. On average, 400 copies of each target per Primary PCR Reaction Chamber, with at most 1 mutation. Perform 10-40 cycles of locus-specific PCR with blocking PNA or LNA to reduce amplification of wild-type DNA. Optional: Use dUTP during PCR reaction (and pre-treat with UDG to avoid carryover contamination of initial sample. Also, all downstream PCR primers should include identical 5' tail sequences, preferably 8-11 bases to suppress amplification of primer dimers.

2. Dilute products of each Primary PCR Reaction Chamber with LDR primers and buffers, and distribute products into Secondary LDR Reaction Chambers. Perform 20 cycles of LDR using allele-specific primers with UniTaq tails, in groups of 16, 32, or 64 primer sets. LDR primers for different mutations of the same gene may be designed to give the same signal in the same subdivision. LDR reactions may be performed in the same reaction chamber, or in 2 separate reaction chambers, and then re-combined.

3. Add UniTaq master mix and UDG and distribute products of each Secondary LDR Reaction Chamber into 384 micro-pores. PCR amplify 1, 2, or 4 potential products in each well using the UniTaq primer sets and determine Ct value in each micro-pore of each subdivision. Use one, two, or four different fluorescent dyes on the UniTaq primers.

Note 1. This design provides the option of using the identical LDR primer sets across the board, or printing different LDR primer sets, which then combine with aliquots of the PCR reaction, and then the products are combined again before distributing onto the micro-pores.

Note 2. Another layer of selectivity can be incorporated into the method by including a 3' blocking group, and an RNA base, in the upstream primer. Upon target-specific hybridization, RNase H2 removes the RNA base to liberate a 3'OH group which is a few bases upstream of the mutation, and suitable for polymerase extension. The blocking LNA or PNA probe comprising wild-type sequence that partially overlaps with the upstream PCR primer will preferentially compete in binding to wild-type sequence over the upstream primer, but not as much to mutant DNA, and thus suppresses amplification of wild-type DNA during each round of PCR.

Note 3. Likewise, further selectivity can be incorporated into the method by including a 3' blocking group, and an RNA base, in the downstream primer, which is removed by RNase H2 upon target-specific hybridization. Further, the identical 5' tails can be extended, to about 24-30 bases. The sequence would allow addition of a "universal" primer (also including a 3' blocking group, and an RNA base), which would be present at higher concentration than the locus-specific primers for the initial PCR amplification step. The universal primer would facilitate amplification of all PCR products during the multiplexed amplification.

Note 4. Alternatively, to minimize dropout of fragments during multiplexed PCR, an initial "pre-amplification" multiplexed PCR is performed for 8-20 cycles in an initial reaction chamber. These products are then distributed into the 24 Primary PCR Reaction Chambers. In one variation, each of the 24 primary reaction chambers contains from 1-4 PCR primer sets with PNA or LNA to suppress amplification of wild-type sequence, and single or multiplexed PCR is performed for an additional 10-30 cycles to enable amplification of 1-4 different fragments containing potential mutations in a single primary reaction chamber. In another variation, 6 sets of 4 primary reaction chambers contains from 4-16 PCR primer sets with PNA or LNA to suppress amplification of wild-type sequence, and multiplexed PCR is performed for an additional 10-30 cycles to enable amplification of 4-16 different fragments containing potential mutations in a single primary reaction chamber.

Note 5. This design also allows combining with methylation detection.

For Identification and Quantification of Low Abundance CpG Methylation in Plasma (when Combined with Mutation; Using Bisulfite-PCR-LDR-Taqman™, or Bisulfite-PCR-LDR-Unitaq Detection. See FIGS. 31, 32, and 30):

1. Digest sample with Bsh1236I in the Initial Reaction Chamber. Treat with Bisulfite. Re-purify DNA strands.

2. Distribute bisulfate treated sample into 24 Primary PCR Reaction Chambers. Highest level of DNA in plasma after RE cleavage=200 genome equivalents. Perform 0-40 cycles of locus-specific PCR with optional blocking PNA or LNA to reduce amplification of wild-type DNA, if needed. Use dUTP during PCR reaction. Also, all downstream PCR primers should include identical 5' tail sequences, preferably 8-11 bases to suppress amplification of primer dimers.

2. Dilute products of each Primary PCR Reaction Chamber with LDR primers and buffers and distribute products into Secondary LDR Reaction Chambers. Perform 20 cycles of LDR using methyl-specific primers with UniTaq tails, in groups of 16, 32, or 64 primer sets. LDR primers for different methylation regions, i.e. top and bottom strand of the same promoter region may be designed to give the same signal in the same subdivision. LDR reactions may be performed in the same reaction chamber, or in 2 separate reaction chambers, and then re-combined.

3. Add UniTaq master mix and UDG and distribute products of each Secondary LDR Reaction Chambers into 384 micro-pores. PCR amplify 1, 2, or 4 potential products in each well using the UniTaq primer sets and determine Ct value in each micro-pore of each subdivision. Use one, two, or four different fluorescent dyes on the UniTaq primers.

Note 1. This design provides the option of using the identical LDR primer sets across the board, or printing different LDR primer sets, which then combine with aliquots of the PCR reaction, and then the products are combined again before distributing onto the micro-pores.

Note 2. Another layer of selectivity can be incorporated into the method by including a 3' blocking group, and an RNA base, in the upstream primer. Upon target-specific hybridization, RNase H2 removes the RNA base to liberate a 3'OH group which is a few bases upstream of the mutation, and suitable for polymerase extension. The blocking LNA or PNA probe comprising wild-type sequence that partially overlaps with the upstream PCR primer will preferentially compete in binding to wild-type sequence over the upstream primer, but not as much to mutant DNA, and thus suppresses amplification of wild-type DNA during each round of PCR.

Note 3. Likewise, further selectivity can be incorporated into the method by including a 3' blocking group, and an RNA base, in the downstream primer, which is removed by RNase H2 upon target-specific hybridization. Further, the identical 5' tails can be extended, to about 24-30 bases. The sequence would allow addition of a "universal" primer (also including a 3' blocking group, and an RNA base), which would be present at higher concentration than the locus-specific primers for the initial PCR amplification step. The universal primer would facilitate amplification of all PCR products during the multiplexed amplification.

Note 4. In another embodiment, to minimize dropout of fragments during multiplexed PCR, an initial "pre-amplification" multiplexed PCR is performed for 8-20 cycles in the initial reaction chamber. These products are then distributed into the 24 Primary PCR Reaction Chambers. In one variation, each of the 24 primary reaction chambers contains from 1-4 PCR primer sets, and single or multiplexed PCR is performed for an additional 10-30 cycles to enable amplification of 1-4 different fragments containing potential methylations in a single primary reaction chamber. In another variation, 6 sets of 4 primary reaction chambers contains from 4-16 PCR primer sets, and multiplexed PCR is performed for an additional 10-30 cycles to enable amplification of 4-16 different fragments containing potential methylations in a single primary reaction chamber.

Note 5. This design also allows combining with mutation detection.

Prophetic Example 8—Use of
PCR-LDR-Taqman™ or PCR-LDR Unitaq
Detection for Low Abundance Mutation and/or
CpG Methylation Identification and Quantification
Directly from Plasma The assay described below would use a cartridge with 48×48=2,304 subdivisions for 221, 1846 micro-well array format, with 96 micro-wells per subdivision, and 4,608 micro-wells per column (acoustic droplet ejection into microtiter array plate): Please see FIGS. 28 and 29.

The assay may be designed to detect and quantify 48, 96, or 192 potential targets. Preparation of the microtiter plate would require spotting UniTaq or Universal Tag primer and target-specific probe sets, and drying them down before use of microtiter plate.

1. Distribute initial sample into 48 wells or Primary PCR Reaction Chambers. Highest level of DNA in plasma=10,000 genome equivalents. On average, 200 copies of each target per Primary PCR Reaction Chamber, with at most 1 mutation. Perform 10-40 cycles of locus-specific PCR with blocking PNA or LNA to reduce amplification of wild-type DNA. Optional: Use dUTP during PCR reaction (and pre-treat with UDG to avoid carryover contamination of initial sample).

2. Dilute products of each well or Primary PCR Reaction Chamber with LDR primers and buffers and distribute into Secondary LDR Reaction Chambers. Perform 20 cycles of LDR using allele-specific primers with UniTaq tails, in groups of 16, 32, or 64 primer sets. LDR primers for different mutations of the same gene may be designed to give the same signal in the same subdivision. LDR reactions may be performed in the same reaction chamber, or in 2 separate reaction chambers, and then re-combined.

3. Add UniTaq master mix and UDG and distribute products of each well or Secondary LDR Reaction Chamber into 48 subdivisions, respectively, containing 96 micro-pores. The subdivisions have been pre-spotted with appropriate UniTaq primers, and/or probes; (see FIGS. 28, and 29). PCR amplify 1, 2, or 4 potential products in each micro-pore using the pre-spotted primer sets and determine Ct value in each micro-pore of each subdivision. Use one, two, or four different fluorescent dyes on the UniTaq primers.

For Identification and Quantification of Low Abundance CpG Methylation in Plasma (when Combined with Mutation; Using Bisulfite-PCR-LDR-Taqman™, or Bisulfite-PCR-LDR-Unitaq Detection. See FIGS. 31 and 32):

1. Digest sample with Bsh1236I in Initial Reaction Chamber. Treat with Bisulfite. Re-purify DNA strands.

2. Distribute bisulfate treated sample into 48 wells or Primary PCR Reaction Chambers. Highest level of DNA in plasma after RE cleavage=200 genome equivalents. Perform 10-40 cycles of locus-specific PCR with optional blocking PNA or LNA to reduce amplification of wild-type DNA, if needed. Optional: Use dUTP during PCR reaction.

3. Dilute products of each well or Primary PCR Reaction Chamber with LDR primers and buffers and distribute into Secondary LDR Reaction Chambers. Perform 20 cycles of LDR using methyl-specific primers with UniTaq tails, in groups of 16, 32, or 64 primer sets. LDR primers for different methylation regions, i.e. top and bottom strand of the same promoter region may be designed to give the same signal in the same subdivision. LDR reactions may be performed in the same reaction chamber, or in 2 separate reaction chambers, and then re-combined.

4. Add UniTaq master mix and UDG and distribute products of each well or Secondary LDR Reaction Chamber into 48 subdivisions, respectively, containing 96 micro-pores. The subdivisions have been pre-spotted with appropriate UniTaq primers, and/or probes; (see FIGS. 31 and 32). PCR amplify 1, 2, or 4 potential products in each micro-pore using the pre-spotted primer sets and determine Ct value in each micro-pore of each subdivision. Use one, two, or four different fluorescent dyes on the UniTaq primers.

See also, notes 1-5 for Example 7 above.

Prophetic Example 9—Use of PCR-PCR-Taqman™ or PCR-PCR Unitaq Detection for Exact Enumeration of Both Rare and Overexpressed lncRNA, mRNA, or Splice Variants The assay described below would use a cartridge with 24×16=384 (or optional 768) subdivisions for 9,216 micro-well or micro-pore array format, with 24 micro-wells or micro-pores per subdivision, and 384 micro-wells or micro-pores per column (using pre-spotted array): Please see FIG. 33 for example with splice variant and FIG. 34.

The assay may be designed to detect and quantify 384 potential targets. Preparation of the cartridge would require spotting 16, 32, or 64 nested PCR primer pairs on the front side of the array, with adding UniTaq or Universal Tag and target-specific probe and primer sets at right angles and drying them down before cartridge assembly.

1. Initial multiplexed reverse-transcription/amplification of the sample—384 potential targets. Perform 7 cycles of multiplexed RT-PCR in the Initial Reaction Chamber, maximum of 128 copies of each original transcript. All reverse transcription and PCR primers should include identical 5' tail sequences, preferably 10-11 bases to suppress amplification of primer dimers.

2. Distribute initial multiplexed products into 6 Primary PCR Reaction Chambers. Average distribution in each Primary PCR Reaction Chamber is 20 copies of each original transcript. Perform 10 cycles of nested PCR using primers with UniTaq tails, in groups of 16, 32, or 64 primer unique sets for each Primary PCR Reaction Chamber, for a maximum of 20,480 copies of each original transcript. For this example, three different sets of transcripts would be accurately quantified, where the minimum number would be on the order of 1 original RNA transcript, yielding 20,480 copies, 100 original RNA transcripts, yielding 2,048,000 copies, and 10,000 original RNA transcripts, yielding 204,800,000 copies.

3. The six Primary PCR Reaction Chambers are designed to retain a certain percentage of the volume of the liquid in the reaction after draining. For this example, the full volume of the nested PCR reaction will be designated as 80 units, and the amount retained as 40 units or less. For this illustration, the multiplexed amplification primer sets for Primary PCR Reaction Chambers 1 & 2 are for low-level transcripts (retaining 40 units of liquid), for Primary PCR Reaction Chambers 3 & 4 are for medium-level transcripts (retaining 10 units of liquid), and for Primary PCR Reaction Chambers 5 & 6 are for high-level transcripts (retaining 3 units of liquid). After the first draining, below are the calculations for liquid and minimum copies remaining:

| | Starting Molecules | Liquid Remaining | Remaining Molecules |
|---|---|---|---|
| PR-Chambers 1 & 2 | 20,480 | 40 µ | 20,480 × 40/80 = 10,240 |
| PR-Chambers 3 & 4 | 2,048,000 | 6 µ | 2,048,000 × 6/80 = 153,600 |
| PR-Chambers 5 & 6 | 204,800,000 | 1.2 µ | 204,800,000 × 1.2/80 = 3,072,000 |

A fresh 40µ of master-mix with antibody to inhibit polymerase is added to the remaining liquid, and drained again:

| | Starting Molecules | Liquid Remaining | Remaining Molecules |
|---|---|---|---|
| PR-Chambers 1 & 2 | 10,240 | 40 µ | 10,240 × 40/80 = 5,120 |
| PR-Chambers 3 & 4 | 153,600 | 6 µ | 153,600 × 6/46 = 20,034 |
| PR-Chambers 5 & 6 | 3,072,000 | 1.2 µ | 3,072,000 × 1.2/41 = 89,912 |

A fresh 40µ of master-mix with antibody to inhibit polymerase is added to the remaining liquid, and drained again:

| | Starting Molecules | Liquid Remaining | Remaining Molecules |
|---|---|---|---|
| PR-Chambers 1 & 2 | 5,120 | 40 µ | 5,120 × 40/80 = 2,560 |
| PR-Chambers 3 & 4 | 20,034 | 6 µ | 20,034 × 6/46 = 2,613 |
| PR-Chambers 5 & 6 | 89,912 | 1.2 µ | 89,912 × 1.2/41 = 2,631 |

A fresh 40µ of master-mix is added to the remaining liquid, and now pushed upward, divided equally 4 Secondary Reaction/Dilution Chambers, A, B, C, and D, which have a total volume of 20 units, and can retain 10 units or less.

|  | Starting Molecules | Liquid Remaining | Remaining Molecules |
|---|---|---|---|
| SR-Chambers 1 & 2 A | 640 | 10 μ | 640 × 10/20 = 320 |
| SR-Chambers 1 & 2 B | 640 | 4 μ | 640 × 4/20 = 128 |
| SR-Chambers 1 & 2 C | 640 | 2 μ | 640 × 2/20 = 64 |
| SR-Chambers 1 & 2 D | 640 | 1 μ | 640 × 1/20 = 32 |

SR-Chambers 3 & 4, as well as 5 & 6 will have about twice the number of molecules as above A fresh 10μ of master-mix is added to the remaining liquid in the upper chambers, and drained again:

|  | Starting Molecules | Liquid Remaining | Remaining Molecules |
|---|---|---|---|
| SR-Chambers 1 & 2 A | 320 | 10 μ | 320 × 10/20 = 160 |
| SR-Chambers 1 & 2 B | 128 | 4 μ | 128 × 4/14 = 37 |
| SR-Chambers 1 & 2 C | 64 | 2 μ | 64 × 2/12 = 11 |
| SR-Chambers s 1 & 2 D | 32 | 1 μ | 32 × 1/11 = 2.9 |

SR-Chambers 3 & 4, as well as 5 & 6 will have about twice the number of molecules as above A fresh 10μ of master-mix is added to the remaining liquid in the upper chambers, and drained again:

|  | Starting Molecules | Liquid Remaining | Remaining Molecules |
|---|---|---|---|
| SR-Chambers 1 & 2 A | 160 | 10 μ | 160 × 10/20 = 80 |
| SR-Chambers 1 & 2 B | 37 | 4 μ | 37 × 4/14 = 11 |
| SR-Chambers 1 & 2 C | 11 | 2 μ | 11 × 2/12 = 1.8 |
| SR-Chambers 1 & 2 D | 2.9 | 1 μ | 2.9 × 1/11 = 0.26 |

SR-Chambers 3 & 4, as well as 5 & 6 will have about twice the number of molecules as above At the end, sufficient mastermix is added as all the remaining products and reagents are moved to a larger mixing chamber, in preparation for moving into the micro-pores.

4. Distribute products of each Secondary Reaction/Dilution Chamber into 384 micro-wells or micro-pores. On average, each A Secondary Reaction/Dilution Chamber will get 5 copies of each original transcript, with progressively less in the B, C, and D Secondary Reaction/Dilution Chambers. PCR amplify 1, 2, or 4 potential products in each well using the UniTaq primer sets and determine Ct value in each micro-pore of each subdivision. Use one, two, or four different fluorescent dyes on the UniTaq primers. Poisson distribution in 24 micro-pores will provide enumeration for very low copy transcripts in the A Secondary Reaction/Dilution Chamber, while Poisson distribution across 24 micro-pores in the B, C, and D Secondary Reaction/Dilution Chambers will provide enumeration for high copy transcripts across three to four orders of magnitude.

Secondary Reaction/Dilution Chambers 1 & 2 will accurately enumerate starting transcripts ranging from 1 (filling on average about 5 of the 24 micro-pores of the "A" column) to about 1,500-3,000 (filling on average about 15-21 of the 24 micro-wells or micro-pores of the "D" column).

Secondary Reaction/Dilution Chambers 3 & 4 will accurately enumerate starting transcripts ranging from 100 (filling on average about 10 of the 24 micro-pores of the "A" column) to about 150,000-300,000 (filling on average about 15-21 of the 24 micro-wells or micro-pores of the "D" column).

Secondary Reaction/Dilution Chambers 5 & 6 will accurately enumerate starting transcripts ranging from 10,000 (filling on average about 10 of the 24 micro-pores of the "A" column) to about 15,000,000-30,000,000 (filling on average about 15-21 of the 24 micro-wells or micro-pores of the "D" column).

Note 1: The success of this assay format depends on there being no primer dimers formed by the UniTaq primers, e.g. with the nested primers. Using 3'-blocked UniTaq primers and RNaseH2 to unblock at an RNA base would solve this problem. The same 3' block/RNase trick may also be used on the nested primer set; however, there is a slight risk such primers would be less effective since sequence drift of the pathogen may prevent the primers from amplifying that particular target.

Note 2: One advantage of using the UniTaq primers is they may be placed very close to each other such that multiple nested products may be generated off a single initial target transcript. This allows primer design with 2 nested primer sets within each transcript region. This would allow double verification for a given transcript. Another advantage of this approach is it would limit the number of PCR primers in the initial multiplexed reaction. A further advantage is that primers can be designed such that those signals are displayed in different subdivisions to mitigate any target-independent (false) signals.

Note 3: As an alternative to designing different sets of chambers with different dilutions, separate heating elements may run different chambers under different conditions, including changing the number of PCR cycles.

Prophetic Example 10—Use of PCR-PCR-Taqman™ or PCR-PCR Unitaq Detection for Exact Enumeration of Both Rare and Overexpressed lncRNA, mRNA, or Splice Variants The assay described below would use a cartridge with 48×48=2,304 subdivisions for 221,1846 micro-well array format, with 96 micro-wells per subdivision, and 4,608 micro-wells per column (acoustic droplet ejection into microtiter array plate): Please see FIG. 33 for example with splice variant.

The assay may be designed to detect and quantify 576, or 1,152 potential targets. Preparation of the microtiter plate would require spotting UniTaq or Universal Tag primer and target-specific probe sets, and drying them down before use of microtiter plate.

1. Initial multiplexed reverse-transcription/amplification of the sample—576, or 1,152 potential targets. Perform 10 cycles of multiplexed PCR, maximum of 1,024 copies of each original RNA molecule in the Initial Reaction Chamber. If needed, use "tandem" PCR primers. Also, all PCR primers may include identical 5' tail sequences, preferably 10-11 bases to suppress amplification of primer dimers.

2. Distribute initial multiplexed products into 48 wells or Primary PCR Reaction Chambers. Average distribution in each well is 20 copies of each original RNA target. Perform 3-4 cycles of nested PCR using primers with UniTaq tails, in groups of 24, or 48 primer sets, for a maximum of 160-320 copies of each original RNA molecule.

3. Distribute products of each well or Primary PCR Reaction Chamber into 2 or 4 sets of 24 or 12 subdivisions respectively containing 96 micro-pores. When using 2 sets, the second set is a 100/1 dilution of the first. When using 4 sets, each set is a 20/1 dilution of the previous set. This allows coverage of RNA molecules present across many orders of magnitude. On average, each initial subdivision will get 12 copies of each original RNA molecule, with a given micro-pore getting one or zero copies of original RNA. If RNA is present in higher numbers, each subdivision will get additional copies. PCR amplify 1, 2, or 4 potential products in each micro-pore using the pre-spotted UniTaq primer sets and determine Ct value in each micro-pore of each subdivision. Use one, two, or four different fluorescent dyes on the UniTaq primers. Poisson distribution in 96 micro-pores across 2 or 4 dilution sets will provide some degree of enumeration for very low copy RNA, as well as higher copy RNA in sample.

See also, notes 1-2 for Example 9 above.

Prophetic Example 11—Use of PCR-PCR-Sequencing for Unknown Pathogen Identification and Genotyping The assay described below would use a cartridge with 48×32=1,536 subdivisions for 4,239,360 micro-pore array format for targeted sequencing, with 2,760 micro-pores per subdivision, and 88,320 micro-pores per column. For multiplexed amplification with immobilized primer, see FIG. 35. For details on driving amplification to completion on solid surface, see FIGS. 36, 37, and 38.

The assay may be designed to identify and genotype 1,536 potential targets. Preparation of the cartridge would require spotting 48×32 PCR primer pairs on the front side of the array, with 32×48 PCR sequencing primers on the back side and drying them down before cartridge assembly.

1. Initial multiplexed amplification of the sample—1,536 potential targets. Perform 10 cycles of PCR in the Initial Reaction Chamber, maximum of 1,024 copies of each original pathogen.

2. Distribute initial multiplexed products into 48 Primary PCR Reaction Chambers. Average distribution in each Primary PCR Reaction Chamber is 20 copies of each original pathogen target. Nested, locus-specific primers are unblocked with RNaseH2 only when bound to target. Perform 5 cycles of nested PCR in groups of 32, maximum of 640 copies of each original pathogen. Optional, remove universal primer sequence from product with UDG/APE1 to improve hybridization of product to immobilized primer in micro-pores.

3. Distribute products of each Primary PCR Reaction Chamber into 88,320 micro-pores. On average, each subdivision (comprising 2,760 micro-pores) will get 20 copies of each original pathogen. PCR amplify multiple products in each micro-pore, and then melt off non-anchored strand.

4. Add 48 sequencing primers for each of the 48 targets in 32 subdivisions at right angles. Allows for sequencing of 1,536 potential targets simultaneously. Poisson distribution in 2,760 micro-pores enables enumeration of low-abundance targets.

PCR-PCR-Sequencing for Unknown Pathogen Identification and Genotyping with Adding Sequencing Primers at the Same 48 Subdivisions (See FIG. 49):

If sequencing primers are added in the same orientation, i.e. without subdivision, there are 48×n potential targets, with 88,320/n micro-pores/subdivision.

There are several ways to approach this. One approach is that in general, bacterial pathogens are present at lower levels than viral pathogens. The original PCR cycles could include an RT-step for Viral pathogens, without the second primer, such that they aren't amplified as much as the bacterial fragments are. Also, the original PCR step could be for fewer cycles, and the nested PCR step could also be for fewer cycles still. Then, even if some pathogens are present at higher numbers, with 88,320 micro-pores/section (i.e. column), even if some are present at 2,000 copies, and others at 5 copies, sequencing 32 targets per subdivision would not be unreasonable. Note, the sets of 32 sequencing primers×48 would also be printed on the device. This would allow for detecting 1,536 potential targets simultaneously in a single sequencing run, as well as take advantage of the Poisson distribution in 2,760 micro-pores.

Another approach is to incorporate 8-12 bases of unique sequence in-between the universal primer and the target-specific sequence of the nested PCR primer on the side that does not get attached to the solid support. This would allow for sequencing sets of potential targets by using the 8-12 bases on the 3' side of more universal sequencing primers.

Another approach is to use different universal primers for each set of nested PCR primers, and then print the desired universal sets within the micro-pores, in 32 sections. This would effectively make sure that each amplification product goes to a defined row and column. The advantage of this approach is that it also allows for separate Taqman™ or LDR detection of various products.

In a variation of this idea, the universal primer sequences are the UniTaq sequences. The desired UniTaq primers are printed within the pores, in 32 sets. This approach does not require immobilization of all the primers, although they can be transiently kept in place using hybridization to dendrimers.

Note that with 4-color LDR-FRET detection, splitting into 48 sections, this still allows for highly accurate enumeration of 192 targets simultaneously. Since each of the 48 sections has a different set of (e.g. 16) targets amplified, one could add all 384 LDR primers simultaneously, and they would sort themselves out. This would allow accurate quantification and enumeration of 768 targets in just 4 LDR reactions.

Prophetic Example 12—Use of PCR-PCR-Sequencing for Unknown Pathogen Identification and Genotyping The assay described below would use a cartridge with 48 double-columns×48 double-rows=2,304 subdivisions for 25,436,160 micro-pore array format for targeted sequencing, with 11,040 micro-pores per subdivision, and 529,920 micro-pores per column. For multiplexed amplification with immobilized primer, see FIG. 35. For details on driving amplification to completion on solid surface, see FIGS. 36, 37, and 38.

The assay may be designed to identify and genotype 2,304 to 9,216 potential targets. Preparation of the cartridge would require spotting 48×48 PCR primer pairs on the front side of the array, with 48×48 PCR sequencing primers on the back side and drying them down before cartridge assembly.

1. Initial multiplexed amplification of the sample—2,304 to 9,216 potential targets. Perform 10 cycles of PCR in the Initial Reaction Chamber, maximum of 1,024 copies of each original pathogen.

2. Distribute initial multiplexed products into 48 wells or Primary PCR Reaction Chambers. Average distribution in each well or Primary PCR Reaction Chamber is 20 copies of each original pathogen target. Nested, locus-specific primers are unblocked with RNaseH2 only when bound to target. Perform 2-3 cycles of nested PCR in groups of 32, maximum of 80 to 160 copies of each original pathogen. Optional, remove universal primer sequence from product with UDG/APE1 to improve hybridization of product to immobilized primer in micro-pores.

3. Distribute products of each well or Primary PCR Reaction Chamber into 529,920 micro-pores. PCR amplify multiple products in each micro-pore and melt off non-anchored strand.

PCR-PCR-Sequencing for Unknown Pathogen Identification and Genotyping with Adding Sequencing Primers at the Same 48 Subdivisions:

If sequencing primers are added in the same orientation, i.e. without subdivision, there are 48×n potential targets, with 529,920/n micro-pores/subdivision.

There are several ways to approach this. One approach is that in general, bacterial pathogens are present at lower levels than viral pathogens. The original PCR cycles could include an RT-step for Viral pathogens, without the second primer, such that they aren't amplified as much as the bacterial fragments are. Also, the original PCR step could be for fewer cycles. Then, even if some pathogens are present at higher numbers, with 529,920 micro-pores/section (column), even if some are present at 2,000 copies, and others at 5 copies, sequencing 32 targets per section (column) would not be unreasonable. Note, the sets of 192 sequencing primers×48 would also be distributed into the device. This would allow for detecting 9,216 potential targets simultaneously in a single sequencing run, as well as take advantage of the Poisson distribution in 529,920 micro-pores.

Another approach is to incorporate 8-16 bases of unique sequence in-between the universal primer and the target-specific sequence of the nested PCR primer on the side that does not get attached to the solid support. This would allow for sequencing sets of potential targets by using the 8-16 bases on the 3' side of more universal sequencing primers. A first set of 8-16 sequencing primers may comprise a common 5' sequence (16 bases), and variable 3' sequences (8 bases). Or, a second set of 64-256 sequencing primers may comprise a common 5' sequence (8 bases), a variable middle sequence (8 bases, 8-16 variants) and hyper-variable 3' sequences (8 bases, 64-256 variants).

Prophetic Example 13—Use of PCR-PCR-Sequencing for Low Abundance Mutation and/or CpG Methylation Identification and Enumeration Directly from Plasma The assay described below would use a cartridge with 48×32=1,536 subdivisions for 4,239,360 micro-pore array format for targeted sequencing, with 2,760 micro-pores per subdivision, and 88,320 micro-pores per column. See FIGS. 40-46, and 48.

1. Distribute initial sample into 48 Primary PCR Reaction Chambers. Highest level of DNA in plasma=10,000 genome equivalents. On average, 200 copies of each target per Primary PCR Reaction Chamber, with at most 1 mutation. Locus-specific primers are unblocked with RNaseH2 only when bound to target. Perform 3 cycles of fragment identifier PCR for both strands, each strand covering slightly different sequences. Yields 4 copies of top strand, and 4 copies of bottom strand.

2. Treat with UDG/APE1, and distribute products of each Primary PCR Reaction Chamber into 88,320 micro-pores. Assuming 75% capture, a given target will have about 1200 copies per section (column), and if a mutation is present, there should be about 3 copies of the "Watson strand" and about 3 copies of the "Crick strand". PCR amplify multiple products in each well using nested target-specific primers and universal primers and melt off non-anchored strand.

3. Add 72 sequencing primers—covers 36 target regions, for both Watson and Crick strand, including overlapping regions when needed. Generate about 80 bases of sequence information, plus 10 bases of unique fragment identifier barcode.

4. Add an additional 72 sequencing primers. The current cartridge easily has room for 4 rounds of sequencing=288 primers—covers 144 target regions, both strands, with accurate enumeration of each mutation.

Note 1: The original nested primers may also be used as sequencing primers.

Note 2: The nested primers may be designed to contain different sets of universal sequences comprising the master universal sequence and then 8-12 bases on the 3' end to uniquely sequence different fragments, such that on average, 72 products are sequenced per individual sequencing primer. Repeat with next sequencing primer to sequence next 72 fragments.

For Identification and Quantification of Low Abundance CpG Methylation in Plasma (when Combined with Mutation; Using Bisulfite-PCR-PCR Sequencing. See FIGS. 51 and 52):

1. Digest sample with Bsh1236I in the Initial Reaction Chamber. Treat with Bisulfite. Re-purify strands.

2. Distribute bisulfate treated sample into 48 Primary PCR Reaction Chambers. Highest level of DNA in plasma after RE cleavage=200 genome equivalents. On average, 4 copies of each target per Primary PCR Reaction Chamber, with at most 1 being methylated. Locus-specific primers are unblocked with RNaseH2 only when bound to target. Perform 3 cycles of fragment identifier PCR for both strands, each strand covering slightly different sequences. Yields 4 copies of top strand, and 4 copies of bottom strand of originally methylated DNA.

3. Treat with UDG/APE1, and distribute products of each Primary PCR Reaction Chamber into 88,320 micro-pores. Assuming 75% capture, a given target will have about 16 copies per Primary PCR Reaction Chamber, and if a methylated region is present, there should be about 3 copies of the "Watson strand" and about 3 copies of the "Crick strand". PCR amplify multiple products in each well using nested target-specific primers and universal primers and melt off non-anchored strand.

4. Add as many sequencing primers as desired to cover methylated regions. (Theoretically, could cover 2,760 methylated regions in one sequencing run, with accurate enumeration of every methylated region.)

Note 1. The original nested primers may also be used as sequencing primers.

For Identification and Quantification of Low Abundance CpG Methylation in Plasma Using Bisulfite-PCR-PCR Sequencing (when Done Alone):

1. Digest sample with Bsh1236I in the Initial Reaction Chamber. Treat with Bisulfite. Re-purify strands.

2. Distribute bisulfate treated sample into 48 Primary PCR Reaction Chambers. Highest level of DNA in plasma after RE cleavage=200 genome equivalents. On average, 4 copies of each target per Primary PCR Reaction Chamber, with at most 1 being methylated. Locus-specific primers are unblocked with RNaseH2 only when bound to target. Perform 11 cycles of fragment identifier PCR for one strand. Yields 1,024 copies of one strand of originally methylated DNA.

3. Treat with UDG/APE1, and distribute products of each Primary PCR Reaction Chamber into 88,320 micro-pores. Assuming 75% capture, a given target will have about 100 copies per section (column), and if a methylated region is present, there should be about 24 copies of that strand. PCR amplify multiple products in each well and melt off non-anchored strand.

4. Add 12 sequencing primers for each 12 targets in 32 subdivisions at right angles. Allows for sequencing of 384 potential methylated targets simultaneously. Poisson distribution in 2,760 micro-pores enables enumeration of methylated targets. Total of 384 potential methylated target regions can be evaluated simultaneously, with accurate enumeration of every methylated region.

Note 1. The original target-specific second primers may also be used as sequencing primers.

Prophetic Example 14—Use of PCR-PCR-Sequencing for Low Abundance Mutation and/or CpG Methylation Identification and Enumeration Directly from Plasma The assay described below would use a cartridge with 48 double-columns×48 double-rows=2,304 subdivisions for 25,436,160 micro-pore array format for targeted sequencing, with 11,040 micro-pores per subdivision, and 529,920 micro-pores per column. See FIGS. 40-46, and 48.

1. Distribute initial sample into 48 wells or Primary PCR Reaction Chambers. Highest level of DNA in plasma=10,000 genome equivalents. On average, 200 copies of each target per Primary PCR Reaction Chamber, with at most 1 mutation. Locus-specific primers are unblocked with RNaseH2 only when bound to target. Perform 3 cycles of fragment identifier PCR for both strands, each strand covering slightly different sequences. Yields 4 copies of top strand, and 4 copies of bottom strand.

2. Treat with UDG/APE1 and distribute products from each Primary PCR Reaction Chambers into 529,920 micro-pores. Assuming 75% capture, a given target will have about 1200 copies per section (column), and if a mutation is present, there should be about 3 copies of the "Watson strand" and about 3 copies of the "Crick strand". PCR amplify multiple products in each well using nested target-specific primers and universal primers and melt off non-anchored strand.

3. Add 256 sequencing primers—covers 128 target regions, for both Watson and Crick strand, including overlapping regions when needed. Generate about 80 bases of sequence information, plus 10 bases of unique fragment identifier barcode. Approximately 307,200 micro-pores out of the 529,920 micro-pores will generate sequence information, with about 75% of these providing reads from a single PCR product per sequencing round.

4. Add an additional 256 sequencing primers as often as needed to sequence as many targeted regions as needed.

Note 1: The original nested primers may also be used as sequencing primers.

Note 2: The nested primers may be designed to contain different sets of universal sequences comprising the master universal sequence and then 8-16 bases on the 3' end to uniquely sequence different fragments, such that on average, 256 products are sequenced per individual sequencing primer. Repeat with next sequencing primer to sequence next 256 fragments.

For Identification and Quantification of Low Abundance CpG Methylation in Plasma (when Combined with Mutation; Using Bisulfite-PCR-PCR Sequencing. See FIG. 51):

1. Digest sample with Bsh1236I in the Initial Reaction Chamber. Treat with Bisulfite. Re-purify strands.

2. Distribute bisulfate treated sample into 48 wells or Primary PCR Reaction Chambers. Highest level of DNA in plasma after RE cleavage=200 genome equivalents. On average, 4 copies of each target per Primary PCR Reaction Chamber, with at most 1 being methylated. Locus-specific primers are unblocked with RNaseH2 only when bound to target. Perform 3 cycles of fragment identifier PCR for both strands, each strand covering slightly different sequences. Yields 4 copies of top strand, and 4 copies of bottom strand of originally methylated DNA.

3. Treat with UDG/APE1 and distribute products from each Primary PCR Reaction Chamber into 529,920 micro-pores. Assuming 75% capture, a given target will have about 16 copies per section (column), and if a methylated region is present, there should be about 3 copies of the "Watson strand" and about 3 copies of the "Crick strand". PCR amplify multiple products in each well using nested target-specific primers and universal primers and melt off non-anchored strand.

4. Add as many sequencing primers as desired to cover methylated regions. Theoretically, could cover 19,200 methylated regions in one sequencing run, with accurate enumeration of every methylated region. Thus, if a master universal sequence is used just for the methylated regions, this single primer could cover all the methylated regions in a single run.

Note 1. The original nested primers may also be used as sequencing primers.

For Identification and Quantification of Low Abundance CpG Methylation in Plasma Using Bisulfite-PCR-PCR Sequencing (when Done Alone):

1. Digest sample with Bsh1236I in Initial Reaction Chamber. Treat with Bisulfite. Re-purify strands.

2. Distribute bisulfate treated sample into 48 wells or Primary PCR Reaction Chambers. Highest level of DNA in plasma after RE cleavage=200 genome equivalents. On average, 4 copies of each target per Primary PCR Reaction Chamber, with at most 1 being methylated. Locus-specific primers are unblocked with RNaseH2 only when bound to target. Perform 11 cycles of fragment identifier PCR for one strand. Yields 1,024 copies of one strand of originally methylated DNA.

3. Treat with UDG/APE1 and distribute products from each Primary PCR Reaction Chamber into 529,920 micro-pores. Assuming 75% capture, a given target will have about 100 copies per section (column), and if a methylated region is present, there should be about 24 copies of that strand. PCR amplify multiple products in each well and melt off non-anchored strand.

4. Add as many sequencing primers as desired to cover methylated regions. Theoretically, could cover 19,200 methylated regions in one sequencing run, with accurate enumeration of every methylated region. Thus, if a master universal sequence is used just for the methylated regions, this single primer could cover all the methylated regions in a single run.

Note 1. The original target-specific second primers may also be used as sequencing primers.

Prophetic Example 15—Use of PCR-PCR-Sequencing for Non-Invasive Pre-Natal Testing (NIPT of Trisomy Directly from Plasma The assay described below would use a cartridge with 48×32=1,536 subdivisions for 4,239,360 micro-pore array format for targeted sequencing, with 2,760 micro-pores per subdivision, and 88,320 micro-pores per column. See FIG. 50.

1. Adjust DNA in plasma/sample to 2,000 genome equivalents. Distribute initial sample into 48 Primary PCR Reaction Chambers. On average, 40 copies of each locus per Primary PCR Reaction Chamber, with different SNPs. Locus-specific primers are unblocked with RNaseH2 only when bound to target. Perform 3 cycles of fragment identifier PCR for both strands, each strand covering slightly different sequences. Yields 4 copies of top strand, and 4 copies of bottom strand.

2. Treat with UDG/APE1 and distribute products of each Primary PCR Reaction Chamber into 88,320 micro-pores. Assuming 75% capture, a given locus will have about 240 copies per section i.e. column (120 for Watson strand and 120 for Crick strand). PCR amplify multiple products in each well using nested locus-specific primers and universal primers and melt off non-anchored strand.

3. Add 368 sequencing primers (or one primer, see note 2 below)—covers 184 locus regions, for both Watson and Crick strand. Generate about 50 bases of sequence information, plus 10 bases of unique fragment identifier barcode.

4. Add an additional 368 (or one primer, see note 2 below) sequencing primers. The current cartridge has room for 4 rounds of sequencing=covers 736 locus regions, both strands, with accurate enumeration of each SNP on both the Watson and Crick strand.

Basic idea is to enumerate how many copies of each strand are present. Since the Watson strands should match the Crick strands in each of the 48 sections, i.e. columns (since they are generated from a given fragment with one of each strand), this is an internal control for loss of strands or other errors. Multiple unique loci on Chromosomes 2 (control), 13, 18, 21, X, and Y are used to establish copy number as well as identify trisomy or other chromosomal copy changes.

The above calculations are based on filling on average about 50% of the micro-pores. (Poisson distribution: mean lambda=0.4; Initial percentage x=0). Under such conditions, approximately 60% of the micro-pores will not give any sequencing reads, about 30% are unique (i.e. single reads), about 7.5% will give double reads, and about 1.3% will give triple reads. On a practical level, the single reads are unambiguous for distinguishing SNPs. The double reads may be used to determine loci, but double reads should not be used to distinguish SNPs. Between the single and double reads, over 90% of the strands are covered, and since that distribution is essentially random, this approach should provide highly accurate enumeration of each strand present in the initial sample.

Note 1: The original nested primers may also be used as sequencing primers.

Note 2: The nested primers may be designed to contain different sets of universal sequences comprising the master universal sequence and then 8-12 bases on the 3' end to uniquely sequence different fragments, such that on average, 368 products are sequenced per individual sequencing primer. Repeat with next sequencing primer to sequence next 368 fragments.

Prophetic Example 16—Use of PCR-PCR-Sequencing for Non-Invasive Pre-Natal Testing (NIPT of Trisomy Directly from Plasma The assay described below would use a cartridge with 48 double-columns×48 double-rows=2,304 subdivisions for 25,436,160 micro-pore array format for targeted sequencing, with 11,040 micro-pores per subdivision, and 529,920 micro-pores per column. See FIG. 50.

1. Adjust DNA in plasma/sample to 2,000 genome equivalents. Distribute initial sample into 48 Primary PCR Reaction Chambers. On average, 40 copies of each locus per Primary PCR Reaction Chamber, with different SNPs. Locus-specific primers are unblocked with RNaseH2 only when bound to target. Perform 3 cycles of fragment identifier PCR for both strands, each strand covering slightly different sequences. Yields 4 copies of top strand, and 4 copies of bottom strand.

2. Treat with UDG/APE1 and distribute products of each Primary PCR Reaction Chamber into 529,920 micro-pores. Assuming 75% capture, a given locus will have about 240 copies per section, i.e. column (120 for Watson strand and 120 for Crick strand). PCR amplify multiple products in each well using nested locus-specific primers and universal primers and melt off non-anchored strand.

3. Add 2,208 sequencing primers (or one primer, see note 2 below)—covers 1,104 locus regions, for both Watson and Crick strand. Generate about 50 bases of sequence information, plus 10 bases of unique fragment identifier barcode.

4. Add an additional 2,208 (or one primer, see note 2 below) sequencing primers.

Basic idea is to enumerate how many copies of each strand are present. Since the Watson strands should match the Crick strands in each of the 48 sections, i.e. columns (since they are generated from a given fragment with one of each strand), this is an internal control for loss of strands or other errors. Multiple unique loci on Chromosomes 2 (control), 13, 18, 21, X, and Y are used to establish copy number as well as identify trisomy or other chromosomal copy changes.

The above calculations are based on filling on average about 50% of the micro-pores. (Poisson distribution: mean lambda=0.4; Initial percentage x=0). Under such conditions, approximately 60% of the micro-pores will not give any sequencing reads, about 30% are unique (i.e. single reads), about 7.5% will give double reads, and about 1.3% will give triple reads. On a practical level, the single reads are unambiguous for distinguishing SNPs. The double reads may be used to determine loci but should not be used to distinguish SNPs. Between the single and double reads, over 90% of the strands are covered, and since that distribution is essentially random, this approach should provide highly accurate enumeration of each strand present in the initial sample.

Note 1: The original nested primers may also be used as sequencing primers.

Note 2: The nested primers may be designed to contain different sets of universal sequences comprising the master universal sequence and then 8-16 bases on the 3' end to uniquely sequence different fragments, such that on average, 368 products are sequenced per individual sequencing primer. Repeat with next sequencing primer to sequence next 1,104 fragments.

Prophetic Example 17—Use of
PCR-PCR-Taqman™ or PCR-PCR Unitaq
Detection for Exact Enumeration of Both Rare and Overexpressed lncRNA, mRNA, or Splice Variants The assay described below would use a cartridge with 48×32=1,536 subdivisions for 4,239,360 micro-pore array format for targeted sequencing, with 2,760 micro-pores per subdivision, and 88,320 micro-pores per column. Please see FIGS. 53 and 54. The assay may be designed to detect and quantify 1,536 potential targets.

1. Initial multiplexed reverse-transcription/amplification of the sample—1,536 potential targets. Perform 9 cycles of PCR in the Initial Reaction Chamber, maximum of 512 copies of each original transcript. All reverse transcription and PCR primers should include identical 5' tail sequences, preferably 10-11 bases to suppress amplification of primer dimers.

2. Distribute initial multiplexed products into 24 Primary PCR Reaction Chambers. Average distribution in each Primary PCR Reaction Chamber is 20 copies of each original transcript. Perform 10 cycles of nested PCR using primers with UniTaq tails, in groups of 32 primer unique sets for each Primary PCR Reaction Chamber, for a maximum of 20,480 copies of each original transcript. For this example, three different sets of transcripts would be accurately quantified, where the minimum number would be on the order of 1 original RNA transcript, yielding 20,480 copies, 100 original RNA transcripts, yielding 2,048,000 copies, and 10,000 original RNA transcripts, yielding 204,800,000 copies.

3. The 24 Primary PCR Reaction Chambers are designed to retain a certain percentage of the volume of the liquid in the reaction after draining. For this example, the full volume of the nested PCR reaction will be designated as 80 units, and the amount retained as 40 units or less. For this illustration, the multiplexed amplification primer sets for Primary PCR Reaction Chambers 1-8 are for low-level transcripts (retaining 40 units of liquid), for Primary PCR Reaction Chambers 9-16 are for medium-level transcripts (retaining 10 units of liquid), and for Primary PCR Reaction Chambers 17-24 are for high-level transcripts (retaining 3 units of liquid). After the first draining, below are the calculations for liquid and minimum copies remaining:

|  | Starting Molecules | Liquid Remaining | Remaining Molecules |
| --- | --- | --- | --- |
| PR-Chambers 1-8 | 20,480 | 40 μ | 20,480 × 40/80 = 10,240 |
| PR-Chambers 9-16 | 2,048,000 | 6 μ | 2,048,000 × 6/80 = 153,600 |
| PR-Chambers 17-24 | 204,800,000 | 1.2 μ | 204,800,000 × 1.2/80 = 3,072,000 |

A fresh 40μ of master-mix with antibody to inhibit polymerase is added to the remaining liquid, and drained again:

|  | Starting Molecules | Liquid Remaining | Remaining Molecules |
| --- | --- | --- | --- |
| PR-Chambers 1-8 | 10,240 | 40 μ | 10,240 × 40/80 = 5,120 |
| PR-Chambers 9-16 | 153,600 | 6 μ | 153,600 × 6/46 = 20,034 |
| PR-Chambers 17-24 | 3,072,000 | 1.2 μ | 3,072,000 × 1.2/41 = 89,912 |

A fresh 40μ of master-mix with antibody to inhibit polymerase is added to the remaining liquid, and drained again:

|  | Starting Molecules | Liquid Remaining | Remaining Molecules |
| --- | --- | --- | --- |
| PR-Chambers 1-8 | 5,120 | 40 μ | 5,120 × 40/80 = 2,560 |
| PR-Chambers 9-16 | 20,034 | 6 μ | 20,034 × 6/46 = 2,613 |
| PR-Chambers 17-24 | 89,912 | 1.2 μ | 89,912 × 1.2/41 = 2,631 |

A fresh 40μ of master-mix is added to the remaining liquid, and now pushed upward, divided equally into Secondary Reaction/Dilution Chambers, A and B, which have a total volume of 20 units, and can retain 10 units or less.

|  | Starting Molecules | Liquid Remaining | Remaining Molecules |
| --- | --- | --- | --- |
| SR-Chambers 1-8 A | 640 | 10 μ | 640 × 10/20 = 320 |
| SR-Chambers 1-8 B | 640 | 0.5 μ | 640 × 0.5/20 = 16 |

SR-Chambers 9-16, as well as 17-24 will have about twice the number of molecules as above A fresh 10μ of master-mix is added to the remaining liquid in the upper chambers, and drained again:

|  | Starting Molecules | Liquid Remaining | Remaining Molecules |
| --- | --- | --- | --- |
| SR-Chambers 1-8 A | 320 | 10 μ | 320 × 10/20 = 160 |
| SR-Chambers 1-8 B | 16 | 0.5 μ | 16 × 0.5/10.5 = 0.76 |

SR-Chambers 9-16, as well as 17-24 will have about twice the number of molecules as above At the end, sufficient mastermix is added as all the remaining products and reagents are moved to a larger mixing chamber, in preparation for moving into the micropores.

4. Distribute products of each Secondary Reaction/Dilution Chamber into 88,320 micro-pores. On average, each A Secondary Reaction/Dilution Chamber will get 5 copies of each original transcript, with about 200-fold less in the B Secondary Reaction/Dilution Chamber. PCR amplify potential products in each micro-pore using the UniTaq primer sets and determine Ct value in each micro-pore of each subdivision. (Optional: the total number of transcripts may be doubled or quadrupled by using two, or four different fluorescent dyes on the UniTaq primers). Poisson distribution in 2,760 micro-pores will provide enumeration for very low copy transcripts in the A Secondary Reaction/Dilution Chambers, while Poisson distribution across 2,760 micro-pores in the B Secondary Reaction/Dilution Chambers will provide enumeration for high copy transcripts across three orders of magnitude.

Secondary Reaction/Dilution Chambers 1-8 will accurately enumerate starting transcripts ranging from 1 (filling on average about 5 of the 2,760 micro-pores of the "A" column) to about 110,000-220,000 (filling on average about 1,766-2,290 of the 2,760 micro-pores of the "B" column).

Secondary Reaction/Dilution Chambers 3 & 4 will accurately enumerate starting transcripts ranging from 100 (filling on average about 10 of the 2,760 micro-pores of the "A" column) to about 11,000,000-22,000,000 (filling on average about 1,766-2,290 of the 2,760 micro-pores of the "B" column).

Secondary Reaction/Dilution Chambers 5 & 6 will accurately enumerate starting transcripts ranging from 10,000 (filling on average about 10 of the 2,760 micro-pores of the "A" column) to about to about 1,100,000,000-2,200,000,000 (filling on average about 1,766-2,290 of the 2,760 micro-pores of the "B" column).

Note 1: The success of this assay format depends on there being no primer dimers formed by the UniTaq primers, e.g. with the nested primers. Using 3'-blocked UniTaq primers and RNaseH2 to unblock at an RNA base would solve this problem. The same 3' block/RNase trick may also be used on the nested primer set, however there is a slight risk such primers would be less effective since sequence drift of the pathogen may prevent the primers from amplifying that particular target.

Note 2: One advantage of using the UniTaq primers is they may be placed very close to each other such that multiple nested products may be generated off a single initial target transcript. This allows primer design with 2 nested primer sets within each transcript region. This would allow double verification for a given transcript. Another advantage of this approach is it would limit the number of PCR primers in the initial multiplexed reaction. A further advantage is that primers can be designed such that those signals are displayed in different sections (columns) to mitigate any target-independent (false) signals.

Note 3: As an alternative to designing different sets of chambers with different dilutions, separate heating elements may run different chambers under different conditions, including varying the number of PCR cycles.

With Adding Sequencing Primers at the Same 48 Sections (i.e. Columns) for Exact Enumeration of Both Rare and Overexpressed lncRNA, mRNA, or Splice Variants:

If sequencing primers are added in the same orientation, i.e. without subdivision, there are 48×n potential targets, with 88,320/n micro-pores/subdivision.

There are two ways to approach this. One approach is that in general, bacterial pathogens are present at lower levels than viral pathogens. The original PCR cycles could include an RT-step for viral pathogens, without the second primer, such that they aren't amplified as much as the bacterial fragments are. Also, the original PCR step could be for fewer cycles, and the nested PCR step could also be for fewer cycles still. Then, even if some pathogens are present at higher numbers, with 88,320 micro-pores/section (column), even if some are present at 2,000 copies, and others at 5 copies, sequencing 32 targets per section would not be unreasonable. Note, the sets of 32 sequencing primers×48 would also be printed on the device. This would allow for detecting 1,536 potential targets simultaneously in a single sequencing run, as well as take advantage of the Poisson distribution in 2,760 micro-pores.

Another approach is to incorporate 8-12 bases of unique sequence in-between the universal primer and the target-specific sequence of the nested PCR primer on the side that does not get attached to the solid support. This would allow for sequencing sets of potential targets by using the 8-12 bases on the 3' side of more universal sequencing primers.

Another approach is to use different universal primers for each set of nested PCR primers, and then print the desired universal sets within the pores, in 32 sections. This would effectively make sure that each amplification product goes to a defined row and column. The advantage of this approach is that it also allows for separate Taqman™ or LDR detection of various products.

In a variation of this idea, the universal primer sequences are the UniTaq sequences. The desired UniTaq primers are printed within the pores, in 32 sets. This approach does not require immobilization of all the primers, although they can be transiently kept in place using hybridization to dendrimers.

Note that with 4-color LDR-FRET detection, splitting into 48 sections, this still allows for highly accurate enumeration of 192 targets simultaneously. Since each of the 48 sections has a different set of (e.g. 16) targets amplified, one could add all 384 LDR primers simultaneously, and they would sort themselves out. This would allow accurate quantification and enumeration of 768 targets in just 4 LDR reactions.

For 384 Potential Targets. (with Adding UniTaq Primer Sets at Right Angles, and Drying them Down Before Assembly.)

Requires spotting 24× of either 16, 32, or 64 nested PCR primer pairs on the front side of the array.

Prophetic Example 18—Example of PCR Primer Design with Split UniTaq Probe (UniRq)

Example of PCR Primer Design with Split UniTaq Probe (UniRq) for FIG. 18:

(Tm=64.6) (186 bp total; 28+28 bp TS DNA)

```
Forward primer sequence: (Ai-Bi'-ti'-TS)
5'-TCAGTATCGGCGTAGTCACCTGTTTTGTTG-A-TCACTATCGGA
(SEQ ID NO: 17) (Upstream-Target-Sequence; 28 bp)
rTCCGG-3' Block Reverse primer sequence: (Ci-Bj-tj-TS)
5'-TCGACGATAGGTTTCCGCACTCACAGGCAGC-T-AGCGATAGTAC
(SEQ ID NO: 18) (Downstream-Target-Sequence;
28 bp) rGTACC-3' Block 1st UniTaq Primer: (F1-Bj,Bi-Q-Ai)
5'-F1-TCACArGGCAGC-A-CAACAAAACA-Q
TCAGTATCGGCGTAGTCACC-3' (SEQ ID NO: 19)

2nd UniTaq primer: Ci
5'-TCGACGATAGGTTTCCGCAC-3' (SEQ ID NO: 20)

Full PCR product (Tm of probe portion hybridizing
to both split complements = 64.6)

5'-F1-TCACArGGCAGC-A-CAACAAAACA-QTCAGTATCGGCG
TAGTCACCTGTTTTGTTG-A-TCACTATCGGA (SEQ ID NO: 21)
(Upstream-Target-Sequence; 28 bp) TCCGATAGTGA-
A-AGCGATAGTAC (SEQ ID NO: 22) (Downstream-
Target-Sequence; 28 bp) GTACTATCGCT-A-GCTGCCTGTGA
GTGCGGAAACCTATCGTCGA-3' (SEQ ID NO: 23)
```

-continued

Notes based on OligoAnalyzer 3.1 Tm calculations:

Internal bold sequences ti & ti' hairpin at 62.6° C., entire structure is given Tm value of 53.1° C.

Internal italic sequences tj & tj' hairpin at 59.7° C., entire structure is given Tm value of 53.1° C.

Separate bold sequences ti & ti' hybridize at 38.6° C.

Separate italic sequences tj & tj' hybridize at 37.2° C.

Separate double underlined sequences Bi & Bi' and Bj & Bj' have Tm of 30.2 and 47.6, respectively Combining the four hairpin regions gives, results in overall hairpin Tm at 64.6.

Potential primer-dimer PCR product (Tm of probe portion hybridizing to both split complements = 54.4)

(Note: Since the primer dimer lacks authentic target sequence TCCGATAGTGA-A-*AGCGATAGTAC* (SEQ ID NO: 24), hybridization of PCR primers to such a product will not liberate the 3' block, and thus will not amplify.)

5'-<u>F1</u>-TCACArGGCAGC-A-<u>CAACAAAACA-Q</u>TCAGTATCGGCG TAGTCACC<u>TGTTTTGTTG</u>-A-TCACTATCGGA (SEQ ID NO: 25) (Upstream-Target-Sequence; 28 bp) (Downstream-Target-Sequence; 28 bp) *GTACTATCGCT*-A-<u>GCTGCCTGTGAG</u> TGCGGAAACCTATCGTCGA-3' (SEQ ID NO: 26)

Prophetic Example 19—Example of PCR Primer Design with Separate Split UniTaq Probe (UniSpTq)

Example of PCR primer design with separate split UniTaq probe:
(Tm=62.6) (156 bp total; 28+28 bp TS DNA)

Forward primer sequence: (Ai-<u>Bi'</u>-ti'-TS)
5'-TCAGTATCGGCGTAGTCACC<u>GAGTTTCCTTG</u>-A-TCACTATCGGA (SEQ ID NO: 27) (Upstream-Target-Sequence; 28 bp) rTCCGG-3' Block Reverse primer sequence: (Ci-Bj-tj-TS)
5'-TCGACGATAGGTTTCCGCAC<u>TCACAGTCAGC</u>-T-*AGCGATAGTAC* (SEQ ID NO: 28) (Downstream-Target-Sequence; 28 bp) *rGTACC*-3' Block 1$^{st}$ UniTaq Primer: (Ai)
5'-TCAGTATCGGCGTAGTCACC-3' (SEQ ID NO: 29)

2$^{nd}$ UniTaq primer: Ci
5'-TCGACGATAGGTTTCCGCAC-3' (SEQ ID NO: 30)

UniTaq Probe: (F1-Bj,Bi-Q)
5'-<u>F1</u>-TCACArGTCAGC-A-<u>CAAGGAAACTC-Q</u>-3' (SEQ ID NO: 31)

Full PCR product (Tm of probe portion hybridizing to both split complements = 62.6)

5'-<u>F1</u>-TCACArGTCAGC-A-<u>CAAGGAAACTC-Q</u>-3'
(SEQ ID NO: 32)

5'-TCAGTATCCGCGTAGTCACC<u>GAGTTTCCTTG</u>-A-TCACTATCGGA (SEQ ID NO: 33) (Upstream-Target-Sequence; 28 bp) TCCGATAGTGA-A-*AGCGATAGTAC* (SEQ ID NO: 34)

(Downstream-Target-Sequence; 28 bp) *GTACTATCGCT*-A-<u>GCTGACTGTGA</u>GTGCGGAAACCTATCGTCGA-3' (SEQ ID NO: 35)

Notes based on OligoAnalyzer 3.1 Tm calculations:

Internal bold sequences ti & ti' hairpin at 62.6° C., entire structure is given Tm value of 53.1° C.

Internal italic sequences tj & tj' hairpin at 59.7° C., entire structure is given Tm value of 53.1° C.

Separate bold sequences ti & ti' hybridize at 38.6° C.

Separate italic sequences tj & tj' hybridize at 37.2° C.

Separate double underlined sequences Bi & Bi' and Bj & Bj' have Tm of 36.4 and 42.7, respectively Combining the four hairpin regions gives an overall hairpin at 62.6.

Potential primer-dimer PCR product (Tm of probe portion hybridizing to both split complements = 51.4)

(Note: Since the primer dimer lacks authentic target sequence TCCGATAGTGA-A-*AGCGATAGTAC* (SEQ ID NO: 36), hybridization of PCR primers to such a product will not liberate the 3' block, and thus will not amplify.)

5'-<u>F1</u>-TCACArGTCAGC-A-<u>CAAGGAAACTC-Q</u>-3' (SEQ ID NO: 37)

5'-TCAGTATCCGCGTAGTCACC<u>GAGTTTCCTTG</u>-A-TCACTATCGGA (SEQ ID NO: 38) (Upstream-Target-Sequence; 28 bp) (Downstream-Target-Sequence; 28 bp) *GTACTATCGCT*-A-<u>GCTGACTGTGA</u>GTGCGGAAACCTATCGTCGA-3' (SEQ ID NO: 39)

Prophetic Example 20—Example of LDR Primer Design with Split UniTaq Probe (UniSpTq)

Example of LDR Primer Design with Split UniTaq Probe (UniSpTq) for FIG. 21:
(Tm=66.6) (170 bp total; 60 bp TS DNA)

Upstream LDR primer sequence: (Ai-<u>Bi'</u>-zi-TS)
5'-TCAGTATCGGCGTAGTCACC<u>CTGTTTTGTTG</u>-A-TCACTATCGGAC (SEQ ID NO: 40) (Upstream-Target-Sequence; 30 bp)-ribose base-first 4 downstream bases-3' Block Downstream LDR primer sequence: (TS-zi'-<u>Bj'</u>-Ci')
5'-(Downstream-Target-Sequence; 30 bp) GTCCGATAGTGA-A-GCTGCCTGTGAGGTGCGGAAACCTATCGTCGA-3' (SEQ ID NO: 41)

1$^{st}$ UniTaq Primer: (F1-Bj,Bi-Q-Ai)
5'-<u>F1</u>-CTCACAGGCAGC-A-<u>CAACAAAACAG-Q</u>TCAGTATCGGCGTAG TCACC-3' (SEQ ID NO: 42)

2$^{nd}$ UniTaq primer: Ci
5'-TCGACGATAGGTTTCCGCAC-3' (SEQ ID NO: 43)

Full length PCR product:
5'-<u>F1</u>-CTCACAGGCAGC-A-<u>CAACAAAACAG-Q</u>TCAGTATCGGCGTAG TCACC<u>CTGTTTTGTTG</u>-A-TCACTATCGGAC (SEQ ID NO: 44) (Upstream-Target-Sequence; 30 bp) (Downstream-Target-Sequence; 30 bp) GTCCGATAGTGA-A-<u>GCTGCCTGTG</u> AGGTGCGGAAACCTATCGTCGA-3' (SEQ ID NO: 45)

Notes based on OligoAnalyzer 3.1 Tm calculations:

Internal bold sequences zi & zi' hairpin at 64° C.; entire structure is given Tm value of 57.4° C.

Separately, bold sequences zi & zi' hybridize at 42.9° C.

Separate double underlined sequences Bi & Bi' and Bj & Bj' have Tm of 35.1 and 50.3, respectively.

Combining the three hairpin regions results in Tm of 66.6

This example demonstrates how to use a split zip-code design with a probe attached to one of the primers, as in traditional UniTaq. Here the advantage is that the probe oligonucleotide will hybridize to either the upstream LDR primer, or the downstream LDR primer, but will only hybridize to both when the two separate LDR probes are covalently linked and can hybridize to each other. As above, the LDR reaction is performed at 10 nM probe, and the product is diluted 10-fold when going into the UniTaq reaction, meaning the maximum LDR primer concentration is 1 nM, or about 250 to 500-fold lower than the UniTaq probe concentration. Thus, as above, the likelihood of three-way hybridization when two of the probes are at 1 nM, drops to zero. However, when there is LDR product, it gets amplified, increasing the overall concentration of product, and now it is just a single molecule hybridizing to itself (the amplified LDR product containing the attached UniTaq probe).

Prophetic Example 21—Example of LDR Primer Design with Separate Split UniTaq

Probe (UniSpTq)

Example of LDR Primer Design with Separate Split UniTaq Probe:

(Tm=65.2) (150 bp total; 60 bp TS DNA)

Upstream LDR primer sequence: (Ai-$\underline{Bi'}$-zi-TS)
5'-TCAGTATCGGCGTAGTCACC$\underline{CGAGTTTCCTTG}$-A-TCACTTTCGGAC (SEQ ID NO: 46) (Upstream-Target-Sequence; 30 bp)-ribose base-first 4 downstream bases-3' Block Downstream LDR primer sequence: (TS-zi'-$\underline{Bj'}$-Ci')
5'-(Downstream-Target-Sequence; 30 bp) GTCCGAAAG TGA-A-$\underline{GCTGACTGTGAG}$GTGCGGAAACCTATCGTCGA-3' (SEQ ID NO: 47)

1$^{st}$ UniTaq Primer: (Ai)
5'-TCAGTATCGGCGTAGTCACC-3' (SEQ ID NO: 48)

2$^{nd}$ UniTaq primer: Ci
5'-TCGACGATAGGTTTCCGCAC-3' (SEQ ID NO: 49)

UniTaq Probe: (F1-Bj,Bi-Q)
$\underline{5'-F1}$-CTCACAGTCAGC-A-$\underline{CAAGGAAACTCG-Q}$-3' (SEQ ID NO: 50)

Full length PCR product:
5'-TCAGTATCGGCGTAGTCACC$\underline{CGAGTTTCCTTG}$-A-TCACTTTCGGAC (SEQ ID NO: 51) (Upstream-Target-Sequence; 30 bp) (Downstream-Target-Sequence; 30 bp) GTCCGAAAGTGA-A-$\underline{GCTGACTGTGAG}$GTGCGGAAACCTATCGTCGA-3' (SEQ ID NO: 52)

Notes based on OligoAnalyzer 3.1 Tm calculations:

Internal bold sequences zi & zi' hairpin at 64° C.; entire structure is given Tm value of 56.3° C.

Separately, bold sequences zi & zi' hybridize at 44.7° C.

Separate double underlined sequences Bi & Bi' and Bj & Bj' have Tm of 43.0 and 45.9, respectively.

Combining the three hairpin regions gives a Tm of 65.2.

This example demonstrates how to use a split zip-code design with a separate probe. Here the advantage is that the probe oligonucleotide will hybridize to either the upstream LDR primer, or the downstream LDR primer, but will only hybridize to both when the two separate LDR probes are covalently linked and can hybridize to each other. More importantly, consider that while the average PCR experiment uses a 100 to 500 nM primer concentration, the LDR reactions described herein use a 10 nM primer concentration. The product is diluted 10-fold when going into the UniTaq reaction, meaning the maximum LDR primer concentration is 1 nM, or about 250 to 500-fold lower than the UniTaq probe concentration. Thus, the likelihood of three-way hybridization when two of the probes are at 1 nM, drops to zero. However, when there is LDR product, it gets amplified, increasing the overall concentration of product, and now it is just two molecules hybridizing to each other (the amplified LDR product and the UniTaq probe).

Prophetic Example 22—Example of qLDR Primer Design with Isothermal RNaseH2 Cleavage of Added Universal Probe (UniLDq)

Example of qLDR Primer Design with Isothermal RNaseH2 Cleavage of Added Universal Probe (UniLDq; FIG. 22):

(Tm=64.8); (145 bp total; 60 bp TS DNA)

Upstream LDR primer sequence: ($\underline{Bi'}$-ti'-TS)
5'-GAGTTTCCTTG-A-TCACTATCGGA (SEQ ID NO: 53)-Upstream-Target-Sequence-TCCGATAGTGA-A-*rAGCGG*-3' Block (SEQ ID NO: 54)

Downstream LDR primer sequence: (TS-*tj'*-$\underline{Bj'}$)
5' AGCGATAGTAC (SEQ ID NO: 55)-downstream-Target-Sequence-*GTACTATCGCT*-A-$\underline{GCTGACTGTGA}$-3' (SEQ ID NO: 56)

Cleavable Probe: (F1-Bj,Bi-Q)
$\underline{5'-F1}$-TCACArGTCAGC-A-$\underline{CAAGGAAACTC-Q}$-3' (SEQ ID NO: 57)

Full length LDR product:
5'-GAGTTTCCTTG-A-TCACTATCGGA (SEQ ID NO: 58) (Upstream-Target-Sequence; 30 bp with 3' TCCGATAGTGA-A-) (SEQ ID NO: 59) (*AGCGATAGTAC* 5' portion of downstream-Target-Sequence (SEQ ID NO: 60); 30 bp) *GTACTATCGCT*-A-$\underline{GCTGACTGTGA}$-3' (SEQ ID NO: 61)

Notes based on OligoAnalyzer 3.1 Tm calculations:

Internal bold sequences ti & ti' hairpin at 67° C., entire structure is given Tm value of 67.7° C.

Internal italic sequences tj & tj' hairpin at 63.7° C., entire structure is given Tm value of 67.7° C.

Separate bold sequences ti & ti' hybridize at 38.6° C.

Separate italic sequences tj & tj' hybridize at 37.2° C.

Separate double underlined sequences Bi & Bi' and Bj & Bj' have Tm of 36.4 and 42.7, respectively.

Combining the 4 double-stranded stem regions gives a Tm value at 64.8.

Prophetic Example 23—qLDR Primer Design with Isothermal RNaseH2 Cleavage of Added Target-Specific Probe (TsLDq)

Example of qLDR Primer Design with Isothermal RNaseH2 Cleavage of Added Target-Specific Probe (TsLDq; FIG. 23): (Tm=62) (84 bp total, example for B-raf V600E mutation).

Upstream LDR = U1-BRAF (52 bases)
5'-CGAGTTTCCTTGG-A-GTCCTAAATAGGTGATTTTGGTCTAGCTACGGA-rGAGAC-3' Block (SEQ ID NO: 62)

Downstream LDR = BRAF (37 bases)
5'-GAAATCTCGATGGAGTGGGTCCCATTTGGT-A-CGAGAT-3'
(SEQ ID NO: 63)

Complete LDR product: 84 bp
5'-CGAGTTTCCTTGG-A-GTCCTAAATAGGTGATTTTGGTCTAGCTACGGA-GAAATCTCGATGGAGTGGGTCCCATTTGGT-A-CGAGAT-3'
(SEQ ID NO: 64)

Cleavable probe:
5'-F1-CGAGArUTTCTCCGT-A-CCAAGGAAACTCG-Q
(SEQ ID NO: 65)

Notes based on OligoAnalyzer 3.1 Tm calculations:

Combined pieces of upstream & downstream LDR primers ACGGAGAAATCTCG (SEQ ID NO: 66), 14-mer, with Tm of 50.5° C.

Double underlined sequences Bi & Bi':
CGAGTTTCCTTGG (SEQ ID NO: 67) has Tm of 47.8° C.

Combining the 2 double-stranded stem regions gives a Tm value at 62° C.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

---

What is claimed:

1. A system for identifying a plurality of nucleic acid molecules in a sample, said system comprising:
   (i) an inlet port and
   (ii) a cartridge defining a space containing:
      multiple primary reaction chambers fluidically coupled to said inlet port to receive material from said inlet port and produce primary reaction chamber products from the material and
      a product capture housing enclosing a solid support with a plurality of separate columns of a plurality of product capture subdivisions configured in separate rows and columns, with each separate product capture subdivision comprising an array of a plurality of individual hydrophilic micro-pores or micro-wells, wherein each of said individual hydrophilic micro-pores or micro-wells is separated by hydrophobic surfaces where primary reaction products are further reacted to create array products which are detected in the micro-pores or micro-wells, wherein one or more of the columns of separate product capture subdivisions receive material which has passed through one of said multiple primary reaction chambers.

2. The system of claim 1 further comprising:
   (iii) an outlet port for discharging material from said product capture housing.

3. The system of claim 1, wherein the space defined by said cartridge further comprises:
   one or more initial reaction chambers into which said inlet port discharges material and from which material is discharged into said multiple primary reaction chambers.

4. The system of claim 1, wherein the space defined by the cartridge further comprises:
   multiple secondary reaction chambers, one or more of which are fluidically coupled to one of said multiple primary reaction chambers to receive material from one of said multiple primary reaction chambers and
   multiple mixing chambers each fluidically coupled to one of said multiple secondary reaction chambers to receive material from one of said multiple secondary reaction chambers and to discharge material to said product capture housing so that each column of separate product capture subdivisions is fluidically coupled to one of said multiple mixing chambers to receive material from one of said multiple mixing chambers.

5. The system of claim 4, wherein at least some of said multiple primary and secondary reaction chambers are configured to maintain a trough of liquid in said multiple primary and secondary reaction chambers.

6. The system of claim 4, wherein said multiple primary and secondary reaction chambers each have an internal baffle to maintain a trough of liquid in said multiple primary and secondary reaction chambers.

7. The system of claim 4, wherein said multiple primary and/or secondary reaction chambers each have one or more of internal baffles to maintain a plurality of troughs of liquid in said multiple primary and secondary reaction chambers.

8. The system of claim 4, wherein each of said mixing chambers include a divider extending from a position proximate to where material enters said mixing chamber to a position proximate to where material leaves said mixing chambers.

9. The system of claim 4, wherein each of said mixing chambers include a first surface which is highly hydrophobic and a second surface spaced from, and less hydrophobic than, the first surface, wherein the first and second surfaces extend from a position proximate to where material enters each of said mixing chambers to a position proximate to where material leaves each of said mixing chambers.

10. The system of claim 4, wherein said primary reaction chambers and/or said secondary reaction chambers comprise an internal surface on to which oligonucleotide primers or probes can be spotted.

11. The system of claim 1, wherein the product capture subdivisions comprise the array of the plurality of individual micro-pores each having opposed first and second open ends with the first end having a large diameter and the second end having a diameter which is smaller than that of the first end.

12. The system of claim 1, wherein the product capture subdivisions comprise the array of the plurality of individual micro-wells each having an open end and a closed end.

13. The system of claim 4, wherein said product capture housing comprises:
a plurality of fluid channels to permit material to pass from said multiple mixing chambers, through a column of the product capture subdivisions into contact with the array of micro-pores or micro-wells in those subdivisions.

14. The system of claim 1 further comprising:
one or more valves for selectively introducing or removing reagents or reactants into or out of the cartridge through said inlet.

15. The system of claim 2 further comprising:
one or more valves for selectively introducing or removing reagents or reactants into or out of said product capture housing through said outlet port and/or through a location in said product capture housing distal from said outlet port.

16. The system of claim 1 further comprising:
one or more heating elements in said cartridge in a position proximate to said primary reaction chamber and/or in a position proximate to said product capture housing.

17. The system of claim 3 further comprising:
one or more heating elements in said cartridge in a position proximate to said initial reaction chambers.

18. The system of claim 4 further comprising:
one or more heating elements in said cartridge in a position proximate to one of said secondary reaction chambers and/or in a position proximate to one of said multiple mixing chambers.

19. A method for preparing a system for identifying a plurality of nucleic acid molecules in a sample, said method comprising:
providing the system of claim 1 and applying universal tag or capture oligonucleotide primers or probes to the micro-pores or micro-wells of the product capture subdivisions on the solid support within said product capture housing, whereby the universal tag or capture oligonucleotide primers or probes are retained within the micro-pores or micro-wells.

20. The method of claim 19, further comprising:
filling the one or more primary reaction chambers with primary reaction oligonucleotide probes or primers each having a first portion comprising a nucleotide sequence complementary to a portion of target nucleic acids in the sample.

21. A process of identifying a plurality of nucleic acid molecules in a sample using the system prepared by the method of claim 20, wherein the primary reaction oligonucleotide probes or primers further comprise a second portion comprising a nucleotide sequence the same or complementary to a portion of the universal tag or capture oligonucleotide primers, retained within the micro-pores or micro-wells and wherein, following said filling the one or more primary reaction chambers and optionally said filling the one or more secondary reaction chambers, if present, said process further comprising:
conducting the primary and/or secondary reactions in said system and
detecting the presence of target nucleic acid molecules in the sample in the micro-wells or micro-pores after said conducting the primary and/or secondary reactions in said system.

22. The system of claim 11 further comprising:
a mesh screen covering the second ends of the micro-pores in said product capture housing.

23. The system of claim 11 further comprising:
a bead placed in the individual micro-pores.

24. The system of claim 13, wherein said plurality of fluid channels are located above and below the solid support.

25. The system of claim 13, wherein said plurality of fluid channels are located above the solid support.

* * * * *

SEQUENCE LISTING

<160> NUMBER OF SEQ ID NOS: 67

<210> SEQ ID NO 1
<211> LENGTH: 24
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (1)..(16)
<223> OTHER INFORMATION: n at positions 1-16 can be a, g, c, or t

<400> SEQUENCE: 1
nnnnnnnnnn nnnnnngtca gcta                                            24

<210> SEQ ID NO 2
<211> LENGTH: 24
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (1)..(16)
<223> OTHER INFORMATION: n at positions 1-16 can be a, g, c, or t

<400> SEQUENCE: 2
nnnnnnnnnn nnnnnngtca atcg                                            24

<210> SEQ ID NO 3
<211> LENGTH: 24
<212> TYPE: DNA
<213> ORGANISM: Artificial Sequence
<220> FEATURE:
<223> OTHER INFORMATION: primer
<220> FEATURE:

<221> NAME/KEY: misc_feature
<222> LOCATION: (1)..(16)
<223> OTHER INFORMATION: n at positions 1-16 can be a, g, c, or t

<400> SEQUENCE: 3
nnnnnnnnnn nnnnnngtca tagc                                          24

<210> SEQ ID NO 4
<211> LENGTH: 24
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (1)..(16)
<223> OTHER INFORMATION: n at positions 1-16 can be a, g, c, or t

<400> SEQUENCE: 4
nnnnnnnnnn nnnnnngtca cgat                                          24

<210> SEQ ID NO 5
<211> LENGTH: 24
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (1)..(16)
<223> OTHER INFORMATION: n at positions 1-16 can be a, g, c, or t

<400> SEQUENCE: 5
nnnnnnnnnn nnnnnnactg gcta                                          24

<210> SEQ ID NO 6
<211> LENGTH: 24
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (1)..(16)
<223> OTHER INFORMATION: n at positions 1-16 can be a, g, c, or t

<400> SEQUENCE: 6
nnnnnnnnnn nnnnnnactg atcg                                          24

<210> SEQ ID NO 7
<211> LENGTH: 24
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (1)..(16)
<223> OTHER INFORMATION: n at positions 1-16 can be a, g, c, or t

<400> SEQUENCE: 7
nnnnnnnnnn nnnnnnactg tagc                                          24

<210> SEQ ID NO 8
<211> LENGTH: 24
<212> TYPE: DNA
<213> ORGANISM: Artificial Sequence
<220> FEATURE:
<223> OTHER INFORMATION: primer

```
<220> FEATURE:
<221> NAME/KEY: misc_feature
<222> LOCATION: (1)..(16)
<223> OTHER INFORMATION: n at positions 1-16 can be a, g, c, or t

<400> SEQUENCE: 8
nnnnnnnnnn nnnnnnactg cgat                                              24

<210> SEQ ID NO 9
<211> LENGTH: 24
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (1)..(16)
<223> OTHER INFORMATION: n at positions 1-16 can be a, g, c, or t

<400> SEQUENCE: 9
nnnnnnnnnn nnnnnntgac gcta                                              24

<210> SEQ ID NO 10
<211> LENGTH: 24
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (1)..(16)
<223> OTHER INFORMATION: n at positions 1-16 can be a, g, c, or t

<400> SEQUENCE: 10
nnnnnnnnnn nnnnnntgac atcg                                              24

<210> SEQ ID NO 11
<211> LENGTH: 24
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (1)..(16)
<223> OTHER INFORMATION: n at positions 1-16 can be a, g, c, or t

<400> SEQUENCE: 11
nnnnnnnnnn nnnnnntgac tagc                                              24

<210> SEQ ID NO 12
<211> LENGTH: 24
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (1)..(16)
<223> OTHER INFORMATION: n at positions 1-16 can be a, g, c, or t

<400> SEQUENCE: 12
nnnnnnnnnn nnnnnntgac cgat                                              24

<210> SEQ ID NO 13
<211> LENGTH: 24
<212> TYPE: DNA
<213> ORGANISM: Artificial Sequence
<220> FEATURE:
```

```
<223> OTHER INFORMATION: primer
<220> FEATURE:
<221> NAME/KEY: misc_feature
<222> LOCATION: (1)..(16)
<223> OTHER INFORMATION: n at positions 1-16 can be a, g, c, or t

<400> SEQUENCE: 13
nnnnnnnnnn nnnnnncagt gcta                                          24

<210> SEQ ID NO 14
<211> LENGTH: 24
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (1)..(16)
<223> OTHER INFORMATION: n at positions 1-16 can be a, g, c, or t

<400> SEQUENCE: 14
nnnnnnnnnn nnnnnncagt atcg                                          24

<210> SEQ ID NO 15
<211> LENGTH: 24
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (1)..(16)
<223> OTHER INFORMATION: n at positions 1-16 can be a, g, c, or t

<400> SEQUENCE: 15
nnnnnnnnnn nnnnnncagt tagc                                          24

<210> SEQ ID NO 16
<211> LENGTH: 24
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (1)..(16)
<223> OTHER INFORMATION: n at positions 1-16 can be a, g, c, or t

<400> SEQUENCE: 16
nnnnnnnnnn nnnnnncagt cgat                                          24

<210> SEQ ID NO 17
<211> LENGTH: 42
<212> TYPE: DNA
<213> ORGANISM: Artificial Sequence
<220> FEATURE:
<223> OTHER INFORMATION: primer

<400> SEQUENCE: 17
tcagtatcgg cgtagtcacc tgttttgttg atcactatcg ga                      42

<210> SEQ ID NO 18
<211> LENGTH: 43
<212> TYPE: DNA
<213> ORGANISM: Artificial Sequence
<220> FEATURE:
<223> OTHER INFORMATION: primer

<400> SEQUENCE: 18
```
tcgacgatag gtttccgcac tcacaggcag ctagcgatag tac 43

```
<210> SEQ ID NO 19
<211> LENGTH: 43
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (6)..(6)
<223> OTHER INFORMATION: n at position 6 can be a, g, c, or u
<220> FEATURE:
<221> NAME/KEY: misc_feature
<222> LOCATION: (6)..(6)
<223> OTHER INFORMATION: n at position 6 is RNA

<400> SEQUENCE: 19
```
tcacanggca gcacaacaaa acatcagtat cggcgtagtc acc 43

```
<210> SEQ ID NO 20
<211> LENGTH: 20
<212> TYPE: DNA
<213> ORGANISM: Artificial Sequence
<220> FEATURE:
<223> OTHER INFORMATION: primer

<400> SEQUENCE: 20
```
tcgacgatag gtttccgcac 20

```
<210> SEQ ID NO 21
<211> LENGTH: 65
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (6)..(6)
<223> OTHER INFORMATION: n at position 6 can be a, g, c, or u
<220> FEATURE:
<221> NAME/KEY: misc_feature
<222> LOCATION: (6)..(6)
<223> OTHER INFORMATION: n at position 6 is RNA

<400> SEQUENCE: 21
```
tcacanggca gcacaacaaa acatcagtat cggcgtagtc acctgttttg ttgatcacta 60
tcgga 65

```
<210> SEQ ID NO 22
<211> LENGTH: 51
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (1)..(28)
<223> OTHER INFORMATION: n at positions 1-28 can be a, g, c, or t

<400> SEQUENCE: 22
```
nnnnnnnnnn nnnnnnnnnn nnnnnnnntc cgatagtgaa agcgatagta c 51

```
<210> SEQ ID NO 23
<211> LENGTH: 71
<212> TYPE: DNA
<213> ORGANISM: Artificial Sequence
<220> FEATURE:
```

```
<223> OTHER INFORMATION: primer
<220> FEATURE:
<221> NAME/KEY: misc_feature
<222> LOCATION: (1)..(28)
<223> OTHER INFORMATION: n at positions 1-28 can be a, g, c, or t

<400> SEQUENCE: 23
nnnnnnnnnn nnnnnnnnnn nnnnnnnngt actatcgcta gctgcctgtg agtgcggaaa      60
cctatcgtcg a                                                          71

<210> SEQ ID NO 24
<211> LENGTH: 23
<212> TYPE: DNA
<213> ORGANISM: Artificial Sequence
<220> FEATURE:
<223> OTHER INFORMATION: primer

<400> SEQUENCE: 24
tccgatagtg aaagcgatag tac                                             23

<210> SEQ ID NO 25
<211> LENGTH: 65
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (6)..(6)
<223> OTHER INFORMATION: n at position 6 can be a, g, c, or u
<220> FEATURE:
<221> NAME/KEY: misc_feature
<222> LOCATION: (6)..(6)
<223> OTHER INFORMATION: n at position 6 is RNA

<400> SEQUENCE: 25
tcacanggca gcacaacaaa acatcagtat cggcgtagtc acctgttttg ttgatcacta      60
tcgga                                                                 65

<210> SEQ ID NO 26
<211> LENGTH: 99
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (1)..(56)
<223> OTHER INFORMATION: n at positions 1-56 can be a, g, c, or t

<400> SEQUENCE: 26
nnnnnnnnnn nnnnnnnnnn nnnnnnnnnn nnnnnnnnnn nnnnnnnnnn nnnnnngtac      60
tatcgctagc tgcctgtgag tgcggaaacc tatcgtcga                            99

<210> SEQ ID NO 27
<211> LENGTH: 43
<212> TYPE: DNA
<213> ORGANISM: Artificial Sequence
<220> FEATURE:
<223> OTHER INFORMATION: primer

<400> SEQUENCE: 27
tcagtatcgg cgtagtcacc gagtttcctt gatcactatc gga                       43

<210> SEQ ID NO 28
<211> LENGTH: 43
```

-continued

```
<212> TYPE: DNA
<213> ORGANISM: Artificial Sequence
<220> FEATURE:
<223> OTHER INFORMATION: primer

<400> SEQUENCE: 28
tcgacgatag gtttccgcac tcacagtcag ctagcgatag tac                    43

<210> SEQ ID NO 29
<211> LENGTH: 20
<212> TYPE: DNA
<213> ORGANISM: Artificial Sequence
<220> FEATURE:
<223> OTHER INFORMATION: primer

<400> SEQUENCE: 29
tcagtatcgg cgtagtcacc                                              20

<210> SEQ ID NO 30
<211> LENGTH: 20
<212> TYPE: DNA
<213> ORGANISM: Artificial Sequence
<220> FEATURE:
<223> OTHER INFORMATION: primer

<400> SEQUENCE: 30
tcgacgatag gtttccgcac                                              20

<210> SEQ ID NO 31
<211> LENGTH: 24
<212> TYPE: DNA
<213> ORGANISM: Artificial Sequence
<220> FEATURE:
<223> OTHER INFORMATION: probe
<220> FEATURE:
<221> NAME/KEY: misc_feature
<222> LOCATION: (6)..(6)
<223> OTHER INFORMATION: n at position 6 can be a, g, c, or u
<220> FEATURE:
<221> NAME/KEY: misc_feature
<222> LOCATION: (6)..(6)
<223> OTHER INFORMATION: n at position 6 is RNA

<400> SEQUENCE: 31
tcacangtca gcacaaggaa actc                                         24

<210> SEQ ID NO 32
<211> LENGTH: 24
<212> TYPE: DNA
<213> ORGANISM: Artificial Sequence
<220> FEATURE:
<223> OTHER INFORMATION: probe
<220> FEATURE:
<221> NAME/KEY: misc_feature
<222> LOCATION: (6)..(6)
<223> OTHER INFORMATION: n at position 6 can be a, g, c, or u
<220> FEATURE:
<221> NAME/KEY: misc_feature
<222> LOCATION: (6)..(6)
<223> OTHER INFORMATION: n at position 6 is RNA

<400> SEQUENCE: 32
tcacangtca gcacaaggaa actc                                         24

<210> SEQ ID NO 33
<211> LENGTH: 43
<212> TYPE: DNA
<213> ORGANISM: Artificial Sequence
<220> FEATURE:
```

<223> OTHER INFORMATION: primer

<400> SEQUENCE: 33
tcagtatccg cgtagtcacc gagtttcctt gatcactatc gga     43

<210> SEQ ID NO 34
<211> LENGTH: 51
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (1)..(28)
<223> OTHER INFORMATION: n at positions 1-28 can be a, g, c, or t

<400> SEQUENCE: 34
nnnnnnnnnn nnnnnnnnnn nnnnnnnntc cgatagtgaa agcgatagta c     51

<210> SEQ ID NO 35
<211> LENGTH: 71
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (1)..(28)
<223> OTHER INFORMATION: n at positions 1-28 can be a, g, c, or t

<400> SEQUENCE: 35
nnnnnnnnnn nnnnnnnnnn nnnnnnnngt actatcgcta gctgactgtg agtgcggaaa     60
cctatcgtcg a     71

<210> SEQ ID NO 36
<211> LENGTH: 23
<212> TYPE: DNA
<213> ORGANISM: Artificial Sequence
<220> FEATURE:
<223> OTHER INFORMATION: primer

<400> SEQUENCE: 36
tccgatagtg aaagcgatag tac     23

<210> SEQ ID NO 37
<211> LENGTH: 24
<212> TYPE: DNA
<213> ORGANISM: Artificial Sequence
<220> FEATURE:
<223> OTHER INFORMATION: probe
<220> FEATURE:
<221> NAME/KEY: misc_feature
<222> LOCATION: (6)..(6)
<223> OTHER INFORMATION: n at position 6 can be a, g, c, or u
<220> FEATURE:
<221> NAME/KEY: misc_feature
<222> LOCATION: (6)..(6)
<223> OTHER INFORMATION: n at position 6 is RNA

<400> SEQUENCE: 37
tcacangtca gcacaaggaa actc     24

<210> SEQ ID NO 38
<211> LENGTH: 43
<212> TYPE: DNA
<213> ORGANISM: Artificial Sequence
<220> FEATURE:
<223> OTHER INFORMATION: primer

<400> SEQUENCE: 38
tcagtatccg cgtagtcacc gagtttcctt gatcactatc gga                43

<210> SEQ ID NO 39
<211> LENGTH: 99
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (1)..(56)
<223> OTHER INFORMATION: n at positions 1-56 can be a, g, c, or t

<400> SEQUENCE: 39
nnnnnnnnnn nnnnnnnnnn nnnnnnnnnn nnnnnnnnnn nnnnnnnnnn nnnnnngtac    60
tatcgctagc tgactgtgag tgcggaaacc tatcgtcga                             99

<210> SEQ ID NO 40
<211> LENGTH: 44
<212> TYPE: DNA
<213> ORGANISM: Artificial Sequence
<220> FEATURE:
<223> OTHER INFORMATION: primer

<400> SEQUENCE: 40
tcagtatcgg cgtagtcacc ctgttttgtt gatcactatc ggac               44

<210> SEQ ID NO 41
<211> LENGTH: 75
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (1)..(30)
<223> OTHER INFORMATION: n at positions 1-30 can be a, g, c, or t

<400> SEQUENCE: 41
nnnnnnnnnn nnnnnnnnnn nnnnnnnnnn gtccgatagt gaagctgcct gtgaggtgcg    60
gaaacctatc gtcga                                                       75

<210> SEQ ID NO 42
<211> LENGTH: 44
<212> TYPE: DNA
<213> ORGANISM: Artificial Sequence
<220> FEATURE:
<223> OTHER INFORMATION: primer

<400> SEQUENCE: 42
ctcacaggca gcacaacaaa acagtcagta tcggcgtagt cacc               44

<210> SEQ ID NO 43
<211> LENGTH: 20
<212> TYPE: DNA
<213> ORGANISM: Artificial Sequence
<220> FEATURE:
<223> OTHER INFORMATION: primer

<400> SEQUENCE: 43
tcgacgatag gtttccgcac                                          20

<210> SEQ ID NO 44

```
<211> LENGTH: 68
<212> TYPE: DNA
<213> ORGANISM: Artificial Sequence
<220> FEATURE:
<223> OTHER INFORMATION: probe

<400> SEQUENCE: 44
ctcacaggca gcacaacaaa acagtcagta tcggcgtagt caccctgttt tgttgatcac      60
tatcggac                                                              68

<210> SEQ ID NO 45
<211> LENGTH: 105
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (1)..(60)
<223> OTHER INFORMATION: n at positions 1-60 can be a, g, c, or t

<400> SEQUENCE: 45
nnnnnnnnnn nnnnnnnnnn nnnnnnnnnn nnnnnnnnnn nnnnnnnnnn nnnnnnnnnn      60
gtccgatagt gaagctgcct gtgaggtgcg gaaacctatc gtcga                     105

<210> SEQ ID NO 46
<211> LENGTH: 45
<212> TYPE: DNA
<213> ORGANISM: Artificial Sequence
<220> FEATURE:
<223> OTHER INFORMATION: primer

<400> SEQUENCE: 46
tcagtatcgg cgtagtcacc cgagtttcct tgatcacttt cggac                      45

<210> SEQ ID NO 47
<211> LENGTH: 75
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (1)..(30)
<223> OTHER INFORMATION: n at positions 1-30 can be a, g, c, or t

<400> SEQUENCE: 47
nnnnnnnnnn nnnnnnnnnn nnnnnnnnnn gtccgaaagt gaagctgact gtgaggtgcg      60
gaaacctatc gtcga                                                      75

<210> SEQ ID NO 48
<211> LENGTH: 20
<212> TYPE: DNA
<213> ORGANISM: Artificial Sequence
<220> FEATURE:
<223> OTHER INFORMATION: primer

<400> SEQUENCE: 48
tcagtatcgg cgtagtcacc                                                  20

<210> SEQ ID NO 49
<211> LENGTH: 20
<212> TYPE: DNA
<213> ORGANISM: Artificial Sequence
<220> FEATURE:
<223> OTHER INFORMATION: primer
```

```
<400> SEQUENCE: 49
tcgacgatag gtttccgcac                                               20

<210> SEQ ID NO 50
<211> LENGTH: 25
<212> TYPE: DNA
<213> ORGANISM: Artificial Sequence
<220> FEATURE:
<223> OTHER INFORMATION: probe

<400> SEQUENCE: 50
ctcacagtca gcacaaggaa actcg                                         25

<210> SEQ ID NO 51
<211> LENGTH: 45
<212> TYPE: DNA
<213> ORGANISM: Artificial Sequence
<220> FEATURE:
<223> OTHER INFORMATION: primer

<400> SEQUENCE: 51
tcagtatcgg cgtagtcacc cgagtttcct tgatcacttt cggac                   45

<210> SEQ ID NO 52
<211> LENGTH: 105
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (1)..(60)
<223> OTHER INFORMATION: n at positions 1-60 can be a, g, c, or t

<400> SEQUENCE: 52
nnnnnnnnnn nnnnnnnnnn nnnnnnnnnn nnnnnnnnnn nnnnnnnnnn nnnnnnnnnn   60
gtccgaaagt gaagctgact gtgaggtgcg gaaacctatc gtcga                  105

<210> SEQ ID NO 53
<211> LENGTH: 23
<212> TYPE: DNA
<213> ORGANISM: Artificial Sequence
<220> FEATURE:
<223> OTHER INFORMATION: primer

<400> SEQUENCE: 53
gagtttcctt gatcactatc gga                                           23

<210> SEQ ID NO 54
<211> LENGTH: 18
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (13)..(13)
<223> OTHER INFORMATION: n at position 13 can be a, g, c, or u
<220> FEATURE:
<221> NAME/KEY: misc_feature
<222> LOCATION: (13)..(13)
<223> OTHER INFORMATION: n at position 13 is RNA

<400> SEQUENCE: 54
tccgatagtg aanagcgg                                                 18
```

<210> SEQ ID NO 55
<211> LENGTH: 11
<212> TYPE: DNA
<213> ORGANISM: Artificial Sequence
<220> FEATURE:
<223> OTHER INFORMATION: primer

<400> SEQUENCE: 55
agcgatagta c                                                          11

<210> SEQ ID NO 56
<211> LENGTH: 23
<212> TYPE: DNA
<213> ORGANISM: Artificial Sequence
<220> FEATURE:
<223> OTHER INFORMATION: primer

<400> SEQUENCE: 56
gtactatcgc tagctgactg tga                                             23

<210> SEQ ID NO 57
<211> LENGTH: 24
<212> TYPE: DNA
<213> ORGANISM: Artificial Sequence
<220> FEATURE:
<223> OTHER INFORMATION: probe
<220> FEATURE:
<221> NAME/KEY: misc_feature
<222> LOCATION: (6)..(6)
<223> OTHER INFORMATION: n at position 6 can be a, g, c, or u
<220> FEATURE:
<221> NAME/KEY: misc_feature
<222> LOCATION: (6)..(6)
<223> OTHER INFORMATION: n at position 6 is RNA

<400> SEQUENCE: 57
tcacangtca gcacaaggaa actc                                            24

<210> SEQ ID NO 58
<211> LENGTH: 23
<212> TYPE: DNA
<213> ORGANISM: Artificial Sequence
<220> FEATURE:
<223> OTHER INFORMATION: primer

<400> SEQUENCE: 58
gagtttcctt gatcactatc gga                                             23

<210> SEQ ID NO 59
<211> LENGTH: 42
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (1)..(30)
<223> OTHER INFORMATION: n at positions 1-30 can be a, g, c, or t

<400> SEQUENCE: 59
nnnnnnnnnn nnnnnnnnnn nnnnnnnnnn tccgatagtg aa                        42

<210> SEQ ID NO 60
<211> LENGTH: 41
<212> TYPE: DNA
<213> ORGANISM: Artificial Sequence
<220> FEATURE:
<223> OTHER INFORMATION: primer

```
<220> FEATURE:
<221> NAME/KEY: misc_feature
<222> LOCATION: (12)..(41)
<223> OTHER INFORMATION: n at positions 12-41 can be a, g, c, or t

<400> SEQUENCE: 60
agcgatagta cnnnnnnnnn nnnnnnnnnn nnnnnnnnnn n                         41

<210> SEQ ID NO 61
<211> LENGTH: 23
<212> TYPE: DNA
<213> ORGANISM: Artificial Sequence
<220> FEATURE:
<223> OTHER INFORMATION: primer

<400> SEQUENCE: 61
gtactatcgc tagctgactg tga                                             23

<210> SEQ ID NO 62
<211> LENGTH: 53
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (48)..(48)
<223> OTHER INFORMATION: n at position 48 can be a, g, c, or u
<220> FEATURE:
<221> NAME/KEY: misc_feature
<222> LOCATION: (48)..(48)
<223> OTHER INFORMATION: n at position 48 is RNA

<400> SEQUENCE: 62
cgagtttcct tggagtccta aataggtgat tttggtctag ctacgganga gac             53

<210> SEQ ID NO 63
<211> LENGTH: 37
<212> TYPE: DNA
<213> ORGANISM: Artificial Sequence
<220> FEATURE:
<223> OTHER INFORMATION: primer

<400> SEQUENCE: 63
gaaatctcga tggagtgggt cccatttggt acgagat                              37

<210> SEQ ID NO 64
<211> LENGTH: 84
<212> TYPE: DNA
<213> ORGANISM: Artificial Sequence
<220> FEATURE:
<223> OTHER INFORMATION: primer

<400> SEQUENCE: 64
cgagtttcct tggagtccta aataggtgat tttggtctag ctacggagaa atctcgatgg      60
agtgggtccc atttggtacg agat                                            84

<210> SEQ ID NO 65
<211> LENGTH: 29
<212> TYPE: DNA
<213> ORGANISM: Artificial Sequence
<220> FEATURE:
<223> OTHER INFORMATION: probe
<220> FEATURE:
<221> NAME/KEY: misc_feature
<222> LOCATION: (6)..(6)
<223> OTHER INFORMATION: n at position 6 can be a, g, c, or u
<220> FEATURE:
```

```
<221> NAME/KEY: misc_feature
<222> LOCATION: (6)..(6)
<223> OTHER INFORMATION: n at position 6 is RNA
<220> FEATURE:
<221> NAME/KEY: misc_feature
<222> LOCATION: (7)..(7)
<223> OTHER INFORMATION: n at position 7 is u
<220> FEATURE:
<221> NAME/KEY: misc_feature
<222> LOCATION: (7)..(7)
<223> OTHER INFORMATION: n at position 7 is an RNA

<400> SEQUENCE: 65
cgagannttc tccgtaccaa ggaaactcg                                    29

<210> SEQ ID NO 66
<211> LENGTH: 14
<212> TYPE: DNA
<213> ORGANISM: Artificial Sequence
<220> FEATURE:
<223> OTHER INFORMATION: primer

<400> SEQUENCE: 66
acggagaaat ctcg                                                    14

<210> SEQ ID NO 67
<211> LENGTH: 13
<212> TYPE: DNA
<213> ORGANISM: Artificial Sequence
<220> FEATURE:
<223> OTHER INFORMATION: primer

<400> SEQUENCE: 67
cgagtttcct tgg                                                     13
```